US006833248B2

(12) United States Patent
Kletzien et al.

(10) Patent No.: US 6,833,248 B2
(45) Date of Patent: Dec. 21, 2004

(54) HUMAN CASPASE-12 MATERIALS AND METHODS

(75) Inventors: Rolf F. Kletzien, Plainwell, MI (US); Ilene M. Reardon, Kalamazoo, MI (US); Katherine L. Weiland, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/851,873

(22) Filed: May 8, 2001

(65) Prior Publication Data

US 2003/0165488 A1 Sep. 4, 2003

Related U.S. Application Data

(60) Provisional application No. 60/203,162, filed on May 9, 2000.

(51) Int. Cl.$^7$ .............................. C12Q 1/37; C12N 9/64
(52) U.S. Cl. ......................... 435/23; 435/226; 435/183; 435/219; 435/212; 435/69.1; 530/350
(58) Field of Search .......................... 435/23, 69.1, 226, 435/183, 219, 212; 530/350

(56) References Cited

PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*
Bitko, et al., "An endoplasmic reticulum–specific stress–activated caspase (caspase–12) is implicated in the apoptosis of A549 epithelial cells by respiratory syncytial virus," *J. Cell. Biochem.* 80:441–454 (2001).
Celesia, "Disorders of membrane channels or channelopathies," *Clin. Neurophysiol.* 112:2–18 (2001).
Deigner, et al., "Apoptosis modulators in the therapy of neurodegenerative diseases," *Exp. Opin. Investig. Drugs* 9:747–764 (2000).
Kaufman, "Stress signaling from the lumen of the endoplasmic reticulum: coordination of gene transcriptional and translational controls," *Genes & Develop.* 13:1211–1233 (1999).
Kumar, "Mechanisms mediating caspase activation in cell death," *Cell Death Differ.* 6:1060–1066 (1999).
Nakagawa, et al., "Caspase–12 mediates endoplasmic–reticulum–specific apoptosis and cytotoxicity by amyloid–β," *Nature* 403:98–103 (2000).

NCBI Database Genbank Accession No. AC009795, National Library of Medicine, (Bethesda, Maryland, US).
NCBI Database Genbank Accession No. AC009799, National Library of Medicine, (Bethesda, Maryland, US).
NCBI Database Genbank Accession No. AP002004, National Library of Medicine, (Bethesda, Maryland, US).
Paschen, "Dependence of vital cell function on endoplasmic reticulum calcium levels: implications for the mechanisms underlying neuronal cell injury in different pathological states," *Cell Calcium* 29:1–11 (2001).
Scaffidi, et al., "FLICE is predominantly expressed as two functionally active isoforms, caspase–8/a and caspase–8/b," *J. Biol. Chem.* 272:26953–26958 (1997).
Shorofsky, et al., "Calcium currents and arrhythmias: insights from molecular biology," *Am. J. Med.* 110:127–140 (2001).
Slee, et al., "Serial killers: ordering caspase activation events in apoptosis," *Cell Death Differ.* 6:1067–1074 (1999).
Stennicke, et al., "Catalytic properties of the caspases," *Cell Death Differ.* 6:1054–1059 (1999).
Takahashi, "Caspase: executioner and undertaker of apoptosis," *Int. J. Hematology* 70:226–232 (1999).
Tzivoni, "End organ protection by calcium–channel blockers," *Clin. Cardiol.* 24:102–106 (2001).
Van de Craen, et al., "Characterization of seven murine caspase family members," *FEBS Lett.* 403:61–69 (1997).
Vanderkish, et al., "The pathogenic activation of calpain: a marker and mediator of cellular toxicity and disease states," *Int. J. Exp. Path.* 81:323–339 (2000).
Yoneda, et al., "Activation of caspase–12, an endoplasmic reticulum (ER) resident caspase, through tumor necrosis factor receptor–associated factor 2 (TRAF2) dependent mechanism in response to ER stress," *J. Biol. Chem.*, Manuscript M010677200, Jan. 29, 2001.
Zeuner, et al., "Caspase activation without death," *Cell Death Differ.* 6:1075–1080 (1999).

* cited by examiner

Primary Examiner—Richard Hutson
(74) Attorney, Agent, or Firm—Marshall, Gerstein & Borun LLP

(57) ABSTRACT

The present invention provides novel human caspase-12 polynucleotides and polypeptides; constructs and recombinant host cells incorporating the polynucleotides; the human caspase-12 polypeptides encoded by the polynucleotides; antibodies to the polypeptides; and methods of making and using all of the foregoing.

5 Claims, 20 Drawing Sheets

```
Human caspase-1     ------------------------------------------------------------ MADKVLKEKRKLFIRSMG
Human caspase-13a   ------------------------------------------------------------ MAEDKHNKNPLKMLESLG
Human caspase-4     ------------------------------------------------------------ MAEGNHRKKPLKVLESLG
Human caspase-5     MFKGILQSGLDNFVINHMLKNNVAGQTSIQTLVPNTDQKSTSVKKDNHKKKTVKRMLEYLG
Human caspase-12    ------------------------------------------------------------ VHMVKLLI
Mouse caspase-12    ------------------------------------------------------------ MAARRTHERDPIYKIKGLA
Mouse caspase-11    ------------------------------------------------------------ MAENKHPDKPLKVLEQLG
conserved amino acids b                                                                   :  :

Human caspase-1     EGTINGLLDELLQTRVLNKEEMEKVKRENATVMDKTRALIDSVIPKGAQACQICITYICE
Human caspase-13a   KELISGLLDDFVEKNVIKLEEEEKKKTIYDAKLQDKARVLVDSIRQKNQEAGQVFVQTFLN
Human caspase-4     KDFLTGVLDNLVEQNVLNWKEEEKKKYYDAKTEDKVRVMADSMQEKQRMAGQMLLQTEFN
Human caspase-5     KDVLHGVFNYLAKHDVLTLKEEERKKYYDAKIEDKALLLVDSLR-KNRVAHQMFTQTLLN
Human caspase-12    KTFLDGIFDDLMENNVINTDEIHLIGKCLKFVVSNAENLVDDITETAQIAGKIFREHLWN
Mouse caspase-12    KDMLDGVFDDLVEKNVLNGDELLKIGESASFILNKAENLVENFLEKTDMAGKIFAGHIAN
Mouse caspase-11    KEVLTEYLEKLVQSNVLKLKEEDKQKFNNAERSDKRWVFVDAMKKKHSKVGEMLLQTEFS
conserved amino acids b   :    :    :         *   *         .

Human caspase-1     EDSYLAGTLGLSADQ------TSGNYLNMQDSQGVLSSFPAPQAVQDN------PAMPTS
Human caspase-13a   ID-------------------------------KNS-----TSIKAPEETVAG----PDESV-
Human caspase-4     ID-------------------------------QIS-----PNKKAHPNMEAG----PPESG-
Human caspase-5     MD-------------------------------QKI-----TSVKPLLQIEAG----PPESA-
Human caspase-12    SKKQLS------------------------------
Human caspase-12    SQEQLSLQFSNDEDDGPQKICTPSSPESKRKVEDDEMEVNAGLAHESHLMLTAPHGLQS
Mouse caspase-12    VD-------------------------------PGS-----HHGEANLEMEE-----PEE---
Mouse caspase-11    
conserved amino acids b     :***   . .    *        .    . :    .

Human caspase-1     SGSEGNVKLCSLEEAQRIWKQKSAEIYPIMQKSSRTRLALIICNEEFDSIPRRTGAEVDI
Human caspase-13a   - GSAATLKLCPHEEFLKLCPHEEFLKLCKERAGEIYPIKERKDRTRLALIICNTEFDHMPPRNGAALDI
Human caspase-4     - ESTDALKLCPHEEFLRLCKERAEEIYPIKERNNRTRLALIICNTEFDHLPPRNGADFDI
Human caspase-5     - ESTNILKLCPREEFLRLCKKNHDEIYPIKKREDRRLALIICNTKFDHLPARNGAHYDI
Human caspase-12    ------------------QIYPVMEKERRTCLASNIRNKEFNYLJNRNGSELDL
Human caspase-12    SEVQDTLKLCPRDQFCKIKTERAKEIYPVMEKEGRTRLALIICNKKFDYLFDRDNADTDI
Mouse caspase-12    -- SLNTLKLCSPEEFTRLCREKTQEIYPIKEANGRTRKALIICNTEFKHLSLRYGAKFDI
conserved amino acids b    :***:.    .  *  .  :.   *  * **  *  :       .  *:
```

FIGURE 1A

```
Human caspase-1      TGMTMLLQNLGY SVDVKKNLTASD MTELEAFAHRP EHKTSDSTFLVF MSHGIREGICGK
Human caspase-13a    LGMKQLLEGLGY TVEVEEKLTARD MESVLWKFAARE EHKSSDSTFLVF MSHGILDGICGT
Human caspase-4      TGMKELLEGLDY SVDVEENLTARD MESALRAFATRP EHKSSDSTFLVL MSHGILEGICGT
Human caspase-5      VGMKRLLQGLGY TVVDEKNLTARD MESVLRAFAARP EHKSSDSTFLVL MSHGILEGICGT
Human caspase-12     LGMXDLLENLGY SVGIKENLTAQE METALRQFAAHP EHQSSDSTFLVV MSHSILNGICGT
Mouse caspase-12     LNMQELLENLGY SVVLKENLTAQE METELMQFAGRP EHQSSDSTFLVF MSHGILEGICGV
Mouse caspase-11     IGMKGLLEDLGY DVVVKEELTAEG MESEMKDFAALS EHQTSDSTFLVL MSHGTLHGICGT
conserved amino acidsb    .*  **:.*.*  *  :::****  **  ..  **   **::********. ***.  .****

Human caspase-1      KHSEQVPDILQL NAIFNMLNTKNC PSLKDKPKVIII QACRGDSPGVVW FKDSVG-VSGNL
Human caspase-13a    MHSEEEPDVLPY DTIFRTFNNRNC LSLKDKPKVIIV QACRGANRGELW VSDSPP-ALADS
Human caspase-4      VHDEKKPDVLLY DTIFQIFNNRNC LSLKDKPKVIIV QACRGANRGELW VRDSPA-SLEVA
Human caspase-5      AHKKKKPDVLLY DTIFQIFNNRNC LSLKDKPKVIIV QACRGEKHGELW VRDSPA-SLAVI
Human caspase-12     KHWDQEPDVLHD DTIFEIFNNRNC QSLKDKPKVIIM QACRGNGAGIVW FTTDSGKASADT
Mouse caspase-12     KHRNKKPDVLHD DTIFKIFNNSNC RSLRNKPKILIM QACRGRYNGTIW VSTNKGIATADT
Mouse caspase-11     MHSEKTPDVLQY DTIYQIFNNCHC PGLRDKPKVIIV QACRGGNSGEMW IRESSK-PQLCR
conserved amino acidsb    *  .. :**:.  ** ..*. ** .:****:::*: *****. ***** .     .

Human caspase-1      SLP-TTEEFEDD AIKKAHIEKDFI AFCSSTPDNVSW RHPTMGSVFIGR LIEHMQEYACSC
Human caspase-13a    FSQ-SSENLEED AVYKTHVEKDFI AFCSSTPHNVSW RDIKKGSLFITR LITCFQKYAWCC
Human caspase-4      SSQ-SSENLEED AVYKTHVEKDFI AFCSSTPHNVSW RDSTMGSIFITQ LITCFQKYSWCC
Human caspase-5      SSQ-SSENLEAD SVCKIHEEKDFI AFCSSTPHNVSW RDRTRGSIFITE LITCFQKYSCCC
Human caspase-12     HGRLLQGNICND AVTKAHVEKDFI AFKSSTPR---- ------------ ------------
Mouse caspase-12     DEERVLSCKWNN SITKAHVETDFI AFKSSTPHNISW KVGKTGSLFISK LIDCFKKYCWCY
Mouse caspase-11     GVD-LPRNMEAD AVKLSHVEKDFI AFYSTTPHHLSY RDKTGGSYFITR LISCFRKHACSC
conserved amino acidsb    * . *.******  *:**     * *  :: ******* *:**

Human caspase-1      DVEEIFRKVRFS FEQPDGRAQMPT TERVTLTRCFYL FPGH
Human caspase-13a    HLBEVFRKVQQS FEKPNVKAQMPT VERLSMTRYFYL FPGN
Human caspase-4      HLEEVFRKVQQS FETPRAKAQMPT IERLSMTRYFYL FPGN
Human caspase-5      HLMEIFRKVQKS FEVPQAKAQMPT IERATLTRDFYL FPGN
Human caspase-12     ----SHS FETPNIILTQLPT IERLSMTRYFYL FPGN
Mouse caspase-12     HLEEIFRKVQHS FEVPGELTQMPT IERVSMTRYFYL FPGN
Mouse caspase-11     HLFDIFLKVQQS FEKASIHSQMPT IDRATLTRYFYL FPGN
conserved amino acidsb    ***. :**::** .*  ::** ******:
```

```
hCaspase12  MADEKPSNGVLVHMVKLLIKTFLDGIFDDLMENNVLNTDEIHLIGKCLKFVVSNAENLVD
KW-Ap       MADEKPSNGVLVHMVKLLIKTFLDGIFDDLMENNVLNTDEIHLIGKCLKFVVSNAENLVD
KW-Bp       MADEKPSNGVLVHMVKLLIKTFLDGIFDDLMENNVLNTDEIHLIGKCLKFVVSNAE-LVD
KW-Cp       MADEKPSNGVLVHMVKLLIKTFLDGIFDDLMENNVLNTDEIHLIGKCLKFVVSNAENLVD
KW-Dp       MADEKPSNGVLVHMVKLLIKTFLDGIFDDLMENNVLNTDEIHLIGKCLKFVVSNAENLVD
KW-Ep       ------------------------------------------------------------
KW-Fp       ------------------------------------------------------------
KW-Hp       ------------------------------------------------------------
KW-Gp       ------------------------------------------------------------
KW-Ip       ------------------------------------------------------------
KW-Jp       MADEKPSNGVLVHMVKLLIKTFLDGIFDDLMENNVLNTDEIHLIGKCLKFVVSNAENLVD
KW-Kp       MADEKPSNGVLVHMVKLLIKTFLDGIFDDLMENNVLNTDEIHLIGKCLKFVVSNAENLVD hCaspase12  DITETAQIAGKIFREHLWNSKKQLSSALLEIQGAQPSGKLKLCPHAHFHELKTKRADEIY
KW-Ap       DITETAQIAGKIFREHLWNSKKQLSSDISSDGEREANMPG--------------------
KW-Bp       DITETAQIAGKIFREHLWNSKKQLSSDISSDGEREANMPG--------------------
KW-Cp       DITETAQIAGKIFREHLWNSKKQLSSDISSDGEREANMPG--------------------
KW-Dp       DITETAQIAGKIFREHLWNSKKQLSSDISSDGEREANMPG--------------------
KW-Ep       ---------------------------------PSGKLKLCPHAHFHELKTKRADEIY
KW-Fp       -----------------------------AQPSGKLKLCPHAHFHELKTKRADEIY
KW-Hp       -----------------------------AQPSGKLKLCPHAHFHELKTKRADEIY
KW-Gp       -----------------------------AQPSGKLKLCPHAHFHELKTKRADEIY
KW-Ip       -----------------------------AQPSGKLKLCPHAHFHELKTKRADEIY
KW-Jp       DITETAQIAGKIFREHLWNSKKQLSSDISSDGEREANMPG--------------------
KW-Kp       DITETAQIAGKIFREHLWNSKKQLSSALLEIQGAQPSGKLKLCPHAHFHELKTKRADEIY hCaspase12  PVMEKERRTCLALNIRNKEFNYLHNRNGSELDLLGMRDLLENLGYSVVIKENLTAQEMET
KW-Ap       -----------LNIRNKEFNYLHNRNGSELDLLGMXDLLENLGYSVVIKENLTAQEMET
KW-Bp       -----------LNIRNKEFNYLHNRNGSELDLLGMXDLLENLGYSVVIKENLTAQEMET
KW-Cp       -----------LNIRNKEFNYLHNRNGSELDLLGMXDLLENLGYSVVIKENLTAQ----
KW-Dp       -----------LNIRNKEFNYLHNRNGSELDLLGMXDLLENLGYSVVIKENLTAQ----
KW-Ep       PVMEKERRTCLALNIRNKEFNYLHNRNGSELDLLGMRDLLENLGYSVVIKENLTA-----
KW-Fp       PVMEKERRTCLALNIRNKEFNYLHNRNGSELDLLGMXDLLENLGYSVVIKESLTAQEMET
KW-Hp       PVMEKERRTCLALNIRNKEFNYLHNRNGSELDLLGMXDLLENLGYSVVIKENLTAQ----
KW-Gp       PVMEKERRTCLALNIRNKEFNYLHNRNGSELDLLGMXDLLENLGYSVVIKENLTAQ----
KW-Ip       PVMEKERRTCLALNIRNKEFNYLHNRNGSELDLLGMXDLLENLGYSVVIKENLTAQEMET
KW-Jp       -----------LNIRNKEFNYLHNRNGSELDLLGMXDLLENLGYSVVIKENLTAQEME-
KW-Kp       PVMEKERRTCLALNIRNKEFNYLHNRNGSELDLLGMXDLLENLGYSVVIKENLTAQEMET
                       ********************** *********** * hCaspase12  ALRQFAAHPEHQSSDSTFLVFMSHGILNGICGTKHWDQEPDVLHDDTIFEIFNNRNCQSL
KW-Ap       ALRQFAAHPEHQSSDSTFLVFMSHSILNGICGTKHWDQEPDVLHDDTIFEIFNNRNCQSL
KW-Bp       ALRQFAAHPEHQSSDSTFLVFMSHSILNGICGTKHWDQEPDVLHDDTIFEIFNNRNCQSL
KW-Cp       ------------------------------------------------------------
KW-Dp       ------------------------------------------------------------
KW-Ep       -------------------SILNGICGTKHWDQEPDVLHDDTIFEIFNNRNCQSL
KW-Fp       ALRQFAAHPEHQSSDSTFLVFMSHSILNGICGTKHWDQEPDVLHDDTIFEIFNNRNCQSL
KW-Hp       ------------------------------------------------------------
KW-Gp       ------------------------------------------------------------
KW-Ip       ALRQFAAHPEHQSSDSTFLAFMSHSILNRICGTKHWDQEPDVLHDDTIFEIFNNRNCQSL
KW-Jp       ---------------STFLVFMSHSILNGICGTKH-------------------------
KW-Kp       ALRQFAAHPEHQSSDSTFLVFMSHSILNGICGTKHWDQEPDVLHDDTIFEIFNNRNCQSL
```

FIGURE 2B

| | |
|---|---|
| hCaspase12 | KDKPKVIIMQACRGNGAGIVWFTTDSGKASADTHGRLLQGNICNDAVTKAHVEKDFIAFK |
| KW-Ap | KDKPKVIIMQACRGNGAGIVWFTTDSGKASADTHGRLLQGNICNDAVTKAHVEKDFIAFK |
| KW-Bp | KDKPKVIIMQACRGNGAGIVWFTTDSGKASADTHGRLLQGNICNDAVTKAHVEKDFIAFK |
| KW-Cp | ---------------GAGIVWFTTDSGKASADTHGRLLQGNICNDAVTKAHVEKDFIAFK |
| KW-Dp | ---------------GAGIVWFTTDSGKASADTHGRLLQGNICNDAVTKAHVEKDFIAFK |
| KW-Ep | KDKPKVIIMQACRG---------------------------------------------- |
| KW-Fp | KDKPKVIIMQAC------------------------------------------------ |
| KW-Hp | ---------------GAGIVWFTTDSGKASADTHGRLLQGNICNDAVTKAHVEKDFIAFK |
| KW-Gp | ----------------------------------------------------MVLGLFGSP |
| KW-Ip | KDKPK------------------------------------------------MVLGLFGSP |
| KW-Jp | ------------------------------------------------------------ |
| KW-Kp | KDKPKVIIMQACRGNGAGIVWFTTDSGKASADTHGRLLQGNICNDAVTKAHVEKDFIAFK |

| | |
|---|---|
| hCaspase12 | SSTPHNVSWRHETNGSVFISQIIYYFREYSWSHHLEEIFQKVQHSFETPNILTQLPTIER |
| KW-Ap | SSTPHNVSWRHETNGSVFISQIIYYFREYSWSHHLEEIFQKVQHSFETPNILTQLPTIER |
| KW-Bp | SSTP------------------------------VQHSFETPNILTQLPTIER |
| KW-Cp | SSTPHNVSWRHETNGSVFISQIIYYFREYSWSHHLEEIFQKVQHSFETPNILTQLPTIER |
| KW-Dp | SSTP------------------------------VQHSFETPNILTQLPTIER |
| KW-Ep | ------------------------------------------------------------ |
| KW-Fp | ------------------------------------------------------------ |
| KW-Hp | SSTPHNVSWRHETNGSVFISQIIYYFREYSWSHHLEEIFQKVQHSFETPNILTQLPTIER |
| KW-Gp | LTVEKPVQILMVGSCKVTSVMMLLQRLMWKRTSLLSNLPHHVQHSFETPNILTQLPTIER |
| KW-Ip | LTWKKPVQILMVGSCKVTSVMMLLQRFMWKRTSLLSNLPHHVQHSFETPNILTQLPTIER |
| KW-Jp | ------------------------------------------------------------ |
| KW-Kp | SSTPHNVSWRHETNGSVFISQIIYYFREYSWSHHLEEIFQKVQHSFETPNILTQLPTIER |

| | |
|---|---|
| hCaspase12 | LSMTRYFYLFPGN |
| KW-Ap | LSMTRYFYLFPGN |
| KW-Bp | LSMTRYFYLFPGN |
| KW-Cp | LSMTRYFYLFPGN |
| KW-Dp | LSMTRYFYLFPGN |
| KW-Ep | ------------- |
| KW-Fp | ------------- |
| KW-Hp | LSMTRYFYLFPGN |
| KW-Gp | LSMTRYFYLFPGN |
| KW-Ip | LSMTRYFYLFPGN |
| KW-Jp | ------------- |
| KW-Kp | LSMTRYFYLFPGN |

Human Caspase-12 compared to Mouse Caspase-12 with CARD domain, ICE-p20 domain, ICE-p10 domain and Active-site amino acids described.

```
hCaspase-12   MADEKPSNGVLVHMVKLLIKTFLDGIFDDLMENNVLNTDEIHLIGKCLKFVVSNAENLVD      60
mCaspase-12   MAARRTHERDPIYKIKGLAKDMLDGVFDDLVEKNVLNGDELLKIGESASFILNKAENLVE      60
              **   :   ::  :*  *:  ****:*::****.*:****  **:: .  *::.*****:

hCaspase-12   DITETAQIAGKIFREHLWNSKKQLS---------------------------------       85
mCaspase-12   NFLEKTDMAGKIFAGHIANSQEQLSLQFSNDEDDGPQKICTPSSPSESKRKVEDDEMEVN     120
              : :.:*  ****   *: :::*                        ↑auto catalytic hCaspase-12   --------SALLEIQGAQPSGKLKLCPHAHFHELKTKRADEIYPVMEKERRTCLALN      134
mCaspase-12   AGLAHESHLMLTAPHGLQSSEVQDTLKLCPRDQFCKIKTERAKEIYPVMEKEGRTRLALI    180
                      *:     . *.     ..******:.:* ::*:**:******** :* ***
                      ↑calpain                          ↑calpain hCaspase-12   IRNKEFNYLHNRNGSELDLLGMRDLLENLGYSVVIKENLTAQEMETALRQFAAHPEHQSS   194
mCaspase-12   ICNKKFDYLFDRDNADTDILNMQELLENLGYSVVLKENLTAQEMETELMQFAGRPEHQSS   240
              * ** *:** :*:.::** * :::*******::*********:*:*. *** hCaspase-12   DSTFLVFMSHGILNGICGTKHWDQEPDVLHDDTIFEIFNNRNCQSLKDKPKVIIMQACRG   254
mCaspase-12   DSTFLVFMSHGILEGICGVKHRNKKPDVLHDDTIFKIFNNSNCRSLRNKPKILIMQACRG   300
              ***********:. :::********:.:::*::******* hCaspase-12   NGAGI VWFTTDSGKASADTHGRLLQGNICNDAVTKAHVEKDFIAFKSSTPHNVSWRHETN   314
mCaspase-12   RYNGT IWVSTNKGIATADTDEERVLSCKWNNSITKAHVETDFIAFKSSTPHNISWKVGKT   360
               :.*:  *.:*:.::*:*** .*:* .: *::.:******.*************:**:  :.
                                                         ↑auto catalytic hCaspase-12   GSVFISQIIYYFREYSWSHHLEEIFQKVQHSFETPNILTQLPTIERLSMTRYFYLFP_GN   373
mCaspase-12   GSLFISKLIDCFKKYCYHLEEIERKVQHSFEVPGELTQMPTIERVSMTRYFYLFP_GN    419
              **:***::*  *::*.:.*****  ************.*.:**:*****:********
```

```
h_Caspase-3   ----------------------------------------------------------------
h_Caspase-7   ----------------------------------------------------------------
h_Caspase-12  --------------------------------------------------------MADE
m_Caspase-12  --------------------------------------------------------MAAR
h_Caspase-4   --------------------------------------------------------MAEG
h_Caspase-13  --------------------------------------------------------MAED
h_Caspase-5   --------------------------MFKGILQSGLDNFVINHMLKNNVAGQTSIQTLVPNTDQKSTSVKKD
h_Caspase-1   ----------------------------------------------------------MAD
h_Caspase-6   ----------------------------------------------------------------
h_Caspase-8   ------------MDFSRNLYDIGEQLDSEDIASLKFLSLDYIPQRKQEPIKDALM
h_Caspase-10  MKSQGQHWYSSSDKNCKVSFREKLLIIDSNLGVQDVENLKFLCIGLVPNKKLEKSSSASD
h_Caspase-9   ----------------------------------------------------------MDE
h_Caspase-2   ----------------------------------------------------------------
h_Caspase-14  --------------------------------------------------MAADRGRRILGVCGM h_Caspase-3   ----------------------------------------------------------------
h_Caspase-7   ----------------------------------------------------------------
h_Caspase-12  KPSNGVLVHMVK----LLIKTFLDGI--FDDLMENNVLNTDEIHLIGKCL-KFVVSNAEN
m_Caspase-12  RTHERDPIYKIK----GLAKDMLDGV--FDDLVEKNVLNGDELLKIGESA-SFILNKAEN
h_Caspase-4   N-HRKKPLKVLE----SLGKDFLTGV--LDNLVEQNVLNWKEEKKYYD-AKTEDKVRV
h_Caspase-13  K-HNKNPLKMLE----SLGKELISGL--LDDFVEKNVLKLEEEEKKIYD-AKLQDKARV
h_Caspase-5   N-HKKKTVKMLE----YLGKDVLHGV--FNYLAKHDVLTLKEEEKKYYD-AKIEDKALI
h_Caspase-1   KVLKEKRKLFIR----SMGEGTINGL--LDELLQTRVLNKEEMEKVKREN-ATVMDKTRA
h_Caspase-6   ----------------------------------------------------------------
h_Caspase-8   LFQRLQEKRMLEESNLSFLKELLFRINRLDLLITYLNTRKEEMERELQTPGRAQISAYRV
h_Caspase-10  VFEHLLAEDLLSEEDPFFLAELLYIIR-QKKLLQHLNCTKEEVERLLPTR--QRVSLFRN
h_Caspase-9   ADRRLLRRCRLR----IVEELQVDQLWDALLSSELFRPHMIEDIQRAGSGSRRDQARQ
h_Caspase-2   HPHHQETLKKNR----VVLAKQLLSELLEHLLEKDIITLEMRELIQAKV--GSFSQNVE
h_Caspase-14  ---------------------------------------------------------------- h_Caspase-3   -----------------MENTEN------SVDSK-SIKNLEPKIIH----GSE-------
h_Caspase-7   ----MADDQGCIEEQGVEDSANED-----SVDAKPDRSSFVPSLFS----KKKKN-----
```

FIGURE 4B

```
h_Caspase-12   LVDDITETAQIAGKIFREHLWNS-----KKQLSSALL--BIQGAQ----PSG----K---
m_Caspase-12   LVENFLEKTDMAGKIFAGHIANS-----QEQLSLQFSNDEDDGPQKICTPSSPSESKRKV
h_Caspase-4    MADSMQEKQRMAGQMLLQTFENID----QISPNKKAHPNMEAGPP----ESGES------
h_Caspase-13   LVDSIRQKNQEAGQVFVQTFLNID----KNSTSIKAPEETVAGPD----ESVGS------
h_Caspase-5    LVDSLR-KNRVAHQMFTQTLLNMD----QKITSVKPLLQIEAGPP----ESAES------
h_Caspase-1    LIDSVIPKGAQACQICITYICEEDS---YLAGTIGLSADQTSGNYLNMQDSQGVLSSFPA
h_Caspase-6    --MSSASGLRRGHPAGGE----EN-----
h_Caspase-8    MLYQISEEVSRSELRSFKFLLQEEISKCKLDDDMNLLDIFIEMEKRVILGEGKLDILKRV
h_Caspase-10   LLYELSEGIDSENLKDMIFLLKDSLP-KTEMTSLSFLAFLEKQGK---IDEDNLTCLEDL
h_Caspase-9    LIIDLETRGSQALPLFISCLEDTG---QDMLASFLRTNRQAAKLSKPTLENLTPVLRP
h_Caspase-2    LLNLLPKRGPQAFDAFCEALRETKQGHLEDMLLTTLSGLQHVLPPLSCDYDLSLPFPVCE
h_Caspase-14   ------------------------------------------------------------ h_Caspase-3    -----------------------------------------SMDS--GISLDN------
h_Caspase-7    -----------------------------------------VTMRS--IKTTRDRVPTY-
h_Caspase-12   -----------------------------------------LKLCPHAHFHELKTKRADE---
m_Caspase-12   EDDEMEVNAGLAHES--HLM--LTAPHGLQSSEVQDTLKLCPRDQFCKIKTERAKE---
h_Caspase-4    -----------------------------------------TDALKLCPHEEFLRLCKERAEE-
h_Caspase-13   -----------------------------------------AATLKLCPHEEFLKLCKERAGE-
h_Caspase-5    -----------------------------------------TNILKLCPREEFLRLCKKNHDE-
h_Caspase-1    -----NPAMPTSSGSEGNVKLCSLEEAQRIWKQKSAE--
h_Caspase-6    PQAVQD-----------------------------------------MTETDAFYKREMFDPAE--
h_Caspase-8    CAQINKSLLKIINDY--EEFSKERSSSLEGSPDEFSNGEELCGVMTISDSPREQDSE---
h_Caspase-10   CKTVVPKLLRNIEKYKREKAIQIVTPPVDKEAESYQGEEELVSQTDVKTFLEALPQESWQ
h_Caspase-9    EIRK--------------------PEVLRPETPRPVDIGSSGFGDVGALESLRGNAD--
h_Caspase-2    SCPLYKKLR---------------LSTDTVEHSLDNKDGPVCLQVKPCTPEFYQTHFQ--
h_Caspase-14   ------------------------------------------------------------ h_Caspase-3    -----------------------------------------SYKMDYPEMGLCIIINNKN
h_Caspase-7    -----------------------------------------QYNMNFEKLGKCIIINNKN
h_Caspase-12   -----------------------------------------IYPVMEKERRTCLALNIRN
m_Caspase-12   -----------------------------------------IYPVMEKEGRTRLALIICN
h_Caspase-4    -----------------------------------------IYPIKERNNRTRLALIICN
```

FIGURE 4C

```
h_Caspase-13  ------------------------------------------IYPIKERKDRTRLALIICN
h_Caspase-5   ------------------------------------------IYPIKKREDRRRLALIICN
h_Caspase-1   ------------------------------------------IYPIMDKSSRTRLALIICN
h_Caspase-6   ------------------------------------------KYKMDHRRRGIALIFNHER
h_Caspase-8   ---------------------------------------SQTLDKVYQMKSKPRGYCLIINNHN
h_Caspase-10  NKHAGSNGNRATNGAPSLVSRGMQGASANTLNSETSTKRAAVYRMNRNHRGLCVIVNNHS
h_Caspase-9   ------------------------------------------LAYILSMEPCGHCLIINNVN
h_Caspase-2   ------------------------------------------LAYRLQSRPRGLALVLSNVH
h_Caspase-14  ------------------------------------------MSNPRSLEEEKYDMSGARLA h_Caspase-3   FH-------KSTGMTSRSGTDVDAANLRETFRNLKYEVRNK-NDLTREEIVELMRDVSKE
h_Caspase-7   FD-------KVTGMGVRNGTDKDAEALFKCFRSLGFDVIVY-NDCSCAKMQDLLKKASEE
h_Caspase-12  K--------EFNYLHNRNGSELDLLGMRDLLENLGYSVVIKENLTAQEMETALRQFAAHP
m_Caspase-12  K--------KFDYLFDRDNADTDILNMQELLENLGYSVVLKENLTAQEMETELMQFAGRP
h_Caspase-4   T--------EFDHLPPRNGADFDITGMKELLEGLDYSVDVEENLTARDMESALRAFATRP
h_Caspase-13  T--------EFDHMPPRNGAALDILGMKQLLEGLGYTVEVEEKLTARDMESVLWKFAARE
h_Caspase-5   T--------KFDHLPARNGAHYDIVGMKRLLQGLGYTVVDEKNLTARDMESVLRAFAARP
h_Caspase-1   E--------EFDSIPRRTGAEVDITGMTMLLQNLGYSVDVKKNLTASDMTTELEAFAHRP
h_Caspase-6   FF-------WHLTLPERRRTCADRDNLTRRFSDLGFEVKCFNDLKAEELLLKIHEVSTVS
h_Caspase-8   FAKAREKVPKLHSIRDRNGTHLDAGALTTTFEELHFEIKPH-DDCTVEQIYEILKIYQLM
h_Caspase-10  F--------TSLKDRQGTHKDAEILSHVFQWLGFTVTHIHNNVTKVEMEMVLQKQKCNP
h_Caspase-9   FCR------E-SGLRTRTGSNIDCEKLRRRFSSPHFMVEVKGDLTAKKMVLALLELAQQD
h_Caspase-2   FTG------EKELEFRSGGDVDHSTLVTLFKLLGYDVHVLCDQTAQEMQEKLQNFAQLP
h_Caspase-14  L--------ILCVTKAREGSEEDLDALEHMFRQLRFESTMKRDPTAEQFQEELEKFQQAI
                       *                                * h_Caspase-3   D--HSKRSSFVCVLLSHGEEG---------IIFGTNG------PVDLKKITNFFRGDRCRSL
h_Caspase-7   D--HTNAACFACILLSHGEEN---------VIYGKDG------VTPIKDLTAHFRGDRCKTL
h_Caspase-12  B--HQSSDSTFLVFMSH_GIIN-------GICGTKHWDQEPDVLHDDTIFEIFNNRNCQSL
m_Caspase-12  E--HQSSDSTFLVFMSHGILE--------GICGVKHRNKKPDVLHDDTIFKIFNNSNCRSL
h_Caspase-4   E--HKSSDSTFLVLMSHGILE--------GICGTVHDEKKPDVLLYDTIFQIFNNRNCLSL
h_Caspase-13  E--HKSSDSTFLVFMSHGILD--------GICGTMHSEEEPDVLPYDTIFRTFNNRNCLSL
```

FIGURE 4D

```
h_Caspase-5     E--HKSSDSTFLVLMSHGILE------GICGTAHKKKKPDVLLYDTIFQIFNNRNCLSL
h_Caspase-1     E--HKTSDSTFLVFMSHGIRE------GICGKKHSEQVPDILQLNAIFNMLNTKNCPSL
h_Caspase-6     ---HADADCFVCVFLSHGEGN------HIYAYDA-------KIEIQTLTGLFKGDKCHSL
h_Caspase-8     D--HSNMDCFICCILSHGDKG------IIYGTDG-------QEAPIYELTSQFTGLKCPSL
h_Caspase-10    A--HADGDCFVFCILTHGRFG------AVYSSDE-------ALIPIREIMSHFTALQCPRL
h_Caspase-9     --HGALDCCVVVILSHGCQASHLQFPGAVYGTDG-------CPVSVEKIVNIFNGTSCPSL
h_Caspase-2     A--HRVTDSCIVALLSHGVEG------AIYGVDG-------KLLQLQEVFQLFDNANCPSL
h_Caspase-14    DSREDPVSCAFVVLMAHGREG------FLKGEDG-------EMVKLENLFEALNKNCQAL
                     .           :::**                               *   * h_Caspase-3     TGKPKLFIIQACRGT--ELDCGIETDSG-------VDDDMAC--------------HKIP
h_Caspase-7     LEKPKLFFIQACRGT--ELDDGIQADSG-------PINDTDANPR-----------YKIP
h_Caspase-12    KDKPKVIIMQAC_RGN--GAGIVWFTTD------SGKASADTHG-RLLQGNIC--NDAVTKA
m_Caspase-12    RNKPKILIMQACRGR--YNGTIWSTN--------KGIATADTDEERVLS--CKWNNSITKA
h_Caspase-4     KDKPKVIIVQACRGA--NRGELWVRDSP------ASLEVASSQSSENLE-------EDAVYKT
h_Caspase-13    KDKPKVIIVQACRGA--NRGELWVSDSP------PALADSFSQSSENLE-------EDAVYKT
h_Caspase-5     KDKPKVIIVQACRGE--KHGELWVRDSP------ASLAVISSQSSENLE-------ADSVCKI
h_Caspase-1     KDKPKVIIIQACRGD--SPGVVWFKDSV------GVSGNLSLPTTEEFE-------DDAIKKA
h_Caspase-6     VGKPKIFIIQACRGN--QHDVPVIPLDV------VDNQTEKLDTNITEVD-------AASVYTL
h_Caspase-8     AGKPKVFFIQACQGDNYQKGIPVETDS-------EEQPYLEMDLS------------SPQTRYI
h_Caspase-10    AEKPKLFFIQACQGEEIQPSVSIEADALN-----PEQAPTSLQ---------------DSI
h_Caspase-9     GGKPKLFFIQACGEQKDHGFEVASTSPEDESPGSNPEPDATPFQEGLRTFDQLDAISSL
h_Caspase-2     QNKPKMFFIQACRGDETDRGVDQQDGKN------HAGSPGCEESDAGKE-------KLPKMRL
h_Caspase-14    RAKPKVYIIQACRGEQRDPGETVGGDE-------IVMVIKDSP--------------QTI
                 *. ::*  *      * h_Caspase-3     VDA-DFLYAYSTAPGYYSWRNSKDGSWFIQSLCAMLKQYA-DKLEFMHILTRVNRKVATE
h_Caspase-7     VEA-DFLFAYSTVPGYYSWRSPGRGSWFVQALCSILEEHG-KDLEIMQILTRVNDRVARH
h_Caspase-12    HVEKDFIAFKSSTPHNVSWRHETNGSVFISQIIYYFREYS-WSHHLEEIFQ---KVQHS
m_Caspase-12    HVETDFIAFKSSTPHNISWKVGKTGSLFISKLIDCFKKYC-WCYHLEEIFR----KVQHS
h_Caspase-4     HVEKDFIAFCSSTPHNVSWRDSTMGSIFITQLITCFQKYS-WCCHLEEVFR----KVQQS
h_Caspase-13    HVEKDFIAFCSSTPHNVSWRDIKKGSLFITRLITCFQKYA-WCCHLEEVFR----KVQQS
h_Caspase-5     HEEKDFIAFCSSTPHNVSWRDRTRGSIFITELITCFQKYS-CCCHLMEIFR----KVQKS
h_Caspase-1     HIEKDFIAFCSSTPDNVSWRHPTMGSVFIGRLIEHMQEYA-CSCDVEEIFR----KVRFS
```

FIGURE 4E

```
h_Caspase-6    PAGADFLMCYSVAEGYYSHRETVNGSWYIQDLCEMLGKYG-SSLEFTELLTLVNRKVSQR
h_Caspase-8    PDEADFLLGMATVNNCVSYRNPAEGTWYIQSLCQSLRERCPRGDDILTILT----EVNYE
h_Caspase-10   PAEADFLLGLATVPGYVSFRHVEEGSWYIQSLCNHLKKLVPRMLKFLEKTM----EIRGR
h_Caspase-9    PTPSDIFVSYSTFPGFVSWRDPKSGSWYVETLDDIFEQWA-HSEDLQSLLL----RVANA
h_Caspase-2    PTRSDMICGYACLKGTAAMRNTKRGSWYIEALAQVFSERA-CDMHVADMLVKVN-ALIKD
h_Caspase-14   PTYTDALHVYSTVEGYIAYRHDQKGSCFIQTLVDVFTKRK---GHILELLT----EVTRR
                  :         *            *  :       :                  :

h_Caspase-3    FESFSFDATFHAKKQIPCIVSMLTKE--LYFYH-----
h_Caspase-7    FESQSDDPHFHEKKQIPCVVSMLTKE--LYFSQ-----
h_Caspase-12   FET----PNILTQLPTIERLSMTRYF--YLFPGN----
m_Caspase-12   FEV----PGELTQMPTIERVSMTRYF--YLFPGN----
h_Caspase-4    FET----PRAKAQMPTIERLSMTRYF--YLFPGN----
h_Caspase-13   FEK----PNVKAQMPTVERLSMTRYF--YLFPGN----
h_Caspase-5    FEV----PQAKAQMPTIERATLTRDF--YLFPGN----
h_Caspase-1    FEQ----PDGRAQMPTTERVTLTRCF--YLFPGH----
h_Caspase-6    RVDFCKDPSAIGKKQVPCFASMLTKK--LHFFPKSN--
h_Caspase-8    VSN--KDDKKNMGKQMPQPTFTLRKK--LVFPSD----
h_Caspase-10   KRTVWG-AKQISATSLPTAISAQTPRPPMRRWSSVS--
h_Caspase-9    VSV-----KGIYKQMPGCFNFLRKK--LFFKTS----
h_Caspase-2    REGYAPGTEFHRCKEMSEYCSTLCRH-LYLFPGHPPT
h_Caspase-14   MAEAELVQEGKARKTNPEIQSTLRKR--LYLQ------
```

Legend:
→ Active-site Residues
* Identical Residues
: Conservative Substitution
. Allowable Substitution CLUSTAL W (1.7) multiple sequence alignment

FIGURE 5A

```
h_Caspase-4    ------------------------------------------------MAEGN-HRKKPLKVLESL
h_Caspase-5    MFKGILQSGLDNFVINHMLKNNVAGQTSIQTLVPNTDQKSTSVKKDN-HKKKTVKMLEYL
h_Caspase-13   ------------------------------------------------MAEDK-HNKNPLKMLESL
h_Caspase-12   ------------------------------------------------MADEKPSNGVLVHMVKLL
h_Caspase-1    ------------------------------------------------MADKVLKEKRKLFIRSM
                                                                 :.  ..

h_Caspase-4    GKDFLTGVLDNLIVEQNVLNWKEEEKKKYYDAKTEDKVRVMADSMQEKQRMAGQMLLQTFF
h_Caspase-5    GKDVLHGVFENYLAKHDVLTLKEEEKKKYYDAKIEDKALILVDSLR-KNRVAHQMFTQTLL
h_Caspase-13   GKELISGLLDDFVEKNVLKLEEEEKKIYDAKLQDKARVLVDSIRQKNQEAGQVFVQTFL
h_Caspase-12   IKTFLDGIFDDLMENNVLNTDEIHLIGKCLKFVVSNAENLVDDITETAQIAGKIFREHLW
h_Caspase-1    GEGTINGLLDELLQTRVLNKEEMEKVKRENATVMDKTRALIDSVIPKGAQACQICITYIC
                           : : .*.*                 .:  :     :     .

h_Caspase-4    N------------------------------IDQISPNKKAHPNMEAG--PPESGESTDALKLCP
h_Caspase-5    N------------------------------MDQKITSVKPLLQIEAG--PPESAESTNILKLCP
h_Caspase-13   N------------------------------IDKNSTSIKAPEETVAG--PDESVGSAATLKLCP
h_Caspase-12   N------------------------------SKKQLSS--ALLEIQGA--QP-SGK---LKLCP
h_Caspase-1    EEDSYLAGTLGLSADQTSGNYLNMQDSQGVLSSFPAPQAVQDNPAMPTSSGSEGNVKLCS
                                                                   :***.

h_Caspase-4    HEEFLRLCKERAEEIYPIKERNNRTRLALIICNTEFDHLPPRNGADFDITGMKELLEGLD
h_Caspase-5    REEFLRLCKKNHDEIYPIKKREDRRLALIICNTKFDHLPARNGAHYDIVGMKRLLQGLG
h_Caspase-13   HEEFLKLCKERAGEIYPIKERKDRTRLALIICNTEEDHMPPRNGAALDILGMKQLLEGLG
h_Caspase-12   HAHFHELKTKRADEIYPVMEKERRTCLALNIRNKEFNYLHNRNGSELDLLGMRDLLENLG
h_Caspase-1    LEEAQRIWKQKSAEIYPIMDKSSRTRLALIICNEEFDSIPRRTGAEVDITGMTMLLQNLG
                   :  ..   ****:  .:  *   *.**.:  :   *  :*  :.**  *..* h_Caspase-4    YSVDVEENLTARDMESALRAFATRPEHKSSDSTFLVLMSHGILEGICGTVHDEKKPDVLL
h_Caspase-5    YTVVDEKNLTARDMESVLRAFAARPEHKSSDSTFLVLMSHGILEGICGTAHKKKKPDVLL
h_Caspase-13   YTVEVEEKLTARDMESVLWKFAAREEIKSSDSTFLVFMSHGILDGICGTMHSEEEPDVLP
h_Caspase-12   YSVVIKENLTAQEMETALRQFAAHPEHQSSDSTFLVFMSHGILNGICGTKHWDQEPDVLH
                * *. *:*** .:*: :*: **.. *::******:*****:.****  :  :****
```

FIGURE 5B

```
h_Caspase-1    YSVDVKKNLTASDMTTELEAFAHRPEHKTSDSTFLVFMSHGIREGICGKKHSEQVPDILQ
               *:*   ::.***  :*. : *   : ::.**********.:** .. :* h_Caspase-4    YDTIFQIFNNRNCLSLKDKPKVIIVQACRGANRGELWVR-DSPASLEVASSQSSE-NLEE
h_Caspase-5    YDTIFQIFNNRNCLSLKDKPKVIIVQACRGEKHGELWVR-DSPASLAVISSQSSE-NLEA
h_Caspase-13   YDTIFRTFNNRNCLSLKDKPKVIIVQACRGANRGELWVS-DSPPALADSFSQSSE-NLEE
h_Caspase-12   DDTIFEIFNNRNCQSLKDKPKVIIMQACRGNGAGI_VWFTTDSGKASADTHGRLLQGNICN
h_Caspase-1    LNAIFNMLNTKNCPSLKDKPKVIIIQACRGDSPGVVWFK-DSVGVSGNLSLPTTE-EFED
               :. **           ** ************:******  .  :.   **      ::

h_Caspase-4    DAVYKTHVEKDFIAFCSSTPHNVSWRDSTMGSIFITQLITCFQKYSWCCHLEEVFRKVQQ
h_Caspase-5    DSVCKIHEEKDFIAFCSSTPHNVSWRDRTRGSIFITELITCFQKYSCCCHLMEIFRKVQK
h_Caspase-13   DAVYKTHVEKDFIAFCSSTPHNVSWRDIKKGSLFITRLITCFQKYAWCCHLEEVFRKVQQ
h_Caspase-12   DAVTKAHVEKDFIAFKSSTPHNVSWRHETNGSVFISQIIYFREYSWSHHLEEIFQKVQH
h_Caspase-1    DAIKKAHIEKDFIAFCSSTPDNVSWRHPTMGSVFIGRLIEHMQEYACSCDVEEIFRKVRF
               *:: *  :*:*****.***.:****.  ..* :*     .  :  * . ::::*:**.:

h_Caspase-4    SFETPRAKAQMPTIERLSMTRYFYLFPGN
h_Caspase-5    SFEVPQAKAQMPTIERATLTRDFYLFPGN
h_Caspase-13   SFEKPNVKAQMPTVERLSMTRYFYLFPGN
h_Caspase-12   SFETPNILTQLPTIERLSMTRYFYLF_PGN
h_Caspase-1    SFEQPDGRAQMPTTERVTLTRCFYLFPGH
               ***.*   :*:** ** ::** ******:

CARD domain    ICE-P20 Domain    ICE-P10 Domain    Active-site Residues
```

1. Brain 2. Heart 3. Kidney 4. Spleen 5. Liver 6. Colon 7. Lung 8. Small Intestine 9. Muscle 10. Stomach 11. Testis 12. Placenta 13. Pituitary 14. Thyroid gland 15. Adrenal gland 16. Pancreas 17. Ovary 18. Uterus 19. Prostate 20. PBL 21. Fetal brain 22. Fetal liver 23. Fat 24. Mammary gland

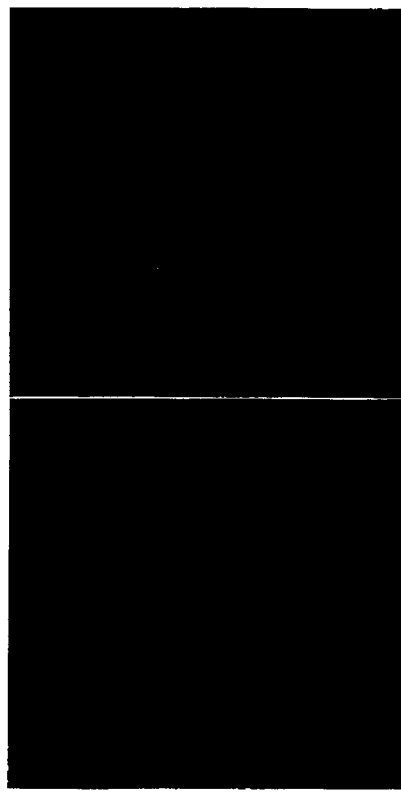
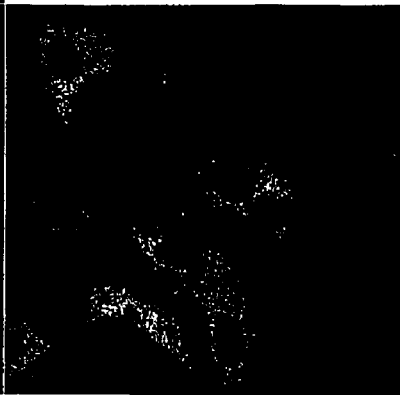
FIGURE 7

FIGURE 12
A. 
Caspase-12
B. 
Caspase-3

SEQUENCE LISTING

<160> NUMBER OF SEQ ID NOS: 105

<210> SEQ ID NO 1
<211> LENGTH: 1026
<212> TYPE: DNA
<213> ORGANISM: Homo sapien
<220> FEATURE:
<221> NAME/KEY: CDS
<222> LOCATION: (1)..(372)

<400> SEQUENCE: 1

```
atg gct gat gag aaa cca tcc aac ggt gtt ctg gtc cac atg gtg aag        48
Met Ala Asp Glu Lys Pro Ser Asn Gly Val Leu Val His Met Val Lys
 1               5                  10                  15 ttg ctg atc aag acc ttt cta gat ggc att ttt gat gat ttg atg gaa        96
Leu Leu Ile Lys Thr Phe Leu Asp Gly Ile Phe Asp Asp Leu Met Glu
            20                  25                  30 aat aat gtg tta aat aca gat gag ata cac ctt ata gga aaa tgt cta       144
Asn Asn Val Leu Asn Thr Asp Glu Ile His Leu Ile Gly Lys Cys Leu
        35                  40                  45 aag ttt gtg gtg agc aat gct gaa aac ctg gtt gat gat atc act gag       192
Lys Phe Val Val Ser Asn Ala Glu Asn Leu Val Asp Asp Ile Thr Glu
    50                  55                  60 aca gct caa att gca ggc aaa ata ttt agg gaa cac ctg tgg aat tcc       240
Thr Ala Gln Ile Ala Gly Lys Ile Phe Arg Glu His Leu Trp Asn Ser
65                  70                  75                  80 aaa aaa cag ctg agt tca gat ata tcc agt gat gga gaa aga gag gcg       288
Lys Lys Gln Leu Ser Ser Asp Ile Ser Ser Asp Gly Glu Arg Glu Ala
                85                  90                  95 aac atg cct ggc ctc aac atc cgc aac aaa gaa ttc aac tat ctt cat       336
Asn Met Pro Gly Leu Asn Ile Arg Asn Lys Glu Phe Asn Tyr Leu His
            100                 105                 110 aat cga aat ggt tct gaa ctt gac ctt ttg ggg atg tgagatctac            382
Asn Arg Asn Gly Ser Glu Leu Asp Leu Leu Gly Met
        115                 120 ttgaaaacct tggatactca gtggttataa aagagaatct cacagctcag gaaatggaaa     442
cagcactaag gcagtttgct gctcacccag agcaccagtc ctcagacagc acattcctgg     502
tgtttatgtc acatagcatc ctgaatgaa tctgtgggac caagcactgg gatcaagagc      562
cagatgttct tcacgatgac accatctttg aaattttcaa caaccgtaac tgccagagtc     622
tgaaagacaa acccaaggtc atcatcatgc aagcctgccg aggcaatggt gctgggattg     682
tttggttcac cactgacagt ggaaaagcca gtgcagatac tcatggtcgg ctcttgcaag     742
gtaacatctg taatgatgct gttacaaagg ctcatgtgga aaaggacttc attgctttca     802
aatcttccac accacataat gtttcttgga gacatgaaac aaatggctct gtcttcattt     862
cccaaattat ctactacttc agagagtatt cttggagtca tcatctagag gaaatttttc     922
aaaaggttca acattcattt gagaccccaa atatactgac ccagctgccc accattgaaa     982
gactatccat gacacgatat ttctatctct ttcctgggaa ttaa                     1026
```

<210> SEQ ID NO 2
<211> LENGTH: 124
<212> TYPE: PRT
<213> ORGANISM: Homo sapiens

<400> SEQUENCE: 2

```
Met Ala Asp Glu Lys Pro Ser Asn Gly Val Leu Val His Met Val Lys
 1               5                  10                  15
```

```
Leu Leu Ile Lys Thr Phe Leu Asp Gly Ile Phe Asp Asp Leu Met Glu
             20                  25                  30

Asn Asn Val Leu Asn Thr Asp Glu Ile His Leu Ile Gly Lys Cys Leu
         35                  40                  45

Lys Phe Val Val Ser Asn Ala Glu Asn Leu Val Asp Asp Ile Thr Glu
     50                  55                  60

Thr Ala Gln Ile Ala Gly Lys Ile Phe Arg Glu His Leu Trp Asn Ser
 65                  70                  75                  80

Lys Lys Gln Leu Ser Ser Asp Ile Ser Ser Asp Gly Glu Arg Glu Ala
                 85                  90                  95

Asn Met Pro Gly Leu Asn Ile Arg Asn Lys Glu Phe Asn Tyr Leu His
             100                 105                 110

Asn Arg Asn Gly Ser Glu Leu Asp Leu Leu Gly Met
         115                 120
```

<210> SEQ ID NO 3
<211> LENGTH: 1026
<212> TYPE: DNA
<213> ORGANISM: Homo sapiens
<220> FEATURE:
<221> NAME/KEY: CDS
<222> LOCATION: (1)..(1023)
<223> OTHER INFORMATION:
<221> NAME/KEY: misc_feature
<222> LOCATION: (373)..(374)..(375)
<223> OTHER INFORMATION: n = a or t or g or c
<221> NAME/KEY: misc_feature
<222> LOCATION: (125)
<223> OTHER INFORMATION: Xaa = any amino acid or no amino acid

<400> SEQUENCE: 3

```
atg gct gat gag aaa cca tcc aac ggt gtt ctg gtc cac atg gtg aag      48
Met Ala Asp Glu Lys Pro Ser Asn Gly Val Leu Val His Met Val Lys
 1               5                  10                  15 ttg ctg atc aag acc ttt cta gat ggc att ttt gat gat ttg atg gaa      96
Leu Leu Ile Lys Thr Phe Leu Asp Gly Ile Phe Asp Asp Leu Met Glu
             20                  25                  30 aat aat gtg tta aat aca gat gag ata cac ctt ata gga aaa tgt cta     144
Asn Asn Val Leu Asn Thr Asp Glu Ile His Leu Ile Gly Lys Cys Leu
         35                  40                  45 aag ttt gtg gtg agc aat gct gaa aac ctg gtt gat gat atc act gag     192
Lys Phe Val Val Ser Asn Ala Glu Asn Leu Val Asp Asp Ile Thr Glu
     50                  55                  60 aca gct caa att gca ggc aaa ata ttt agg gaa cac ctg tgg aat tcc     240
Thr Ala Gln Ile Ala Gly Lys Ile Phe Arg Glu His Leu Trp Asn Ser
 65                  70                  75                  80 aaa aaa cag ctg agt tca gat ata tcc agt gat gga gaa aga gag gcg     288
Lys Lys Gln Leu Ser Ser Asp Ile Ser Ser Asp Gly Glu Arg Glu Ala
                 85                  90                  95 aac atg cct ggc ctc aac atc cgc aac aaa gaa ttc aac tat ctt cat     336
Asn Met Pro Gly Leu Asn Ile Arg Asn Lys Glu Phe Asn Tyr Leu His
             100                 105                 110 aat cga aat ggt tct gaa ctt gac ctt ttg ggg atg nnn gat cta ctt     384
Asn Arg Asn Gly Ser Glu Leu Asp Leu Leu Gly Met Xaa Asp Leu Leu
         115                 120                 125 gaa aac ctt gga tac tca gtg gtt ata aaa gag aat ctc aca gct cag     432
Glu Asn Leu Gly Tyr Ser Val Val Ile Lys Glu Asn Leu Thr Ala Gln
     130                 135                 140 gaa atg gaa aca gca cta agg cag ttt gct gct cac cca gag cac cag     480
Glu Met Glu Thr Ala Leu Arg Gln Phe Ala Ala His Pro Glu His Gln
145                 150                 155                 160
```

-continued

| | | |
|---|---|---|
| tcc tca gac agc aca ttc ctg gtg ttt atg tca cat agc atc ctg aat<br>Ser Ser Asp Ser Thr Phe Leu Val Phe Met Ser His Ser Ile Leu Asn<br>                        165                      170                    175 | 528 |
| gga atc tgt ggg acc aag cac tgg gat caa gag cca gat gtt ctt cac<br>Gly Ile Cys Gly Thr Lys His Trp Asp Gln Glu Pro Asp Val Leu His<br>180 185 190 | 576 |
| gat gac acc atc ttt gaa att ttc aac aac cgt aac tgc cag agt ctg<br>Asp Asp Thr Ile Phe Glu Ile Phe Asn Asn Arg Asn Cys Gln Ser Leu<br>195 200 205 | 624 |
| aaa gac aaa ccc aag gtc atc atc atg caa gcc tgc cga ggc aat ggt<br>Lys Asp Lys Pro Lys Val Ile Ile Met Gln Ala Cys Arg Gly Asn Gly<br>210 215 220 | 672 |
| gct ggg att gtt tgg ttc acc act gac agt gga aaa gcc agt gca gat<br>Ala Gly Ile Val Trp Phe Thr Thr Asp Ser Gly Lys Ala Ser Ala Asp<br>225 230 235 240 | 720 |
| act cat ggt cgg ctc ttg caa ggt aac atc tgt aat gat gct gtt aca<br>Thr His Gly Arg Leu Leu Gln Gly Asn Ile Cys Asn Asp Ala Val Thr<br>245 250 255 | 768 |
| aag gct cat gtg gaa aag gac ttc att gct ttc aaa tct tcc aca cca<br>Lys Ala His Val Glu Lys Asp Phe Ile Ala Phe Lys Ser Ser Thr Pro<br>260 265 270 | 816 |
| cat aat gtt tct tgg aga cat gaa aca aat ggc tct gtc ttc att tcc<br>His Asn Val Ser Trp Arg His Glu Thr Asn Gly Ser Val Phe Ile Ser<br>275 280 285 | 864 |
| caa att atc tac tac ttc aga gag tat tct tgg agt cat cat cta gag<br>Gln Ile Ile Tyr Tyr Phe Arg Glu Tyr Ser Trp Ser His His Leu Glu<br>290 295 300 | 912 |
| gaa att ttt caa aag gtt caa cat tca ttt gag acc cca aat ata ctg<br>Glu Ile Phe Gln Lys Val Gln His Ser Phe Glu Thr Pro Asn Ile Leu<br>305 310 315 320 | 960 |
| acc cag ctg ccc acc att gaa aga cta tcc atg aca cga tat ttc tat<br>Thr Gln Leu Pro Thr Ile Glu Arg Leu Ser Met Thr Arg Tyr Phe Tyr<br>325 330 335 | 1008 |
| ctc ttt cct ggg aat taa<br>Leu Phe Pro Gly Asn<br>340 | 1026 |

<210> SEQ ID NO 4
<211> LENGTH: 341
<212> TYPE: PRT
<213> ORGANISM: Homo sapiens
<220> FEATURE:
<221> NAME/KEY: misc_feature
<222> LOCATION: 125
<223> OTHER INFORMATION: Xaa = any amino acid or no amino acid

<400> SEQUENCE: 4

Met Ala Asp Glu Lys Pro Ser Asn Gly Val Leu Val His Met Val Lys
1               5                   10                  15

Leu Leu Ile Lys Thr Phe Leu Asp Gly Ile Phe Asp Asp Leu Met Glu
            20                  25                  30

Asn Asn Val Leu Asn Thr Asp Glu Ile His Leu Ile Gly Lys Cys Leu
        35                  40                  45

Lys Phe Val Val Ser Asn Ala Glu Asn Leu Val Asp Asp Ile Thr Glu
    50                  55                  60

Thr Ala Gln Ile Ala Gly Lys Ile Phe Arg Glu His Leu Trp Asn Ser
65                  70                  75                  80

Lys Lys Gln Leu Ser Ser Asp Ile Ser Ser Asp Gly Glu Arg Glu Ala
                85                  90                  95

```
Asn Met Pro Gly Leu Asn Ile Arg Asn Lys Glu Phe Asn Tyr Leu His
            100                 105                 110
Asn Arg Asn Gly Ser Glu Leu Asp Leu Leu Gly Met Xaa Asp Leu Leu
        115                 120                 125
Glu Asn Leu Gly Tyr Ser Val Val Ile Lys Glu Asn Leu Thr Ala Gln
    130                 135                 140
Glu Met Glu Thr Ala Leu Arg Gln Phe Ala Ala His Pro Glu His Gln
145                 150                 155                 160
Ser Ser Asp Ser Thr Phe Leu Val Phe Met Ser His Ser Ile Leu Asn
                165                 170                 175
Gly Ile Cys Gly Thr Lys His Trp Asp Gln Glu Pro Asp Val Leu His
            180                 185                 190
Asp Asp Thr Ile Phe Glu Ile Phe Asn Asn Arg Asn Cys Gln Ser Leu
        195                 200                 205
Lys Asp Lys Pro Lys Val Ile Met Gln Ala Cys Arg Gly Asn Gly
    210                 215                 220
Ala Gly Ile Val Trp Phe Thr Thr Asp Ser Gly Lys Ala Ser Ala Asp
225                 230                 235                 240
Thr His Gly Arg Leu Leu Gln Gly Asn Ile Cys Asn Asp Ala Val Thr
                245                 250                 255
Lys Ala His Val Glu Lys Asp Phe Ile Ala Phe Lys Ser Ser Thr Pro
            260                 265                 270
His Asn Val Ser Trp Arg His Glu Thr Asn Gly Ser Val Phe Ile Ser
        275                 280                 285
Gln Ile Ile Tyr Tyr Phe Arg Glu Tyr Ser Trp Ser His His Leu Glu
    290                 295                 300
Glu Ile Phe Gln Lys Val Gln His Ser Phe Glu Thr Pro Asn Ile Leu
305                 310                 315                 320
Thr Gln Leu Pro Thr Ile Glu Arg Leu Ser Met Thr Arg Tyr Phe Tyr
                325                 330                 335
Leu Phe Pro Gly Asn
            340

<210> SEQ ID NO 5
<211> LENGTH: 915
<212> TYPE: DNA
<213> ORGANISM: Homo sapiens
<220> FEATURE:
<221> NAME/KEY: CDS
<222> LOCATION: (1)..(372)

<400> SEQUENCE: 5 atg gct gat gag aaa cca tcc aac ggt gtt ctg gtc cac atg gtg aag      48
Met Ala Asp Glu Lys Pro Ser Asn Gly Val Leu Val His Met Val Lys
  1               5                  10                  15 ttg ctg atc aag acc ttt cta gat ggc att ttt gat gat ttg atg gaa      96
Leu Leu Ile Lys Thr Phe Leu Asp Gly Ile Phe Asp Asp Leu Met Glu
             20                  25                  30 aat aat gtg tta aat aca gat gag ata cac ctt ata gga aaa tgt cta     144
Asn Asn Val Leu Asn Thr Asp Glu Ile His Leu Ile Gly Lys Cys Leu
         35                  40                  45 aag ttt gtg gtg agc aat gct gaa aac ctg gtt gat gat atc act gag     192
Lys Phe Val Val Ser Asn Ala Glu Asn Leu Val Asp Asp Ile Thr Glu
     50                  55                  60 aca gct caa att gca ggc aaa ata ttt agg gaa cac ctg tgg aat tcc     240
Thr Ala Gln Ile Ala Gly Lys Ile Phe Arg Glu His Leu Trp Asn Ser
 65                  70                  75                  80
```

```
aaa aaa cag ctg agt tca gat ata tcc agt gat gga gaa aga gag gcg    288
Lys Lys Gln Leu Ser Ser Asp Ile Ser Ser Asp Gly Glu Arg Glu Ala
                 85                  90                  95 aac atg cct ggc ctc aac atc cgc aac aaa gaa ttc aac tat ctt cat    336
Asn Met Pro Gly Leu Asn Ile Arg Asn Lys Glu Phe Asn Tyr Leu His
            100                 105                 110 aat cga aat ggt tct gaa ctt gac ctt ttg ggg atg tgagatctac         382
Asn Arg Asn Gly Ser Glu Leu Asp Leu Leu Gly Met
        115                 120 ttgaaaacct tggatactca gtggttataa aagagaatct cacagctcag gaaatggaaa    442
cagcactaag gcagtttgct gctcacccag agcaccagtc ctcagacagc acattcctgg    502
tgtttatgtc acatagcatc ctgaatggaa tctgtgggac caagcactgg gatcaagagc    562
cagatgttct tcacgatgac accatctttg aaattttcaa caaccgtaac tgccagagtc    622
tgaaagacaa acccaaggtc atcatcatgc aagcctgccg aggcaatggt gctgggattg    682
tttggttcac cactgacagt ggaaaagcca gtgcagatac tcatggtcgg ctcttgcaag    742
gtaacatctg taatgatgct gttacaaagg ctcatgtgga aaaggacttc attgctttca    802
aatcttccac accagttcaa cattcatttg agaccccaaa tatactgacc cagctgccca    862
ccattgaaag actatccatg acacgatatt tctatctctt tcctgggaat taa          915
```

<210> SEQ ID NO 6
<211> LENGTH: 124
<212> TYPE: PRT
<213> ORGANISM: Homo sapiens

<400> SEQUENCE: 6

```
Met Ala Asp Glu Lys Pro Ser Asn Gly Val Leu Val His Met Val Lys
  1               5                  10                  15

Leu Leu Ile Lys Thr Phe Leu Asp Gly Ile Phe Asp Asp Leu Met Glu
             20                  25                  30

Asn Asn Val Leu Asn Thr Asp Glu Ile His Leu Ile Gly Lys Cys Leu
         35                  40                  45

Lys Phe Val Val Ser Asn Ala Glu Asn Leu Val Asp Asp Ile Thr Glu
     50                  55                  60

Thr Ala Gln Ile Ala Gly Lys Ile Phe Arg Glu His Leu Trp Asn Ser
 65                  70                  75                  80

Lys Lys Gln Leu Ser Ser Asp Ile Ser Ser Asp Gly Glu Arg Glu Ala
                 85                  90                  95

Asn Met Pro Gly Leu Asn Ile Arg Asn Lys Glu Phe Asn Tyr Leu His
            100                 105                 110

Asn Arg Asn Gly Ser Glu Leu Asp Leu Leu Gly Met
        115                 120
```

<210> SEQ ID NO 7
<211> LENGTH: 916
<212> TYPE: DNA
<213> ORGANISM: Homo sapiens
<220> FEATURE:
<221> NAME/KEY: CDS
<222> LOCATION: (1)..(912)
<223> OTHER INFORMATION:
<221> NAME/KEY: misc_feature
<222> LOCATION: (373)..(375)
<223> OTHER INFORMATION: n = a or t or g or c
<221> NAME/KEY: misc_feature
<222> LOCATION: 125
<223> OTHER INFORMATION: Xaa = any amino acid or no amino acid

<400> SEQUENCE: 7

-continued

| | |
|---|---|
| atg gct gat gag aaa cca tcc aac ggt gtt ctg gtc cac atg gtg aag<br>Met Ala Asp Glu Lys Pro Ser Asn Gly Val Leu Val His Met Val Lys<br>1                  5                      10               15 | 48 |
| ttg ctg atc aag acc ttt cta gat ggc att ttt gat gat ttg atg gaa<br>Leu Leu Ile Lys Thr Phe Leu Asp Gly Ile Phe Asp Asp Leu Met Glu<br>                  20                   25                  30 | 96 |
| aat aat gtg tta aat aca gat gag ata cac ctt ata gga aaa tgt cta<br>Asn Asn Val Leu Asn Thr Asp Glu Ile His Leu Ile Gly Lys Cys Leu<br>           35                     40                  45 | 144 |
| aag ttt gtg gtg agc aat gct gaa aac ctg gtt gat gat atc act gag<br>Lys Phe Val Val Ser Asn Ala Glu Asn Leu Val Asp Asp Ile Thr Glu<br>50                    55                    60 | 192 |
| aca gct caa att gca ggc aaa ata ttt agg gaa cac ctg tgg aat tcc<br>Thr Ala Gln Ile Ala Gly Lys Ile Phe Arg Glu His Leu Trp Asn Ser<br>65                    70                    75                  80 | 240 |
| aaa aaa cag ctg agt tca gat ata tcc agt gat gga gaa aga gag gcg<br>Lys Lys Gln Leu Ser Ser Asp Ile Ser Ser Asp Gly Glu Arg Glu Ala<br>                  85                   90                  95 | 288 |
| aac atg cct ggc ctc aac atc cgc aac aaa gaa ttc aac tat ctt cat<br>Asn Met Pro Gly Leu Asn Ile Arg Asn Lys Glu Phe Asn Tyr Leu His<br>           100                   105                  110 | 336 |
| aat cga aat ggt tct gaa ctt gac ctt ttg ggg atg nnn gat cta ctt<br>Asn Arg Asn Gly Ser Glu Leu Asp Leu Leu Gly Met Xaa Asp Leu Leu<br>           115                   120                  125 | 384 |
| gaa aac ctt gga tac tca gtg gtt ata aaa gag aat ctc aca gct cag<br>Glu Asn Leu Gly Tyr Ser Val Val Ile Lys Glu Asn Leu Thr Ala Gln<br>           130                   135                  140 | 432 |
| gaa atg gaa aca gca cta agg cag ttt gct gct cac cca gag cac cag<br>Glu Met Glu Thr Ala Leu Arg Gln Phe Ala Ala His Pro Glu His Gln<br>145                   150                   155                  160 | 480 |
| tcc tca gac agc aca ttc ctg gtg ttt atg tca cat agc atc ctg aat<br>Ser Ser Asp Ser Thr Phe Leu Val Phe Met Ser His Ser Ile Leu Asn<br>                  165                   170                  175 | 528 |
| gga atc tgt ggg acc aag cac tgg gat caa gag cca gat gtt ctt cac<br>Gly Ile Cys Gly Thr Lys His Trp Asp Gln Glu Pro Asp Val Leu His<br>           180                   185                  190 | 576 |
| gat gac acc atc ttt gaa att ttc aac aac cgt aac tgc cag agt ctg<br>Asp Asp Thr Ile Phe Glu Ile Phe Asn Asn Arg Asn Cys Gln Ser Leu<br>           195                   200                  205 | 624 |
| aaa gac aaa ccc aag gtc atc atc atg caa gcc tgc cga ggc aat ggt<br>Lys Asp Lys Pro Lys Val Ile Ile Met Gln Ala Cys Arg Gly Asn Gly<br>           210                   215                  220 | 672 |
| gct ggg att gtt tgg ttc acc act gac agt gga aaa gcc agt gca gat<br>Ala Gly Ile Val Trp Phe Thr Thr Asp Ser Gly Lys Ala Ser Ala Asp<br>225                   230                   235                  240 | 720 |
| act cat ggt cgg ctc ttg caa ggt aac atc tgt aat gat gct gtt aca<br>Thr His Gly Arg Leu Leu Gln Gly Asn Ile Cys Asn Asp Ala Val Thr<br>                  245                   250                  255 | 768 |
| aag gct cat gtg gaa aag gac ttc att gct ttc aaa tct tcc aca cca<br>Lys Ala His Val Glu Lys Asp Phe Ile Ala Phe Lys Ser Ser Thr Pro<br>           260                   265                  270 | 816 |
| cgt tca aca ttc att tga gac ccc aaa tat act gac cca gct gcc cac<br>Arg Ser Thr Phe Ile     Asp Pro Lys Tyr Thr Asp Pro Ala Ala His<br>           275                   280                  285 | 864 |
| cat tga aag act atc cat gac acg ata ttt cta tct ctt tcc tgg gaa<br>His     Lys Thr Ile His Asp Thr Ile Phe Leu Ser Leu Ser Trp Glu<br>           290                   295                  300 | 912 |
| ttaa | 916 |

<210> SEQ ID NO 8
<211> LENGTH: 277
<212> TYPE: PRT
<213> ORGANISM: Homo sapiens
<220> FEATURE:
<221> NAME/KEY: misc_feature
<222> LOCATION: 125
<223> OTHER INFORMATION: Xaa = any amino acid or no amino acid

<400> SEQUENCE: 8

Met Ala Asp Glu Lys Pro Ser Asn Gly Val Leu Val His Met Val Lys
  1               5                  10                  15
Leu Leu Ile Lys Thr Phe Leu Asp Gly Ile Phe Asp Asp Leu Met Glu
             20                  25                  30
Asn Asn Val Leu Asn Thr Asp Glu Ile His Leu Ile Gly Lys Cys Leu
         35                  40                  45
Lys Phe Val Val Ser Asn Ala Glu Asn Leu Val Asp Asp Ile Thr Glu
     50                  55                  60
Thr Ala Gln Ile Ala Gly Lys Ile Phe Arg Glu His Leu Trp Asn Ser
 65                  70                  75                  80
Lys Lys Gln Leu Ser Ser Asp Ile Ser Ser Asp Gly Glu Arg Glu Ala
                 85                  90                  95
Asn Met Pro Gly Leu Asn Ile Arg Asn Lys Glu Phe Asn Tyr Leu His
            100                 105                 110
Asn Arg Asn Gly Ser Glu Leu Asp Leu Leu Gly Met Xaa Asp Leu Leu
        115                 120                 125
Glu Asn Leu Gly Tyr Ser Val Val Ile Lys Glu Asn Leu Thr Ala Gln
    130                 135                 140
Glu Met Glu Thr Ala Leu Arg Gln Phe Ala Ala His Pro Glu His Gln
145                 150                 155                 160
Ser Ser Asp Ser Thr Phe Leu Val Phe Met Ser His Ser Ile Leu Asn
                165                 170                 175
Gly Ile Cys Gly Thr Lys His Trp Asp Gln Glu Pro Asp Val Leu His
            180                 185                 190
Asp Asp Thr Ile Phe Glu Ile Phe Asn Asn Arg Asn Cys Gln Ser Leu
        195                 200                 205
Lys Asp Lys Pro Lys Val Ile Ile Met Gln Ala Cys Arg Gly Asn Gly
    210                 215                 220
Ala Gly Ile Val Trp Phe Thr Thr Asp Ser Gly Lys Ala Ser Ala Asp
225                 230                 235                 240
Thr His Gly Arg Leu Leu Gln Gly Asn Ile Cys Asn Asp Ala Val Thr
                245                 250                 255
Lys Ala His Val Glu Lys Asp Phe Ile Ala Phe Lys Ser Ser Thr Pro
            260                 265                 270
Arg Ser Thr Phe Ile
        275

<210> SEQ ID NO 9
<211> LENGTH: 874
<212> TYPE: DNA
<213> ORGANISM: Homo sapiens
<220> FEATURE:
<221> NAME/KEY: misc_feature
<222> LOCATION: 22
<223> OTHER INFORMATION: n = a or t or g or c

<400> SEQUENCE: 9
atggctgatg agaaaccatc cnacggtgtt ctggtccaca tggtgaagtt gctgatcaag      60

```
accttctag atggcatttt tgatgatttg atggaaaata atgtgttaaa tacagatgag    120 atacaccta taggaaaatg tctaaagttt gtggtgagca atgctgaaaa cctggttgat    180
gatatcactg agacagctca aattgcaggc aaaatattta gggaacacct gtggaattcc    240
aaaaaacagc tgagttcaga tatatccagt gatggagaaa gagaggcgaa catgcctggc    300
ctcaacatcc gcaacaaaga attcaactat cttcataatc gaaatggttc tgaacttgac    360
cttttgggga tgtgagatct acttgaaaac cttggatact cagtggttat aaaagagaat    420
ctcacagctc agatggtgct gggattgttt ggttcaccac tgacagtgga aaagccagtg    480
cagatactca tggtcggctc ttgcaaggta acatctgtaa tgatgctgtt acaaaggctc    540
atgtggaaaa ggacttcatt gctttcaaat cttccacacc acataatgtt tcttggagac    600
atgaaacaaa tggctctgtc ttcatttccc aaattatcta ctacttcaga gagtattctt    660
ggagtcatca tctagaggaa attttttcaaa aggttcaaca ttcatttgag accccaaata    720
tactgaccca gctgcccacc attgaaagac tatccatgac acgatatttc tatctctttc    780
ctgggaatta aaaatcgaat tcccgcggcc gccatggcgg ccgggagcat gcgacgtcgg    840
gcccaattcg ccctatagtg agtcgtatta caat                                874

<210> SEQ ID NO 10
<211> LENGTH: 765
<212> TYPE: DNA
<213> ORGANISM: Homo sapiens

<400> SEQUENCE: 10
atggctgatg agaaaccatc caacggtgtt ctggtccaca tggtgaagtt gctgatcaag     60 accttctag atggcatttt tgatgatttg atggaaaata atgtgttaaa tacagatgag    120 atacaccta taggaaaatg tctaaagttt gtggtgagca atgctgaaaa cctggttgat    180
gatatcactg agacagctca aattgcaggc aaaatattta gggaacacct gtggaattcc    240
aaaaaacagc tgagttcaga tatatccagt gatggagaaa gagaggcgaa catgcctggc    300
ctcaacatcc gcaacaaaga attcaactat cttcataatc gaaatggttc tgaacttgac    360
cttttgggga tgtgagatct acttgaaaac cttggatact cagtggttat aaaagagaat    420
ctcacagctc agatggtgct gggattgttt ggttcaccac tgacagtgga aaagccagtg    480
cagatactca tggtcggctc ttgcaaggta acatctgtaa tgatgctgtt acaaaggctc    540
atgtggaaaa ggacttcatt gctttcaaat cttccacacc acgttcaaca ttcatttgag    600
accccaaata tactgaccca gctgcccact attgaaagac tatccatgac acgatatttc    660
tatctctttc ctgggaatta aaaatcgaat tcccgcggcc gccatggcgg ccgggagcat    720
gcgacgtcgg gcccaattcg ccctatagtg agtcgtatta caatt                     765

<210> SEQ ID NO 11
<211> LENGTH: 29
<212> TYPE: DNA
<213> ORGANISM: Homo sapiens

<400> SEQUENCE: 11
tttcaattgc caggaaagag gtagaaata                                        29

<210> SEQ ID NO 12
<211> LENGTH: 27
<212> TYPE: DNA
<213> ORGANISM: Homo sapiens
```

```
<400> SEQUENCE: 12
ggtctagatg gmatttttga tgatttg                                         27

<210> SEQ ID NO 13
<211> LENGTH: 25
<212> TYPE: DNA
<213> ORGANISM: Homo sapiens

<400> SEQUENCE: 13
ttccaattcc aaaaaacagc tgagt                                           25

<210> SEQ ID NO 14
<211> LENGTH: 23
<212> TYPE: DNA
<213> ORGANISM: Homo sapiens

<400> SEQUENCE: 14
caccagagca ccagtcctca gac                                             23

<210> SEQ ID NO 15
<211> LENGTH: 26
<212> TYPE: DNA
<213> ORGANISM: Homo sapiens

<400> SEQUENCE: 15
caatgtgaca taaacaccag gaatgt                                          26

<210> SEQ ID NO 16
<211> LENGTH: 26
<212> TYPE: DNA
<213> ORGANISM: Homo sapiens

<400> SEQUENCE: 16
ccgcctcggc aggcttgcat gatgat                                          26

<210> SEQ ID NO 17
<211> LENGTH: 25
<212> TYPE: DNA
<213> ORGANISM: Homo sapiens

<400> SEQUENCE: 17
gtcagatagt caaactttgt attgc                                           25

<210> SEQ ID NO 18
<211> LENGTH: 26
<212> TYPE: DNA
<213> ORGANISM: Homo sapiens

<400> SEQUENCE: 18
tcatatatcc agtgatggag aaagag                                          26

<210> SEQ ID NO 19
<211> LENGTH: 24
<212> TYPE: DNA
<213> ORGANISM: Homo sapiens

<400> SEQUENCE: 19
cttgggaaat gaagacagag ccat                                            24

<210> SEQ ID NO 20
<211> LENGTH: 23
<212> TYPE: DNA
<213> ORGANISM: Homo sapiens
```

```
<400> SEQUENCE: 20
acccaggaat atctctggaa gca                                           23

<210> SEQ ID NO 21
<211> LENGTH: 23
<212> TYPE: DNA
<213> ORGANISM: Homo sapiens

<400> SEQUENCE: 21
ccactcagct gtttttgga att                                            23

<210> SEQ ID NO 22
<211> LENGTH: 28
<212> TYPE: DNA
<213> ORGANISM: Homo sapiens

<400> SEQUENCE: 22
cctgaatgga atctgtggga ccaagcac                                      28

<210> SEQ ID NO 23
<211> LENGTH: 28
<212> TYPE: DNA
<213> ORGANISM: Homo sapiens

<400> SEQUENCE: 23
gtgcttggtc ccacagattc cattcagg                                      28

<210> SEQ ID NO 24
<211> LENGTH: 24
<212> TYPE: DNA
<213> ORGANISM: Homo sapiens

<400> SEQUENCE: 24
accaagcact gggatcaaga gcca                                          24

<210> SEQ ID NO 25
<211> LENGTH: 24
<212> TYPE: DNA
<213> ORGANISM: Homo sapiens

<400> SEQUENCE: 25
tggctcttga tcccagtgct tgga                                          24

<210> SEQ ID NO 26
<211> LENGTH: 27
<212> TYPE: DNA
<213> ORGANISM: Homo sapiens

<400> SEQUENCE: 26
ttgcctgcaa tttgagctgt ctcagtg                                       27

<210> SEQ ID NO 27
<211> LENGTH: 24
<212> TYPE: DNA
<213> ORGANISM: Homo sapiens

<400> SEQUENCE: 27
gccatggctg atgagaaacc atcc                                          24

<210> SEQ ID NO 28
<211> LENGTH: 33
<212> TYPE: DNA
```

<213> ORGANISM: Homo sapiens

<400> SEQUENCE: 28

| tttaattccc aggaaagaga tagaaatatc gtg | 33 |
|---|---|

<210> SEQ ID NO 29
<211> LENGTH: 26
<212> TYPE: DNA
<213> ORGANISM: Homo sapiens

<400> SEQUENCE: 29

| gtgatatcat caaccaggtt ttcagc | 26 |
|---|---|

<210> SEQ ID NO 30
<211> LENGTH: 292
<212> TYPE: DNA
<213> ORGANISM: Homo sapiens

<400> SEQUENCE: 30

| taagaggttg aaaagtgtct aaaggtggag gtggagggga agcagcttgt tcttctctct | 60 |
|---|---|
| ggagccatta cctgagctgt gagattctct tttataacca ctgagtatcc aaggttttca | 120 |
| agtagatctc acatccccaa aaggtcaagt tcagaaccat ttcgattatg aagatagttg | 180 |
| aattctttgt tgcggatgtt gaggccaggc atgttccgcc tctctttctc catcactgga | 240 |
| tatatctgca attaatacac acagaatgac tttccccagg acttttctct tt | 292 |

<210> SEQ ID NO 31
<211> LENGTH: 686
<212> TYPE: DNA
<213> ORGANISM: Homo sapiens

<400> SEQUENCE: 31

| gaaatgaatg ttgaaaggct ttggattaga catgaggtat ttatcttgat gtaaagggta | 60 |
|---|---|
| cagtctgaca tggagtgtca attctaagag gtagtgtaca acgttgagaa gacagaatac | 120 |
| ccatgggctt ggtcctatga aacctgcaaa ctctcttcat tccaggactt tcctggttca | 180 |
| tggtggaaga tgctttctga gacttgaaaa gagtcgtatc tcatctatag cctactttct | 240 |
| ttttcaggtt cagcaagcat ttgaaagtcc cggaggcaac agtccaaatg cccaccatag | 300 |
| aacgagtgtc catgacaaga tatttctacc tctttcctgg caattgaaaa tggttaagca | 360 |
| ttgagagttg ttggtggtgt atgaaataaa tgaaagtgtg atattggagg tgagttccga | 420 |
| tgaccaatga cagttgagta cttggatggc caaattagtg tactttgttg atgtagtctg | 480 |
| gtgattgatt atctggtatc ttttattcga tttttttttgc attttgggtt cccccaactc | 540 |
| tataattaat caggcaatca atcaatcaag gacgtaagga aaaccaaggc caaatgagat | 600 |
| aataaaaaac ccagggtagc acttattaaa atagaaacat actcctgcat ccattactat | 660 |
| ttatattcat tacatctcat actcta | 686 |

<210> SEQ ID NO 32
<211> LENGTH: 533
<212> TYPE: DNA
<213> ORGANISM: Homo sapiens

<400> SEQUENCE: 32

| gtccttgcac cagaggcttt ggcatcacct gagaaattgt tataaatgaa aattcatggg | 60 |
|---|---|
| cccattctca cctatcaaat aaaaattatt tggactagga tgcaggaagc tctgcttact | 120 |
| aagctttcta ggtgattctt atgcacgtta aaatttggga accactaccc tagaatgggg | 180 |

```
atctaaagtt ctgtccatat ctaagattct atcattttca cagatgagaa accatccaac      240
ggtgttctgg tccacatggt gaagttgctg atcaagacct ttctagatgg cattttgat       300 gatttgatgg aaaataatgt gttaaataca gatgagatac accttatagg aaaatgtcta      360
aagtttgtgg tgagcaatgc tgaaaacctg gttgatgata tcactgagac agctcaaatt      420
gcaggcaaaa tatttaggga acacctgtgg aattccaaaa aacagctgag ttcaggtgag      480
tattgggggc taacagctag aaattcattc ttattctttc tctactcttc tta             533

<210> SEQ ID NO 33
<211> LENGTH: 563
<212> TYPE: DNA
<213> ORGANISM: Homo sapiens

<400> SEQUENCE: 33
cttggagtca ggaaggattg tcaagatgaa ttaagagctt tgggatttct tataaaaatt      60
cacaaatggt tctccaaagt tttctggggc ataacattga aaataaaaga agaccctacc      120
ttttgaaaaa tttcctctag atgatgactc caagaatact ctctgaagta gtagataatt      180
tgggaaatga agacagagcc atttgtttca tgtctccaag aaacattatc tacaaataaa      240
aggcatcaaa atattggagg atgtgatctt ttatacatgt ggaagactcc tggagacata      300
actttgggaa aaaaaatctg attttgtttc tttggagaag agagggaaac caatgctaaa      360
taaagatgga cctccaactt ccataccagg cccagaaaaa gccatcatgg gaccttcctc      420
actcataaat caccttgatt ttctagtagg ctagaccgaa gtgatatcct ctgggtttgc      480
aagtagtgga aaagagtgta agtcctttca gcactaacta cataacagaa aaataataca      540
gccttgacat tccttgattc tgg                                              563

<210> SEQ ID NO 34
<211> LENGTH: 528
<212> TYPE: DNA
<213> ORGANISM: Homo sapiens

<400> SEQUENCE: 34
tatgtctatg catatgtgta tgtgcgtgtg tatgtgtatg tgtgtgcata tgtggatgtt      60
tgtgcatatg agtatgtgtg tgcatatgtg tatgtgtgtg tgtatgtgta tgtgtgtgta      120
tttataaata tctcttcttt aatgagacat aatgtctctc ccagatggtg ctgggattgt      180
ttggttcacc actgacagtg gaaaagccag tgcagatact catggtcggc tcttgcaagg      240
taacatctgt aatgatgctg ttacaaaggc tcatgtggaa aaggacttca ttgctttcaa      300
atcttccaca ccacgtaagt gatttcagag agaataattt ctaaatttct tagtaggttt      360
ctagatagta ggcttggcta tgatcatatc ttatcaccga acagagcatt tcttctctaa      420
ttaccaggat attttaggtg gagaaaagat ttaaaatgct gagactttca taattagaaa      480
gctataaatc ttgatttggg aagaaacgtt caaagttaac aggacttt                   528

<210> SEQ ID NO 35
<211> LENGTH: 555
<212> TYPE: DNA
<213> ORGANISM: Homo sapiens

<400> SEQUENCE: 35
tccttactca taaactctg tagctaagtt aattacacat ataatcacac atctaatatc       60
aagtatgggg cagaagaaag cccaggcctt gaaacagctc cttcattccc gtgatgtcga      120
```

```
agtgagcccc attccttgga gtcagatagt caaactttgt attgcttata atgagagcca    180
ggtatttgca gatctttctg tttttttttt tattagattg atctgcagga gatggagatg    240
aaatgacttt gattacctga gtctcttttc aatctccata tgtttcacaa ttttgttttt    300
ttaaaacctc gtatagctgc cctcttccct aacctctatc aaaagacact gctttcctct    360
ctctcaagag cccagagcaa gaaccaggac atatctggat gattagtcaa gaatcttaaa    420
gaaactagaa taattcctac tcccttcctt cttattttc ttctgcatct actcaaacat     480
ttcttatatt caggttcaaa tcaaatttca taaaaactga gagatgtcat ctgcaccagt    540
aaaaatgaat atagc                                                     555

<210> SEQ ID NO 36
<211> LENGTH: 532
<212> TYPE: DNA
<213> ORGANISM: Homo sapiens

<400> SEQUENCE: 36
tcttttgata gaggttaggg aagagggcag ctatacgagg ttttaaaaaa caaaattgtg    60
aaacatatgg aggattgaaa aggagactca ggtaatcaaa gtcatttcat ctccatctcc    120
tgcagatcaa tctaataaaa aaaaaaacag aaagatctgc aaatacctgg ctctcattat    180
aagcaataca aagtttgact atctgactcc aagggaatgg ggctcacttc gacatcacgg    240
gaatgaagga gctgtttcaa ggcctgggct tcttctgccc catacttgat attagatgtg    300
tgattatatg tgtaattaac ttagctacag agttttatga gtaaggagag ttaagcctag    360
caattttgta atatagtaag aactacatga catgatatat gtagaaaact aattatagtt    420
ctgttcatac ttaaattgct caataaagat aatgatggca acaatgatag tggtgatgtt    480
gatgatgata atgacgcaat ttggttgacc atgaaatagg aggagtcagc ca            532

<210> SEQ ID NO 37
<211> LENGTH: 576
<212> TYPE: DNA
<213> ORGANISM: Homo sapiens

<400> SEQUENCE: 37
gtgtgtgttc atctattttg tttattatat ggtgaaagga cagcatggca tgatctgcaa    60
acaacttggg agcctagtgg ccattttttg ttgcttactc actgtggtaa tatgagggag    120
tttcttcatc ttttggagcc tctattcctt cctctgtaaa gtgggataat tccagttatt    180
tctcaagccc ctataaaagc caagagaata acacaatgt tgtagtaga aagtcagtcc      240 caagaatcaa aatacaatca ctacacaatc tcttgcaatg cttacaaact gccacttttg    300
atcaactgtt gctaggtttt tgttgactt tatgcggaaa gtggttaaat gtaaggttgt     360
aaacatgtcg tccaaatctg taagataat tcccaagcta tgcttttatt aaaaaaaaa      420 tcctcaaaac aaaaatgtaa acaaaaaata gtgaaggtca tagcccaaga catacccatc    480
tgtatcatca tagataacgt gtccaggaga gacagcacaa ggggctccat cttcatcaca    540
caactcatcg catgcttcca gagatattcc tggcgc                              576

<210> SEQ ID NO 38
<211> LENGTH: 611
<212> TYPE: DNA
<213> ORGANISM: Homo sapiens

<400> SEQUENCE: 38
```

```
cacagccctc cctggggtct caaaatcaag atttacagct ttctaattgg ggactcactg      60
cctcggcagg cttgcatgat gatgaccttg ggtttgtctt tcagactctg gcagttacgg     120
ttgttgaaaa tttcaaagta tggtgtcatc gtgaagaaca tctggctctt gatcccagtg     180
cttggtccca cagattccat tcaggatgct atgtgacata aacaccagga atgtgctgtc     240
tgaggactgg tgctctgggt gagcagcaaa ctgccttagt gctgtttcca tttcctgaaa     300
gagacccttg agtcactatc gaggaagtct ccatgtgtat gtagtttgta atcaaataat     360
gggtagggtt cacaaaaagg agccagcact aaggaatcag atggtttaga ctgaatagga     420
ttataagata aacagtgttc tgacataaaa ctagaaaatt tagctgtata gaatattaaa     480
gttagtaggg tttttatgta gtatcttgcc cagtggtttt tagtaaaacc ttaggtttct     540
gaagatgctg ggagatggaa taaaatgaag gccaagtgag atgacaatac accaatagga     600
ccattttgct a                                                          611
```

<210> SEQ ID NO 39
<211> LENGTH: 76
<212> TYPE: PRT
<213> ORGANISM: Artificial Sequence
<220> FEATURE:
<223> OTHER INFORMATION: Description of Artificial Sequence: peptide

<400> SEQUENCE: 39

```
Arg Glu Lys Ser Trp Gly Lys Ser Phe Cys Val Tyr Leu Gln Ile Tyr
 1               5                  10                  15

Pro Val Met Glu Lys Glu Arg Arg Asn Met Pro Gly Leu Asn Ile Arg
            20                  25                  30

Asn Lys Glu Arg Asn Tyr Leu His Asn Arg Asn Gly Ser Glu Leu Asp
        35                  40                  45

Leu Leu Gly Met Asp Leu Leu Glu Asn Leu Gly Tyr Ser Val Val Ile
    50                  55                  60

Lys Glu Asn Leu Thr Ala Gln Val Met Ala Pro Glu
65                  70                  75
```

<210> SEQ ID NO 40
<211> LENGTH: 47
<212> TYPE: PRT
<213> ORGANISM: Artificial Sequence
<220> FEATURE:
<223> OTHER INFORMATION: Description of Artificial Sequence: peptide

<400> SEQUENCE: 40

```
His Leu Pro Thr Phe Phe Phe Arg Phe Ser Lys His Leu Lys Val Pro
 1               5                  10                  15

Glu Ala Thr Val Gln Met Pro Thr Ile Glu Arg Val Ser Met Thr Arg
            20                  25                  30

Tyr Phe Tyr Leu Phe Pro Gly Asn Lys Trp Leu Ser Ile Glu Ser
        35                  40                  45
```

<210> SEQ ID NO 41
<211> LENGTH: 177
<212> TYPE: PRT
<213> ORGANISM: Artificial Sequence
<220> FEATURE:
<223> OTHER INFORMATION: Description of Artificial Sequence: peptide
<221> NAME/KEY: misc_feature
<222> LOCATION: (15)..(45)..(62)..(68)
<223> OTHER INFORMATION: Xaa = any amino acid or no amino acid

<400> SEQUENCE: 41

```
Val Leu Ala Pro Glu Ala Leu Ala Ser Pro Glu Lys Leu Leu Xaa Met
 1               5                  10                  15

Lys Ile His Gly Pro Ile Leu Thr Tyr Gln Ile Lys Ile Ile Trp Thr
            20                  25                  30

Arg Met Gln Glu Ala Leu Leu Thr Lys Leu Ser Arg Xaa Phe Leu Cys
        35                  40                  45

Thr Leu Lys Phe Gly Asn His Tyr Pro Arg Met Gly Ile Xaa Ser Ser
    50                  55                  60

Val His Ile Xaa Asp Ser Ile Ile Phe Thr Asp Glu Lys Pro Ser Asn
65                  70                  75                  80

Gly Val Leu Val His Met Val Lys Leu Leu Ile Lys Thr Phe Leu Asp
                85                  90                  95

Gly Ile Phe Asp Asp Leu Met Glu Asn Asn Val Leu Asn Thr Asp Glu
                100                 105                 110

Ile His Leu Ile Gly Lys Cys Leu Lys Phe Val Val Ser Asn Ala Glu
            115                 120                 125

Asn Leu Val Asp Asp Ile Thr Glu Thr Ala Gln Ile Ala Gly Lys Ile
    130                 135                 140

Phe Arg Glu His Leu Trp Asn Ser Lys Lys Gln Leu Ser Ser Gly Glu
145                 150                 155                 160

Tyr Trp Gly Leu Thr Ala Arg Asn Ser Phe Leu Phe Leu Tyr Ser
                165                 170                 175

Ser
```

<210> SEQ ID NO 42
<211> LENGTH: 99
<212> TYPE: PRT
<213> ORGANISM: Artificial Sequence
<220> FEATURE:
<223> OTHER INFORMATION: Description of Artificial Sequence: peptide
<221> NAME/KEY: misc_feature
<222> LOCATION: (18)..(80)
<223> OTHER INFORMATION: Xaa = any amino acid or no amino acid

<400> SEQUENCE: 42

```
Met Ser Pro Gly Val Phe His Met Tyr Lys Arg Ser His Pro Pro Ile
 1               5                  10                  15

Phe Xaa Cys Leu Leu Phe Val Asp Asn Val Ser Trp Arg His Glu Thr
            20                  25                  30

Asn Gly Ser Val Phe Ile Ser Gln Ile Ile Tyr Tyr Phe Arg Glu Tyr
        35                  40                  45

Ser Trp Ser His His Leu Glu Glu Ile Phe Gln Lys Val Gly Ser Ser
    50                  55                  60

Phe Ile Phe Asn Val Met Pro Gln Lys Thr Leu Glu Asn His Leu Xaa
65                  70                  75                  80

Ile Phe Ile Arg Asn Pro Lys Ala Leu Asn Ser Ser Xaa Gln Ser Phe
                85                  90                  95

Leu Thr Pro
```

<210> SEQ ID NO 43
<211> LENGTH: 99
<212> TYPE: PRT
<213> ORGANISM: Artificial Sequence
<220> FEATURE:
<223> OTHER INFORMATION: Description of Artificial Sequence: peptide
<221> NAME/KEY: misc_feature
<222> LOCATION:
<223> OTHER INFORMATION: Xaa = any amino acid or no amino acid

```
<400> SEQUENCE: 43

Cys Val Cys Met Cys Met Cys Val Tyr Leu Xaa Ile Ser Leu Leu Xaa
 1               5                  10                  15

Asp Ile Met Ser Leu Pro Asp Gly Ala Gly Ile Val Trp Phe Thr Thr
                20                  25                  30

Asp Ser Gly Lys Ala Ser Ala Asp Thr His Gly Arg Leu Leu Gln Gly
            35                  40                  45

Asn Ile Cys Asn Asp Ala Val Thr Lys Ala His Val Glu Lys Asp Phe
        50                  55                  60

Ile Ala Phe Lys Ser Ser Thr Pro Arg Lys Xaa Phe Gln Arg Glu Xaa
 65                  70                  75                  80

Phe Leu Asn Phe Leu Val Gly Phe Xaa Ile Val Gly Leu Ala Met Ile
                85                  90                  95

Ile Ser Tyr

<210> SEQ ID NO 44
<211> LENGTH: 50
<212> TYPE: PRT
<213> ORGANISM: Artificial Sequence
<220> FEATURE:
<223> OTHER INFORMATION: Description of Artificial Sequence:peptide
<221> NAME/KEY: misc_feature
<222> LOCATION:
<223> OTHER INFORMATION: Xaa = any amino acid or no amino acid

<400> SEQUENCE: 44

Ala Leu Ile Ile Ser Asn Thr Lys Phe Asp Tyr Leu Thr Pro Arg Asn
 1               5                  10                  15

Gly Ala His Phe Asp Ile Thr Gly Met Lys Glu Leu Phe Gln Gly Leu
                20                  25                  30

Gly Phe Leu Leu Pro His Thr Xaa Tyr Xaa Met Cys Asp Tyr Met Cys
            35                  40                  45

Asn Xaa
     50

<210> SEQ ID NO 45
<211> LENGTH: 47
<212> TYPE: PRT
<213> ORGANISM: Artificial Sequence
<220> FEATURE:
<223> OTHER INFORMATION: Description of Artificial Sequence: peptide

<400> SEQUENCE: 45

Ala Leu Ile Ile Ser Asn Thr Lys Phe Asp Tyr Leu Thr Pro Arg Glu
 1               5                  10                  15

Trp Gly Ser Leu Arg His His Gly Asn Glu Gly Ala Val Ser Arg Pro
                20                  25                  30

Gly Leu Leu Leu Pro His Thr Tyr Met Cys Asp Thr Met Cys Asn
            35                  40                  45

<210> SEQ ID NO 46
<211> LENGTH: 48
<212> TYPE: PRT
<213> ORGANISM: Artificial Sequence
<220> FEATURE:
<223> OTHER INFORMATION: Description of Artificial Sequence: peptide

<400> SEQUENCE: 46

Leu Ser Leu Ala Ile Gln Ser Leu Thr Ile Leu Gln Gly Asn Gly Ala
 1               5                  10                  15
```

-continued

His Phe Asp Ile Thr Gly Met Lys Glu Leu Phe Gln Gly Leu Gly Phe
                20                  25                  30

Phe Cys Pro Ile Leu Asp Ile Arg Cys Val Ile Ile Cys Val Ile Asn
            35                  40                  45

<210> SEQ ID NO 47
<211> LENGTH: 51
<212> TYPE: PRT
<213> ORGANISM: Artificial Sequence
<220> FEATURE:
<223> OTHER INFORMATION: Description of Artificial Sequence: peptide

<400> SEQUENCE: 47

Ser Lys Gln Lys Cys Lys Gln Lys Ile Val Lys Val Ile Ala Gln Asp
  1               5                  10                  15

Ile Pro Ile Cys Ile Ile Ile Asp Asn Val Ser Arg Arg Asp Ser Thr
                20                  25                  30

Arg Gly Ser Ile Phe Ile Thr Gln Ile Leu Ala Cys Phe Gln Arg Tyr
            35                  40                  45

Ser Trp Arg
        50

<210> SEQ ID NO 48
<211> LENGTH: 89
<212> TYPE: PRT
<213> ORGANISM: Artificial Sequence
<220> FEATURE:
<223> OTHER INFORMATION: Description of Artificial Sequence: peptide

<400> SEQUENCE: 48

Gly Ser Leu Leu Leu Thr Gln Ser Thr Ser Pro Gln Thr Ala His Ser
  1               5                  10                  15

Trp Cys Leu Cys His Ile Ala Ser Met Glu Ser Val Gly Pro Ser Thr
                20                  25                  30

Gly Ile Lys Ser Gln Met Phe Phe Thr Met Thr Pro Tyr Phe Glu Ile
            35                  40                  45

Phe Asn Asn Arg Asn Cys Gln Ser Leu Lys Asp Lys Pro Lys Val Ile
 50                  55                  60

Ile Met Gln Ala Cys Arg Gly Ser Glu Ser Pro Ile Arg Lys Leu Ile
65                  70                  75                  80

Leu Ile Leu Arg Pro Gln Gly Gly Leu
                85

<210> SEQ ID NO 49
<211> LENGTH: 92
<212> TYPE: PRT
<213> ORGANISM: Artificial Sequence
<220> FEATURE:
<223> OTHER INFORMATION: Description of Artificial Sequence: peptide

<400> SEQUENCE: 49

Ile Leu Ser Tyr Ser Val Thr Ile Phe Leu Ser Ala Gly Ser Phe Leu
  1               5                  10                  15

Thr Leu Pro Ile Ile Leu Gln Thr Thr Tyr Thr Trp Arg Leu Pro Arg
                20                  25                  30

Leu Lys Gly Leu Phe Gln Glu Met Glu Thr Ala Leu Arg Gln Phe Ala
            35                  40                  45

Ala His Pro Glu His Gln Ser Ser Asp Ser Thr Phe Leu Val Phe Met
 50                  55                  60

Ser His Ser Ile Leu Asn Gly Ile Cys Gly Thr Lys His Trp Asp Gln

```
                    65                  70                  75                  80
              Glu Pro Asp Val Leu His Asp Thr Ile Leu Asn
                                    85                  90

<210> SEQ ID NO 50
<211> LENGTH: 1026
<212> TYPE: DNA
<213> ORGANISM: Homo sapien
<220> FEATURE:
<221> NAME/KEY: CDS
<222> LOCATION: (1)..(372)

<400> SEQUENCE: 50 atg gct gat gag aaa cca tcc aac ggt gtt ctg gtc cac atg gtg aag       48
Met Ala Asp Glu Lys Pro Ser Asn Gly Val Leu Val His Met Val Lys
  1               5                  10                  15 ttg ctg atc aag acc ttt cta gat ggc att ttt gat gat ttg atg gaa      96
Leu Leu Ile Lys Thr Phe Leu Asp Gly Ile Phe Asp Asp Leu Met Glu
             20                  25                  30 aat aat gtg tta aat aca gat gag ata cac ctt ata gga aaa tgt cta     144
Asn Asn Val Leu Asn Thr Asp Glu Ile His Leu Ile Gly Lys Cys Leu
         35                  40                  45 aag ttt gtg gtg agc aat gct gaa aac ctg gtt gat gat atc act gag     192
Lys Phe Val Val Ser Asn Ala Glu Asn Leu Val Asp Asp Ile Thr Glu
     50                  55                  60 aca gct caa att gca ggc aaa ata ttt agg gaa cac ctg tgg aat tcc     240
Thr Ala Gln Ile Ala Gly Lys Ile Phe Arg Glu His Leu Trp Asn Ser
 65                  70                  75                  80 aaa aaa cag ctg agt tca gat ata tcc agt gat gga gaa aga gag gcg     288
Lys Lys Gln Leu Ser Ser Asp Ile Ser Ser Asp Gly Glu Arg Glu Ala
                 85                  90                  95 aac atg cct ggc ctc aac atc cgc aac aaa gaa ttc aac tat ctt cat     336
Asn Met Pro Gly Leu Asn Ile Arg Asn Lys Glu Phe Asn Tyr Leu His
            100                 105                 110 aat cga aat ggt tct gaa ctt gac ctt ttg ggg atg tgagatctac           382
Asn Arg Asn Gly Ser Glu Leu Asp Leu Leu Gly Met
        115                 120 ttgaaaacct tggatactca gtggttataa aagagaatct cacagctcag gaaatggaaa    442
cagcactaag gcagtttgct gctcacccag agcaccagtc ctcagacagc acattcctgg    502
tgtttatgtc acatagcatc ctgaatggaa tctgtgggac caagcactgg gatcaagagc    562
cagatgttct tcacgatgac accatctttg aaattttcaa caaccgtaac tgccagagtc    622
tgaaagacaa acccaaggtc atcatcatgc aagcctgccg aggcaatggt gctgggattg    682
tttggttcac cactgacagt ggaaaagcca gtgcagatac tcatggtcgg ctcttgcaag    742
gtaacatctg taatgatgct gttacaaagg ctcatgtgga aaaggacttc attgctttca    802
aatcttccac accacataat gtttcttgga gacatgaaac aaatggctct gtcttcattt    862
cccaaattat ctactacttc agagagtatt cttggagtca tcatctagag gaaattttttc   922 aaaaggttca acattcattt gagacccaa atatactgac ccagctgccc accattgaaa     982
gactatccat gacacgatat ttctatctct ttcctgggaa ttaa                    1026

<210> SEQ ID NO 51
<211> LENGTH: 340
<212> TYPE: PRT
<213> ORGANISM: Homo sapiens

<400> SEQUENCE: 51

Met Ala Asp Glu Lys Pro Ser Asn Gly Val Leu Val His Met Val Lys
```

```
            1               5                   10                  15
Leu Leu Ile Lys Thr Phe Leu Asp Gly Ile Phe Asp Asp Leu Met Glu
                20                  25                  30

Asn Asn Val Leu Asn Thr Asp Glu Ile His Leu Ile Gly Lys Cys Leu
                35                  40                  45

Lys Phe Val Val Ser Asn Ala Glu Asn Leu Val Asp Asp Ile Thr Glu
                50                  55                  60

Thr Ala Gln Ile Ala Gly Lys Ile Phe Arg Glu His Leu Trp Asn Ser
 65                  70                  75                  80

Lys Lys Gln Leu Ser Ser Ile Tyr Pro Val Met Glu Lys Glu Arg Arg
                85                  90                  95

Thr Cys Leu Ala Leu Asn Ile Arg Asn Lys Glu Phe Asn Tyr Leu His
                100                 105                 110

Asn Arg Asn Gly Ser Glu Leu Asp Leu Leu Gly Met Asp Leu Leu Glu
                115                 120                 125

Asn Leu Gly Tyr Ser Val Val Ile Lys Glu Asn Leu Thr Ala Gln Glu
                130                 135                 140

Met Glu Thr Ala Leu Arg Gln Phe Ala Ala His Pro Glu His Gln Ser
145                 150                 155                 160

Ser Asp Ser Thr Phe Leu Val Phe Met Ser His Ser Ile Leu Asn Gly
                165                 170                 175

Ile Cys Gly Thr Lys His Trp Asp Gln Glu Pro Asp Val Leu His Asp
                180                 185                 190

Asp Thr Ile Phe Glu Ile Phe Asn Asn Arg Asn Cys Gln Ser Leu Lys
                195                 200                 205

Asp Lys Pro Lys Val Ile Ile Met Gln Ala Cys Arg Gly Asn Gly Ala
                210                 215                 220

Gly Ile Val Trp Phe Thr Thr Asp Ser Gly Lys Ala Ser Ala Asp Thr
225                 230                 235                 240

His Gly Arg Leu Leu Gln Gly Asn Ile Cys Asn Asp Ala Val Thr Lys
                245                 250                 255

Ala His Val Glu Lys Asp Phe Ile Ala Phe Lys Ser Ser Thr Pro His
                260                 265                 270

Asn Val Ser Trp Arg His Glu Thr Asn Gly Ser Val Phe Ile Ser Gln
                275                 280                 285

Ile Ile Tyr Tyr Phe Arg Glu Tyr Ser Trp Ser His His Leu Glu Glu
                290                 295                 300

Ile Phe Gln Lys Val Gln His Ser Phe Glu Thr Pro Asn Ile Leu Thr
305                 310                 315                 320

Gln Leu Pro Thr Ile Glu Arg Leu Ser Met Thr Arg Tyr Phe Tyr Leu
                325                 330                 335

Phe Pro Gly Asn
                340

<210> SEQ ID NO 52
<211> LENGTH: 1001
<212> TYPE: DNA
<213> ORGANISM: Homo sapiens

<400> SEQUENCE: 52
atggctgatg agaaaccatc caacggtgtt ctggtccaca tggtgaagtt gctgatcaag      60
acctttctag atggcatttt tgatgatttg atggaaaata atgtgttaaa tacagatgag     120
atacacctta taggaaaatg tctaaagttt gtggtgagca atgctgaaaa cctggttgat     180
```

-continued

```
gatatcactg agacagctca aattgcaggc aaaatattta gggaacacct gtggaattcc    240
aaaaaacagc tgagttcaga tatatccagt gatggagaaa gagaggcgaa catgcctggc    300
ctcaacatcc gcaacaaaga attcaactat cttcataatc gaaatggttc tgaacttgac    360
cttttgggga tgtgagatct acttgaaaac cttggatact cagtggttat aaaagagaat    420
ctcacagctc aggaaatgga acagcacta aggcagtttg ctgctcaccc agagcaccag      480
tcctcagaca gcacattcct ggtgtttatg tcacatagca tcctgaatgg aatctgtggg    540
accaagcact gggatcaaga gccagatgtt cttcacgatg acaccatctt tgaaattttc    600
aacaaccgta actgccagag tctgaaagac aaacccaagg tcatcatcat gcaagcctgc    660
cgaggcaatg gtgctgggat tgtttggttc accactgaca gtggaaaagc cagtgcagat    720
actcatggtc ggctcttgca aggtaacatc tgtaatgatg ctgttacaaa ggctcatgtg    780
gaaaaggact tcattgcttt caaatcttcc acaccacgtt caacattcat tgagacccc    840 aaatatactg acccagctgc ccaccattga aagactatcc atgacacgat atttctatct    900
ctttcctggg aattaaaaat cgaattcccg cggccgccat ggcggccggg agcatgcgac    960
gtcgggccca attcgcccta tagtgagtcg tattacaatt c                       1001
```

<210> SEQ ID NO 53
<211> LENGTH: 303
<212> TYPE: PRT
<213> ORGANISM: Homo sapiens

<400> SEQUENCE: 53

```
Met Ala Asp Glu Lys Pro Ser Asn Gly Val Leu Val His Met Val Lys
1               5                   10                  15

Leu Leu Ile Lys Thr Phe Leu Asp Gly Ile Phe Asp Asp Leu Met Glu
            20                  25                  30

Asn Asn Val Leu Asn Thr Asp Glu Ile His Leu Ile Gly Lys Cys Leu
        35                  40                  45

Lys Phe Val Val Ser Asn Ala Glu Asn Leu Val Asp Asp Ile Thr Glu
    50                  55                  60

Thr Ala Gln Ile Ala Gly Lys Ile Phe Arg Glu His Leu Trp Asn Ser
65                  70                  75                  80

Lys Lys Gln Leu Ser Ser Ile Tyr Pro Val Met Glu Lys Glu Arg Arg
                85                  90                  95

Thr Cys Leu Ala Leu Asn Ile Arg Asn Lys Glu Phe Asn Tyr Leu His
            100                 105                 110

Asn Arg Asn Gly Ser Glu Leu Asp Leu Leu Gly Met Asp Leu Leu Glu
        115                 120                 125

Asn Leu Gly Tyr Ser Val Val Ile Lys Glu Asn Leu Thr Ala Gln Glu
    130                 135                 140

Met Glu Thr Ala Leu Arg Gln Phe Ala Ala His Pro Glu His Gln Ser
145                 150                 155                 160

Ser Asp Ser Thr Phe Leu Val Phe Met Ser His Ser Ile Leu Asn Gly
                165                 170                 175

Ile Cys Gly Thr Lys His Trp Asp Gln Glu Pro Asp Val Leu His Asp
            180                 185                 190

Asp Thr Ile Phe Glu Ile Phe Asn Asn Arg Asn Cys Gln Ser Leu Lys
        195                 200                 205

Asp Lys Pro Lys Val Ile Ile Met Gln Ala Cys Arg Gly Asn Gly Ala
    210                 215                 220

Gly Ile Val Trp Phe Thr Thr Asp Ser Gly Lys Ala Ser Ala Asp Thr
```

```
                225                 230                 235                 240
His Gly Arg Leu Leu Gln Gly Asn Ile Cys Asn Asp Ala Val Thr Lys
                    245                 250                 255
Ala His Val Glu Lys Asp Phe Ile Ala Phe Lys Ser Ser Thr Pro Val
                260                 265                 270
Gln His Ser Phe Glu Thr Pro Asn Ile Leu Thr Gln Leu Pro Thr Ile
            275                 280                 285
Glu Arg Leu Ser Met Thr Arg Tyr Phe Tyr Leu Phe Pro Gly Asn
        290                 295                 300

<210> SEQ ID NO 54
<211> LENGTH: 874
<212> TYPE: DNA
<213> ORGANISM: Homo sapiens
<220> FEATURE:
<221> NAME/KEY: misc_feature
<222> LOCATION:
<223> OTHER INFORMATION: n = a or t or g or c

<400> SEQUENCE: 54
atggctgatg agaaaccatc cnacggtgtt ctggtccaca tggtgaagtt gctgatcaag      60
acctttctag atggcatttt tgatgatttg atggaaaata atgtgttaaa tacagatgag     120
atacacctta taggaaaatg tctaaagttt gtggtgagca atgctgaaaa cctggttgat     180
gatatcactg agacagctca aattgcaggc aaaatattta gggaacacct gtggaattcc     240
aaaaaacagc tgagttcaga tatatccagt gatggagaaa gagaggcgaa catgcctggc     300
ctcaacatcc gcaacaaaga attcaactat cttcataatc gaaatggttc tgaacttgac     360
cttttgggga tgtgagatct acttgaaaac cttggatact cagtggttat aaaagagaat     420
ctcacagctc agatggtgct gggattgttt ggttcaccac tgacagtgga aaagccagtg     480
cagatactca tggtcggctc ttgcaaggta acatctgtaa tgatgctgtt acaaaggctc     540
atgtggaaaa ggacttcatt gctttcaaat cttccacacc acataatgtt tcttggagac     600
atgaaacaaa tggctctgtc ttcatttccc aaattatcta ctacttcaga gagtattctt     660
ggagtcatca tctagaggaa atttttcaaa aggttcaaca ttcatttgag accccaaata     720
tactgaccca gctgcccacc attgaaagac tatccatgac acgatatttc tatctctttc     780
ctgggaatta aaaatcgaat tcccgcggcc gccatggcgg ccgggagcat gcgacgtcgg     840
gcccaattcg ccctatagtg agtcgtatta caat                                874

<210> SEQ ID NO 55
<211> LENGTH: 261
<212> TYPE: PRT
<213> ORGANISM: Homo sapiens
<220> FEATURE:
<221> NAME/KEY: misc_feature
<222> LOCATION: 8
<223> OTHER INFORMATION: Xaa = any amino acid or no amino acid

<400> SEQUENCE: 55

Met Ala Asp Glu Lys Pro Ser Xaa Gly Val Leu Val His Met Val Lys
1               5                   10                  15
Leu Leu Ile Lys Thr Phe Leu Asp Gly Ile Phe Asp Asp Leu Met Glu
            20                  25                  30
Asn Asn Val Leu Asn Thr Asp Glu Ile His Leu Ile Gly Lys Cys Leu
        35                  40                  45
Lys Phe Val Val Ser Asn Ala Glu Asn Leu Val Asp Asp Ile Thr Glu
    50                  55                  60
```

Thr Ala Gln Ile Ala Gly Lys Ile Phe Arg Glu His Leu Trp Asn Ser
65                  70                  75                  80

Lys Lys Gln Leu Ser Ser Ile Tyr Pro Val Met Glu Lys Glu Arg Arg
            85                  90                  95

Thr Cys Leu Ala Leu Asn Ile Arg Asn Lys Glu Phe Asn Tyr Leu His
                100                 105                 110

Asn Arg Asn Gly Ser Glu Leu Asp Leu Gly Met Asp Leu Leu Glu
            115                 120                 125

Asn Leu Gly Tyr Ser Val Val Ile Lys Glu Asn Leu Thr Ala Gln Gly
    130                 135                 140

Ala Gly Ile Val Trp Phe Thr Thr Asp Ser Gly Lys Ala Ser Ala Asp
145                 150                 155                 160

Thr His Gly Arg Leu Leu Gln Gly Asn Ile Cys Asn Asp Ala Val Thr
                165                 170                 175

Lys Ala His Val Glu Lys Asp Phe Ile Ala Phe Lys Ser Ser Thr Pro
            180                 185                 190

His Asn Val Ser Trp Arg His Glu Thr Asn Gly Ser Val Phe Ile Ser
        195                 200                 205

Gln Ile Ile Tyr Tyr Phe Arg Glu Tyr Ser Trp Ser His His Leu Glu
    210                 215                 220

Glu Ile Phe Gln Lys Val Gln His Ser Phe Glu Thr Pro Asn Ile Leu
225                 230                 235                 240

Thr Gln Leu Pro Thr Ile Glu Arg Leu Ser Met Thr Arg Tyr Phe Tyr
                245                 250                 255

Leu Phe Pro Gly Asn
            260

<210> SEQ ID NO 56
<211> LENGTH: 765
<212> TYPE: DNA
<213> ORGANISM: Homo sapiens

<400> SEQUENCE: 56
atggctgatg agaaaccatc caacggtgtt ctggtccaca tggtgaagtt gctgatcaag      60
acctttctag atggcatttt tgatgatttg atggaaaata atgtgttaaa tacagatgag     120
atacaccttt aggaaaatg tctaaagttt gtggtgagca atgctgaaaa cctggttgat     180
gatatcactg agacagctca aattgcaggc aaaatattta gggaacacct gtggaattcc     240
aaaaaacagc tgagttcaga tatatccagt gatggagaaa gagaggcgaa catgcctggc     300
ctcaacatcc gcaacaaaga attcaactat cttcataatc gaaatggttc tgaacttgac     360
cttttgggga tgtgagatct acttgaaaac cttggatact cagtggttat aaaagagaat     420
ctcacagctc agatggtgct gggattgttt ggttcaccac tgacagtgga aaagccagtg     480
cagatactca tggtcggctc ttgcaaggta acatctgtaa tgatgctgtt acaaggctc     540 atgtggaaaa ggacttcatt gctttcaaat cttccacacc acgttcaaca ttcatttgag     600
accccaaata tactgaccca gctgcccact attgaaagac tatccatgac acgatatttc     660
tatctctttc ctgggaatta aaaatcgaat tcccgcggcc gccatggcgg ccgggagcat     720
gcgacgtcgg gcccaattcg ccctatagtg agtcgtatta caatt                     765

<210> SEQ ID NO 57
<211> LENGTH: 224
<212> TYPE: PRT
<213> ORGANISM: Homo sapien

<400> SEQUENCE: 57

Met Ala Asp Glu Lys Pro Ser Asn Gly Val Leu Val His Met Val Lys
1               5                   10                  15

Leu Leu Ile Lys Thr Phe Leu Asp Gly Ile Phe Asp Asp Leu Met Glu
            20                  25                  30

Asn Asn Val Leu Asn Thr Asp Glu Ile His Leu Ile Gly Lys Cys Leu
        35                  40                  45

Lys Phe Val Val Ser Asn Ala Glu Asn Leu Val Asp Asp Ile Thr Glu
    50                  55                  60

Thr Ala Gln Ile Ala Gly Lys Ile Phe Arg Glu His Leu Trp Asn Ser
65                  70                  75                  80

Lys Lys Gln Leu Ser Ser Ile Tyr Pro Val Met Glu Lys Glu Arg Arg
                85                  90                  95

Thr Cys Leu Ala Leu Asn Ile Arg Asn Lys Glu Phe Asn Tyr Leu His
            100                 105                 110

Asn Arg Asn Gly Ser Glu Leu Asp Leu Leu Gly Met Asp Leu Leu Glu
        115                 120                 125

Asn Leu Gly Tyr Ser Val Val Ile Lys Glu Asn Leu Thr Ala Gln Gly
    130                 135                 140

Ala Gly Ile Val Trp Phe Thr Thr Asp Ser Gly Lys Ala Ser Ala Asp
145                 150                 155                 160

Thr His Gly Arg Leu Leu Gln Gly Asn Ile Cys Asn Asp Ala Val Thr
                165                 170                 175

Lys Ala His Val Glu Lys Asp Phe Ile Ala Phe Lys Ser Ser Thr Pro
            180                 185                 190

Val Gln His Ser Phe Glu Thr Pro Asn Ile Leu Thr Gln Leu Pro Thr
        195                 200                 205

Ile Glu Arg Leu Ser Met Thr Arg Tyr Phe Tyr Leu Phe Pro Gly Asn
    210                 215                 220

<210> SEQ ID NO 58
<211> LENGTH: 439
<212> TYPE: DNA
<213> ORGANISM: Homo sapiens

<400> SEQUENCE: 58
cccagtggca agttaaagct tgtcctcat gctcacttcc atgaactaaa gacaaaaagg     60
gcagatgaga tatatccagt gatggagaaa gagaggcgaa catgcctggc ctcaacatcc    120
gcaacaaaga attcaactat cttcataatc gaaatggttc tgaacttgac cttttgggga   180
tgcgagatct acttgaaaac cttggatact cagtggttat aaaagagaat ctcacagcta   240
gcatcctgaa tggaatctgt gggaccaagc actgggatca agagccagat gttcttcacg   300
atgacaccat ctttgaaatt ttcaacaacc gtaactgcca gagtctgaaa gacaaaccca   360
aggtcatcat catgcaagcc tgccgaggcg gaatcactag tgaattcgcg gccgcctgca   420
ggtcgaccat atgggagag                                                439

<210> SEQ ID NO 59
<211> LENGTH: 129
<212> TYPE: PRT
<213> ORGANISM: Homo sapien

<400> SEQUENCE: 59

Pro Ser Gly Lys Leu Lys Leu Cys Pro His Ala His Phe His Glu Leu
1               5                   10                  15

-continued

Lys Thr Lys Arg Ala Asp Glu Ile Tyr Pro Val Met Glu Lys Glu Arg
            20                  25                  30

Arg Thr Cys Leu Ala Leu Asn Ile Arg Asn Lys Glu Phe Asn Tyr Leu
        35                  40                  45

His Asn Arg Asn Gly Ser Glu Leu Asp Leu Leu Gly Met Asp Leu Leu
    50                  55                  60

Glu Asn Leu Gly Tyr Ser Val Val Ile Lys Glu Asn Leu Thr Ala Ser
65                  70                  75                  80

Ile Leu Asn Gly Ile Cys Gly Thr Lys His Trp Asp Gln Glu Pro Asp
                85                  90                  95

Val Leu His Asp Asp Thr Ile Phe Glu Ile Phe Asn Asn Arg Asn Cys
            100                 105                 110

Gln Ser Leu Lys Asp Lys Pro Lys Val Ile Ile Met Gln Ala Cys Arg
        115                 120                 125

Gly

<210> SEQ ID NO 60
<211> LENGTH: 477
<212> TYPE: DNA
<213> ORGANISM: Homo sapiens

<400> SEQUENCE: 60 gcccaacccca gtggcaagtt aaagctttgt cctcatgctc acttccatga actaaagaca     60
aaaagggcag atgagatata tccagtgatg gagaaagaga ggcgaacatg cctggcctca    120
acatccgcaa caaagaattc aactatcttc ataatcgaaa tggttctgaa cttgaccttt    180
tggggatgtg agatctactt gaaaaccttg gatactcagt ggtttataaaa gagagtctca    240 cagctcagga aatggaaaca gcactaaggc agtttgctgc tcacccagag caccagtcct    300
cagacagcac attcctggtg tttatgtcac atagcatcct gaatggaatc tgtgggacca    360
agcactggga tcaagagcca gatgttcttc acgatgacac catctttgaa attttcaaca    420
accgtaactg ccagagtctg aaagacaaac ccaaggtcat catcatgcaa gcctgcc       477

<210> SEQ ID NO 61
<211> LENGTH: 158
<212> TYPE: PRT
<213> ORGANISM: Homo sapiens

<400> SEQUENCE: 61

Ala Gln Pro Ser Gly Lys Leu Lys Leu Cys Pro His Ala His Phe His
1               5                   10                  15

Glu Leu Lys Thr Lys Arg Ala Asp Glu Ile Tyr Pro Val Met Glu Lys
            20                  25                  30

Glu Arg Arg Thr Cys Leu Ala Leu Asn Ile Arg Asn Lys Glu Phe Asn
        35                  40                  45

Tyr Leu His Asn Arg Asn Gly Ser Glu Leu Asp Leu Leu Gly Met Asp
    50                  55                  60

Leu Leu Glu Asn Leu Gly Tyr Ser Val Val Ile Lys Glu Ser Leu Thr
65                  70                  75                  80

Ala Gln Glu Met Glu Thr Ala Leu Arg Gln Phe Ala Ala His Pro Glu
                85                  90                  95

His Gln Ser Ser Asp Ser Thr Phe Leu Val Phe Met Ser His Ser Ile
            100                 105                 110

Leu Asn Gly Ile Cys Gly Thr Lys His Trp Asp Gln Glu Pro Asp Val
        115                 120                 125

```
Leu His Asp Asp Thr Ile Phe Glu Ile Phe Asn Asn Arg Asn Cys Gln
    130                 135                 140

Ser Leu Lys Asp Lys Pro Lys Val Ile Ile Met Gln Ala Cys
145                 150                 155
```

<210> SEQ ID NO 62
<211> LENGTH: 497
<212> TYPE: DNA
<213> ORGANISM: Homo sapiens

<400> SEQUENCE: 62

```
gcccaaccca gtggcaagtt aaagctttgt cctcatgctc acttccatga actcaagaca      60
aaaagggcag atgagatata tccagtgatg gagaaagaga ggcgaacatg cctggcctca     120
acatccgcaa caaagaattc aactatcttc ataatcgaaa tggttctgaa cttgaccttt     180
tggggatgtg agatctactt gaaaaccttg gatactcagt ggtttataaaa gagaatctca    240
cagctcagat ggtgctggga ttgtttggtt caccactgac agtggaaaag ccagtgcaga     300
tactcatggt cggctcttgc aaggtaacat ctgtaatgat gctgttacaa aggctcatgt     360
ggaaaaggac ttcattgctt tcaaatcttc cacaccacgt tcaacattca tttgagaccc     420
caaatatact gacccagctg cccaccattg aaagactatc catgacacga tatttctatc    480
tctttcctgg gaattaa                                                    497
```

<210> SEQ ID NO 63
<211> LENGTH: 163
<212> TYPE: PRT
<213> ORGANISM: Homo sapien

<400> SEQUENCE: 63

```
Ala Gln Pro Ser Gly Lys Leu Lys Leu Cys Pro His Ala His Phe His
1               5                   10                  15

Glu Leu Lys Thr Lys Arg Ala Asp Glu Ile Tyr Pro Val Met Glu Lys
            20                  25                  30

Glu Arg Arg Thr Cys Leu Ala Leu Asn Ile Arg Asn Lys Glu Phe Asn
        35                  40                  45

Tyr Leu His Asn Arg Asn Gly Ser Glu Leu Asp Leu Leu Gly Met Asp
    50                  55                  60

Leu Leu Glu Asn Leu Gly Tyr Ser Val Val Ile Lys Glu Asn Leu Thr
65                  70                  75                  80

Ala Gln Gly Ala Gly Ile Val Trp Phe Thr Thr Asp Ser Gly Lys Ala
                85                  90                  95

Ser Ala Asp Thr His Gly Arg Leu Leu Gln Gly Asn Ile Cys Asn Asp
            100                 105                 110

Ala Val Thr Lys Ala His Val Glu Lys Asp Phe Ile Ala Phe Lys Ser
        115                 120                 125

Ser Thr Pro Val Gln His Ser Phe Glu Thr Pro Asn Ile Leu Thr Gln
    130                 135                 140

Leu Pro Thr Ile Glu Arg Leu Ser Met Thr Arg Tyr Phe Tyr Leu Phe
145                 150                 155                 160

Pro Gly Asn
```

<210> SEQ ID NO 64
<211> LENGTH: 661
<212> TYPE: DNA
<213> ORGANISM: Homo sapiens

```
<400> SEQUENCE: 64
gcccaaccca gtggcaagtt aaagctttgt cctcatgctc acttccatga actaaagaca      60
aaaagggcag atgagatata tccagtgatg gagaaagaga ggcgaacatg cctggcctca     120
acatccgcaa caaagaattc aactatcttc ataatcgaaa tggttctgaa cttgaccttt     180
agggatgtg  agatctactt gaaaaccttg gatactcagt ggttataaaa gagaatctca     240
cagctcagat ggtgctggga ttgtttggtt caccactgac agtggaaaag ccagtgcaga     300
tactcatggt cggctcttgc aaggtaacat ctgtaatgat gctgttacaa aggctcatgt     360
ggaaaaggac ttcattgctt tcaaatcttc cacaccacat aatgtttctt ggagacatga     420
aacaaatggc tctgtcttca tttcccaaat tatctactac ttcagagagt attcttggag     480
tcatcatcta gaggaaatct ttcaaaaggt tcaacattca tttgagaccc caaatatact     540
gacccagctg cccaccattg aaagactatc catgacacga tatttctatc tctttcctgg     600
gaattaaaaa tcgaattccc gcggccgcca tggcggccgg gagcatgcga cgtcgggccc     660
a                                                                    661
```

<210> SEQ ID NO 65
<211> LENGTH: 200
<212> TYPE: PRT
<213> ORGANISM: Homo sapiens

<400> SEQUENCE: 65

```
Ala Gln Pro Ser Gly Lys Leu Lys Leu Cys Pro His Ala His Phe His
  1               5                  10                  15

Glu Leu Lys Thr Lys Arg Ala Asp Glu Ile Tyr Pro Val Met Glu Lys
             20                  25                  30

Glu Arg Arg Thr Cys Leu Ala Leu Asn Ile Arg Asn Lys Glu Phe Asn
         35                  40                  45

Tyr Leu His Asn Arg Asn Gly Ser Glu Leu Asp Leu Leu Gly Met Asp
     50                  55                  60

Leu Leu Glu Asn Leu Gly Tyr Ser Val Val Ile Lys Glu Asn Leu Thr
 65                  70                  75                  80

Ala Gln Gly Ala Gly Ile Val Trp Phe Thr Thr Asp Ser Gly Lys Ala
                 85                  90                  95

Ser Ala Asp Thr His Gly Arg Leu Leu Gln Gly Asn Ile Cys Asn Asp
            100                 105                 110

Ala Val Thr Lys Ala His Val Glu Lys Asp Phe Ile Ala Phe Lys Ser
        115                 120                 125

Ser Thr Pro His Asn Val Ser Trp Arg His Glu Thr Asn Gly Ser Val
    130                 135                 140

Phe Ile Ser Gln Ile Ile Tyr Tyr Phe Arg Glu Tyr Ser Trp Ser His
145                 150                 155                 160

His Leu Glu Glu Ile Phe Gln Lys Val Gln His Ser Phe Glu Thr Pro
                165                 170                 175

Asn Ile Leu Thr Gln Leu Pro Thr Ile Glu Arg Leu Ser Met Thr Arg
            180                 185                 190

Tyr Phe Tyr Leu Phe Pro Gly Asn
        195                 200
```

<210> SEQ ID NO 66
<211> LENGTH: 758
<212> TYPE: DNA
<213> ORGANISM: Homo sapiens

<400> SEQUENCE: 66

```
gcccaaccca gtggcaagtt aaagctttgt cctcatgctc acttccatga actaaagaca      60
aaaagggcag atgagatata tccagtgatg gagaaagaga ggcgaacatg cctggcctca     120
acatccgcaa caaagaattc aactatcttc ataatcgaaa tggttctgaa cttgacctttt    180
tggggatgtg agatctactt gaaaaccttg gatactcagt ggttataaaa gagaatctca     240
cagctcagga aatggaaaca gcactaaggc agtttgctgc tcacccagag caccagtcct    300
cagacagcac attcctggcg tttatgtcac atagcatcct gaatagaatc tgtgggacca     360
agcactggga tcaagagcca gatgttcttc acgatgacac catctttgaa attttcaaca     420
accgtaactg ccagagtctg aaagacaaac ccaagatggt gctgggattg tttggttcac     480
cactgacagt ggaaaaagcc agtgcagata ctcatggtcg gctcttgcaa ggtaacatct     540
gtaatgatgc tgttacaaag gttcatgtgg aaaaggactt cattgctttc aaatcttcca     600
caccacgttc aacattcatt tgagacccca aatatactga cccagctgcc caccattgaa     660
agactatcca tgacacgata tttctatctc tttcctggga attaaaaatc gaattcccgc     720
ggccgccagg cggccgggag catgcgacgt cgggccca                              758
```

<210> SEQ ID NO 67
<211> LENGTH: 232
<212> TYPE: PRT
<213> ORGANISM: Homo sapien

<400> SEQUENCE: 67

```
Ala Gln Pro Ser Gly Lys Leu Lys Leu Cys Pro His Ala His Phe His
 1               5                  10                  15
Glu Leu Lys Thr Lys Arg Ala Asp Glu Ile Tyr Pro Val Met Glu Lys
            20                  25                  30
Glu Arg Arg Thr Cys Leu Ala Leu Asn Ile Arg Asn Lys Glu Phe Asn
        35                  40                  45
Tyr Leu His Asn Arg Asn Gly Ser Glu Leu Asp Leu Leu Gly Met Asp
    50                  55                  60
Leu Leu Glu Asn Leu Gly Tyr Ser Val Val Ile Lys Glu Asn Leu Thr
65                  70                  75                  80
Ala Gln Glu Met Glu Thr Ala Leu Arg Gln Phe Ala Ala His Pro Glu
                85                  90                  95
His Gln Ser Ser Asp Ser Thr Phe Leu Ala Phe Met Ser His Ser Ile
            100                 105                 110
Leu Asn Arg Ile Cys Gly Thr Lys His Trp Asp Gln Glu Pro Asp Val
        115                 120                 125
Leu His Asp Asp Thr Ile Phe Glu Ile Phe Asn Asn Arg Asn Cys Gln
    130                 135                 140
Ser Leu Lys Asp Lys Pro Lys Gly Ala Gly Ile Val Trp Phe Thr Thr
145                 150                 155                 160
Asp Val Glu Lys Ala Ser Ala Asp Thr His Gly Arg Leu Leu Gln Gly
                165                 170                 175
Asn Ile Cys Asn Asp Ala Val Thr Lys Val His Val Glu Lys Asp Phe
            180                 185                 190
Ile Ala Phe Lys Ser Ser Thr Pro Val Gln His Ser Phe Glu Thr Pro
        195                 200                 205
Asn Ile Leu Thr Gln Leu Pro Thr Ile Glu Arg Leu Ser Met Thr Arg
    210                 215                 220
Tyr Phe Tyr Leu Phe Pro Gly Asn
```

-continued

<210> SEQ ID NO 68
<211> LENGTH: 503
<212> TYPE: DNA
<213> ORGANISM: Homo sapiens

<400> SEQUENCE: 68

```
atggctgatg agaaaccatc caacggtgtt ctggtccaca tggtgaagtt gctgatcaag      60
acctttctag atggcatttt tgatgatttg atggaaaata atgtgttaaa tacagatgag     120
atacaccta taggaaaatg tctaaagttt gtggtgagca atgctgaaaa cctggttgat     180
gatatcactg agacagctca gattgcaggc aaaatattta gggaacacct gtggaattcc     240
aaaaaacagc tgagttcaga tatatccagt gatggagaaa gagaggcgaa catgcctggc     300
ctcaacatcc gcaacaaaga attcaactat cttcataatc gaatggttc tgaacttgac      360
cttttgggga tgtgagatct acttgaaaac cttggatact cagtggttat aaaagagaat     420
ctcacagctc aggaaatgga acagcacat tcctggtgtt tatgtcacat agcatcctga     480
atggaatctg tgggaccaag cac                                              503
```

<210> SEQ ID NO 69
<211> LENGTH: 166
<212> TYPE: PRT
<213> ORGANISM: Homo sapien

<400> SEQUENCE: 69

```
Met Ala Asp Glu Lys Pro Ser Asn Gly Val Leu Val His Met Val Lys
1               5                   10                  15
Leu Leu Ile Lys Thr Phe Leu Asp Gly Ile Phe Asp Asp Leu Met Glu
            20                  25                  30
Asn Asn Val Leu Asn Thr Asp Glu Ile His Leu Ile Gly Lys Cys Leu
        35                  40                  45
Lys Phe Val Val Ser Asn Ala Glu Asn Leu Val Asp Asp Ile Thr Glu
    50                  55                  60
Thr Ala Gln Ile Ala Gly Lys Ile Phe Arg Glu His Leu Trp Asn Ser
65                  70                  75                  80
Lys Lys Gln Leu Ser Ser Ile Tyr Pro Val Met Glu Lys Glu Arg Arg
                85                  90                  95
Thr Cys Leu Ala Leu Asn Ile Arg Asn Lys Glu Phe Asn Tyr Leu His
            100                 105                 110
Asn Arg Asn Gly Ser Glu Leu Asp Leu Leu Gly Met Asp Leu Leu Glu
        115                 120                 125
Asn Leu Gly Tyr Ser Val Val Ile Lys Glu Asn Leu Thr Ala Gln Glu
    130                 135                 140
Met Glu Ser Thr Phe Leu Val Phe Met Ser His Ser Ile Leu Asn Gly
145                 150                 155                 160
Ile Cys Gly Thr Lys His
                165
```

<210> SEQ ID NO 70
<211> LENGTH: 1129
<212> TYPE: DNA
<213> ORGANISM: Homo sapiens

<400> SEQUENCE: 70

```
tgattgccat ggctgatgag aaaccatcca acggtgttct ggtccacatg gtgaagttgc      60
```

-continued

```
tgatcaagac ctttctagat ggcattttg atgatttgat ggaaaataat gtgttaaata      120
cagatgagat acaccttata ggaaaatgtc taaagtttgt ggtgagcaat gctgaaaacc      180
tggttgatga tatcactgag acagctcaaa ttgcaggcaa aatatttagg gaacacctgt      240
ggaattccaa aaaacagctg agttcagctc ttctggaaat ccagggtgcc caacccagtg      300
gcaagtaaaa gctttgtcct catgctcact tccatgaact aaagacaaaa agggcagatg      360
agatatatcc agtgatggag aaagagaggc gaacatgcct ggcctcaaca tccgcaacaa      420
agaattcaac tatcttcata atcgaaatgg ttctgaactt gaccttttgg ggatgtgaga      480
tctacttgaa aaccttggat actcagtggt tataaaagag aatctcacag ctcaggaaat      540
ggaaacagca ctaaggcagt ttgctgctca cccagagcac cagtcctcag acagcacatt      600
cctggtgttt atgtcacata gcatcctgaa tggaatctgt gggaccaagc actgggatca      660
agagccagat gttcttcacg atgacaccat ctttgaaatt ttcaacaacc gtaactgcca      720
gagtctgaaa gacaaaccca aggtcatcat catgcaagcc tgccgaggca atggtgctgg      780
gattgtttgg ttcaccactg acagtggaaa agccagtgca gatactcatg gtcggctctt      840
gcaaggtaac atctgtaatg atgctgttac aaaggctcat gtggaaaagg acttcattgc      900
tttcaaatct tccacaccac ataatgtttc ttggagacat gaaacaaatg gctctgtctt      960
catttcccaa attatctact acttcagaga gtattcttgg agtcatcatc tagaggaaat     1020
ttttcaaaag gttcaacatt catttgagac cccaaatata ctgacccagc tgcccaccat     1080
tgaaagacta tccatgacac gatatttcta tctctttcct gggaattaa              1129
```

<210> SEQ ID NO 71
<211> LENGTH: 372
<212> TYPE: PRT
<213> ORGANISM: Homo sapiens

<400> SEQUENCE: 71

```
Met Ala Asp Glu Lys Pro Ser Asn Gly Val Leu Val His Met Val Lys
1               5                   10                  15

Leu Leu Ile Lys Thr Phe Leu Asp Gly Ile Phe Asp Asp Leu Met Glu
            20                  25                  30

Asn Asn Val Leu Asn Thr Asp Glu Ile His Leu Ile Gly Lys Cys Leu
        35                  40                  45

Lys Phe Val Val Ser Asn Ala Glu Asn Leu Val Asp Asp Ile Thr Glu
    50                  55                  60

Thr Ala Gln Ile Ala Gly Lys Ile Phe Arg Glu His Leu Trp Asn Ser
65                  70                  75                  80

Lys Lys Gln Leu Ser Ser Ala Leu Leu Glu Ile Gln Gly Ala Gln Pro
                85                  90                  95

Ser Gly Lys Leu Lys Leu Cys Pro His Ala His Phe His Glu Leu Lys
            100                 105                 110

Thr Lys Arg Ala Asp Glu Ile Tyr Pro Val Met Glu Lys Glu Arg Arg
        115                 120                 125

Thr Cys Leu Ala Leu Asn Ile Arg Asn Lys Glu Phe Asn Tyr Leu His
    130                 135                 140

Asn Arg Asn Gly Ser Glu Leu Asp Leu Leu Gly Met Asp Leu Glu
145                 150                 155                 160

Asn Leu Gly Tyr Ser Val Val Ile Lys Glu Asn Leu Thr Ala Gln Glu
                165                 170                 175

Met Glu Thr Ala Leu Arg Gln Phe Ala Ala His Pro Glu His Gln Ser
            180                 185                 190
```

```
Ser Asp Ser Thr Phe Leu Val Phe Met Ser His Ser Ile Leu Asn Gly
        195                 200                 205

Ile Cys Gly Thr Lys His Trp Asp Gln Glu Pro Asp Val Leu His Asp
        210                 215                 220

Asp Thr Ile Phe Glu Ile Phe Asn Asn Arg Asn Cys Gln Ser Leu Lys
225                 230                 235                 240

Asp Lys Pro Lys Val Ile Ile Met Gln Ala Cys Arg Gly Asn Gly Ala
                245                 250                 255

Gly Ile Val Trp Phe Thr Thr Asp Ser Gly Lys Ala Ser Ala Asp Thr
            260                 265                 270

His Gly Arg Leu Leu Gln Gly Asn Ile Cys Asn Asp Ala Val Thr Lys
        275                 280                 285

Ala His Val Glu Lys Asp Phe Ile Ala Phe Lys Ser Ser Thr Pro His
        290                 295                 300

Asn Val Ser Trp Arg His Glu Thr Asn Gly Ser Val Phe Ile Ser Gln
305                 310                 315                 320

Ile Ile Tyr Tyr Phe Arg Glu Tyr Ser Trp Ser His His Leu Glu Glu
                325                 330                 335

Ile Phe Gln Lys Val Gln His Ser Phe Glu Thr Pro Asn Ile Leu Thr
            340                 345                 350

Gln Leu Pro Thr Ile Glu Arg Leu Ser Met Thr Arg Tyr Phe Tyr Leu
        355                 360                 365

Phe Pro Gly Asn
    370

<210> SEQ ID NO 72
<211> LENGTH: 1130
<212> TYPE: DNA
<213> ORGANISM: Homo sapiens

<400> SEQUENCE: 72
tgattgccat ggctgatgag aaaccatcca acggtgttct ggtccacatg gtgaagttgc      60
tgatcaagac ctttctagat ggcatttttg atgatttgat ggaaaataat gtgttaaata     120
cagatgagat acaccttata ggaaaatgtc taaagtttgt ggtgagcaat gctgaaaacc     180
tggttgatga tatcactgag acagctcaaa ttgcaggcaa atatttaggg aacaccctgt     240
ggaattccaa aaaacagctg agttcagctc ttctggaaat ccagggtgcc aacccagtg      300
gcaagttaaa gctttgtcct catgctcact ccatgaacta aagacaaaaa agggcagatg     360
agatatatcc agtgatggag aaagagaggc gaacatgcct ggccctcaac atccgcaaca     420
aagaattcaa ctatcttcat aatcgaaatg gttctgaact tgacctttg gggatgcgag      480
atctacttga aaaccttgga tactcagtgg ttataaaaga gaatctcaca gctcaggaaa     540
tggaaacagc actaaggcag tttgctgctc acccagagca ccagtcctca gacagcacat     600
tcctggtgtt tatgtcacat agcatcctga atggaatctg tgggaccaag cactgggatc     660
aagagccaga tgttcttcac gatgacacca tctttgaaat tttcaacaac cgtaactgcc     720
agagtctgaa agacaaaccc aaggtcatca tcatgcaagc ctgccgaggc aatggtgctg     780
ggattgtttg gttcaccact gacagtggaa aagccagtgc agatactcat ggtcggctct     840
tgcaaggtaa catctgtaat gatgctgtta caaaggctca tgtggaaaag gacttcattg     900
ctttcaaatc ttccacacca cataatgttt cttggagaca tgaaacaaat ggctctgtct     960
tcatttccca aattatctac tacttcagag agtattcttg gagtcatcat ctagaggaaa    1020
```

-continued

```
tttttcaaaa ggttcaacat tcatttgaga ccccaaatat actgacccag ctgcccacca    1080
ttgaaagact atccatgaca cgatatttct atctctttcc tgggaattaa               1130

<210> SEQ ID NO 73
<211> LENGTH: 373
<212> TYPE: PRT
<213> ORGANISM: Homo sapiens

<400> SEQUENCE: 73

Met Ala Asp Glu Lys Pro Ser Asn Gly Val Leu Val His Met Val Lys
1               5                   10                  15

Leu Leu Ile Lys Thr Phe Leu Asp Gly Ile Phe Asp Asp Leu Met Glu
            20                  25                  30

Asn Asn Val Leu Asn Thr Asp Glu Ile His Leu Ile Gly Lys Cys Leu
        35                  40                  45

Lys Phe Val Val Ser Asn Ala Glu Asn Leu Val Asp Asp Ile Thr Glu
    50                  55                  60

Thr Ala Gln Ile Ala Gly Lys Ile Phe Arg Glu His Leu Trp Asn Ser
65                  70                  75                  80

Lys Lys Gln Leu Ser Ser Ala Leu Leu Glu Ile Gln Gly Ala Gln Pro
                85                  90                  95

Ser Gly Lys Leu Lys Leu Cys Pro His Ala His Phe His Glu Leu Lys
            100                 105                 110

Thr Lys Arg Ala Asp Glu Ile Tyr Pro Val Met Glu Lys Glu Arg Arg
        115                 120                 125

Thr Cys Leu Ala Leu Asn Ile Arg Asn Lys Glu Phe Asn Tyr Leu His
    130                 135                 140

Asn Arg Asn Gly Ser Glu Leu Asp Leu Leu Gly Met Arg Asp Leu Leu
145                 150                 155                 160

Glu Asn Leu Gly Tyr Ser Val Val Ile Lys Glu Asn Leu Thr Ala Gln
                165                 170                 175

Glu Met Glu Thr Ala Leu Arg Gln Phe Ala Ala His Pro Glu His Gln
            180                 185                 190

Ser Ser Asp Ser Thr Phe Leu Val Phe Met Ser His Ser Ile Leu Asn
        195                 200                 205

Gly Ile Cys Gly Thr Lys His Trp Asp Gln Glu Pro Asp Val Leu His
    210                 215                 220

Asp Asp Thr Ile Phe Glu Ile Phe Asn Asn Arg Asn Cys Gln Ser Leu
225                 230                 235                 240

Lys Asp Lys Pro Lys Val Ile Met Gln Ala Cys Arg Gly Asn Gly
                245                 250                 255

Ala Gly Ile Val Trp Phe Thr Thr Asp Ser Gly Lys Ala Ser Ala Asp
            260                 265                 270

Thr His Gly Arg Leu Leu Gln Gly Asn Ile Cys Asn Asp Ala Val Thr
        275                 280                 285

Lys Ala His Val Glu Lys Asp Phe Ile Ala Phe Lys Ser Ser Thr Pro
    290                 295                 300

His Asn Val Ser Trp Arg His Glu Thr Asn Gly Ser Val Phe Ile Ser
305                 310                 315                 320

Gln Ile Ile Tyr Tyr Phe Arg Gln Tyr Ser Trp Ser His His Leu Glu
                325                 330                 335

Glu Ile Phe Gln Lys Val Gln His Ser Phe Glu Thr Pro Asn Ile Leu
            340                 345                 350

Thr Gln Leu Pro Thr Ile Glu Arg Leu Ser Met Thr Arg Tyr Phe Tyr
```

-continued

```
                355                 360                 365
Leu Phe Pro Gly Asn
    370

<210> SEQ ID NO 74
<211> LENGTH: 867
<212> TYPE: DNA
<213> ORGANISM: Homo sapiens

<400> SEQUENCE: 74
tcagctcttc tggaaatcca gggtgcccaa cccagtggca agttaaagct ttgtcctcat      60
gctcacttcc atgaactaaa gacaaaaagg gcagatgaga tatatccagt gatggagaaa    120
gagaggcgaa catgcctggc cctcaacatc cgcaacaaag aattcaacta tcttcataat    180
cgaaatggtt ctgaacttga cctttgggg atgcgagatc tacttgaaaa ccttggatac     240
tcagtggtta taaagagaa tctcacagct caggaaatgg aaacagcact aaggcagttt     300
gctgctcacc cagagcacca gtcctcagac agcacattcc tggtgtttat gtcacatagc    360
atcctgaatg gaatctgtgg gaccaagcac tgggatcaag agccagatgt tcttcacgat    420
gacaccatct ttgaaatttt caacaaccgt aactgccaga gtctgaaaga caaacccaag    480
gtcatcatca tgcaagcctg ccgaggcaat ggtgctggga ttgtttggtt caccactgac    540
agtggaaaag ccagtgcaga tactcatggt cggctcttgc aaggtaacat ctgtaatgat    600
gctgttacaa aggctcatgt ggaaaaggac ttcattgctt tcaaatcttc cacaccacat    660
aatgtttctt ggagacatga aacaaatggc tctgtcttca tttcccaaat tatctactac    720
ttcagagagt attcttggag tcatcatcta gaggaaattt ttcaaaaggt tcaacattca    780
tttgagaccc caaatatact gacccagctg cccaccattg aaagactatc catgacacga    840
tatttctatc tctttcctgg gaattaa                                         867

<210> SEQ ID NO 75
<211> LENGTH: 288
<212> TYPE: PRT
<213> ORGANISM: Homo sapiens

<400> SEQUENCE: 75

Ser Ala Leu Leu Glu Ile Gln Gly Ala Gln Pro Ser Gly Lys Leu Lys
1               5                   10                  15

Leu Cys Pro His Ala His Phe His Glu Leu Lys Thr Lys Arg Ala Asp
            20                  25                  30

Glu Ile Tyr Pro Val Met Glu Lys Glu Arg Arg Thr Cys Leu Ala Leu
        35                  40                  45

Asn Ile Arg Asn Lys Glu Phe Asn Tyr Leu His Asn Arg Asn Gly Ser
    50                  55                  60

Glu Leu Asp Leu Leu Gly Met Arg Asp Leu Leu Glu Asn Leu Gly Tyr
65                  70                  75                  80

Ser Val Val Ile Lys Glu Asn Leu Thr Ala Gln Glu Met Glu Thr Ala
                85                  90                  95

Leu Arg Gln Phe Ala Ala His Pro Glu His Gln Ser Ser Asp Ser Thr
            100                 105                 110

Phe Leu Val Phe Met Ser His Ser Ile Leu Asn Gly Ile Cys Gly Thr
        115                 120                 125

Lys His Trp Asp Gln Glu Pro Asp Val Leu His Asp Asp Thr Ile Phe
    130                 135                 140

Glu Ile Phe Asn Asn Arg Asn Cys Gln Ser Leu Lys Asp Lys Pro Lys
```

```
            145                 150                 155                 160
Val Ile Ile Met Gln Ala Cys Arg Gly Asn Gly Ala Gly Ile Val Trp
                    165                 170                 175

Phe Thr Thr Asp Ser Gly Lys Ala Ser Ala Asp Thr His Gly Arg Leu
                180                 185                 190

Leu Gln Gly Asn Ile Cys Asn Asp Ala Val Thr Lys Ala His Val Glu
            195                 200                 205

Lys Asp Phe Ile Ala Phe Lys Ser Ser Thr Pro His Asn Val Ser Trp
        210                 215                 220

Arg His Glu Thr Asn Gly Ser Val Phe Ile Ser Gln Ile Ile Tyr Tyr
225                 230                 235                 240

Phe Arg Glu Tyr Ser Trp Ser His His Leu Glu Glu Ile Phe Gln Lys
                245                 250                 255

Val Gln His Ser Phe Glu Thr Pro Asn Ile Leu Thr Gln Leu Pro Thr
            260                 265                 270

Ile Glu Arg Leu Ser Met Thr Arg Tyr Phe Tyr Leu Phe Pro Gly Asn
        275                 280                 285

<210> SEQ ID NO 76
<211> LENGTH: 1130
<212> TYPE: DNA
<213> ORGANISM: Homo sapiens

<400> SEQUENCE: 76
tgattgccat ggctgatgag aaaccatcca acggtgttct ggtccacatg gtgaagttgc      60
tgatcaagac ctttctagat ggcattttg atgatttgat ggaaaataat gtgttaaata     120
cagatgagat acaccttata ggaaaatgtc taaagtttgt ggtgagcaat gctgaaaacc     180
tggttgatga tatcactgag acagctcaaa ttgcaggcaa atatttagg gaacacctgt      240 ggaattccaa aaaacagctg agttcagctc ttctggaaat ccagggtgcc caacccagtg     300
gcaagttaaa gctttgtcct catgctcact tccatgaact aaagacaaaa agggcagatg     360
agatatatcc agtgatggag aaagagaggc gaacatgcct ggccctcaac atccgcaaca     420
aagaattcaa ctatcttcat aatcgaaatg gttctgaact tgacctttg gggatgcgag      480 atctacttga aaaccttgga tactcagtgg ttataaaaga gaatctcaca gctcaggaaa     540
tggaaacagc actaaggcag tttgctgctc acccagagca ccagtcctca gacagcacat     600
tcctggtgtt tatgtcacat ggcatcctga atggaatctg tgggaccaag cactgggatc     660
aagagccaga tgttcttcac gatgacacca tctttgaaat tttcaacaac cgtaactgcc     720
agagtctgaa agacaaaccc aaggtcatca tcatgcaagc ctgccgaggc aatggtgctg     780
ggattgtttg gttcaccact gacagtggaa aagccagtgc agatactcat ggtcggctct     840
tgcaaggtaa catctgtaat gatgctgtta caaaggctca tgtggaaaag gacttcattg     900
ctttcaaatc ttccacacca cataatgttt cttggagaca tgaaacaaat ggctctgtct     960
tcatttccca aattatctac tacttcagag agtattcttg gagtcatcat ctagaggaaa    1020
ttttccaaaa ggttcaacat tcatttgaga ccccaaatat actgacccag ctgcccacca    1080
ttgaaagact atccatgaca cgatatttct atctctttcc tgggaattaa                1130

<210> SEQ ID NO 77
<211> LENGTH: 373
<212> TYPE: PRT
<213> ORGANISM: Homo sapiens

<400> SEQUENCE: 77
```

```
Met Ala Asp Glu Lys Pro Ser Asn Gly Val Leu Val His Met Val Lys
1               5                   10                  15

Leu Leu Ile Lys Thr Phe Leu Asp Gly Ile Phe Asp Asp Leu Met Glu
            20                  25                  30

Asn Asn Val Leu Asn Thr Asp Glu Ile His Leu Ile Gly Lys Cys Leu
            35                  40                  45

Lys Phe Val Val Ser Asn Ala Glu Asn Leu Val Asp Asp Ile Thr Glu
    50                  55                  60

Thr Ala Gln Ile Ala Gly Lys Ile Phe Arg Glu His Leu Trp Asn Ser
65                  70                  75                  80

Lys Lys Gln Leu Ser Ser Ala Leu Leu Glu Ile Gln Gly Ala Gln Pro
                85                  90                  95

Ser Gly Lys Leu Lys Leu Cys Pro His Ala His Phe His Glu Leu Lys
                100                 105                 110

Thr Lys Arg Ala Asp Glu Ile Tyr Pro Val Met Glu Lys Glu Arg Arg
            115                 120                 125

Thr Cys Leu Ala Leu Asn Ile Arg Asn Lys Glu Phe Asn Tyr Leu His
    130                 135                 140

Asn Arg Asn Gly Ser Glu Leu Asp Leu Leu Gly Met Arg Asp Leu Leu
145                 150                 155                 160

Glu Asn Leu Gly Tyr Ser Val Val Ile Lys Glu Asn Leu Thr Ala Gln
                165                 170                 175

Glu Met Glu Thr Ala Leu Arg Gln Phe Ala Ala His Pro Glu His Gln
                180                 185                 190

Ser Ser Asp Ser Thr Phe Leu Val Phe Met Ser His Gly Ile Leu Asn
            195                 200                 205

Gly Ile Cys Gly Thr Lys His Trp Asp Gln Glu Pro Asp Val Leu His
        210                 215                 220

Asp Asp Thr Ile Phe Glu Ile Phe Asn Asn Arg Asn Cys Gln Ser Leu
225                 230                 235                 240

Lys Asp Lys Pro Lys Val Ile Met Gln Ala Cys Arg Gly Asn Gly
                245                 250                 255

Ala Gly Ile Val Trp Phe Thr Thr Asp Ser Gly Lys Ala Ser Ala Asp
                260                 265                 270

Thr His Gly Arg Leu Leu Gln Gly Asn Ile Cys Asn Asp Ala Val Thr
        275                 280                 285

Lys Ala His Val Glu Lys Asp Phe Ile Ala Phe Lys Ser Ser Thr Pro
    290                 295                 300

His Asn Val Ser Trp Arg His Glu Thr Asn Gly Ser Val Phe Ile Ser
305                 310                 315                 320

Gln Ile Ile Tyr Tyr Phe Arg Glu Tyr Ser Trp Ser His Leu Glu
                325                 330                 335

Glu Ile Phe Gln Lys Val Gln His Ser Phe Glu Thr Pro Asn Ile Leu
            340                 345                 350

Thr Gln Leu Pro Thr Ile Glu Arg Leu Ser Met Thr Arg Tyr Phe Tyr
        355                 360                 365

Leu Phe Pro Gly Asn
        370

<210> SEQ ID NO 78
<211> LENGTH: 867
<212> TYPE: DNA
<213> ORGANISM: Homo sapiens
```

-continued

```
<400> SEQUENCE: 78
tcagctcttc tggaaatcca gggtgcccaa cccagtggca agttaaagct ttgtcctcat      60
gctcacttcc atgaactaaa gacaaaaagg gcagatgaga tatatccagt gatggagaaa     120
gagaggcgaa catgcctggc cctcaacatc cgcaacaaag aattcaacta tcttcataat     180
cgaaatggtt ctgaacttga cctttggg atgcgagatc tacttgaaaa ccttggatac      240
tcagtggtta taaaagagaa tctcacagct caggaaatgg aaacagcact aaggcagttt     300
gctgctcacc cagagcacca gtcctcagac agcacattcc tggtgtttat gtcacatggc     360
atcctgaatg gaatctgtgg gaccaagcac tgggatcaag agccagatgt tcttcacgat     420
gacaccatct ttgaaatttt caacaaccgt aactgccaga gtctgaaaga caaacccaag     480
gtcatcatca tgcaagcctg ccgaggcaat ggtgctggga ttgtttggtt caccactgac     540
agtggaaaag ccagtgcaga tactcatggt cggctcttgc aaggtaacat ctgtaatgat     600
gctgttacaa aggctcatgt ggaaaaggac ttcattgctt tcaaatcttc cacaccacat     660
aatgtttctt ggagacatga aacaaatggc tctgtcttca tttcccaaat tatctactac     720
ttcagagagt attcttggag tcatcatcta gaggaaattt ttcaaaaggt tcaacattca     780
tttgagaccc caaatatact gacccagctg cccaccattg aaagactatc catgacacga     840
tatttctatc tctttcctgg gaattaa                                        867

<210> SEQ ID NO 79
<211> LENGTH: 288
<212> TYPE: PRT
<213> ORGANISM: Homo sapiens

<400> SEQUENCE: 79

Ser Ala Leu Leu Glu Ile Gln Gly Ala Gln Pro Ser Gly Lys Leu Lys
  1               5                  10                  15

Leu Cys Pro His Ala His Phe His Glu Leu Lys Thr Lys Arg Ala Asp
             20                  25                  30

Glu Ile Tyr Pro Val Met Glu Lys Glu Arg Arg Thr Cys Leu Ala Leu
         35                  40                  45

Asn Ile Arg Asn Lys Glu Phe Asn Tyr Leu His Asn Arg Asn Gly Ser
     50                  55                  60

Glu Leu Asp Leu Leu Gly Met Arg Asp Leu Leu Glu Asn Leu Gly Tyr
 65                  70                  75                  80

Ser Val Val Ile Lys Glu Asn Leu Thr Ala Gln Glu Met Glu Thr Ala
                 85                  90                  95

Leu Arg Gln Phe Ala Ala His Pro Glu His Gln Ser Ser Asp Ser Thr
            100                 105                 110

Phe Leu Val Phe Met Ser His Gly Ile Leu Asn Gly Ile Cys Gly Thr
        115                 120                 125

Lys His Trp Asp Gln Glu Pro Asp Val Leu His Asp Thr Ile Phe
    130                 135                 140

Glu Ile Phe Asn Asn Arg Asn Cys Gln Ser Leu Lys Asp Lys Pro Lys
145                 150                 155                 160

Val Ile Ile Met Gln Ala Cys Arg Gly Asn Gly Ala Gly Ile Val Trp
                165                 170                 175

Phe Thr Thr Asp Ser Gly Lys Ala Ser Ala Asp Thr His Gly Arg Leu
            180                 185                 190

Leu Gln Gly Asn Ile Cys Asn Asp Ala Val Thr Lys Ala His Val Glu
        195                 200                 205
```

```
Lys Asp Phe Ile Ala Phe Lys Ser Ser Thr Pro His Asn Val Ser Trp
    210                 215                 220

Arg His Glu Thr Asn Gly Ser Val Phe Ile Ser Gln Ile Ile Tyr Tyr
225                 230                 235                 240

Phe Arg Glu Tyr Ser Trp Ser His His Leu Glu Glu Ile Phe Gln Lys
                245                 250                 255

Val Gln His Ser Phe Glu Thr Pro Asn Ile Leu Thr Gln Leu Pro Thr
                260                 265                 270

Ile Glu Arg Leu Ser Met Thr Arg Tyr Phe Tyr Leu Phe Pro Gly Asn
            275                 280                 285

<210> SEQ ID NO 80
<211> LENGTH: 404
<212> TYPE: PRT
<213> ORGANISM: Homo Sapien

<400> SEQUENCE: 80

Met Ala Asp Lys Val Leu Lys Glu Lys Arg Lys Leu Phe Ile Arg Ser
1               5                   10                  15

Met Gly Glu Gly Thr Ile Asn Gly Leu Leu Asp Glu Leu Leu Gln Thr
            20                  25                  30

Arg Val Leu Asn Lys Glu Glu Met Glu Lys Val Lys Arg Glu Asn Ala
        35                  40                  45

Thr Val Met Asp Lys Thr Arg Ala Leu Ile Asp Ser Val Ile Pro Lys
    50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Leu Ser Ser Phe Pro
            100                 105                 110

Ala Pro Gln Ala Val Gln Asp Asn Pro Ala Met Pro Thr Ser Ser Gly
        115                 120                 125

Ser Glu Gly Asn Val Lys Leu Cys Ser Leu Glu Glu Ala Gln Arg Ile
    130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
            180                 185                 190

Leu Gln Asn Leu Gly Tyr Ser Val Asp Val Lys Lys Asn Leu Thr Ala
        195                 200                 205

Ser Asp Met Thr Thr Glu Leu Glu Ala Phe Ala His Arg Pro Glu His
    210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
                245                 250                 255

Gln Leu Asn Ala Ile Phe Asn Met Leu Asn Thr Lys Asn Cys Pro Ser
            260                 265                 270

Leu Lys Asp Lys Pro Lys Val Ile Ile Ile Gln Ala Cys Arg Gly Asp
        275                 280                 285

Ser Pro Gly Val Val Trp Phe Lys Asp Ser Val Gly Val Ser Gly Asn
    290                 295                 300
```

-continued

Leu Ser Leu Pro Thr Thr Glu Glu Phe Glu Asp Asp Ala Ile Lys Lys
305                 310                 315                 320

Ala His Ile Glu Lys Asp Phe Ile Ala Phe Cys Ser Ser Thr Pro Asp
            325                 330                 335

Asn Val Ser Trp Arg His Pro Thr Met Gly Ser Val Phe Ile Gly Arg
            340                 345                 350

Leu Ile Glu His Met Gln Glu Tyr Ala Cys Ser Cys Asp Val Glu Glu
        355                 360                 365

Ile Phe Arg Lys Val Arg Phe Ser Phe Glu Gln Pro Asp Gly Arg Ala
    370                 375                 380

Gln Met Pro Thr Thr Glu Arg Val Thr Leu Thr Arg Cys Phe Tyr Leu
385                 390                 395                 400

Phe Pro Gly His

<210> SEQ ID NO 81
<211> LENGTH: 377
<212> TYPE: PRT
<213> ORGANISM: Homo sapiens

<400> SEQUENCE: 81

Met Ala Glu Asp Lys His Asn Lys Asn Pro Leu Lys Met Leu Glu Ser
1               5                   10                  15

Leu Gly Lys Glu Leu Ile Ser Gly Leu Leu Asp Asp Phe Val Glu Lys
            20                  25                  30

Asn Val Leu Lys Leu Glu Glu Glu Lys Lys Ile Tyr Asp Ala
            35                  40                  45

Lys Leu Gln Asp Lys Ala Arg Val Leu Val Asp Ser Ile Arg Gln Lys
    50                  55                  60

Asn Gln Glu Ala Gly Gln Val Phe Val Gln Thr Phe Leu Asn Ile Asp
65                  70                  75                  80

Lys Asn Ser Thr Ser Ile Lys Ala Pro Glu Thr Val Ala Gly Pro
                85                  90                  95

Asp Glu Ser Val Gly Ser Ala Ala Thr Leu Lys Leu Cys Pro His Glu
            100                 105                 110

Glu Phe Leu Lys Leu Cys Lys Glu Arg Ala Gly Glu Ile Tyr Pro Ile
        115                 120                 125

Lys Glu Arg Lys Asp Arg Thr Arg Leu Ala Leu Ile Ile Cys Asn Thr
    130                 135                 140

Glu Phe Asp His Met Pro Pro Arg Asn Gly Ala Ala Leu Asp Ile Leu
145                 150                 155                 160

Gly Met Lys Gln Leu Leu Glu Gly Leu Gly Tyr Thr Val Glu Val Glu
                165                 170                 175

Glu Lys Leu Thr Ala Arg Asp Met Glu Ser Val Leu Trp Lys Phe Ala
            180                 185                 190

Ala Arg Glu Glu His Lys Ser Ser Asp Ser Thr Phe Leu Val Phe Met
        195                 200                 205

Ser His Gly Ile Leu Asp Gly Ile Cys Gly Thr Met His Ser Glu Glu
    210                 215                 220

Glu Pro Asp Val Leu Pro Tyr Asp Thr Ile Phe Arg Thr Phe Asn Asn
225                 230                 235                 240

Arg Asn Cys Leu Ser Leu Lys Asp Lys Pro Lys Val Ile Ile Val Gln
                245                 250                 255

Ala Cys Arg Gly Ala Asn Arg Gly Glu Leu Trp Val Ser Asp Ser Pro
            260                 265                 270

```
Pro Ala Leu Ala Asp Ser Phe Ser Gln Ser Ser Glu Asn Leu Glu Glu
        275                 280                 285

Asp Ala Val Tyr Lys Thr His Val Glu Lys Asp Phe Ile Ala Phe Cys
        290                 295                 300

Ser Ser Thr Pro His Asn Val Ser Trp Arg Asp Ile Lys Lys Gly Ser
305                 310                 315                 320

Leu Phe Ile Thr Arg Leu Ile Thr Cys Phe Gln Lys Tyr Ala Trp Cys
                325                 330                 335

Cys His Leu Glu Glu Val Phe Arg Lys Val Gln Gln Ser Phe Glu Lys
                340                 345                 350

Pro Asn Val Lys Ala Gln Met Pro Thr Val Glu Arg Leu Ser Met Thr
                355                 360                 365

Arg Tyr Phe Tyr Leu Phe Pro Gly Asn
        370                 375

<210> SEQ ID NO 82
<211> LENGTH: 377
<212> TYPE: PRT
<213> ORGANISM: Homo sapiens

<400> SEQUENCE: 82

Met Ala Glu Gly Asn His Arg Lys Lys Pro Leu Lys Val Leu Glu Ser
1               5                   10                  15

Leu Gly Lys Asp Phe Leu Thr Gly Val Leu Asp Asn Leu Val Glu Gln
                20                  25                  30

Asn Val Leu Asn Trp Lys Glu Glu Lys Lys Lys Tyr Tyr Asp Ala
            35                  40                  45

Lys Thr Glu Asp Lys Val Arg Val Met Ala Asp Ser Met Gln Glu Lys
    50                  55                  60

Gln Arg Met Ala Gly Gln Met Leu Leu Gln Thr Phe Phe Asn Ile Asp
65                  70                  75                  80

Gln Ile Ser Pro Asn Lys Lys Ala His Pro Asn Met Glu Ala Gly Pro
                85                  90                  95

Pro Glu Ser Gly Glu Ser Thr Asp Ala Leu Lys Leu Cys Pro His Glu
                100                 105                 110

Glu Phe Leu Arg Leu Cys Lys Glu Arg Ala Glu Glu Ile Tyr Pro Ile
            115                 120                 125

Lys Glu Arg Asn Asn Arg Thr Arg Leu Ala Leu Ile Ile Cys Asn Thr
    130                 135                 140

Glu Phe Asp His Leu Pro Pro Arg Asn Gly Ala Asp Phe Asp Ile Thr
145                 150                 155                 160

Gly Met Lys Glu Leu Leu Glu Gly Leu Asp Tyr Ser Val Asp Val Glu
                165                 170                 175

Glu Asn Leu Thr Ala Arg Asp Met Glu Ser Ala Leu Arg Ala Phe Ala
            180                 185                 190

Thr Arg Pro Glu His Lys Ser Ser Asp Ser Thr Phe Leu Val Leu Met
    195                 200                 205

Ser His Gly Ile Leu Glu Gly Ile Cys Gly Thr Val His Asp Glu Lys
210                 215                 220

Lys Pro Asp Val Leu Leu Tyr Asp Thr Ile Phe Gln Ile Phe Asn Asn
225                 230                 235                 240

Arg Asn Cys Leu Ser Leu Lys Asp Lys Pro Lys Val Ile Ile Val Gln
                245                 250                 255

Ala Cys Arg Gly Ala Asn Arg Gly Glu Leu Trp Val Arg Asp Ser Pro
```

```
                260                 265                 270
Ala Ser Leu Glu Val Ala Ser Ser Gln Ser Ser Glu Asn Leu Glu Glu
        275                 280                 285

Asp Ala Val Tyr Lys Thr His Val Glu Lys Asp Phe Ile Ala Phe Cys
    290                 295                 300

Ser Ser Thr Pro His Asn Val Ser Trp Arg Asp Ser Thr Met Gly Ser
305                 310                 315                 320

Ile Phe Ile Thr Gln Leu Ile Thr Cys Phe Gln Lys Tyr Ser Trp Cys
                325                 330                 335

Cys His Leu Glu Glu Val Phe Arg Lys Val Gln Gln Ser Phe Glu Thr
            340                 345                 350

Pro Arg Ala Lys Ala Gln Met Pro Thr Ile Glu Arg Leu Ser Met Thr
        355                 360                 365

Arg Tyr Phe Tyr Leu Phe Pro Gly Asn
    370                 375

<210> SEQ ID NO 83
<211> LENGTH: 418
<212> TYPE: PRT
<213> ORGANISM: Homo sapiens

<400> SEQUENCE: 83

Met Phe Lys Gly Ile Leu Gln Ser Gly Leu Asp Asn Phe Val Ile Asn
1               5                   10                  15

His Met Leu Lys Asn Asn Val Ala Gly Gln Thr Ser Ile Gln Thr Leu
            20                  25                  30

Val Pro Asn Thr Asp Gln Lys Ser Thr Ser Val Lys Lys Asp Asn His
        35                  40                  45

Lys Lys Lys Thr Val Lys Met Leu Glu Tyr Leu Gly Lys Asp Val Leu
    50                  55                  60

His Gly Val Phe Asn Tyr Leu Ala Lys His Asp Val Leu Thr Leu Lys
65                  70                  75                  80

Glu Glu Glu Lys Lys Lys Tyr Tyr Asp Ala Lys Ile Glu Asp Lys Ala
                85                  90                  95

Leu Ile Leu Val Asp Ser Leu Arg Lys Asn Arg Val Ala His Gln Met
            100                 105                 110

Phe Thr Gln Thr Leu Leu Asn Met Asp Gln Lys Ile Thr Ser Val Lys
        115                 120                 125

Pro Leu Leu Gln Ile Glu Ala Gly Pro Pro Glu Ser Ala Glu Ser Thr
    130                 135                 140

Asn Ile Leu Lys Leu Cys Pro Arg Glu Glu Phe Leu Arg Leu Cys Lys
145                 150                 155                 160

Lys Asn His Asp Glu Ile Tyr Pro Ile Lys Lys Arg Glu Asp Arg Arg
                165                 170                 175

Arg Leu Ala Leu Ile Ile Cys Asn Thr Lys Phe Asp His Leu Pro Ala
            180                 185                 190

Arg Asn Gly Ala His Tyr Asp Ile Val Gly Met Lys Arg Leu Leu Gln
        195                 200                 205

Gly Leu Gly Tyr Thr Val Val Asp Glu Lys Asn Leu Thr Ala Arg Asp
    210                 215                 220

Met Glu Ser Val Leu Arg Ala Phe Ala Ala Arg Pro Glu His Lys Ser
225                 230                 235                 240

Ser Asp Ser Thr Phe Leu Val Leu Met Ser His Gly Ile Leu Glu Gly
                245                 250                 255
```

```
Ile Cys Gly Thr Ala His Lys Lys Lys Pro Asp Val Leu Leu Tyr
            260                 265                 270

Asp Thr Ile Phe Gln Ile Phe Asn Asn Arg Asn Cys Leu Ser Leu Lys
            275                 280                 285

Asp Lys Pro Lys Val Ile Val Gln Ala Cys Arg Gly Glu Lys His
            290                 295                 300

Gly Glu Leu Trp Val Arg Asp Ser Pro Ala Ser Leu Ala Val Ile Ser
305                 310                 315                 320

Ser Gln Ser Ser Glu Asn Leu Glu Ala Asp Ser Val Cys Lys Ile His
                    325                 330                 335

Glu Glu Lys Asp Phe Ile Ala Phe Cys Ser Ser Thr Pro His Asn Val
            340                 345                 350

Ser Trp Arg Asp Arg Thr Arg Gly Ser Ile Phe Ile Thr Glu Leu Ile
            355                 360                 365

Thr Cys Phe Gln Lys Tyr Ser Cys Cys His Leu Met Glu Ile Phe
            370                 375                 380

Arg Lys Val Gln Lys Ser Phe Glu Val Pro Gln Ala Lys Ala Gln Met
385                 390                 395                 400

Pro Thr Ile Glu Arg Ala Thr Leu Thr Arg Asp Phe Tyr Leu Phe Pro
            405                 410                 415

Gly Asn

<210> SEQ ID NO 84
<211> LENGTH: 419
<212> TYPE: PRT
<213> ORGANISM: Mouse

<400> SEQUENCE: 84

Met Ala Ala Arg Arg Thr His Glu Arg Asp Pro Ile Tyr Lys Ile Lys
1               5                   10                  15

Gly Leu Ala Lys Asp Met Leu Asp Gly Val Phe Asp Asp Leu Val Glu
            20                  25                  30

Lys Asn Val Leu Asn Gly Asp Glu Leu Leu Lys Ile Gly Glu Ser Ala
            35                  40                  45

Ser Phe Ile Leu Asn Lys Ala Glu Asn Leu Val Glu Asn Phe Leu Glu
    50                  55                  60

Lys Thr Asp Met Ala Gly Lys Ile Phe Ala Gly His Ile Ala Asn Ser
65                  70                  75                  80

Gln Glu Gln Leu Ser Leu Gln Phe Ser Asn Asp Glu Asp Asp Gly Pro
                85                  90                  95

Gln Lys Ile Cys Thr Pro Ser Ser Pro Ser Glu Ser Lys Arg Lys Val
            100                 105                 110

Glu Asp Asp Glu Met Glu Val Asn Ala Gly Leu Ala His Glu Ser His
            115                 120                 125

Leu Met Leu Thr Ala Pro His Gly Leu Gln Ser Ser Glu Val Gln Asp
            130                 135                 140

Thr Leu Lys Leu Cys Pro Arg Asp Gln Phe Cys Lys Ile Lys Thr Glu
145                 150                 155                 160

Arg Ala Lys Glu Ile Tyr Pro Val Met Glu Lys Glu Gly Arg Thr Arg
                165                 170                 175

Leu Ala Leu Ile Ile Cys Asn Lys Lys Phe Asp Tyr Leu Phe Asp Arg
            180                 185                 190

Asp Asn Ala Asp Thr Asp Ile Leu Asn Met Gln Glu Leu Leu Glu Asn
            195                 200                 205
```

```
Leu Gly Tyr Ser Val Val Leu Lys Glu Asn Leu Thr Ala Gln Glu Met
    210                 215                 220

Glu Thr Glu Leu Met Gln Phe Ala Gly Arg Pro Glu His Gln Ser Ser
225                 230                 235                 240

Asp Ser Thr Phe Leu Val Phe Met Ser His Gly Ile Leu Glu Gly Ile
                245                 250                 255

Cys Gly Val Lys His Arg Asn Lys Lys Pro Asp Val Leu His Asp Asp
            260                 265                 270

Thr Ile Phe Lys Ile Phe Asn Asn Ser Asn Cys Arg Ser Leu Arg Asn
                275                 280                 285

Lys Pro Lys Ile Leu Ile Met Gln Ala Cys Arg Gly Arg Tyr Asn Gly
    290                 295                 300

Thr Ile Trp Val Ser Thr Asn Lys Gly Ile Ala Thr Ala Asp Thr Asp
305                 310                 315                 320

Glu Glu Arg Val Leu Ser Cys Lys Trp Asn Asn Ser Ile Thr Lys Ala
                325                 330                 335

His Val Glu Thr Asp Phe Ile Ala Phe Lys Ser Ser Thr Pro His Asn
            340                 345                 350

Ile Ser Trp Lys Val Gly Lys Thr Gly Ser Leu Phe Ile Ser Lys Leu
        355                 360                 365

Ile Asp Cys Phe Lys Lys Tyr Cys Trp Cys Tyr His Leu Glu Glu Ile
    370                 375                 380

Phe Arg Lys Val Gln His Ser Phe Glu Val Pro Gly Glu Leu Thr Gln
385                 390                 395                 400

Met Pro Thr Ile Glu Arg Val Ser Met Thr Arg Tyr Phe Tyr Leu Phe
                405                 410                 415

Pro Gly Asn

<210> SEQ ID NO 85
<211> LENGTH: 373
<212> TYPE: PRT
<213> ORGANISM: Mouse

<400> SEQUENCE: 85

Met Ala Glu Asn Lys His Pro Asp Lys Pro Leu Lys Val Leu Glu Gln
1               5                   10                  15

Leu Gly Lys Glu Val Leu Thr Glu Tyr Leu Glu Lys Leu Val Gln Ser
            20                  25                  30

Asn Val Leu Lys Leu Lys Glu Glu Asp Lys Gln Lys Phe Asn Asn Ala
        35                  40                  45

Glu Arg Ser Asp Lys Arg Trp Val Phe Val Asp Ala Met Lys Lys Lys
    50                  55                  60

His Ser Lys Val Gly Glu Met Leu Leu Gln Thr Phe Phe Ser Val Asp
65                  70                  75                  80

Pro Gly Ser His His Gly Glu Ala Asn Leu Glu Met Glu Glu Pro Glu
                85                  90                  95

Glu Ser Leu Asn Thr Leu Lys Leu Cys Ser Pro Glu Glu Phe Thr Arg
            100                 105                 110

Leu Cys Arg Glu Lys Thr Gln Glu Ile Tyr Pro Ile Lys Glu Ala Asn
        115                 120                 125

Gly Arg Thr Arg Lys Ala Leu Ile Ile Cys Asn Thr Glu Phe Lys His
    130                 135                 140

Leu Ser Leu Arg Tyr Gly Ala Lys Phe Asp Ile Ile Gly Met Lys Gly
145                 150                 155                 160
```

```
Leu Leu Glu Asp Leu Gly Tyr Asp Val Val Lys Glu Glu Leu Thr
            165                 170                 175

Ala Glu Gly Met Glu Ser Glu Met Lys Asp Phe Ala Ala Leu Ser Glu
            180                 185                 190

His Gln Thr Ser Asp Ser Thr Phe Leu Val Leu Met Ser His Gly Thr
            195                 200                 205

Leu His Gly Ile Cys Gly Thr Met His Ser Glu Lys Thr Pro Asp Val
210                 215                 220

Leu Gln Tyr Asp Thr Ile Tyr Gln Ile Phe Asn Asn Cys His Cys Pro
225                 230                 235                 240

Gly Leu Arg Asp Lys Pro Lys Val Ile Val Gln Ala Cys Arg Gly
            245                 250                 255

Gly Asn Ser Gly Glu Met Trp Ile Arg Glu Ser Ser Lys Pro Gln Leu
            260                 265                 270

Cys Arg Gly Val Asp Leu Pro Arg Asn Met Glu Ala Asp Ala Val Lys
            275                 280                 285

Leu Ser His Val Glu Lys Asp Phe Ile Ala Phe Tyr Ser Thr Thr Pro
290                 295                 300

His His Leu Ser Tyr Arg Asp Lys Thr Gly Gly Ser Tyr Phe Ile Thr
305                 310                 315                 320

Arg Leu Ile Ser Cys Phe Arg Lys His Ala Cys Ser Cys His Leu Phe
                325                 330                 335

Asp Ile Phe Leu Lys Val Gln Gln Ser Phe Glu Lys Ala Ser Ile His
                340                 345                 350

Ser Gln Met Pro Thr Ile Asp Arg Ala Thr Leu Thr Arg Tyr Phe Tyr
            355                 360                 365

Leu Phe Pro Gly Asn
    370

<210> SEQ ID NO 86
<211> LENGTH: 29
<212> TYPE: DNA
<213> ORGANISM: Primer

<400> SEQUENCE: 86
ccggatccta attcccagga aagagatac                                29

<210> SEQ ID NO 87
<211> LENGTH: 21
<212> TYPE: DNA
<213> ORGANISM: Primer

<400> SEQUENCE: 87
gcccaaccca gtggcaagtt a                                        21

<210> SEQ ID NO 88
<211> LENGTH: 24
<212> TYPE: DNA
<213> ORGANISM: Primer

<400> SEQUENCE: 88
gctttaactt gccactgggt tggg                                     24

<210> SEQ ID NO 89
<211> LENGTH: 34
<212> TYPE: DNA
<213> ORGANISM: Primer

<400> SEQUENCE: 89
```

```
ttcaattctt tgttgcgcat gttgagggcc aggc                                  34

<210> SEQ ID NO 90
<211> LENGTH: 25
<212> TYPE: DNA
<213> ORGANISM: Primer

<400> SEQUENCE: 90
gtagatctcg catccccaaa aggtc                                            25

<210> SEQ ID NO 91
<211> LENGTH: 29
<212> TYPE: DNA
<213> ORGANISM: Primer

<400> SEQUENCE: 91
gggatcccat ggctgatgag aaaccatcc                                        29

<210> SEQ ID NO 92
<211> LENGTH: 31
<212> TYPE: DNA
<213> ORGANISM: Primer

<400> SEQUENCE: 92
cggatccctc agctcttctg gaaatccagg g                                     31

<210> SEQ ID NO 93
<211> LENGTH: 35
<212> TYPE: DNA
<213> ORGANISM: Primer

<400> SEQUENCE: 93
gggatccgga agccatggct gatgagaaac catcc                                 35

<210> SEQ ID NO 94
<211> LENGTH: 36
<212> TYPE: DNA
<213> ORGANISM: Primer

<400> SEQUENCE: 94
ggtgtttatg tcacatggca tcctgaatgg aatctg                                36

<210> SEQ ID NO 95
<211> LENGTH: 36
<212> TYPE: DNA
<213> ORGANISM: Primer

<400> SEQUENCE: 95
cagattccat tcaggatgcc atgtgacata aacacc                                36

<210> SEQ ID NO 96
<211> LENGTH: 29
<212> TYPE: DNA
<213> ORGANISM: Primer

<400> SEQUENCE: 96
cacggatccc gccgccatgg cagctcttc                                        29

<210> SEQ ID NO 97
<211> LENGTH: 435
<212> TYPE: PRT
<213> ORGANISM: Homo sapiens
```

```
<400> SEQUENCE: 97

Met Ala Ala Asp Arg Gly Arg Arg Ile Leu Gly Val Cys Gly Met His
1               5                   10                  15

Pro His His Gln Glu Thr Leu Lys Lys Asn Arg Val Val Leu Ala Lys
            20                  25                  30

Gln Leu Leu Ser Glu Leu Leu Glu His Leu Leu Glu Lys Asp Ile
        35                  40                  45

Ile Thr Leu Glu Met Arg Glu Leu Ile Gln Ala Lys Val Gly Ser Phe
    50                  55                  60

Ser Gln Asn Val Glu Leu Leu Asn Leu Leu Pro Lys Arg Gly Pro Gln
65                  70                  75                  80

Ala Phe Asp Ala Phe Cys Glu Ala Leu Arg Glu Thr Lys Gln Gly His
                85                  90                  95

Leu Glu Asp Met Leu Leu Thr Thr Leu Ser Gly Leu Gln His Val Leu
            100                 105                 110

Pro Pro Leu Ser Cys Asp Tyr Asp Leu Ser Leu Pro Phe Pro Val Cys
            115                 120                 125

Glu Ser Cys Pro Leu Tyr Lys Lys Leu Arg Leu Ser Thr Asp Thr Val
130                 135                 140

Glu His Ser Leu Asp Asn Lys Asp Gly Pro Val Cys Leu Gln Val Lys
145                 150                 155                 160

Pro Cys Thr Pro Glu Phe Tyr Gln Thr His Phe Gln Leu Ala Tyr Arg
                165                 170                 175

Leu Gln Ser Arg Pro Arg Gly Leu Ala Leu Val Leu Ser Asn Val His
            180                 185                 190

Phe Thr Gly Glu Lys Glu Leu Glu Phe Arg Ser Gly Gly Asp Val Asp
            195                 200                 205

His Ser Thr Leu Val Thr Leu Phe Lys Leu Leu Gly Tyr Asp Val His
            210                 215                 220

Val Leu Cys Asp Gln Thr Ala Gln Glu Met Gln Glu Lys Leu Gln Asn
225                 230                 235                 240

Phe Ala Gln Leu Pro Ala His Arg Val Thr Asp Ser Cys Ile Val Ala
                245                 250                 255

Leu Leu Ser His Gly Val Glu Gly Ala Ile Tyr Gly Val Asp Gly Lys
            260                 265                 270

Leu Leu Gln Leu Gln Glu Val Phe Gln Leu Phe Asp Asn Ala Asn Cys
        275                 280                 285

Pro Ser Leu Gln Asn Lys Pro Lys Met Phe Phe Ile Gln Ala Cys Arg
290                 295                 300

Gly Asp Glu Thr Asp Arg Gly Val Asp Gln Gln Asp Gly Lys Asn His
305                 310                 315                 320

Ala Gly Ser Pro Gly Cys Glu Glu Ser Asp Ala Gly Lys Glu Lys Leu
                325                 330                 335

Pro Lys Met Arg Leu Pro Thr Arg Ser Asp Met Ile Cys Gly Tyr Ala
            340                 345                 350

Cys Leu Lys Gly Thr Ala Ala Met Arg Asn Thr Lys Arg Gly Ser Trp
            355                 360                 365

Tyr Ile Glu Ala Leu Ala Gln Val Phe Ser Glu Arg Ala Cys Asp Met
    370                 375                 380

His Val Ala Asp Met Leu Val Lys Val Asn Ala Leu Ile Lys Asp Arg
385                 390                 395                 400

Glu Gly Tyr Ala Pro Gly Thr Glu Phe His Arg Cys Lys Glu Met Ser
                405                 410                 415
```

-continued

```
Glu Tyr Cys Ser Thr Leu Cys Arg His Leu Tyr Leu Phe Pro Gly His
            420                 425                 430
Pro Pro Thr
        435

<210> SEQ ID NO 98
<211> LENGTH: 277
<212> TYPE: PRT
<213> ORGANISM: Homo sapiens

<400> SEQUENCE: 98

Met Glu Asn Thr Glu Asn Ser Val Asp Ser Lys Ser Ile Lys Asn Leu
1               5                   10                  15
Glu Pro Lys Ile Ile His Gly Ser Glu Ser Met Asp Ser Gly Ile Ser
            20                  25                  30
Leu Asp Asn Ser Tyr Lys Met Asp Tyr Pro Glu Met Gly Leu Cys Ile
        35                  40                  45
Ile Ile Asn Asn Lys Asn Phe His Lys Ser Thr Gly Met Thr Ser Arg
    50                  55                  60
Ser Gly Thr Asp Val Asp Ala Ala Asn Leu Arg Glu Thr Phe Arg Asn
65                  70                  75                  80
Leu Lys Tyr Glu Val Arg Asn Lys Asn Asp Leu Thr Arg Glu Glu Ile
                85                  90                  95
Val Glu Leu Met Arg Asp Val Ser Lys Glu Asp His Ser Lys Arg Ser
            100                 105                 110
Ser Phe Val Cys Val Leu Leu Ser His Gly Glu Glu Gly Ile Ile Phe
        115                 120                 125
Gly Thr Asn Gly Pro Val Asp Leu Lys Lys Ile Thr Asn Phe Phe Arg
    130                 135                 140
Gly Asp Arg Cys Arg Ser Leu Thr Gly Lys Pro Lys Leu Phe Ile Ile
145                 150                 155                 160
Gln Ala Cys Arg Gly Thr Glu Leu Asp Cys Gly Ile Glu Thr Asp Ser
                165                 170                 175
Gly Val Asp Asp Asp Met Ala Cys His Lys Ile Pro Val Asp Ala Asp
            180                 185                 190
Phe Leu Tyr Ala Tyr Ser Thr Ala Pro Gly Tyr Tyr Ser Trp Arg Asn
        195                 200                 205
Ser Lys Asp Gly Ser Trp Phe Ile Gln Ser Leu Cys Ala Met Leu Lys
    210                 215                 220
Gln Tyr Ala Asp Lys Leu Glu Phe Met His Ile Leu Thr Arg Val Asn
225                 230                 235                 240
Arg Lys Val Ala Thr Glu Phe Glu Ser Phe Ser Phe Asp Ala Thr Phe
                245                 250                 255
His Ala Lys Lys Gln Ile Pro Cys Ile Val Ser Met Leu Thr Lys Glu
            260                 265                 270
Leu Tyr Phe Tyr His
        275

<210> SEQ ID NO 99
<211> LENGTH: 293
<212> TYPE: PRT
<213> ORGANISM: Homo sapiens

<400> SEQUENCE: 99

Met Ser Ser Ala Ser Gly Leu Arg Arg Gly His Pro Ala Gly Gly Glu
1               5                   10                  15
```

```
Glu Asn Met Thr Glu Thr Asp Ala Phe Tyr Lys Arg Glu Met Phe Asp
             20                  25                  30

Pro Ala Glu Lys Tyr Lys Met Asp His Arg Arg Gly Ile Ala Leu
         35                  40                  45

Ile Phe Asn His Glu Arg Phe Phe Trp His Leu Thr Leu Pro Glu Arg
     50                  55                  60

Arg Arg Thr Cys Ala Asp Arg Asp Asn Leu Thr Arg Arg Phe Ser Asp
 65                  70                  75                  80

Leu Gly Phe Glu Val Lys Cys Phe Asn Asp Leu Lys Ala Glu Glu Leu
                 85                  90                  95

Leu Leu Lys Ile His Glu Val Ser Thr Val Ser His Ala Asp Ala Asp
            100                 105                 110

Cys Phe Val Cys Val Phe Leu Ser His Gly Glu Gly Asn His Ile Tyr
            115                 120                 125

Ala Tyr Asp Ala Lys Ile Glu Ile Gln Thr Leu Thr Gly Leu Phe Lys
        130                 135                 140

Gly Asp Lys Cys His Ser Leu Val Gly Lys Pro Lys Ile Phe Ile Ile
145                 150                 155                 160

Gln Ala Cys Arg Gly Asn Gln His Asp Val Pro Val Ile Pro Leu Asp
                165                 170                 175

Val Val Asp Asn Gln Thr Glu Lys Leu Asp Thr Asn Ile Thr Glu Val
            180                 185                 190

Asp Ala Ala Ser Val Tyr Thr Leu Pro Ala Gly Ala Asp Phe Leu Met
        195                 200                 205

Cys Tyr Ser Val Ala Glu Gly Tyr Tyr Ser His Arg Glu Thr Val Asn
210                 215                 220

Gly Ser Trp Tyr Ile Gln Asp Leu Cys Glu Met Leu Gly Lys Tyr Gly
225                 230                 235                 240

Ser Ser Leu Glu Phe Thr Glu Leu Leu Thr Leu Val Asn Arg Lys Val
                245                 250                 255

Ser Gln Arg Arg Val Asp Phe Cys Lys Asp Pro Ser Ala Ile Gly Lys
            260                 265                 270

Lys Gln Val Pro Cys Phe Ala Ser Met Leu Thr Lys Lys Leu His Phe
        275                 280                 285

Phe Pro Lys Ser Asn
        290

<210> SEQ ID NO 100
<211> LENGTH: 303
<212> TYPE: PRT
<213> ORGANISM: Homo sapiens

<400> SEQUENCE: 100

Met Ala Asp Asp Gln Gly Cys Ile Glu Glu Gln Gly Val Glu Asp Ser
 1               5                  10                  15

Ala Asn Glu Asp Ser Val Asp Ala Lys Pro Asp Arg Ser Ser Phe Val
             20                  25                  30

Pro Ser Leu Phe Ser Lys Lys Lys Asn Val Thr Met Arg Ser Ile
         35                  40                  45

Lys Thr Thr Arg Asp Arg Val Pro Thr Tyr Gln Tyr Asn Met Asn Phe
     50                  55                  60

Glu Lys Leu Gly Lys Cys Ile Ile Ile Asn Asn Lys Asn Phe Asp Lys
 65                  70                  75                  80

Val Thr Gly Met Gly Val Arg Asn Gly Thr Asp Lys Asp Ala Glu Ala
```

```
                    85                  90                  95
Leu Phe Lys Cys Phe Arg Ser Leu Gly Phe Asp Val Ile Val Tyr Asn
                100                 105                 110

Asp Cys Ser Cys Ala Lys Met Gln Asp Leu Leu Lys Lys Ala Ser Glu
            115                 120                 125

Glu Asp His Thr Asn Ala Ala Cys Phe Ala Cys Ile Leu Leu Ser His
        130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Cys Arg Gly Thr Glu Leu Asp
            180                 185                 190

Asp Gly Ile Gln Ala Asp Ser Gly Pro Ile Asn Asp Thr Asp Ala Asn
        195                 200                 205

Pro Arg Tyr Lys Ile Pro Val Glu Ala Asp Phe Leu Phe Ala Tyr Ser
    210                 215                 220

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
                245                 250                 255

Glu Ile Met Gln Ile Leu Thr Arg Val Asn Asp Arg Val Ala Arg His
            260                 265                 270

Phe Glu Ser Gln Ser Asp Asp Pro His Phe His Glu Lys Lys Gln Ile
        275                 280                 285

Pro Cys Val Val Ser Met Leu Thr Lys Glu Leu Tyr Phe Ser Gln
    290                 295                 300

<210> SEQ ID NO 101
<211> LENGTH: 479
<212> TYPE: PRT
<213> ORGANISM: Homo sapiens

<400> SEQUENCE: 101

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
                20                  25                  30

Arg Lys Gln Glu Pro Ile Lys Asp Ala Leu Met Leu Phe Gln Arg Leu
            35                  40                  45

Gln Glu Lys Arg Met Leu Glu Glu Ser Asn Leu Ser Phe Leu Lys Glu
        50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160
```

-continued

```
Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Leu Glu Gly Ser
            180                 185                 190

Pro Asp Glu Phe Ser Asn Gly Glu Glu Leu Cys Gly Val Met Thr Ile
            195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
    290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
        355                 360                 365

Ile Pro Val Glu Thr Asp Ser Glu Glu Gln Pro Tyr Leu Glu Met Asp
    370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
        435                 440                 445

Glu Val Ser Asn Lys Asp Asp Lys Lys Asn Met Gly Lys Gln Met Pro
    450                 455                 460

Gln Pro Thr Phe Thr Leu Arg Lys Lys Leu Val Phe Pro Ser Asp
465                 470                 475

<210> SEQ ID NO 102
<211> LENGTH: 416
<212> TYPE: PRT
<213> ORGANISM: Homo sapiens

<400> SEQUENCE: 102

Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Ser
            20                  25                  30

Glu Leu Phe Arg Pro His Met Ile Glu Asp Ile Gln Arg Ala Gly Ser
        35                  40                  45

Gly Ser Arg Arg Asp Gln Ala Arg Gln Leu Ile Ile Asp Leu Glu Thr
    50                  55                  60
```

```
Arg Gly Ser Gln Ala Leu Pro Leu Phe Ile Ser Cys Leu Glu Asp Thr
 65                  70                  75                  80

Gly Gln Asp Met Leu Ala Ser Phe Leu Arg Thr Asn Arg Gln Ala Ala
             85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
        115                 120                 125

Val Asp Ile Gly Ser Gly Phe Gly Asp Val Gly Ala Leu Glu Ser
130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
                180                 185                 190

Arg Phe Ser Ser Pro His Phe Met Val Glu Val Lys Gly Asp Leu Thr
            195                 200                 205

Ala Lys Lys Met Val Leu Ala Leu Leu Glu Leu Ala Gln Gln Asp His
210                 215                 220

Gly Ala Leu Asp Cys Cys Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
            275                 280                 285

Gly Glu Gln Lys Asp His Gly Phe Glu Val Ala Ser Thr Ser Pro Glu
290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
            355                 360                 365

Asp Ile Phe Glu Gln Trp Ala His Ser Glu Asp Leu Gln Ser Leu Leu
370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415

<210> SEQ ID NO 103
<211> LENGTH: 521
<212> TYPE: PRT
<213> ORGANISM: Homo sapiens

<400> SEQUENCE: 103

Met Lys Ser Gln Gly Gln His Trp Tyr Ser Ser Asp Lys Asn Cys
1               5                   10                  15

Lys Val Ser Phe Arg Glu Lys Leu Leu Ile Ile Asp Ser Asn Leu Gly
```

```
                   20              25              30
Val Gln Asp Val Glu Asn Leu Lys Phe Leu Cys Ile Gly Leu Val Pro
             35              40              45
Asn Lys Lys Leu Glu Lys Ser Ser Ala Ser Asp Val Phe Glu His
         50              55              60
Leu Leu Ala Glu Asp Leu Leu Ser Glu Glu Asp Pro Phe Phe Leu Ala
 65              70              75              80
Glu Leu Leu Tyr Ile Ile Arg Gln Lys Lys Leu Leu Gln His Leu Asn
                 85              90              95
Cys Thr Lys Glu Glu Val Glu Arg Leu Leu Pro Thr Arg Gln Arg Val
             100             105             110
Ser Leu Phe Arg Asn Leu Leu Tyr Glu Leu Ser Glu Gly Ile Asp Ser
         115             120             125
Glu Asn Leu Lys Asp Met Ile Phe Leu Leu Lys Asp Ser Leu Pro Lys
     130             135             140
Thr Glu Met Thr Ser Leu Ser Phe Leu Ala Phe Leu Glu Lys Gln Gly
145             150             155             160
Lys Ile Asp Glu Asp Asn Leu Thr Cys Leu Glu Asp Leu Cys Lys Thr
                 165             170             175
Val Val Pro Lys Leu Leu Arg Asn Ile Glu Lys Tyr Lys Arg Glu Lys
             180             185             190
Ala Ile Gln Ile Val Thr Pro Pro Val Asp Lys Glu Ala Glu Ser Tyr
         195             200             205
Gln Gly Glu Glu Glu Leu Val Ser Gln Thr Asp Val Lys Thr Phe Leu
     210             215             220
Glu Ala Leu Pro Gln Glu Ser Trp Gln Asn Lys His Ala Gly Ser Asn
225             230             235             240
Gly Asn Arg Ala Thr Asn Gly Ala Pro Ser Leu Val Ser Arg Gly Met
                 245             250             255
Gln Gly Ala Ser Ala Asn Thr Leu Asn Ser Glu Thr Ser Thr Lys Arg
             260             265             270
Ala Ala Val Tyr Arg Met Asn Arg Asn His Arg Gly Leu Cys Val Ile
         275             280             285
Val Asn Asn His Ser Phe Thr Ser Leu Lys Asp Arg Gln Gly Thr His
     290             295             300
Lys Asp Ala Glu Ile Leu Ser His Val Phe Gln Trp Leu Gly Phe Thr
305             310             315             320
Val His Ile His Asn Asn Val Thr Lys Val Glu Met Glu Met Val Leu
                 325             330             335
Gln Lys Gln Lys Cys Asn Pro Ala His Ala Asp Gly Asp Cys Phe Val
             340             345             350
Phe Cys Ile Leu Thr His Gly Arg Phe Gly Ala Val Tyr Ser Ser Asp
         355             360             365
Glu Ala Leu Ile Pro Ile Arg Glu Ile Met Ser His Phe Thr Ala Leu
     370             375             380
Gln Cys Pro Arg Leu Ala Glu Lys Pro Lys Leu Phe Phe Ile Gln Ala
385             390             395             400
Cys Gln Gly Glu Glu Ile Gln Pro Ser Val Ser Ile Glu Ala Asp Ala
                 405             410             415
Leu Asn Pro Glu Gln Ala Pro Thr Ser Leu Gln Asp Ser Ile Pro Ala
             420             425             430
Glu Ala Asp Phe Leu Leu Gly Leu Ala Thr Val Pro Gly Tyr Val Ser
         435             440             445
```

```
Phe Arg His Val Glu Glu Gly Ser Trp Tyr Ile Gln Ser Leu Cys Asn
            450                 455                 460

His Leu Lys Lys Leu Val Pro Arg Met Leu Lys Phe Leu Glu Lys Thr
465                 470                 475                 480

Met Glu Ile Arg Gly Arg Lys Arg Thr Val Trp Gly Ala Lys Gln Ile
                485                 490                 495

Ser Ala Thr Ser Leu Pro Thr Ala Ile Ser Ala Gln Thr Pro Arg Pro
                500                 505                 510

Pro Met Arg Arg Trp Ser Ser Val Ser
            515                 520

<210> SEQ ID NO 104
<211> LENGTH: 377
<212> TYPE: PRT
<213> ORGANISM: Homo sapiens

<400> SEQUENCE: 104

Met Ala Glu Asp Lys His Asn Lys Asn Pro Leu Lys Met Leu Glu Ser
1               5                   10                  15

Leu Gly Lys Glu Leu Ile Ser Gly Leu Leu Asp Asp Phe Val Glu Lys
            20                  25                  30

Asn Val Leu Lys Leu Glu Glu Glu Lys Lys Lys Ile Tyr Asp Ala
        35                  40                  45

Lys Leu Gln Asp Lys Ala Arg Val Leu Val Asp Ser Ile Arg Gln Lys
    50                  55                  60

Asn Gln Glu Ala Gly Gln Val Phe Val Gln Thr Phe Leu Asn Ile Asp
65                  70                  75                  80

Lys Asn Ser Thr Ser Ile Lys Ala Pro Glu Glu Thr Val Ala Gly Pro
                85                  90                  95

Asp Glu Ser Val Gly Ser Ala Ala Thr Leu Lys Leu Cys Pro His Glu
                100                 105                 110

Glu Phe Leu Lys Leu Cys Lys Glu Arg Ala Gly Glu Ile Tyr Pro Ile
            115                 120                 125

Lys Glu Arg Lys Asp Arg Thr Arg Leu Ala Leu Ile Ile Cys Asn Thr
    130                 135                 140

Glu Phe Asp His Met Pro Pro Arg Asn Gly Ala Ala Leu Asp Ile Leu
145                 150                 155                 160

Gly Met Lys Gln Leu Leu Glu Gly Leu Gly Tyr Thr Val Glu Val Glu
                165                 170                 175

Glu Lys Leu Thr Ala Arg Asp Met Glu Ser Val Leu Trp Lys Phe Ala
            180                 185                 190

Ala Arg Glu Glu His Lys Ser Ser Asp Ser Thr Phe Leu Val Phe Met
        195                 200                 205

Ser His Gly Ile Leu Asp Gly Ile Cys Gly Thr Met His Ser Glu Glu
    210                 215                 220

Glu Pro Asp Val Leu Pro Tyr Asp Thr Ile Phe Arg Thr Phe Asn Asn
225                 230                 235                 240

Arg Asn Cys Leu Ser Leu Lys Asp Lys Pro Lys Val Ile Ile Val Gln
                245                 250                 255

Ala Cys Arg Gly Ala Asn Arg Gly Glu Leu Trp Val Ser Asp Ser Pro
                260                 265                 270

Pro Ala Leu Ala Asp Ser Phe Ser Gln Ser Ser Glu Asn Leu Glu Glu
            275                 280                 285

Asp Ala Val Tyr Lys Thr His Val Glu Lys Asp Phe Ile Ala Phe Cys
```

```
                    290                 295                 300
Ser Ser Thr Pro His Asn Val Ser Trp Arg Asp Ile Lys Lys Gly Ser
305                 310                 315                 320

Leu Phe Ile Thr Arg Leu Ile Thr Cys Phe Gln Lys Tyr Ala Trp Cys
                325                 330                 335

Cys His Leu Glu Glu Val Phe Arg Lys Val Gln Gln Ser Phe Glu Lys
                340                 345                 350

Pro Asn Val Lys Ala Gln Met Pro Thr Val Glu Arg Leu Ser Met Thr
                355                 360                 365

Arg Tyr Phe Tyr Leu Phe Pro Gly Asn
    370                 375

<210> SEQ ID NO 105
<211> LENGTH: 242
<212> TYPE: PRT
<213> ORGANISM: Homo sapiens

<400> SEQUENCE: 105

Met Ser Asn Pro Arg Ser Leu Glu Glu Glu Lys Tyr Asp Met Ser Gly
1               5                   10                  15

Ala Arg Leu Ala Leu Ile Leu Cys Val Thr Lys Ala Arg Glu Gly Ser
                20                  25                  30

Glu Glu Asp Leu Asp Ala Leu Glu His Met Phe Arg Gln Leu Arg Phe
            35                  40                  45

Glu Ser Thr Met Lys Arg Asp Pro Thr Ala Glu Gln Phe Gln Glu Glu
        50                  55                  60

Leu Glu Lys Phe Gln Gln Ala Ile Asp Ser Arg Glu Asp Pro Val Ser
65                  70                  75                  80

Cys Ala Phe Val Val Leu Met Ala His Gly Arg Glu Gly Phe Leu Lys
                85                  90                  95

Gly Glu Asp Gly Glu Met Val Lys Leu Glu Asn Leu Phe Glu Ala Leu
                100                 105                 110

Asn Asn Lys Asn Cys Gln Ala Leu Arg Ala Lys Pro Lys Val Tyr Ile
            115                 120                 125

Ile Gln Ala Cys Arg Gly Glu Gln Arg Asp Pro Gly Glu Thr Val Gly
        130                 135                 140

Gly Asp Glu Ile Val Met Val Ile Lys Asp Ser Pro Gln Thr Ile Pro
145                 150                 155                 160

Thr Tyr Thr Asp Ala Leu His Val Tyr Ser Thr Val Glu Gly Tyr Ile
                165                 170                 175

Ala Tyr Arg His Asp Gln Lys Gly Ser Cys Phe Ile Gln Thr Leu Val
                180                 185                 190

Asp Val Phe Thr Lys Arg Lys Gly His Ile Leu Glu Leu Leu Thr Glu
            195                 200                 205

Val Thr Arg Arg Met Ala Glu Ala Glu Leu Val Gln Glu Gly Lys Ala
        210                 215                 220

Arg Lys Thr Asn Pro Glu Ile Gln Ser Thr Leu Arg Lys Arg Leu Tyr
225                 230                 235                 240

Leu Gln
```

HUMAN CASPASE-12 MATERIALS AND METHODS

This application claims the benefit of provisional application No. 60/203,162 filed May 9, 2000.

FIELD OF THE INVENTION

The present invention relates generally to novel caspase polynucleotides and polypeptides.

DESCRIPTION OF RELATED ART

Cysteine-dependent aspartate-specific proteases (caspases) are a family of proteases that cleave their substrates at aspartic acid (D)-X bonds. They are highly specific endopeptidases that catalyze limited proteolysis [Stennicke et al., *Cell Death Differen.* (1999) 6:1054–1059]. To date 14 mammalian caspases have been identified. Caspase-2, -3, -6, -7, -8, -9 and -10 are major players in the execution phase of apoptosis, whereas caspase-1, -4, -5, and -11 are involved in cytokine processing. The function of caspase-13, and -14 have not been determined, although based on structure caspase-13 is more similar to those caspases active in cytokine processing whereas caspase-14 appears to be closely related to caspases associated with cell death [Slee et al., *Cell Death Differen.* (1999) 6:1067–1074].

Caspases are initially expressed within cells as zymogens with low or no detectable enzymatic activity. The general primary structure of an unprocessed caspase consists of an amino-terminal prodomain, followed by a large subunit and a small subunit. Proteolytic processing of the zymogen either in trans or cis results in one or more cleavages at specific aspartic acid residues present between the large and small subunits. In most caspases, cleavage also occurs between the prodomain and the large subunit. The mature active caspase is a heterotetramer, which consists of two large (~20 kDa) and two small (~10 kDa) subunits. Residues from both subunits contribute to the two substrate-binding pockets which recognize at least four amino acids ($P_1$, $P_2$, $P_3$, and $P_4$) located N-terminal to the cleavage site in substrates. A highly conserved pentapeptide (QACXG) containing the catalytic cysteine, present in the large subunit, leads to the absolute requirement for an Asp at the $P_1$ position. Residues found at positions $P_2$, $P_3$ and $P_4$ on substrates vary greatly and determine substrate specificity within the caspase family [Stennicke et al., *Cell Death Differen.* (1999) 6:1054–1059; Takahashi, *Int J Hematology* (1999) 70:226–232; Slee et al., *Cell Death Differen.* (1999) 6:1067–1074].

Caspases can be divided into two groups based on the length of their N-terminal prodomains. Caspases with long prodomains such as caspase-1, -2, -4, -8, -9, and -10 contain regions such as caspase-recruiting domains (CARD) or death effector domains (DED), that mediate interactions with other proteins. These interactions cause oligomerization of the caspases which is thought to trigger autoprocessing of these proteins. Once activated, these caspases cleave downstream caspases which contain short prodomains and are incapable of autocatalysis, creating a proteolytic cascade [Slee et al., *Cell Death Differen.* (1999) 6:1067–1074; Kumar, *Cell Death Differen.* (1999) 6:1060–1066]].

Initial expression as relatively inert zymogens is especially important since most caspases are expressed constitutively. Regulation of caspase activity may also occur by controlling the subcellular localization of caspases. For example, most caspases are present in the cytosol, however, a number of their substrates are localized in organelles such as the nucleus. Catalytically inactive isoforms of caspases, e.g., caspase-9, which are generated by alternative splicing, can interfere with caspase activation thereby inhibiting apoptosis. Some caspases, e.g., caspase-9 can be regulated by post-translational modifications: phosphorylation inhibits its processing and activation. Negative regulators of caspases called inhibitors of apoptosis (IAPs) have also been identified. It is thought that IAPs protect from cell death by interfering with the catalytic activity of caspases or by preventing the processing and activation of caspases [Takahashi, *Int J Hematology* (1999) 70:226–232; Slee et al., *Cell Death Differen.* (1999) 6:1067–1074; Kumar, *Cell Death Differen.* (1999) 6:1060–1066].

Currently, two distinct pathways have been identified that lead to caspase activation in apoptosis: the cell surface death receptor pathway and the mitochondria-initiated pathway. The cell surface death receptor pathway is initiated by ligation of cell surface death receptors, e.g., Fas and tumor necrosis factor receptor 1 (TNFR1), leading to ligand-induced receptor trimerization, recruitment of intracellular receptor-associated proteins as well as caspases with long prodomains, and ultimately to the activation of caspases. The mitochondria-initiated pathway begins with the release of cytochrome c from the mitochondria in response to various stimuli, e.g., DNA damage. Cytosolic cytochrome c binds to apoptotic protease activating factor 1 (Apaf1) forming an Apaf1-cytochrome c multimeric complex, which then associates with caspase-9 thereby triggering the activation of several downstream caspases. Both pathways lead to enzymatically active caspases that cleave substrates including poly (ADP-ribose) polymerase (PARP), PKCδ, and cPLA$_2$ [Takahashi, *Int J Hematology* (1999) 70:226–232; Slee et al., *Cell Death Differen.* (1999) 6:1067–1074; Kumar, *Cell Death Differen.* (1999) 6:1060–1066].

Caspases have also been shown to be important for the processing of the cytokines interleukin-1β (IL-1β) and interleukin-18 (IL-18). Both IL-1β and IL-18 are expressed as inactive precursor proteins that are proteolytically processed by caspases to yield active cytokines involved in inflammatory responses. IL-1β is a multifunctional protein present in a number of different cell types. For example, IL-1β is a growth factor for acute myeloid leukemia cells, is produced by murine monocytes that migrate into Peyer's patches during inflammation, and is associated with prolonged longevity of peripheral blood monocytes in vitro. IL-18 is a crucial cytokine involved in IFN-γ production in Th1 cells and natural killer cells during inflammation [Zeuner et al., *Cell Death Differen.* (1999) 6:1075–1080].

Recent studies have also uncovered possible physiological roles for caspases apart from apoptosis. Pro-apoptotic caspase-3 is suggested to be involved in processes such as T cell proliferation, IL-2 release in PHA-stimulated Jurkat T cells, IL-16 processing in CD8$^+$ and CD4$^+$ T cells, and in cell cycle control [Zeuner et al., *Cell Death Differen.* (1999) 6:1075–1080]. Caspases have also been implicated in regulating terminal lens fiber differentiation. The mature lens fibers do not undergo cell death, however, they do exhibit nuclear degeneration similar to that seem in apoptosis. Finally, caspases have been shown to mediate CD95 inhibition of erythroid differentiation by cleaving specific transcription factors [Zeuner et al., *Cell Death Differen.* (1999) 6:1075–1080]. Although the most extensively examined process associated with caspase is apoptosis, they appear to function in several other processes.

Of interest to the present invention is Van de Craen et al., *FEBS Lett.* (1997) 403:61–69, which describes the identification and cloning of murine caspase-12. Murine caspase-12 is predominantly expressed in skeletal muscle and lung, and moderately expressed in brain, heart, spleen, liver, kidney and testis. Northen analysis indicates the presence of several different size murine caspase-12 transcripts suggesting that different isoforms of murine caspase-12 may exist. Transient transfection of murine caspase-12 into HeLa and Rat1 cells resulted in the induction of apoptosis [Van de Craen et al., *FEBS Lett.* (1997) 403:61–69].

Nakagawa et al., Nature (2000) 403: 98–103, suggests a potential role for mouse caspase-12 in neurodegenerative disease. Nakagawa et al. reported that cortical neurons isolated from caspase-12 null mutant mice were relatively resistant to induction of apoptosis by β-amyloid. Compared to neurons from wild-type animals, neurons from the caspase-12 null mice could be induced to undergo apoptosis by stimuli that trigger cell death pathways which act through the plasma membrane or mitochondria but not through the stress pathways of the endoplasmic reticulum. To date, the human ortholog of mouse caspase-12 has not been identified and isolated.

There thus exists a need in the art for identification and characterization of additional caspases to further elucidate the role of this important family of molecules in pathological conditions and to develop improved treatments for such conditions.

SUMMARY OF THE INVENTION

The present invention provides purified polynucleotides encoding heretofore unknown human caspase-12 polypeptides, including species homologs, analogs, and variants especially allelic variants thereof; antisense polynucleotide molecules; constructs and recombinant host cells incorporating the polynucleotides; human caspase-12 polypeptides encoded by the polynucleotides; antibodies to the polypeptides; kits employing the polynucleotides and polypeptides; and methods of making and using all of the foregoing.

The invention is based on cloning of cDNA encoding multiple isoforms of human caspase-12. Partial human caspase-12 amino acid sequences derived from computer-aided analysis of partial human DNA sequences are set forth in SEQ ID NOS: 39, 41, 42, 43, 48 and 49. Nucleotide sequences representing four different human caspase-12 isoforms (designated isoforms A or KW-A, B or KW-B, C or KW-C and D or KW-D) are set forth in SEQ ID NOS: 1 and 3 (KW-A), 5 and 7 (KW-B), 9 (KW-C) and 10 (KW-D). Deduced amino acid sequences for isoforms A and B are set forth in SEQ ID NOS: 2 and 4 (for SEQ ID NOS: 1 and 3, respectively) and 6 and 8 (for SEQ ID NOS: 5 and 7, respectively). An alignment of the amino acid sequence of isoform A (SEQ ID NO: 4), with amino acid sequences of other members of the caspase family is shown in FIG. 1. All four of these human caspase-12 isoforms, and indeed all isoforms known to date, show 60% identity over their entire length to murine caspase-12 at the amino acid level. Predicted cleavage sites within isoform KW-A (SEQ ID NO: 4) based on alignment with other caspases are described below.

Nucleotide sequences of updated versions of KW-A, KW-B, KW-C and KW-D are set forth in SEQ ID NOS: 50, 52, 54 and 56, respectively. The corresponding deduced amino acid sequences are set forth in SEQ ID NOS: 51, 53, 55 and 57, respectively. Nucleotide sequences of additional human caspase-12 isoforms KW-E, KW-F, KW-G, KW-H, KW-I, KW-J, and KW-K are set forth in SEQ ID NOS: 58, 60, 62, 64, 66, 68 and 70, respectively. The corresponding deduced amino acid sequences are set forth in SEQ ID NOS: 59, 61, 63, 65, 67, 69 and 71, respectively. FIG. 2 displays an alignment of all eleven isoforms together with a non-naturally occurring variant containing a Ser-205 to Gly mutation (SEQ ID NO: 77) designated hCaspase-12.

A modified KW-K nucleotide sequence, in which the internal stop codon has been eliminated by changing the T at position 476 to a C and in which a C has been added after position 403 to maintain the open reading frame (designated RIK-2) appears in SEQ ID NO: 72; the deduced amino acid sequence is set forth in SEQ ID NO: 73. A further modification of this nucleotide sequence to delete the CARD region (designated RIK-4) appears in SEQ ID NO: 74; the deduced amino acid sequence is set forth in SEQ ID NO: 75. Yet another modification of RIK-2 to incorporate a Ser205 to Gly mutation by changing the A at position 621 to a G appears in SEQ ID NO: 76; the deduced amino acid sequence is set forth in SEQ ID NO: 77. A further modification of RIK-4 to incorporate the same Ser205 to Gly mutation appears in SEQ ID NO: 78; the deduced amino acid sequence is set forth in SEQ ID NO: 79.

In one embodiment, the invention provides purified and isolated polynucleotides (e.g., cDNA, genomic DNA, synthetic DNA, RNA, or combinations thereof, single or double stranded) that comprise nucleotide sequences encoding the amino acid sequences of the polypeptides of the invention. Such polynucleotides are useful for recombinant expression of protein and also for detecting expression of human caspase-12 in cells (e.g., using Northern hybridization and in situ hybridization assays). Such polynucleotides are also useful to design antisense and other molecules for suppressing the expression of any one of the human caspase-12 polynucleotides or polypeptides of the invention in a cultured cell or animal (for therapeutic purposes or to provide a model for diseases characterized by aberrant expression of any one of the human caspase-12 molecules of the invention). Polynucleotides of the invention are also useful in gene therapy methods. Specifically excluded from the definition of polynucleotides of the invention are entire isolated chromosomes of native host cells.

Exemplary human caspase-12 polynucleotides are set forth in SEQ ID NOS: 1, 3, 5, 7, 9, 10, 50, 52, 54, 56, 58, 60, 62, 64, 66, 68, 70, 72, 74, 76 or 78. It will be appreciated that numerous other nucleotide sequences exist that also encode human caspase-12 polypeptides of SEQ ID NOS: 2, 4, 6, 8, 51, 53, 55, 57, 59, 61, 63, 65, 67, 69, 71, 73, 75, 77 or 79 due to the well-known degeneracy of the universal genetic code.

The invention also provides a purified and isolated polynucleotide comprising a nucleotide sequence that encodes a caspase polypeptide, which is preferably capable of biological activity alone or in association with other caspase subunits or domains, wherein the polynucleotide hybridizes to any of the nucleotide sequences set forth in SEQ ID NOS: 1, 3, 5, 7, 9, 10, 50, 52, 54, 56, 58, 60, 62, 64, 66, 68, 70, 72, 74, 76 or 78; or the non-coding strands complementary to these sequences, under the following exemplary moderately stringent hybridization conditions for human caspase-12:

(a) hybridization for 16 hours at 42° C. in a hybridization solution comprising 50% formamide, 1% SDS, 1 M NaCl, 10% Dextran sulphate; and (b) washing 2 times for 30 minutes at 60° C. in a wash solution comprising 0.1% SSC, 1% SDS. Alternatively, highly stringent conditions include washes at 68° C. Polynucleotides that encode a human allelic variant are highly preferred.

The invention also provides a purified and isolated polynucleotide comprising a nucleotide sequence that encodes a caspase polypeptide, which is preferably capable of biological activity alone or in association with other caspase subunits or domains, wherein the caspase-encoding portion of the polynucleotide is at least about 99%, at least about 98%, at least about 95%, at least about 90%, at least about 85%, at least about 80%, at least about 75%, or at least about 70% identical over its full length to one of the nucleotide sequences set forth in SEQ ID NOS: 1, 3, 5, 7, 9, 10, 50, 52, 54, 56, 58, 60, 62, 64, 66, 68, 70, 72, 74, 76 or 78 or a subunit- or domain-encoding portion thereof.

Polynucleotides may comprise at least about 100, or at least about 500, contiguous nucleotides of SEQ ID NOS: 1, 3, 5, 7, 9, 10, 50, 52, 54, 56, 58, 60, 62, 64, 66, 68, 70, 72, 74, 76 or 78. Preferred polynucleotides of the invention comprise a portion of any one of the sequences set forth in SEQ ID NOS: 1, 3, 5, 7, 9, 10, 50, 52, 54, 56, 58, 60, 62, 64, 66, 68, 70, 72, 74, 76 or 78 that encodes at least one subunit, domain or truncation of a caspase (e.g. the prodomain, the large subunit and/or the small subunit). The invention also includes polynucleotides differing from the sequences set forth in SEQ ID NOS: 1, 3, 5, 7, 9, 10, 50, 52, 54, 56, 58, 60, 62, 64, 66, 68, 70, 72, 74, 76 or 78; and from the complementary strands of these sequences by at least one nucleotide. Other preferred polynucleotides of the invention encode a portion of the amino acid sequence of SEQ ID NOS: 2, 4, 6, 8, 51, 53, 55, 57, 59, 61, 63, 65, 67, 69, 71, 73, 75, 77 or 79 that comprises a subunit, domain or truncation thereof.

Fragment polynucleotides of at least 18 consecutive polynucleotides that are capable of specifically hybridizing to any one of SEQ ID NOS: 1, 3, 5, 7, 9, 10, 50, 52, 54, 56, 58, 60, 62, 64, 66, 68, 70, 72, 74, 76 or 78 are also contemplated, as are kits comprising such fragments.

Also included within the scope of the invention are polynucleotides encoding human caspase-12 isoforms or variants with amino acid insertions (including fusion proteins), deletions, and/or substitutions, or other allelic variants or splice variants. Specifically contemplated are polynucleotides encoding any one of the amino acid sequences of the polypeptides of the invention fused to a nucleotide sequence encoding a heterologous amino acid sequence.

In a related embodiment, the invention provides DNA constructs comprising any one of the polynucleotides of the invention. Such constructs are useful, e.g., for amplifying the polynucleotides in host cells to create useful quantities thereof. In preferred embodiments, the constructs comprise any one of the polynucleotides of the invention operatively linked to an expression control sequence. Such constructs are useful for recombinant production of polypeptides of the invention.

In another related embodiment, the invention provides host cells that are transformed or transfected (stably or transiently) with polynucleotides of the invention or constructs of the invention or host cells modified to permit or increase expression of endogenous human caspase-12 polynucleotides. Cells can be modified (e.g., by homologous recombination) to provide increased expression of the human caspase-12 polynucleotides of the invention by replacing, in whole or in part, the naturally occurring promoter with all or part of a heterologous promoter so that the cell expresses the human caspase-12 polynucleotides at higher levels. The heterologous promoter is inserted in such a manner that it is operatively linked to sequences encoding any one of the human caspase-12 polypeptides of the invention. Cells can also be modified to provide increased expression by inserting DNA encoding a heterologous transcription factor that up-regulates human caspase-12 expression. Such host cells are useful for amplifying the polynucleotides and also for expressing any one of the human caspase-12 polypeptide isoforms including a subunit or fragment thereof encoded by the polynucleotide. Such host cells are also useful in assays as described herein.

In another embodiment, the invention provides purified and isolated human caspase-12 polypeptides comprising the amino acid sequence set forth in SEQ ID NOS: 2, 4, 6, 8, 51, 53, 55, 57, 59, 61, 63, 65, 67, 69, 71, 73, 75, 77 or 79; or fragments thereof comprising an epitope specific to any one of the human caspase-12 polypeptides of the invention. By "epitope specific to" is meant a portion of any one of the human caspase-12 polypeptides of the invention that is recognizable by an antibody that is specific for one or more of the human caspase-12 polypeptides of the invention, as defined in detail below. An exemplary embodiment is a purified and isolated polypeptide comprising the complete amino acid sequence set forth in SEQ ID NOS: 2, 4, 6, 8, 51, 53, 55, 57, 59, 61, 63, 65, 67, 69, 71, 73, 75, 77 or 79. Also provided are polypeptides comprising a specific subunit, domain or truncation of the polypeptide having an amino acid sequence of SEQ ID NOS: 2, 4, 6, 8, 51, 53, 55, 57, 59, 61, 63, 65, 67, 69, 71, 73, 75, 77 or 79 (e.g. the prodomain, the large subunit and/or the small subunit).

Polypeptides comprising the amino acid sequence set forth in any one of SEQ ID NOS: 39, 41, 42, 43, 48 or 49 are also contemplated.

Although SEQ ID NOS: 2, 4, 6, 8, 51, 53, 55, 57, 59, 61, 63, 65, 67, 69, 71, 73, 75, 77 or 79 provide a particular human sequence, the invention is intended to include within its scope variants with amino acid insertions (including fusion proteins), deletions, and/or substitutions; other human allelic variants, splice variants, or isoforms of the human caspase-12 polypeptides of the invention.

Polypeptides of the invention include polypeptides that are encoded by polynucleotides that hybridize under stringent, preferably highly stringent conditions, to the nucleotide sequences of SEQ ID NOS: 1, 3, 5, 7, 9, 10, 50, 52, 54, 56, 58, 60, 62, 64, 66, 68, 70, 72, 74, 76 or 78, or the non-coding strand thereof.

Polypeptides of the invention also include polypeptides that are at least about 99%, at least about 98%, at least about 95%, at least about 90%, at least about 85%, at least about 80%, at least about 75%, or at least about 70% identical to one of the amino acid sequences set forth in SEQ ID NOS: 2, 4, 6, 8, 51, 53, 55, 57, 59, 61, 63, 65, 67, 69, 71, 73, 75, 77 or 79 or at least 30 contiguous amino acids thereof.

Polypeptides may comprise at least about 20, or at least about 40, contiguous amino acids of SEQ ID NOS: 2, 4, 6, 8, 51, 53, 55, 57, 59, 61, 63, 65, 67, 69, 71, 73, 75, 77 or 79. In a preferred embodiment, a caspase-12 polypeptide comprises at least one subunit of a human caspase-12. By "subunit" is meant a portion of a caspase that is proteolytically cleaved in trans or cis and which portion then associates with the same or different subunits of a caspase to perform an enzymatic activity.

In still another related embodiment, the invention provides a method for producing a human caspase-12 polypeptide (including variants and fragments) comprising the steps of growing a host cell of the invention in a nutrient medium and isolating the polypeptide or variant thereof from the cell or the medium.

In still another embodiment, the invention provides antibodies (e.g., monoclonal and polyclonal antibodies, single chain antibodies, chimeric antibodies, bifunctional/ bispecific antibodies, humanized antibodies, human antibodies, and complementary determining region (CDR)-grafted antibodies, including compounds which include CDR and/or antigen-binding sequences, which specifically recognize a polypeptide of the invention) and other binding proteins specific for any one of the human caspase-12 polypeptides of the invention. Antibodies are useful for detecting or quantitating human caspase-12 polypeptides or for inhibiting the activity of human caspase-12. Antibody specificity and cross-reactivity is described in greater detail below. The determination of whether an antibody is specific for any one of the human caspase-12 polypeptides of the invention or is cross-reactive with another known caspase may be made using Western blotting assays or several other assays well known in the literature.

In one preferred variation, the invention provides monoclonal antibodies. Hybridomas that produce such antibodies are also intended as aspects of the invention. In yet another variation, the invention provides a humanized antibody. Humanized antibodies are useful for in vivo therapeutic applications.

In another variation, the invention provides a cell-free composition comprising polyclonal antibodies, wherein at least one of the antibodies is an antibody of the invention specific for one or more of the human caspase-12 isoforms. Antisera isolated from an animal is an exemplary composition, as is a composition comprising an antibody fraction of an antisera that has been resuspended in water or in another diluent, excipient, or carrier.

In still another related embodiment, the invention provides an anti-idiotypic antibody specific for an antibody that is specific for one or more of the human caspase-12 polypeptide isoforms.

Also within the scope of the invention are compositions comprising polypeptides, polynucleotides, antibodies, or other modulators of the invention that have been formulated with, e.g., a pharmaceutically acceptable carrier.

The invention also provides assays to identify compounds that bind to and/or inhibit human caspase-12. One such assay comprises the steps of: (a) contacting a composition comprising a human caspase-12 polypeptide with a test compound; and (b) measuring binding between the compound and human caspase-12. The binding may be measured by any one of numerous methods known in the art. Exemplary assay formats are described herein.

The invention also provides a method for identifying a modulator (e.g., inhibitor or enhancer/activator) of human caspase-12 enzymatic activity comprising the steps of: (a) contacting a human caspase-12 substrate and a composition comprising a human caspase-12 polypeptide in the presence and in the absence of a putative modulator compound; (b) detecting proteolytic (enzymatic) activity of the human caspase-12 substrate; and (c) identifying a putative modulator compound in view of decreased or increased proteolytic activity of human caspase-12 in the presence of the putative modulator, as compared to proteolysis in the absence of the putative modulator. Also provided are methods to identify modulators of binding of human caspase-12 to adaptor molecules, receptor molecules, substrates or other ligands, e.g., comprising the steps of (a) contacting a human caspase-12 polypeptide with a binding partner in the presence and absence of a test compound, and (b) detecting binding of the caspase polypeptide to the binding partner, wherein a decrease in binding indicates that the test compound is an inhibitor of binding.

Further, the invention provides a method for identifying a candidate activator of human caspase-12 comprising the steps of contacting a composition comprising a caspase polypeptide lacking an active site sequence, a caspase polypeptide having an active site sequence and a substrate, and measuring enzymatic activity of said composition in the presence and absence of a test compound, wherein a change in enzymatic activity means that the test compound is a candidate modulator.

A number of the caspases identified have been characterized as important effector molecules for apoptosis, whereas other caspases are involved in cytokine processing associated with inflammation. The invention provides a method for treating a disease or disorder associated with inappropriate apoptosis or abnormal inflammation (including any diseases or disorders described in further detail herein) caused by activation of human caspase-12 comprising the step of administering to a mammal in need of such treatment an amount of a caspase inhibitor of the invention (e.g., antibodies, antisense polynucleotides, or other inhibitors, including inhibitors identified by the screening methods of the invention) that is sufficient to inhibit activation of human caspase-12 (i.e., a therapeutically effective amount), thereby inhibiting apoptosis or inhibiting cytokine processing. The invention also provides a method of inducing apoptosis by administering human caspase-12 polynucleotides or polypeptides or agonists of the invention for therapeutic use as anti-viral or anti-tumor agents. Treatment methods using small molecules that mimic, agonize or antagonize the activation of human caspase-12, including small molecules identified by the screening methods of the invention, are also contemplated. Treatment of individuals having any of these disorders is contemplated as an aspect of the invention.

Use of any of the human caspase-12 polynucleotides, polypeptides, inhibitors or agonists of the invention in preparation of a medicament for the treatment of any of the disorders described herein is also contemplated. Thus, the invention provides a method of using one or more of these products, such as a compound that binds to and/or inhibits human caspase-12, in the manufacture of a medicament for preventing or treating a disorder involving, e.g., inappropriate apoptosis and/or excessive cell proliferation, such as an inflammatory disease, a neurodegenerative disease, cancer, a cardiovascular disease and, indeed, any disorder or disease characterized by a gradual and prolonged development of apoptosis.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIG. 1A through FIG. 1B shows an alignment of the amino acid sequences of a human caspase-12 isoform designated KW-A (SEQ ID NO: 4) with other members of the caspase family: human caspase-1 (SEQ ID NO: 80), putative human caspase-13 (SEQ ID NO: 81), human caspase-4 (SEQ ID NO: 82), human caspase-5 (SEQ ID NO: 83), mouse caspase-12 (SEQ ID NO: 84) and mouse caspase-11 (SEQ ID NO: 85). Legend: $^a$translated amino acid sequence from putative human caspase 13 in EMBL database; $^{b}$"*" means amino acid is identical for all sequences; ":" means amino acids are considered conservative substitutions among all sequences; "." means amino acids may be considered conservative substitutions among all sequences.

FIG. 2A through FIG. 2B shows an alignment of the amino acid sequences of isoforms KW-A (SEQ ID NO: 51), KW-B (SEQ ID NO: 53), KW-C (SEQ ID NO: 55), KW-D (SEQ ID NO: 57), KW-E (SEQ ID NO: 59), KW-F (SEQ ID NO: 61), KW-G (SEQ ID NO: 63), KW-H (SEQ ID NO: 65), KW-I (SEQ ID NO: 67), KW-J (SEQ ID NO: 69), and KW-K (SEQ ID NO: 71) as well as hCaspase-12. For purposes of this Figure only, "X" means a stop codon.

FIG. 3 shows an alignment of a non-naturally occurring variant human caspase-12 isoform, designated hCaspase-12 (SEQ ID NO: 77) in the Figure and described in more detail in Example 3B below, with murine caspase-12 (SEQ ID NO: 84). Legend for Domains as calculated by PFAM: CARD Domain=XXXXXXX; ICE-p20 Domain; YYYYYYY; ICE-p10 Domain: ZZZZZZZ; Active-Site Residues: H . . . C; Calpain and Auto-catalytic cleavage sites determined for Mouse Caspase-12.

FIG. 4A through FIG. 4E shows an alignment of the amino acid sequences of the non-naturally occurring variant hCaspase-12 (SEQ ID NO: 77), murine caspase-12 (SEQ ID NO: 84), human caspase-1 (SEQ ID NO: 80), human caspase-2 (SEQ ID NO: 97), human caspase-3 (SEQ ID NO: 98), human caspase-4 (SEQ ID NO: 82), human caspase-5 (SEQ ID NO: 83), human caspase-6 (SEQ ID NO: 99), human caspase-7 (SEQ ID NO: 100), human caspase-8 (SEQ ID NO: 101), human caspase-9 (SEQ ID NO: 102), human caspase-10 (SEQ ID NO: 103), human caspase-13 (SEQ ID NO: 104), and human caspase-14 (SEQ ID NO: 105).

FIG. 5A through FIG. 5B shows an alignment of the amino acid sequences of hCaspase-12 (SEQ ID NO: 77) and the most closely related human caspases, caspase-4, -5, -13 and -1.

FIG. 7 presents immunocytochemical data demonstrating dual fluorescence immunostaining in a single cell. Caspase-12 protein is visualized as red fluorescence in FIG. 7-A; GRP 78 is visualized as green fluorescence in FIG. 7-B. An image overlay of the caspase-12 scan with the GRP 78 scan is shown in FIG. 7-C.

FIG. 8-A shows a Western blot of procaspase-3 incubated with either recombinant human caspase-12 or the ΔCARD variant of human caspase-12. FIG. 8-B shows a Western blot of these same materials detected with antibody specific to the active enzyme.

FIG. 9-A shows Western blots of hCaspase-12 and RIK-5 proteins obtained from culture undergoing apoptosis. FIGS. 9-B and 9-C are control Western blots using antibodies to caspase-8 (Upstate Biotechnology) and caspase-3 (Santa Cruz Biotechnology), respectively.

FIG. 10-C is a Western blot showing induction of human caspase-12 in cultures treated with 40 μM β-amyloid [25–35] (BACHEM) for 40 hours. FIG. 10-D depicts a control Western blot using an antibody against GRP 78 (Santa Cruz Biotechnology).

FIG. 12 shows Western blots illustrating inhibition of caspase activation by caspase (ZVAD-fmk) or calpain (calpeptin) inhibitors in SH-EP cells subjected to ER stress. SH-EP cells were treated with 2 μM A23187 for 40 hours to induce expression of endogenous caspase-12. One culture was pre-incubated with 50 μM ZVAD-fmk, and another was pre-incubated with 10 μM calpeptin (Calbiochem) for 1 hour prior to UV irradiation. Cultures were harvested 6.5 hours after UV irradiation, lysates were prepared and proteins were resolved by NuPAGE gel electrophoresis. Detection relied on antibodies to caspase-12 as described above in Example 8A.

DETAILED DESCRIPTION OF THE INVENTION

1. Definitions

Figure 6:
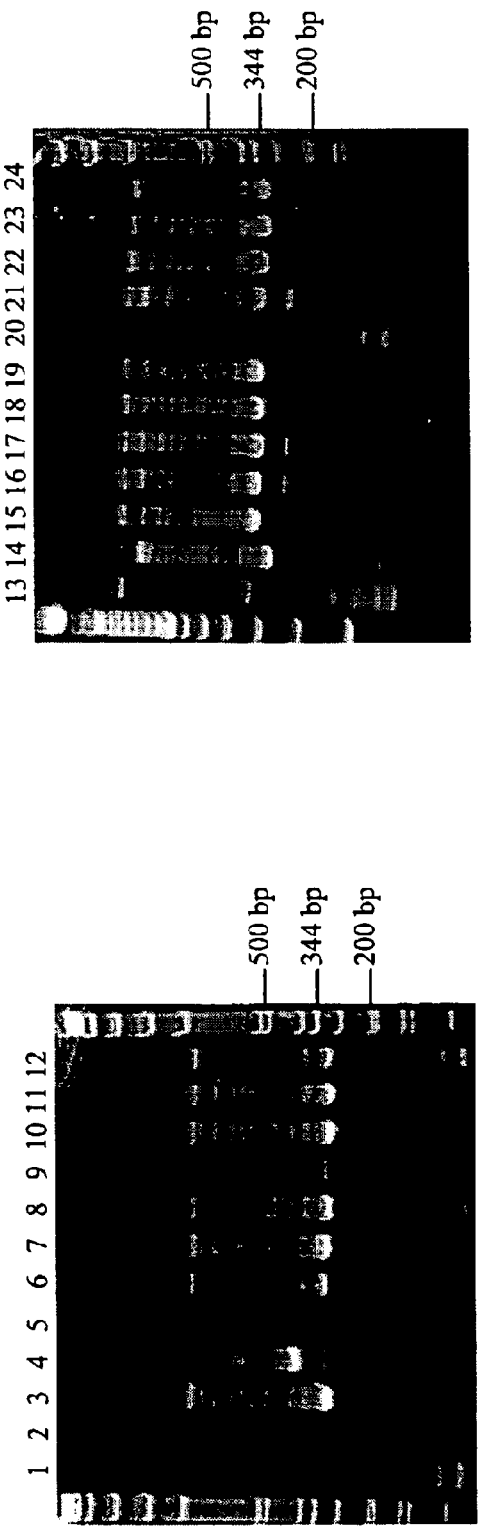
FIG. 6 shows the PCR products from the KW231/KW241 amplification of cDNA from multiple human tissues using the Sure-RACE system (OriGene Technologies, Inc.).

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art. "Synthesized" as used herein and understood in the art, refers to polynucleotides or polypeptides produced by purely chemical, as opposed to enzymatic, methods. "Wholly" synthesized DNA or amino acid sequences are therefore produced entirely by chemical means, and "partially" synthesized DNAs or polypeptides embrace those wherein only portions of the resulting DNA or polypeptide were produced by chemical means. By the term "region" is meant a physically contiguous portion of the primary structure of a biomolecule. In the case of proteins, a region is defined by a contiguous portion of the amino acid sequence of that protein. The term "domain" is herein defined as referring to a structural part of a biomolecule that contributes to a known or suspected function of the biomolecule. Domains may be co-extensive with regions or portions thereof; domains may also incorporate a portion of a biomolecule that is distinct from a particular region, in addition to all or part of that region. Examples of human caspase-12 protein domains include, but are not limited to, the N-terminal prodomain, the predicted CARD domain within the prodomain, the large subunit, the small subunit, and the catalytic domain.

As used herein, the term "activity" refers to a variety of measurable indicia suggesting or revealing binding, either direct or indirect; affecting a response, i.e. having a measurable affect in response to some exposure or stimulus, including, for example, the affinity of a compound for directly binding a polypeptide or polynucleotide of the invention, or, for example, measurement of amounts of upstream or downstream proteins or other similar functions after some stimulus or event, or enzymatic activity such as proteolysis of a substrate.

As used herein, the term "antibody" is meant to refer to complete, intact antibodies, and Fab, Fab', F(ab)$_2$, and other fragments thereof. Complete, intact antibodies include monoclonal and polyclonal antibodies, single chain antibodies, chimeric antibodies, bifunctional/bispecific antibodies, humanized antibodies, human antibodies, and complementary determining region (CDR)-grafted antibodies, including any compounds which include CDR and/or antigen-binding sequences from antibodies.

As used herein, the term "binding" means the physical or chemical interaction between two proteins or compounds or associated proteins or compounds or combinations thereof. Binding includes ionic, non-ionic, hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates.

As used herein, the term "compound" means any identifiable chemical or molecule, including, but not limited to, small molecule, peptide, protein, sugar, nucleotide, or nucleic acid, and such compound can be natural or synthetic, inorganic or organic.

As used herein, the term "complementary" refers to Watson-Crick base pairing between nucleotide units of a nucleic acid molecule.

As used herein, the term "contacting" means bringing together, either directly or indirectly, a compound into physical proximity to a polypeptide or polynucleotide of the invention. The polypeptide or polynucleotide can be in any number of buffers, salts, solutions etc. Contacting includes, for example, placing the compound into a beaker, microtiter plate, cell culture flask, or a microarray, such as a gene chip, or the like, which contains a nucleic acid molecule or polypeptide of the invention.

As used herein, the phrase "homologous nucleotide sequence," or "homologous amino acid sequence," or variations thereof, refers to sequences characterized by a homology, at the nucleotide level or amino acid level, of at least the specified percentage. Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. A homologous nucleotide sequence does not, however, include the nucleotide sequence encoding other known caspases. Homologous amino acid sequences include those amino acid sequences which contain conservative amino acid substitutions and which polypeptides have the same binding and/or activity. A homologous amino acid sequence does not, however, include the amino acid sequence encoding other known caspases. Percent homology can be determined by, for example, the GAP program (Wisconsin Sequence Analysis Package, Version 10 for Unix, Genetics Computer Group, University Research Park, Madison Wis.), using the default settings, which uses the algorithm of Needleman and Wunsch [*J. Mol. Biol.* 48:443–453 (1970)], which is incorporated herein by reference in its entirety).

As used herein, the term "isolated" nucleic acid molecule refers to a nucleic acid molecule (DNA or RNA) that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

As used herein, the terms "modulates" or "modifies" means an increase or decrease in the amount, quality, or effect of a particular activity or protein.

As used herein, the term "oligonucleotide" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar or complementary DNA or RNA in a particular cell or tissue. Oligonucleotides comprise portions of a DNA sequence having at least about 10 nucleotides and as many as about 50 nucleotides, preferably about 15 to 30 nucleotides. They are chemically synthesized and may be used as probes.

As used herein, the term "probe" refers to nucleic acid sequences of variable length, preferably between at least about 10 and as many as about 6,000 nucleotides, depending on use. Exemplary probe sizes include at least about 15, 16, 17, 18, 19, 20, 30, 50, 100, 200, 300, and 400 nucleotides. They are used in the detection of identical, similar, or complementary nucleic acid sequences. Longer length probes are usually obtained from a natural or recombinant source, are highly specific and much slower to hybridize than oligomers. They may be single- or double-stranded and designed to have specificity in PCR, hybridization membrane-based, or ELISA-like technologies.

The term "preventing" refers to decreasing the probability that an organism contracts or develops an abnormal condition, including any disease or disorder described herein.

The term "treating" refers to having a therapeutic effect and at least partially alleviating or abrogating an abnormal condition in the organism, including any disease or disorder described herein.

The term "therapeutic effect" refers to the inhibition of activation factors causing or contributing to the abnormal condition or the reduction in adverse effects resulting from the abnormal condition (including any disease or disorder described herein.). A therapeutic effect relieves to some extent one or more of the symptoms of the abnormal condition.

The term "administering" relates to a method of incorporating a compound into cells or tissues of an organism. An abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques and carrier techniques.

By "amplification" it is meant increased numbers of DNA or RNA in a cell compared with normal cells. "Amplification" as it refers to RNA can be the detectable presence of RNA in cells, since in some normal cells there is no basal expression of RNA. In other normal cells, a basal level of expression exists, therefore in these cases amplification is the detection of at least 1–2-fold, and preferably more, compared to the basal level.

As used herein, the phrase "stringent hybridization conditions" or "stringent conditions" refers to conditions under which a probe, primer, or oligonucleotide will hybridize to its target sequence, but to no other sequences. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g. 10 to 50 nucleotides) and at least about 60° C. for longer probes, primers or oligonucleotides. Stringent conditions may also be achieved with the addition of destabilizing agents, such as formamide.

The amino acid sequences are presented in the amino to carboxy direction, from left to right. The amino and carboxy groups are not presented in the sequence. The nucleotide sequences are presented by single strand only, in the 5' to 3' direction, from left to right. Nucleotides and amino acids are represented in the manner recommended by the IUPAC-IUB Biochemical Nomenclature Commission or (for amino acids) by three letter code.

Genomic DNA of the invention comprises the protein-coding region for a polypeptide of the invention and is also intended to include allelic variants thereof. It is widely understood that, for many genes, genomic DNA is transcribed into RNA transcripts that undergo one or more splicing events wherein intron (i.e., non-coding regions) of the transcripts are removed, or "spliced out." RNA transcripts that can be spliced by alternative mechanisms, and therefore be subject to removal of different RNA sequences but still encode a human caspase-12 polypeptide, are referred to in the art as splice variants which are embraced by the invention. Splice variants comprehended by the invention therefore are encoded by the same original genomic DNA sequences but arise from distinct mRNA transcripts. Allelic variants are modified forms of a wild-type gene sequence, the modification resulting from recombination during chromosomal segregation or exposure to conditions which give rise to genetic mutation. Allelic variants, like wild-type genes, are naturally occurring sequences (as opposed to non-naturally occurring variants which arise from in vitro manipulation). Multiple isoforms can result from allelic or splice variants.

The invention also comprehends cDNA that is obtained through reverse transcription of an RNA polynucleotide encoding a human caspase-12 polypeptide (conventionally followed by second strand synthesis of a complementary strand to provide a double-stranded DNA).

2. Nucleic Acids of the Invention

The present invention provides purified and isolated polynucleotides (e.g., DNA sequences and RNA transcripts, both sense and complementary antisense strands, both single and double stranded, including allelic or splice variants thereof) encoding human caspase-12 polypeptides. DNA polynucleotides of the invention include genomic DNA, cDNA, and DNA that has been chemically synthesized in whole or in part.

Exemplary DNA sequences encoding human caspase-12 polypeptides of the invention are set out in SEQ ID NOS: 1, 3, 5, 7, 9, 10, 50, 52, 54, 56, 58, 60, 62, 64, 66, 68, 70, 72, 74, 76 or 78. Nucleotides 1–1023 of SEQ ID NOS: 1, 3, and 50, nucleotides 1–913 of SEQ ID NOS: 5, 7, and 52, nucleotides 1–788 of SEQ ID NO: 9, nucleotides 1–678 of SEQ ID NO: 10, nucleotides 1–389 of SEQ ID NO: 58, nucleotides 1–477 of SEQ ID NO: 60, nucleotides 1–494 of SEQ ID NO: 62, nucleotides 1–604 of SEQ ID NO: 64, nucleotides 1–702 of SEQ ID NO: 66, nucleotides 1–503 of SEQ ID NO: 68, nucleotides 9–1126 of SEQ ID NO: 70, nucleotides 9–1127 of SEQ ID NO: 72, nucleotides 1–864 of SEQ ID NO: 74, nucleotides 9–1127 of SEQ ID NO: 76, and nucleotides 1–864 of SEQ ID NO: 78, respectively, represent approximately the coding sequences of these human caspase-12 isoforms or variants (which may be surrounded by upstream and downstream untranslated sequences). Nucleotides 7–270, 287–681, and 760–1023 of SEQ ID NO: 3 represent approximately the putative CARD domain, and large and small subunits, respectively, of isoform A. Nucleotides 7–270, 287–681, and 760–913 of SEQ ID NO: 7 represent approximately the putative CARD domain, and large and small subunits, respectively, of isoform B. Nucleotides 7–255, 287–446, and 525–788 of SEQ ID NO: 9 represent approximately the putative CARD domain, and large and small subunits, respectively, of isoform C. Nucleotides 7–255, 287–446, and 525–678 of SEQ ID NO: 10 represent approximately the putative CARD domain, and large and small subunits, respectively, of isoform D.

The following table shows which nucleotides and amino acids represent approximately the putative CARD domain, A subunit (small subunit) and B subunit (large subunit) of the isoforms. The bridge peptide is found between the A and B subunits.

| Isoform | CARD domain | A subunit | B subunit |
|---|---|---|---|
| KW-A | nt 7–270 of SEQ ID NO:50<br>aa 3–86 of SEQ ID NO:51 | nt 287–681 of SEQ ID NO:50<br>aa 96–227 of SEQ ID NO:51 | nt 760–1023 of SEQ ID NO:50<br>aa 254–341 of SEQ ID NO:51 |
| KW-B | nt 7–270 of SEQ ID NO:52<br>aa 3–86 of SEQ ID NO:53 | nt 287–681 of SEQ ID NO:52<br>aa 96–227 of SEQ ID NO:53 | nt 760–913 of SEQ ID NO:52<br>aa 254–304 of SEQ ID NO:53 |
| KW-C | nt 7–255 of SEQ ID NO:54<br>aa 3–86 of SEQ ID NO:55 | nt 287–446 of SEQ ID NO:54<br>aa 96–148 of SEQ ID NO:55 | nt 525–788 of SEQ ID NO:54<br>aa 175–262 of SEQ ID NO:55 |
| KW-D | nt 7–255 of SEQ ID NO:56<br>aa 3–86 of SEQ ID NO:57 | nt 287–446 of SEQ ID NO:56<br>aa 96–148 of SEQ ID NO:57 | nt 525–678 of SEQ ID NO:56<br>aa 175–225 of SEQ ID NO:57 |
| KW-E | none | nt 97–389 of SEQ ID NO:58<br>aa 33–130 of SEQ ID NO:59 | none |
| KW-F | none | nt 103–477 of SEQ ID NO:60<br>aa 35–159 of SEQ ID NO:61 | none |
| KW-G | none | nt 103–262 of SEQ ID NO:62<br>aa 35–87 of SEQ ID NO:63 | nt 371–494 of SEQ ID NO:62<br>aa 114–164 of SEQ ID NO:63 |
| KW-H | none | nt 103–262 of SEQ ID NO:64<br>aa 35–87 of SEQ ID NO:65 | nt 371–604 of SEQ ID NO:64<br>aa 114–200 of SEQ ID NO:65 |
| KW-I | none | nt 103–469 of SEQ ID NO:66<br>aa 35–156 of SEQ ID NO:67 | nt 549–702 of SEQ ID NO:66<br>aa 183–233 of SEQ ID NO:67 |
| KW-J | nt 1–258 of SEQ ID NO:68<br>aa 3–86 of SEQ ID NO:69 | nt 287–503 of SEQ ID NO:68<br>aa 96–167 of SEQ ID NO:69 | none |
| KW-K | nt 15–284 of SEQ ID NO:70<br>aa 3–92 of SEQ ID NO:71 | nt 389–784 of SEQ ID NO:70<br>aa 128–259 of SEQ ID NO:71 | nt 863–1126 of SEQ ID NO:70<br>aa 286–373 of SEQ ID NO:71 |

The worker of skill in the art will readily appreciate that the DNA of the invention comprises a double-stranded molecule, for example the molecule having the sequence set forth in SEQ ID NOS: 1, 3, 5, 7, 9, 10, 50, 52, 54, 56, 58, 60, 62, 64, 66, 68, 70, 72, 74, 76 or 78 along with the complementary molecules (the "non-coding strand" or "complement") having a sequence deducible from the sequences of SEQ ID NOS: 1, 3, 5, 7, 9, 10, 50, 52, 54, 56, 58, 60, 62, 64, 66, 68, 70, 72, 74, 76 or 78 according to Watson-Crick base pairing rules for DNA. Other exemplary polynucleotides of the invention encode the human caspase-12 polypeptides of SEQ ID NOS: 2,4, 6, 8, 51, 53, 55, 57, 59, 61, 63, 65, 67, 69, 71, 73, 75, 77 or 79 or fragments thereof; and differ in sequence from the polynucleotides of SEQ ID NOS: 1, 3, 5, 7, 9, 10, 50, 52, 54, 56, 58, 60, 62, 64, 66, 68, 70, 72, 74, 76 or 78 by virtue of the well-known degeneracy of the universal genetic code.

The invention includes polynucleotides encoding a caspase or a subunit, domain or truncation thereof, which nucleotides are at least about 99%, at least about 98%, at least about 95%, at least about 90%, at least about 85%, at least about 80%, at least about 75%, or at least about 70% identical to one of the nucleotide sequences set forth in SEQ ID NOS: 1, 3, 5, 7, 9, 10, 50, 52, 54, 56, 58, 60, 62, 64, 66, 68, 70, 72, 74, 76 or 78 or a subunit- or domain-encoding portion thereof. Polynucleotides encoding naturally occurring isoforms of human caspase-12 are specifically contemplated, which preferably have at least about 98% identity to 100 contiguous nucleotides of the nucleotide sequences of SEQ ID NOS: 1, 3, 5, 7, 9, 10, 50, 52, 54, 56, 58, 60, 62, 64, 66, 68, 70, 72, 74, 76 or 78 or a subunit- or domain-encoding portion, or a non-coding strand thereof.

The invention further embraces species homologs of the human caspase-12 polynucleotides of the invention. Species homologs, sometimes referred to as "orthologs," generally share at least 35%, at least 40%, at least 45%, at least 50%, at least 60%, at least 65%, at least 70%, at least 75%, at least 80%, at least 85%, at least 90%, at least 95%, at least 98%, or at least 99% homology with human DNA of the invention. Percent sequence "homology" with respect to polynucleotides of the invention is defined herein as the percentage of nucleotide bases in the candidate sequence that are identical to a contiguous region of nucleotides in any of the human caspase-12 polynucleotides set forth in SEQ ID NOS: 1, 3, 5, 7, 9, 10, 50, 52, 54, 56, 58, 60, 62, 64, 66, 68, 70, 72, 74, 76 or 78; after aligning the sequences and introducing gaps, if necessary, to achieve the maximum percent sequence identity. Although described in greater detail in the context of amino acid sequence comparisons (see below), a variety of algorithms for performing sequence comparisons are known in the art. By way of non-limiting example, the GCG Package (Wisconsin Package 10, Genetics Computer Group, Madison Wis., January, 1999) is available to compare sequences at the nucleic acid level as well as the amino acid level. In comparing polynucleotide sequences using either the GCG Package referenced above or the algorithm described by Needleman et al., *J. Mol Biol.* (1970) 48:443–453), the following default parameters are preferred: comparison matrix: match=+10, mismatch=0, with a gap penalty of 50 and a gap length penalty of 3. Other algorithms which may be used include the BLAST family of algorithms (blastn, blastp, blastx, tblastn, tblastx and the like) (Altschul et al., *Nucl. Acids Res.* (1997) 25:3389–3402), as well as the FASTA family (fasta, fastx, tfasta and tfastx) (Pearson et al., *Proc. Natl. Acad. Sci.* (*USA*) (1988) 85:2444–48).

The invention also embraces polynucleotides encoding a caspase or a subunit domain, or truncation thereof, which polynucleotides hybridize under moderately stringent or high stringency conditions to the non-coding strand, or complement, of any of the polynucleotides in SEQ ID NOS: 1, 3, 5, 7, 9, 10, 50, 52, 54, 56, 58, 60, 62, 64, 66, 68, 70, 72, 74, 76 or 78. Such polynucleotides preferably encode at least one subunit or domain of human caspase-12 or a fragment thereof capable of enzymatic or ligand-binding activity (including binding to substrate, adaptor or receptor molecules) alone or in association with other caspase subunits or fragments.

For human caspase-12, exemplary moderately stringent hybridization conditions are as follows: hybridization at 42° C. in a hybridization solution comprising 50% formamide, 1% SDS, 1 M NaCl, 10% Dextran sulfate, and washing twice for 30 minutes at 60° C. in a wash solution comprising 0.1×SSC and 1% SDS. Highly stringent conditions include washes at 68° C. in a wash solution comprising 0.1×SSC and 1% SDS. It is understood in the art that conditions of equivalent stringency can be achieved through variation of temperature and buffer, or salt concentration as described Ausubel, et al. (Eds.), *Current Protocols in Molecular Biology*, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook et al., (Eds.), *Molecular Cloning: A Laboratory Manual,* Cold Spring Harbor Laboratory Press: Cold Spring Harbor, N.Y. (1989), pp. 9.47 to 9.51.

The polynucleotide sequence information provided by the invention makes possible large scale expression of the encoded polypeptide by techniques well known and routinely practiced in the art. Polynucleotides of the invention also permit identification and isolation of polynucleotides encoding human caspase-12 polypeptides, such as human allelic variants and species homologs, by well known techniques including Southern and/or Northern hybridization, and polymerase chain reaction (PCR). Examples of related polynucleotides include human and non-human genomic sequences, including allelic variants, as well as polynucleotides encoding polypeptides homologous to human caspase-12 isoforms and structurally related polypeptides sharing one or more biological, immunological, and/or physical properties of any one of the human caspase-12 polypeptides of the invention. Non-human species genes encoding proteins homologous to human caspase-12 can also be identified by Southern and/or PCR analysis and are useful in animal models for disorders associated with human caspase-12. Knowledge of the sequence of a human caspase-12 polynucleotide also makes possible, through use of Southern hybridization or polymerase chain reaction (PCR), the identification of genomic DNA sequences that comprise regulatory sequences such as promoters, operators, enhancers, repressors, and the like, that control expression of human caspase-12 polynucleotides of the invention or levels of expression of human caspase-12 that may correlate with a disease state or states. Polynucleotides of the invention are also useful in hybridization assays to detect the capacity of cells to express human caspase-12 polynucleotides of the invention. Polynucleotides of the invention may also provide a basis for diagnostic methods useful for identifying a genetic alteration(s) in the human caspase-12 locus that underlies a disease state or states, which information is useful for diagnosis and for selection of therapeutic strategies.

The disclosure herein of a full-length polynucleotide encoding a human caspase-12 polypeptide makes readily available to the worker of ordinary skill in the art every possible fragment of the full-length polynucleotide. The invention therefore provides fragments of human caspase-12 polynucleotides comprising at least 14–15, and preferably at least 16, 17, 18, 20, 25, 50, or 75 consecutive nucleotides of a polynucleotide encoding human caspase-12. Preferably, fragment polynucleotides of the invention comprise sequences unique to the polynucleotide sequence encoding human caspase-12, and therefore hybridize under highly stringent or moderately stringent conditions only (i.e., "specifically") to polynucleotides encoding a human caspase-12 polypeptide (or fragments thereof). Insofar as it is anticipated that caspase-12 is autoprocessed at a cleavage site extending from amino acid 108 to amino acid 117 of hCaspase-12 (SEQ ID NO: 77), with cleavage involving a peptide bond of residue 114 (Lys), preferred polynucleotide fragments would extend from either terminus of the corresponding polynucleotide sequence encoding hCaspase-12 (SEQ ID NO: 76) to the codon adjacent the codon encoding the Lys residue or to the codon encoding the Lys residue itself (e.g., polynucleotides encoding peptides having residues 1–113, 1–114, 114–373, or 115–373 of SEQ ID NO: 77).

Polynucleotide fragments of genomic sequences of the invention comprise not only sequences unique to the coding region, but also include fragments of the full-length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern and Northern hybridization analyses to determine the number of fragments of genomic DNA and RNA to which a polynucleotide will hybridize. Polynucleotides of the invention can be labeled in a manner that permits their detection, including radioactive, fluorescent, and enzymatic labeling.

Fragment polynucleotides can also encode epitopes specific to human caspase-12. Fragment polynucleotides are particularly useful as probes for detection of full-length or fragments of human caspase-12 polynucleotides. One or more polynucleotides can be included in kits that are used to detect the presence of a polynucleotide encoding human caspase-12, or used to detect variations in a polynucleotide sequence encoding human caspase-12.

Also made available by the invention are antisense polynucleotides which recognize and hybridize to polynucleotides encoding human caspase-12. Full-length and fragment anti-sense polynucleotides are provided. Fragment antisense molecules of the invention include those that specifically recognize and hybridize to one or more RNAs of human caspase-12 (as determined by sequence comparison of DNAs encoding human caspase-12 polypeptides to DNA encoding other known molecules). Identification of sequences unique to polynucleotides encoding human caspase-12 polypeptides of the invention, can be deduced through use of any publicly available sequence database, and/or through use of commercially available sequence comparison programs. The uniqueness of selected sequences in an entire genome can be further verified by hybridization analyses. After identification of the desired sequences, isolation through restriction digestion or amplification using any of the various polymerase chain reaction techniques well known in the art can be performed. Antisense polynucleotides are particularly relevant to regulating expression of one or more of the human caspase-12 polypeptide isoforms and/or polynucleotide isoforms by those cells expressing mRNA encoding a human caspase-12 polypeptide of the invention.

Antisense oligonucleotides, or fragments of a nucleotide sequence set forth in SEQ ID NOS: 1, 3, 5, 7, 9, 10, 50, 52, 54, 56, 58, 60, 62, 64, 66, 68, 70, 72, 74, 76 or 78; or sequences complementary or homologous thereto, derived from the nucleotide sequences of the present invention encoding human caspase-12 polypeptides are useful as diagnostic tools for probing gene expression in various tissues. For example, tissue can be probed in situ with oligonucleotide probes carrying detectable groups by conventional autoradiography techniques to investigate native expression of this enzyme or pathological conditions relating thereto. Antisense oligonucleotides are preferably directed to regulatory regions of a nucleotide sequence of SEQ ID NOS: 1, 3, 5, 7, 9, 10, 50, 52, 54, 56, 58, 60, 62, 64, 66, 68, 70, 72, 74, 76 or 78; or mRNA corresponding thereto, including, but not limited to, the initiation codon, TATA box, enhancer sequences, and the like.

Antisense nucleic acids (preferably 10 to 20 base pair oligonucleotides) capable of specifically binding to DNA comprising expression control sequences or RNA of human caspase-12 are introduced into cells (e.g., by a viral vector or colloidal dispersion system such as a liposome). The antisense nucleic acid binds to the target nucleotide sequence encoding a human caspase-12 polypeptide in the cell and prevents transcription or translation of the target sequence. Phosphorothioate and methylphosphonate antisense oligonucleotides are specifically contemplated for therapeutic use by the invention. The antisense oligonucleotides may be further modified by poly-L-lysine, transferrin, polylysine, or cholesterol moieties at their 5' end. Suppressing the expression of a human caspase-12 polynucleotide and/or polypeptide at either the transcriptional or translational level is useful to general cellular and/or animal models for diseases characterized by aberrant expression.

The invention further embraces methods to modulate transcription of human caspase-12 through use of oligonucleotide-directed triple helix formation. For a review, see Lavrovsky, et al., Biochem. Mol. Med. 62:11–22 (1997). Triple helix formation is accomplished using sequence specific oligonucleotides which hybridize to double stranded DNA in the major groove as defined in the Watson-Crick model. Hybridization of a sequence specific oligonucleotide can thereafter modulate activity of DNA-binding proteins, including, for example, transcription factors and polymerases. Preferred target sequences for hybridization include promoter and enhancer regions to permit transcriptional regulation of the expression of human caspase-12. In addition to use of oligonucleotides, triple helix formation techniques of the invention also embrace use of peptide nucleic acids as described in Corey, TIBTECH 15:224–229 (1997).

Oligonucleotides which are capable of triple helix formation are also useful for site-specific covalent modification of target DNA sequences. Oligonucleotides useful for covalent modification are coupled to various DNA damaging agents as described in Lavrovsky, et al., supra.

The human caspase-12 polynucleotide and polypeptide sequences taught in the present invention facilitate the design of novel transcription factors for modulating expression of human caspase-12 polynucleotides in native cells and animals, and cells transformed or transfected with polynucleotides encoding human caspase-12 polypeptides. For example, the $Cys_2$-$His_2$ zinc finger proteins, which bind DNA via their zinc finger domains, have been shown to be amenable to structural changes that lead to the recognition of different target sequences. These artificial zinc finger proteins recognize specific target sites with high affinity and low dissociation constants, and are able to act as gene switches to modulate gene expression. Knowledge of the particular target sequence that regulates expression of human caspase-12 polynucleotides of the present invention facilitates the engineering of zinc finger proteins specific for the target sequence using known methods such as those that combine structure-based modeling and screening of phage display libraries [Segal et al., Proc Natl Acad Sci USA 96:2758–2763 (1999); Liu et al., Proc Natl Acad Sci USA 94: 5525–30 (1997); Greisman et al., Science 275: 657–61 (1997); Choo et al., J Mol Biol 273:525–32 (1997)]. Each zinc finger domain usually recognizes three or more base pairs. Since a recognition sequence of 18 base pairs is generally sufficient in length to render it unique in any known genome, a zinc finger protein consisting of 6 tandem repeats of zinc fingers would be expected to ensure specificity for a particular sequence [Segal et al., Proc Natl Acad Sci USA 96:2758–2763 (1999)]. The artificial zinc finger repeats, designed based on sequences specific for human caspase-12 polynucleotides, are fused to activation or repression domains to promote or suppress expression of human caspase-12 polynucleotides [Liu et al., Proc Natl Acad Sci USA 94: 5525–30 (1997)]. Alternatively, the zinc finger domains can be fused to the TATA box-binding factor (TBP) with varying lengths of linker region between the zinc finger peptide and the TBP to create either transcriptional activators or repressors [Kim et al, Proc Natl Acad Sci USA 94: 3616–3620 (1997)]. Such proteins, and polynucleotides that encode them, have utility for modulating expression of human caspase-12 polynucleotides and polypeptides in vivo in both native cells, animals and humans; and/or cells transfected with sequences encoding human caspase-12 polynucleotides and polypeptides. The novel transcription factor can be delivered to the target cells by transfecting constructs that express the transcription factor (gene therapy), or by introducing the protein. Engineered zinc finger proteins can also be designed to bind RNA sequences for use in therapeutics as alternatives to antisense or catalytic RNA methods [McColl et al., Proc Natl Acad Sci USA 96:9521–6 (1999); Wu et al., Proc Natl Acad Sci USA 92:344–348 (1995)]. The present invention contemplates methods of designing such transcription factors based on the gene sequence of the invention, as well as customized zinc finger proteins, that are useful to modulate expression of human caspase-12 polynucleotide or polypeptide in cells (native or transformed) whose genetic complement includes these sequences.

With the knowledge of the nucleotide sequence information disclosed in the present invention, one skilled in the art can identify and obtain nucleotide sequences which encode human caspase-12 polypeptides from different sources (i.e., different tissues or different organisms) through a variety of means well known to the skilled artisan and as disclosed by, for example, Sambrook et al., "Molecular cloning: a laboratory manual", Second Edition, Cold Spring Harbor Press, Cold Spring Harbor, N.Y. (1989), which is incorporated herein by reference in its entirety.

For example, polynucleotides that encode a full-length human caspase-12 polypeptide including additional isoforms may be obtained by screening of mRNA, cDNA, or genomic DNA with oligonucleotide probes or PCR primers generated from the human caspase-12 gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al.

A nucleic acid molecule comprising any of the human caspase-12 nucleotide sequences described above can alternatively be synthesized by use of the polymerase chain reaction (PCR) procedure, with the PCR oligonucleotide primers produced from the nucleotide sequences provided herein. See U.S. Pat. No. 4,683,195 to Mullis et al. and U.S. Pat. No. 4,683,202 to Mullis. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

A wide variety of alternative cloning and in vitro amplification methodologies are well known to those skilled in the art. Examples of these techniques are found in, for example, Berger et al., Guide to Molecular Cloning Techniques, Methods Enzymol. 152 Academic Press, Inc., San Diego, Calif. (Berger), which is incorporated herein by reference in its entirety.

The nucleic acid molecules of the present invention, and fragments derived therefrom, are useful for screening for polymorphisms associated with certain disorders, as well as for genetic mapping. Knowledge of such polymorphisms allows design of suitable hybridization or PCR or restriction fragment length polymorphism (RFLP) assays to detect the polymorphisms.

Autonomously replicating recombinant expression constructs such as plasmid and viral DNA vectors incorporating polynucleotides of the invention are also provided. Expression constructs wherein polynucleotides, encoding a human caspase-12 polypeptide of the invention, are operatively linked to an endogenous or exogenous expression control DNA sequence and a transcription terminator are also provided. Expression control DNA sequences include promoters, enhancers, and operators, and are generally selected based on the expression systems in which the expression construct is to be utilized. Preferred promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate, and preferably promote, homologous recombination in a host cell. Preferred constructs of the invention also include sequences necessary for replication in a host cell.

Expression constructs are preferably utilized for production of an encoded protein, but also may be utilized simply to amplify a polynucleotide encoding a human caspase-12 polypeptide of the invention.

Another aspect of the present invention is directed to vectors, or recombinant expression vectors, comprising any of the nucleic acid molecules described above. Vectors are used herein either to amplify DNA or RNA encoding a human caspase-12 polypeptide and/or to express DNA which encodes a human caspase-12 polypeptide. Preferred vectors include, but are not limited to, plasmids, phages, phagemids, cosmids, viral particles or viruses, any other episome known in the art, and artificial chromosomes (e.g., bacterial and yeast) as well as integratable DNA fragments (i.e., fragments integratable into the host genome by homologous recombination). Preferred viral particles include, but are not limited to, adenoviruses, baculoviruses, parvoviruses, herpesviruses, poxviruses, adeno-associated viruses, Semliki Forest viruses, vaccinia viruses, and retroviruses. Preferred expression vectors include, but are not limited to, pcDNA3 (Invitrogen) and pSVL (Pharmacia Biotech). Other expression vectors include, but are not limited to, pSPORT™ vectors, pGEM™ vectors (Promega), pPROEXvectors™ (LTI, Bethesda, Md.), Bluescript™ vectors (Stratagene), pQE™ vectors (Qiagen), pSE420™ (Invitrogen), and pYES2™ (Invitrogen).

Preferred expression vectors are replicable DNA constructs in which a DNA sequence encoding a human caspase-12 polypeptide is operably linked or connected to suitable control sequences capable of effecting the expression of the human caspase-12 polynucleotide in a suitable host. DNA regions are operably linked or connected when they are functionally related to each other. For example, a promoter is operably linked or connected to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences in the expression vector will vary depending upon the host selected and the transformation method chosen. Generally, control sequences include a transcriptional promoter, an optional operator sequence to control transcription, a sequence encoding suitable mRNA ribosomal binding and sequences which control the termination of transcription and translation.

Preferred vectors preferably contain a promoter that is recognized by the host organism. The promoter sequences of the present invention may be prokaryotic, eukaryotic or viral. Examples of suitable prokaryotic sequences include the $P_R$ and $P_L$ promoters of bacteriophage lambda (The bacteriophage Lambda, Hershey, A. D., Ed., Cold Spring Harbor Press, Cold Spring Harbor, N.Y. (1973), which is incorporated herein by reference in its entirety; Lambda II, Hendrix, R. W., Ed., Cold Spring Harbor Press, Cold Spring Harbor, N.Y. (1980), which is incorporated herein by reference in its entirety); the trp, recA, heat shock, and lacZ promoters of *E. coli* and the SV40 early promoter (Benoist et al. *Nature*, 1981, 290, 304–310, which is incorporated herein by reference in its entirety). Additional promoters include, but are not limited to those of mouse mammary tumor virus, long terminal repeat of human immunodeficiency virus, Maloney Murine Leukemia Virus, cytomegalovirus immediate early promoter, Epstein Barr virus, Rous Sarcoma Virus, human actin, human myosin, human hemoglobin, human muscle creatine, and human metallothionein.

Additional regulatory sequences can also be included in preferred vectors. Preferred examples of suitable regulatory sequences are represented by the Shine-Dalgarno of the replicase gene of the phage MS-2 and of the gene cII of bacteriophage lambda. The Shine-Dalgarno sequence may be directly followed by DNA encoding a human caspase-12 polypeptide and result in the expression of the mature human caspase-12 protein.

Moreover, suitable expression vectors can include an appropriate marker that allows the screening of the transformed host cells. The transformation of the selected host is carried out using any one of the various techniques well known to the expert in the art and described in Sambrook et al., supra.

An origin of replication can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and a human caspase-12 DNA. An example of a suitable marker is dihydrofolate reductase (DHFR) or thymidine kinase (see, U.S. Pat. No. 4,399,216).

Nucleotide sequences encoding human caspase-12 polypeptides may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al., *Mol. Cell. Biol.* (1983) 3, 280, Cosman et al., *Mol. Immunol.* (1986) 23, 935, Cosman et al., *Nature* (1984) 312, 768, EP-A-0367566, and WO 91/18982, each of which is incorporated herein by reference in its entirety.

3. Hosts

According to another aspect of the invention, host cells are provided, including prokaryotic and eukaryotic cells, comprising a polynucleotide of the invention (or construct/ vector of the invention) in a manner which permits expression of the encoded human caspase-12 polypeptide. Polynucleotides of the invention may be introduced into the host cell as part of a circular plasmid, or as linear DNA comprising an isolated protein coding region or using a viral vector. Methods for introducing DNA into the host cell well known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, and mammalian cells systems.

Host cells of the invention are a valuable source of immunogen for development of antibodies specifically immunoreactive with a human caspase-12 polypeptide of the invention. Host cells of the invention are also useful in methods for large scale production of human caspase-12 polypeptides wherein the cells are grown in a suitable culture medium and the desired polypeptide products are isolated from the cells or from the medium in which the cells are grown by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those wherein the desired protein is expressed and purified as a fusion protein having a specific tag, label, or chelating moiety that is recognized by a specific binding partner or agent. The purified protein can be cleaved to yield the desired protein, or be left as an intact fusion protein. Cleavage of the fusion component may produce a form of the desired protein having additional amino acid residues as a result of the cleavage process.

Knowledge of DNA sequences encoding a human caspase-12 polypeptide of the invention allows for modification of cells to permit, or increase, expression of endogenous genes corresponding to human caspase-12. Cells can be modified (e.g., by homologous recombination) to provide increased expression by replacing, in whole or in part, the naturally occurring promoter that controls expression of human caspase-12, with all or part of a heterologous promoter so that the cells express the human caspase-12 polynucleotide at higher levels. The heterologous promoter is inserted in such a manner that it is operatively linked to endogenous sequences encoding human caspase-12. [See, for example, PCT International Publication No. WO 94/12650, PCT International Publication No. WO 92/20808, and PCT International Publication No. WO 91/09955.] It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the sequence encoding a human caspase-12 polypeptide, amplification of the marker DNA by standard selection methods results in co-amplification of the human caspase-12 sequences in the cells.

The DNA sequence information provided by the present invention also makes possible the development through, e.g. homologous recombination or "knock-out" strategies [Capecchi, Science 244:1288–1292 (1989)], of animals that fail to express one or more functional human caspase-12 polypeptides or that express a specific variant of human caspase-12 or that over-express one or more human caspase-12 polypeptides of the invention. Such animals (especially small laboratory animals such as rats, rabbits, and mice) are useful as models for studying the in vivo activities of human caspase-12 polypeptides and modulators of human caspase-12 polypeptides and/or polynucleotides.

Another aspect of the present invention is directed to transformed host cells having an expression vector comprising any of the nucleic acid molecules described above. Expression of the nucleotide sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera Escherichia, Bacillus, Salmonella, Pseudomonas, Streptomyces, and Staphylococcus.

If a eukaryotic expression vector is employed, then the appropriate host cell would be any eukaryotic cell capable of expressing the cloned sequence. Preferably, eukaryotic cells are cells of higher eukaryotes. Suitable eukaryotic cells include, but are not limited to, non-human mammalian tissue culture cells and human tissue culture cells. Preferred host cells include, but are not limited to, insect cells, HeLa cells, Chinese hamster ovary cells (CHO cells), African green monkey kidney cells (COS cells), human 293 cells, and murine 3T3 fibroblasts. Propagation of such cells in cell culture has become a routine procedure (see, Tissue Culture, Academic Press, Kruse and Patterson, eds. (1973), which is incorporated herein by reference in its entirety).

In addition, a yeast host may be employed as a host cell. Preferred yeast cells include, but are not limited to, the genera Saccharomyces, Pichia, and Kluveromyces. Preferred yeast hosts are *S. cerevisiae* and *P. pastoris*. Preferred yeast vectors can contain an origin of replication sequence from a 2μ yeast plasmid, an autonomously replication sequence (ARS), a promoter region, sequences for polyadenylation, sequences for transcription termination, and a selectable marker gene. Shuttle vectors for replication in both yeast and *E. coli* are also included herein.

Alternatively, insect cells may be used as host cells. In a preferred embodiment, the polypeptides of the invention are expressed using a Baculovirus expression system (see, Luckow et al., *Bio/Technology* (1988) 6, 47, Baculovirus Expression Vectors: A Laboratory Manual, O'Rielly et al. (Eds.), W. H. Freeman and Company, New York (1992) and U.S. Pat. No. 4,879,236, each of which is incorporated herein by reference in its entirety). In addition, the MAX-BAC™ complete Baculovirus expression system (Invitrogen) can, for example, be used for production in insect cells.

4. Polypeptides of the Invention

The invention also provides purified and isolated human caspase-12 polypeptides encoded by polynucleotides of the invention. Exemplary polypeptides comprise any of the amino acid sequences set out in SEQ ID NOS: 2, 4, 6, 8, 51, 53, 55, 57, 59, 61, 63, 65, 67, 69, 71, 73, 75, 77 or 79, or fragments thereof, including epitopes specific to human caspase-12, or a caspase subunit or domain or other fragment capable of enzymatic or ligand-binding activity (including binding to substrate, adaptor, or receptor molecules) alone or in association with other subunits or fragments.

The invention also embraces human caspase-12 polypeptides that have at least 99%, at least 95%, at least 90%, at least 85%, at least 80%, at least 75%, at least 70%, at least 65%, at least 60%, at least 55% or at least 50% identity and/or homology to one or more of the preferred polypeptides of the invention. Percent amino acid sequence "identity" with respect to the preferred polypeptides of the invention is defined herein as the percentage of amino acid residues in the candidate sequence that are identical with the residues in any one of the human caspase-12 polypeptide sequences after aligning both sequences and introducing gaps, if necessary, to achieve the maximum percent sequence identity, and not considering any conservative substitutions as part of the sequence identity. Percent sequence "homology" with respect to preferred polypeptides of the invention is defined herein as the percentage of amino acid residues in the candidate sequence that are identical with the residues in any one of the human caspase-12 polypeptide sequence after aligning the sequences and introducing gaps, if necessary, to achieve the maximum percent sequence identity, and also considering any conservative substitutions as part of the sequence identity.

Percent homology is calculated as the percentage of amino acid residues in the smaller of two sequences which align with identical amino acid residue in the sequence being compared, when four gaps in a length of 100 amino acids may be introduced to maximize alignment [Dayhoff, in *Atlas of Protein Sequence and Structure*, Vol. 5, p. 124, National Biochemical Research Foundation, Washington, D.C. (1972), incorporated herein by reference].

Percent amino acid sequence "identity" with respect to the preferred polypeptides of the invention is defined herein as the percentage of amino acid residues in the candidate sequence that are identical with the residues in any one of the reference caspase-12 polypeptide sequences after aligning both sequences and introducing gaps, if necessary, to achieve the maximum percent sequence identity, and not considering any conservative substitutions as part of the sequence identity. Percent sequence "similarity" with respect to preferred polypeptides of the invention is defined herein as the percentage of amino acid residues in the candidate sequence that are identical with the residues in any one of the reference caspase-12 polypeptide sequences after aligning the sequences and introducing gaps, if necessary, to achieve the maximum percent sequence identity, and also considering any conservative substitutions as part of the sequence similarity. In one aspect, percent similarity is calculated as the percentage of amino acid residues in the smaller of two sequences which align with identical amino acid residue in the sequence being compared, when four gaps in a length of 100 amino acids are introduced to maximize alignment (Dayhoff, in *Atlas of Protein Sequence and Structure* (1972) 5:124, National Biochemical Research Foundation, Washington, D.C., incorporated herein by reference).

Sequence alignment of polypeptides for purposes of sequence comparison also can be done using a variety of multiple alignment servers, most of which are presently available on the Internet, e.g., Clustal W, MAP, PIMA, Block Maker, MSA, MEME, and Match-Box. Preferably Clustal W (Higgins et al., *Gene* (1988) 73:237–244; Higgins et al., *Meth. Enzymol.* (1996) 266:383–402) is employed for sequence alignment of polypeptides (and also, polynucleotides). Similarly, the program BLASTP compares an amino acid query sequence against a protein database, and TBLASTN compares a protein query sequence against a nucleotide sequence database dynamically translated in all six reading frames (both strands), and can be employed in the invention. Determinations of whether two amino acid sequences are substantially homologous (i.e., similar or identical) can also be based on FASTA searches in accordance with Pearson et al., *Proc. Natl. Acad. Sci. USA* (1988) 85:2444–2448.

In particular, preferred methods to determine identity and/or similarity are designed to give the largest match between the sequences tested. Methods to determine identity and similarity are codified in publicly available computer programs (e.g., such as those previously described). Preferred computer program methods to determine identity and similarity between two sequences include, but are not limited to, the GCG Package (Wisconsin Package 10, Genetics Computer Group, Madison, Wis., January, 1999), including the algorithm described by Needleman et al., above, as well as BLASTP, BLASTN, and the like ((Altschul et al., above), or FASTA-type algorithms (Pearson et al., above). The BLAST X program is publicly available from the National Center for Biotechnology Information (NCBI) and other sources (Altschul et al., *BLAST Manual*, NCB NLM NIH Bethesda, Md. 20894; Altschul et al., *J. Mol. Biol.* (1990) 215:403–410). The well known Smith Waterman algorithm may also be used to determine identity.

By way of example, using the computer program GCG Package identified above, two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the program. A standard comparison matrix (see Dayhoff et al., in: *Atlas of Protein Sequence and Structure*, (1978) vol. 5, supp. 3 for the PAM250 comparison matrix; see Henikoff et al., *Proc. Natl. Acad. Sci USA,* (1992) 89:10915–10919 for the BLOSUM 62 comparison matrix) is also used by the algorithm.

Preferred parameters for polypeptide sequence comparison include the following:

Algorithm: Needleman et al., J. Mol. Biol. (1970) 48:443–453, Comparison matrix: BLOSUM 62 from Henikoff and Henikoff, *Proc. Natl. Acad. Sci. USA* (1992)89:10915–10919.

Gap Penalty: 12

Gap Length Penalty: 4

Threshold of Similarity: 0

The GAP program is useful with the above parameters. The aforementioned parameters are the default parameters for polypeptide comparisons (along with no penalty for end gaps) using the GAP algorithm.

Other exemplary algorithms, gap opening penalties, gap extension penalties, comparison matrices, thresholds of similarity, etc. may be used by those of skill in the art, including those set forth in the Program Manual, Wisconsin Package, Version 10, January, 1999. The particular choices to be made will depend on the specific comparison to be made, such as DNA to DNA, protein to protein, protein to DNA; and additionally, whether the comparison is between pairs of sequences (in which case GAP or BestFit are generally preferred) or between one sequence and a large database of sequences (in which case FASTA or BLAST are preferred).

Certain alignment schemes for aligning two amino acid sequences may result in matching of only a short region of the two sequences, and this small aligned region may have very high sequence identity even though there is no significant relationship between the two full-length sequences. Accordingly, in a preferred embodiment, the selected alignment method will result in an alignment that spans at least about 66 contiguous amino acids of the claimed full-length polypeptide.

A polypeptide also may be considered homologous to a caspase-12 polypeptide of the invention if polynucleotides encoding the two polypeptides hybridize with one another. A higher degree of homology is shown if the hybridization occurs under hybridization conditions of greater stringency. Control of hybridization conditions and the relationships between hybridization conditions and degree of homology are understood by those skilled in the art (see, e.g., Sambrook et al., (Eds.), *Molecular Cloning: A Laboratory Manual,* Cold Spring Harbor Laboratory Press: Cold Spring Harbor, N.Y. (1989), pp. 9.47 to 9.51), and as described herein (see above).

Polypeptides of the invention include human caspase-12 polypeptides that are encoded by polynucleotides that hybridize under stringent, preferably highly stringent conditions, to the nucleotide sequences of SEQ ID NOS: 1, 3, 5, 7, 9, 10, 50, 52, 54, 56, 58, 60, 62, 64, 66, 68, 70, 72, 74, 76 or 78, or the non-coding strand thereof.

Polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. Glycosylated and non-glycosylated forms of human caspase-12 polypeptides are embraced.

The invention also embraces variant (or analog) human caspase-12 polypeptides. In one example, insertion variants are provided wherein one or more amino acid residues supplement an amino acid sequence of a human caspase-12 polypeptide. Insertions may be located at either or both termini of the protein, or may be positioned within internal regions of a human caspase-12 polypeptide sequence. Insertional variants with additional residues at either or both termini can include for example, fusion proteins and proteins including amino acid tags or labels.

Insertion variants include human caspase-12 polypeptides wherein one or more amino acid residues are added to a human caspase-12 polypeptide sequence, or to a fragment thereof that is capable of biological activity.

Variant products of the invention also include human caspase-12 polypeptides with additional amino terminal residues. The additional amino terminal residues may be derived from another protein, or may include one or more residues that are not identifiable as being derived from a specific protein. Human caspase-12 polypeptide products with an additional methionine residue at position −1 (Met$^-$$_1$-human caspase-12 polypeptide product) are contemplated, as are variants with additional methionine and lysine residues at positions −2 and −1 (Met$^{-2}$-Lys$^{-1}$-human caspase-12 polypeptide product). Variants of human caspase-12 polypeptides with additional Met, Met-Lys, Lys residues (or one or more basic residues in general) are particularly useful for enhanced recombinant protein production in bacterial host cell.

The invention also embraces human caspase-12 polypeptide variants having additional amino acid residues which result from use of specific expression systems. For example, use of commercially available vectors that express a desired polypeptide as part of glutathione-S-transferase (GST) fusion product provides the desired polypeptide having an additional glycine residue at position −1 after cleavage of the GST component from the desired polypeptide. Variants which result from expression in other vector systems are also contemplated.

Insertional variants also include fusion proteins wherein the amino and/or carboxy termini of a human caspase-12 polypeptide is fused to another polypeptide, such as a constant region of an immunoglobulin chain or fragment thereof, or a targeting moiety such as an antibody or fragment thereof.

In another aspect, the invention provides deletion variants wherein one or more amino acid residues in a human caspase-12 polypeptide are removed. Deletions can be effected at one or both termini of the human caspase-12 polypeptide, or with removal of one or more residues within the amino acid sequence of a human caspase-12 polypeptide. Deletion variants, therefore, include all fragments of a human caspase-12 polypeptide.

The invention also embraces polypeptide fragments of one or more of the sequence set out in SEQ ID NOS: 2, 4, 6, 8, 51, 53, 55, 57, 59, 61, 63, 65, 67, 69, 71, 73, 75, 77 or 79; wherein the fragments are capable of biological (e.g., intracellular signaling) alone or in association with other subunits or fragments, or maintain immunological properties of a human caspase-12 polypeptide. Fragments comprising at least 21, 22, 23, 24, 25, 30, 50, 75, 90, 150, or 200 consecutive amino acids of SEQ ID NOS: 2, 4, 6, 8, 51, 53, 55, 57, 59, 61, 63, 65, 67, 69, 71, 73, 75, 77 or 79 are comprehended by the invention. Preferred polypeptide fragments display antigenic properties unique to or specific for one or more of human caspase-12 isoforms and species homologs. Fragments of the invention having the desired biological and immunological properties can be prepared by any of the methods well known and routinely practiced in the art.

Specific deletion variants contemplated by the invention include variants lacking part or all of the prodomain and/or bridge peptide. Specific fragments include fragments corresponding to a subunit, protein interaction, or receptor-recognition domain. Exemplary polypeptide fragments are those that include the predicted prodomain corresponding to approximately amino acids 3–86 of SEQ ID NO: 4 (isoform A), the predicted large subunit corresponding to approximately amino acids 96–227 of SEQ ID NO: 4, the predicted bridge peptide corresponding to approximately amino acids 228–253 of SEQ ID NO: 4, and the predicted small subunit corresponding to approximately amino acids 254–341 of SEQ ID NO: 4, and other corresponding fragments in SEQ ID NO: 8 (isoform B) and the translated amino acid sequences corresponding to the nucleotide sequences of SEQ ID NOS: 9 and 10 (isoforms C and D). Putative domains within the amino acid sequence of human caspase-12 isoform-A (SEQ ID NO: 4) were predicted using the pfam model (Bateman et al., Nucl. Acids Res. 28:263–266 (2000) and the Motifs program in the GCG Package referenced above. In still another aspect, the invention provides substitution variants of human caspase-12 polypeptides. Substitution variants include those polypeptides wherein one or more amino acid residues of a human caspase-12 polypeptide are removed and replaced with alternative residues. In one aspect, the substitutions are conservative in nature, however, the invention embraces substitutions that are also non-conservative. Conservative substitutions for this purpose may be defined as set out in Tables A, B, or C below.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A (from WO 97/09433, page 10, published Mar. 13, 1997 (PCT/GB96/02197, filed Sep. 6, 1996), immediately below.

TABLE A

Conservative Substitutions I

| SIDE CHAIN CHARACTERISTIC | AMINO ACID |
|---|---|
| Aliphatic | |
| Non-polar | G A P I L V |
| Polar-uncharged | C S T M N Q |
| Polar-charged | D E K R |
| Aromatic | H F W Y |
| Other | N Q D E |

Alternatively, conservative amino acids can be grouped as described in Lehninger, [Biochemistry, Second Edition; Worth Publishers, Inc. NY:NY (1975), pp.71–77] as set out in Table B, immediately below.

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still an another alternative, exemplary conservative substitutions are set out in Table C, immediately below.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Specific substitution variants contemplated include variants in which Asp-X cleavage sites have been altered. Exemplary substitutions include those in which the residue X of the Asp-X cleavage site(s) is/are substituted with another amino acid, preferably a neutral amino acid (e.g., Gly, Ala, Cys, Ser, Leu or Phe). Variants in which amino acid substitutions are made within the active site of human caspase-12, QACRG, that result in proteins retaining proteolytic activity are also contemplated. Exemplary substitutions include substitutions of the first two amino acid residues in the caspase-12 active site, e.g., Q to A, Q to N or A to S. Proteolytically processed human caspase-12 polypeptides comprising one or more subunits or fragments and lacking prodomain and/or bridge regions are also contemplated. Such processed polypeptides may be in multimeric form, e.g., heterotetrameric form, and display enzymatic activity.

It should be understood that the definition of polypeptides of the invention is intended to include polypeptides bearing modifications other than the insertion, deletion, or substitution of amino acid residues. By way of example, the modifications may be covalent in nature, and include for example, chemical bonding with polymers, lipids, other organic, and inorganic moieties. Such derivatives may be prepared to increase circulating half-life of a polypeptide, or may be designed to improve targeting capacity for the polypeptide to desired cells, tissues, or organs. Similarly, the invention further embraces human caspase-12 polypeptides that have been covalently modified to include one or more water soluble polymer attachments such as polyethylene glycol, polyoxyethylene glycol, or polypropylene glycol. Variants of a human caspase-12 polypeptide that display ligand binding properties of one or more native human caspase-12 polypeptides and are expressed at higher levels, and variants that provide for constitutively active human caspase-12 polypeptides are particularly useful in assays of the invention. Such variants also are useful in cellular and animal models for diseases characterized by aberrant expression/activity of one or more human caspase-12 polypeptides of the invention.

In a related embodiment, the present invention provides compositions comprising purified polypeptides of the invention. Preferred compositions comprise, in addition to one or more polypeptides of the invention, a pharmaceutically acceptable (i.e., sterile and non-toxic) liquid, semisolid, or solid diluents that serve as pharmaceutical vehicles, excipients, or media. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil, and cocoa butter.

5. Antibodies

Also comprehended by the present invention are antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for any one of the human caspase-12 polypeptide isoforms including human caspase-12 subunits or fragments thereof. Preferred antibodies of the invention are human antibodies which can be produced and identified according to methods described in WO93/11236, published Jun. 20, 1993, which is incorporated herein by reference in its entirety. Antibody fragments, including Fab, Fab', F(ab')$_2$, and F$_v$, are also provided by the invention. The term "specific for," when used to describe antibodies of the invention, indicates that the variable regions of the antibodies of the invention recognize and bind one or more of the human caspase-12 polypeptides exclusively (i.e., able to distinguish human caspase-12 polypeptides from known polypeptides by virtue of measurable differences in binding affinity, despite the possible existence of localized sequence identity, homology, or similarity between human caspase-12 polypeptides and other polypeptides). Antibodies capable of fortuitously cross-reacting with any one of the human caspase-12 polypeptides of the invention that can be generated from polypeptides previously described in the literature (e.g., due to the existence of a similar epitope in both polypeptides) are considered "cross-reactive" antibodies. Such cross-reactive antibodies are not antibodies that are "specific" for any one of the human caspase-12 polypeptides of the invention. It will be understood that specific antibodies may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), *Antibodies A Laboratory Manual;* Cold Spring Harbor Laboratory; Cold Spring Harbor, N.Y. (1988), Chapter 6. Antibodies that recognize and bind fragments of one or more human caspase-12 polypeptide isoforms of the invention are also contemplated, provided that the antibodies are, first and foremost, specific for one or more human caspase-12 polypeptide isoforms. Antibodies of the invention can be produced using any method well known and routinely practiced in the art.

It is well known that antibodies contain relatively small antigen binding domains that can be isolated chemically or by recombinant techniques. Such domains are useful molecules that bind any one of the caspase-like polypeptides themselves. These domains may be reintroduced into human antibodies, or fused to toxins or other polypeptides. Thus, in still another embodiment, the invention provides a polypeptide comprising a fragment of an antibody specific for one or more human caspase-12 polypeptides of the invention, wherein the fragment and the polypeptide bind to one or more of the different human caspase-12 polypeptide isoforms of the invention. By way of non-limiting example, the invention provides polypeptides that are single chain antibodies and CDR-grafted antibodies.

Non-human antibodies may be humanized by any methods known in the art. In one method, the non-human CDRs are inserted into a human antibody or consensus antibody framework sequence. Further changes can then be introduced into the antibody framework to modulate affinity or immunogenicity.

Antibodies of the invention are useful for, for example, therapeutic purposes (by modulating activity of human caspase-12 polypeptides), diagnostic purposes to detect or quantitate human caspase-12 polypeptides, as well as purification of human caspase-12 polypeptides. Kits comprising an antibody of the invention for any of the purposes described herein are also comprehended. In general, a kit of the invention also includes a control antigen for which the antibody is immunospecific.

Specific binding molecules, including natural binding partners and synthetic compounds, can be identified or developed using isolated or recombinant human caspase-12 polypeptide products, variants thereof, or preferably, cells expressing such products. Binding partners are useful for purifying human caspase-12 polypeptide products and detecting or quantifying the amount of human caspase-12 polypeptide products in fluid and tissue samples using known immunological procedures. Binding molecules are also manifestly useful in modulating (i.e., blocking, inhibiting or stimulating) biological activities of human caspase-12 polypeptides, especially those activities involved in enzymatic activity.

6. Screening for Binding Partners and/or Modulators

The nucleotide and amino acid sequence information provided by the present invention also makes possible the identification of binding partner compounds with which human caspase-12 polypeptides or polynucleotides will interact. Methods to identify binding partner compounds include solution assays, in vitro assays wherein human caspase-12 polypeptides are immobilized, and cell based assays. Identification of binding partner compounds of human caspase-12 polypeptides provides candidates for therapeutic or prophylactic intervention in pathologies associated with normal or aberrant biological activity of human caspase-12.

The invention includes several assay systems for identifying binding partners for human caspase-12 polypeptides. In solution assays, methods of the invention comprise the steps of (a) contacting human caspase-12 polypeptides with one or more candidate binding partner compounds and (b) identifying the compounds that bind to the human caspase-12 polypeptide(s). Identification of the compounds that bind to human caspase-12 polypeptides can be achieved by isolating the human caspase-12 polypeptide/binding partner complex, and separating the human caspase-12 polypeptide from the binding partner compound. An additional step of characterizing the physical, biological, and/or biochemical properties of the binding partner compound is also comprehended in another embodiment of the invention. In one aspect, the human caspase-12 polypeptide/binding partner complex is isolated using an antibody immunospecific for either the human caspase-12 polypeptide or the candidate binding partner compound.

In still other embodiments, either the human caspase-12 polypeptide or the candidate binding partner compound comprises a label or tag that facilitates its isolation, and methods of the invention to identify binding partner compounds include a step of isolating the human caspase-12 polypeptide/binding partner complex through interaction with the label or tag. An exemplary tag of this type is a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

In one variation of an in vitro assay, the invention provides a method comprising the steps of (a) contacting an immobilized human caspase-12 polypeptide with a candidate binding partner compound and (b) detecting binding of the candidate compound to the human caspase-12 polypeptide. In an alternative embodiment, the candidate binding partner compound is immobilized and binding of human caspase-12 polypeptide is detected. Immobilization is accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin moiety. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

Agents, e.g., antibodies or organic/inorganic chemical compounds that modulate (i.e., increase, decrease, or block) the activity or expression of human caspase-12 polypeptides may be identified by incubating a putative modulator with a cell expressing a human caspase-12 polypeptide or polynucleotide and determining the effect of the putative modulator on the activity or expression of the human caspase-12 polypeptide or polynucleotide. The selectivity of a compound that modulates the activity of a human caspase-12 polypeptide or polynucleotide can be evaluated by comparing its effects on the human caspase-12 polypeptide or polynucleotide to its effect on other related compounds. Selective modulators may include, for example, antibodies and other proteins, peptides, or organic molecules which specifically bind to human caspase-12 polypeptides or to a nucleic acid encoding a human caspase-12 polypeptide. Modulators of human caspase-12 polypeptide activity will be therapeutically useful in treatment of diseases and physiological conditions in which normal or aberrant activity of human caspase-12 polypeptide is involved.

Methods of the invention to identify modulators include variations on any of the methods described above to identify binding partner compounds, the variations including techniques wherein a binding partner compound has been identified and the binding assay is carried out in the presence and absence of a candidate modulator. A modulator is identified in those instances where binding between human caspase-12 polypeptides and the binding partner compound changes in the presence of the candidate modulator compared to binding in the absence of the candidate modulator compound. A modulator that increases binding between a human caspase-12 polypeptide and the binding partner compound is described as an enhancer or activator, and a modulator that decreases binding between a human caspase-12 polypeptide and the binding partner compound is described as an inhibitor.

The invention also comprehends high throughput screening (HTS) assays to identify compounds that interact with or inhibit biological activity (i.e., inhibit enzymatic activity, binding activity, etc.) of a human caspase-12 polypeptide. HTS assays permit screening of large numbers of compounds in an efficient manner. Cell-based HTS systems are contemplated to investigate the interaction between human caspase-12 polypeptides and their binding partners. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and human caspase-12 polypeptides.

Another aspect of the present invention is directed to methods of identifying compounds that bind to either a human caspase-12 polypeptide or nucleic acid molecules encoding a human caspase-12 polypeptide, comprising contacting a human caspase-12 polypeptide, or a nucleic acid molecule encoding the same, with a compound, and determining whether the compound binds the human caspase-12 polypeptide or a nucleic acid molecule encoding the same. Binding can be determined by binding assays which are well known to the skilled artisan, including, but not limited to, gel-shift assays, Western blots, radiolabeled competition assay, phage-based expression cloning, co-fractionation by chromatography, co-precipitation, cross linking, interaction trap/two-hybrid analysis, southwestern analysis, ELISA, and the like, which are described in, for example, *Current Protocols in Molecular Biology* (1999) John Wiley & Sons, NY, which is incorporated herein by reference in its entirety. The compounds to be screened (which may include compounds which are suspected to bind a human caspase-12 polypeptide, or a nucleic acid molecule encoding the same) include, but are not limited to, extracellular, intracellular, biologic or chemical origin. The methods of the invention also embrace ligands including substrates, adaptor or receptor molecules that are attached to a label, such as a radiolabel (e.g., $^{125}I$, $^{35}S$, $^{32}P$, $^{33}P$, $^{3}H$), a fluorescence label, a chemiluminescent label, an enzymic label or an immunogenic label. Modulators falling within the scope of the invention include, but are not limited to, non-peptide molecules such as non-peptide mimetics, non-peptide allosteric effectors, and peptides. The human caspase-12 polypeptide or polynucleotide employed in such a test may either be free in solution, attached to a solid support, borne on a cell surface or located intracellularly or associated with a portion of a cell. One skilled in the art can, for example, measure the formation of complexes between a human caspase-12 polypeptide and the compound being tested. Alternatively, one skilled in the art can examine the diminution in complex formation between a human caspase-12 polypeptide and its substrate caused by the compound being tested.

Another aspect of the present invention is directed to methods of identifying compounds which modulate (i.e., increase or decrease) activity of a human caspase-12 polypeptide comprising contacting a human caspase-12 polypeptide with a compound, and determining whether the compound modifies activity of the human caspase-12 polypeptide. The activity in the presence of the test compared is measured to the activity in the absence of the test compound. Where the activity of the sample containing the test compound is higher than the activity in the sample lacking the test compound, the compound will have increased activity. Similarly, where the activity of the sample containing the test compound is lower than the activity in the sample lacking the test compound, the compound will have inhibited activity.

The present invention is particularly useful for screening compounds by using the human caspase-12 polypeptides in any of a variety of drug screening techniques. The compounds to be screened (which may include compounds which are suspected to bind a human caspase-12 polypeptide, or a nucleic acid molecule encoding the same) include, but are not limited to, extracellular, intracellular, biologic or chemical origin. The human caspase-12 polypeptide or polynucleotide employed in such a test may either be free in solution, attached to a solid support, borne on a cell surface or located intracellularly or associated with a portion of a cell. One skilled in the art can, for example, measure the formation of complexes between a human caspase-12 polypeptide and the compound being tested. Alternatively, one skilled in the art can examine the diminution in complex formation between a human caspase-12 polypeptide and its substrate caused by the compound being tested.

The activity of human caspase-12 polypeptides of the invention can be determined by, for example, examining their ability to bind or cleave chemically synthesized or naturally occurring peptide ligands. Alternatively, the activity of the human caspase-12 polypeptides can be assayed by examining their ability to bind to adaptor molecules, receptor molecules, substrates or other ligands. The activity of the human caspase-12 polypeptides can also be determined by examining the activity of effector molecules including, but not limited to other downstream caspases that are activated by human caspase-12. Thus, modulators of human caspase-12 polypeptide activity may alter a human caspase-12 function, such as a binding property of a human caspase-12 polypeptide or an activity such as enzymatic activity. In various embodiments of the method, the assay may take the form of binding assays to natural binding partners, proteolysis assays of human caspase-12 substrates, as well as other binding or function-based assays of caspase activity that are generally known in the art. Biological activities of caspase-12 according to the invention include, but are not limited to, the binding of a natural or an unnatural ligand, as well as any one of the functional activities of caspases known in the art. Non-limiting examples of caspase activities include proteolysis of substrates and binding to substrates, ligands, adaptor or receptor molecules.

The modulators of the invention exhibit a variety of chemical structures, which can be generally grouped into non-peptide mimetics of natural caspase ligands, peptide and non-peptide allosteric effectors of caspases, and peptides that may function as activators or inhibitors (competitive, uncompetitive and non-competitive) (e.g., antibody products) of caspases. The invention does not restrict the sources for suitable modulators, which may be obtained from natural sources such as plant, animal or mineral extracts, or non-natural sources such as small molecule libraries, including the products of combinatorial chemical approaches to library construction, and peptide libraries.

Other assays can be used to examine enzymatic activity including, but not limited to, photometric, radiometric, HPLC, electrochemical, and the like, which are described in, for example, *Enzyme Assays: A Practical Approach*, eds. R. Eisenthal and M. J. Danson (1992) Oxford University Press, which is incorporated herein by reference in its entirety.

cDNAs encoding human caspase-12 polypeptides can be used in drug discovery programs; assays capable of testing thousands of unknown compounds per day in high-throughput screens (HTSs) are thoroughly documented. The literature is replete with examples of the use of radiolabeled ligands in HTS binding assays for drug discovery (see Williams, *Medicinal Research Reviews* (1991) 11, 147–184.; Sweetnam, et al, *J. Natural Products* (1993) 56, 441–455 for review). Immobilized caspases are preferred for binding assay HTS because they allow for better specificity (higher relative purity), provide the ability to generate large amounts of caspase material, and can be used in a broad variety of formats (see Hodgson, *Bio/Technology* (1992) 10:973–980; each of which is incorporated herein by reference in its entirety).

A variety of heterologous systems is available for functional expression of recombinant polypeptides that are well known to those skilled in the art. Such systems include bacteria (Strosberg, et al., *Trends in Pharmacological Sciences* (1992) 13:95–98), yeast (Pausch, Trends in Biotechnology (1997) 15:487–494), several kinds of insect cells (Vanden Broeck, *Int. Rev. Cytology* (1996) 164:189–268), amphibian cells (Jayawickreme et al., *Current Opinion in Biotechnology* (1997) 8: 629–634) and several mammalian cell lines (CHO, HEK293, COS, etc.; see Gerhardt, et al., *Eur. J. Pharmacology* (1997) 334:1–23). These examples do not preclude the use of other possible cell expression systems, including cell lines obtained from nematodes (PCT application WO 98/37177).

In preferred embodiments of the invention, methods of screening for compounds which modulate the activity of human caspase-12 polypeptides comprise contacting test compounds with a human caspase-12 polypeptide and assaying for the presence of a complex between the compound and the human caspase-12 polypeptide. In such assays, the ligand is typically labeled. After suitable incubation, free ligand is separated from that present in bound form, and the amount of free or uncomplexed label is a measure of the ability of the particular compound to bind to the human caspase-12 polypeptide In another embodiment of the invention, high throughput screening for compounds having suitable binding affinity to a human caspase-12 polypeptide is employed. Briefly, large numbers of different small peptide test compounds are synthesized on a solid substrate. The peptide test compounds are contacted with a human caspase-12 polypeptide and washed. Bound human caspase-12 polypeptides are then detected by methods well known in the art. Purified polypeptides of the invention can also be coated directly onto plates for use in the aforementioned drug screening techniques. In addition, non-neutralizing antibodies can be used to capture the protein and immobilize it on the solid support.

Generally, an expressed human caspase-12 polypeptide can be used for HTS binding assays in conjunction with a substrate, ligand, adaptor or receptor molecule that is labeled with a suitable radioisotope, including, but not limited to, $^{125}$I, $^{3}$H, $^{35}$S or $^{32}$P, by methods that are well known to those skilled in the art. Alternatively, the substrate, ligand, adaptor or receptor molecule may be labeled by well-known methods with a suitable fluorescent derivative (Baindur, et al., *Drug Dev. Res.*, (1994) 33:373–398; Rogers, *Drug Discovery Today* (1997) 2:156–160). Radioactive ligand specifically bound to immobilized human caspase-12 can be detected in HTS assays in one of several standard ways, including filtration of the caspase-ligand complex to separate bound ligand from unbound ligand (Williams, *Med. Res. Rev.* (1991)11, 147–184; Sweetnam, et al., *J. Natural Products* (1993) 56, 441–455). Alternative methods include a scintillation proximity assay (SPA) or a FlashPlate format in which such separation is unnecessary (Nakayama, *Cur. Opinion Drug Disc. Dev.* (1998) 1:85–91 Bosse, et al., *J. Biomolecular Screening* (1998) 3: 285–292.). Binding of fluorescent ligands can be detected in various ways, including fluorescence energy transfer (FRET), direct spectrophotofluorometric analysis of bound ligand, or fluorescence polarization (Rogers, *Drug Discovery Today* (1997) 2, 156–160; Hill, *Cur. Opinion Drug Disc. Dev.* (1998) 1, 92–97).

The invention contemplates a multitude of assays to screen and identify inhibitors of substrate, ligand, adaptor or receptor binding to human caspase-12. In one example, human caspase-12 is immobilized and interaction with a binding partner is assessed in the presence and absence of a candidate modulator such as an inhibitor compound. In another example, interaction between human caspase-12 and its binding partner is assessed in a solution assay, both in the presence and absence of a candidate inhibitor compound. In either assay, an inhibitor is identified as a compound that decreases binding between the human caspase-12 and its binding partner. Another contemplated assay involves a variation of the di-hybrid assay wherein an inhibitor of protein/protein interactions is identified by detection of a positive signal in a transformed or transfected host cell, as described in PCT publication number WO 95/20652, published Aug. 3, 1995.

Candidate modulators contemplated by the invention include compounds selected from libraries of either potential activators or potential inhibitors. There are a number of different libraries used for the identification of small molecule modulators, including: (1) chemical libraries, (2) natural product libraries, and (3) combinatorial libraries comprised of random peptides, oligonucleotides or organic molecules. Chemical libraries consist of random chemical structures, some of which are analogs of known compounds or analogs of compounds that have been identified as "hits" or "leads" in other drug discovery screens, some of which are derived from natural products, and some of which arise from non-directed synthetic organic chemistry. Natural product libraries are collections of microorganisms, animals, plants, or marine organisms that are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see Science 282:63–68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701–707 (1997). Identification of modulators through use of the various libraries described herein permits modification of the candidate "hit" (or "lead") to optimize the capacity of the "hit" to modulate activity.

Still other candidate inhibitors contemplated by the invention can be designed and include soluble forms of binding partners, as well as such binding partners as chimeric, or fusion, proteins. A "binding partner" as used herein broadly encompasses non-peptide modulators, as well as peptide modulator including antibodies, antibody fragments, and modified compounds comprising antibody domains that are immunospecific for human caspase-12.

Other assays may be used to identify specific ligands of human caspase-12, including assays that identify ligands of the target protein through measuring direct binding of test ligands to the target protein, as well as assays that identify ligands of target proteins through affinity ultrafiltration with ion spray mass spectroscopy/HPLC methods or other physical and analytical methods. Alternatively, such binding interactions are evaluated indirectly using the yeast two-hybrid system described in Fields et al., Nature, 340:245–246 (1989), and Fields et al., Trends in Genetics, 10:286–292 (1994), both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene. For example, when the first protein is human caspase-12, or subunit or fragment thereof, that is known to interact with another protein or nucleic acid, this assay can be used to detect agents that interfere with the binding interaction. Expression of the reporter gene is monitored as different test agents are added to the system. The presence of an inhibitory agent results in lack of a reporter signal.

The yeast two-hybrid assay can also be used to identify proteins that bind to human caspase-12. In an assay to identify proteins that bind to human caspase-12, or subunit or fragment thereof, a fusion polynucleotide encoding both a human caspase-12 (or subunit or fragment) and a UAS binding domain (i.e., a first protein) may be used. In addition, a large number of hybrid genes each encoding a different second protein fused to an activation domain are produced and screened in the assay. Typically, the second protein is encoded by one or more members of a total cDNA or genomic DNA fusion library, with each second protein-coding region being fused to the activation domain. This system is applicable to a wide variety of proteins, and it is not even necessary to know the identity or function of the second binding protein. The system is highly sensitive and can detect interactions not revealed by other methods; even transient interactions may trigger transcription to produce a stable mRNA that can be repeatedly translated to yield the reporter protein.

Other assays may be used to search for agents that bind to the target protein. One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method which distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al., Anal. Chem., 69:1683–1691 (1997), incorporated herein by reference. This technique screens combinatorial libraries of 20–30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide that shares one or more antigenic determinants with human caspase-12. Radiolabeled competitive binding studies are described in A. H. Lin et al. *Antimicrobial Agents and Chemotherapy* (1997) vol. 41, no. 10. pp. 2127–2131, the disclosure of which is incorporated herein by reference in its entirety.

In other embodiments of the invention, the polypeptides of the invention are employed as a research tool for identification, characterization and purification of interacting, regulatory proteins. Appropriate labels are incorporated into the polypeptides of the invention by various methods known in the art and the polypeptides are used to capture interacting molecules. For example, molecules are incubated with the labeled polypeptides, washed to removed unbound polypeptides, and the polypeptide complex is quantified. Data obtained using different concentrations of polypeptide are used to calculate values for the number, affinity, and association of polypeptide with the protein complex.

Labeled polypeptides are also useful as reagents for the purification of molecules with which the polypeptide interacts including, but not limited to, inhibitors. In one embodiment of affinity purification, a polypeptide is covalently coupled to a chromatography column. Cells and their membranes are extracted, and various cellular subcomponents are passed over the column. Molecules bind to the column by virtue of their affinity to the polypeptide. The polypeptide-complex is recovered from the column, dissociated and the recovered molecule is subjected to protein sequencing. This amino acid sequence is then used to identify the captured molecule or to design degenerate oligonucleotides for cloning the corresponding gene from an appropriate cDNA library.

Alternatively, compounds may be identified which exhibit similar properties to the ligand for human caspase-12, but which are smaller and exhibit a longer half time than the endogenous ligand in a human or animal body. When an organic compound is designed, a molecule according to the invention is used as a "lead" compound. The design of mimetics to known pharmaceutically active compounds is a well-known approach in the development of pharmaceuticals based on such "lead" compounds. Mimetic design, synthesis and testing are generally used to avoid randomly screening a large number of molecules for a target property. Furthermore, structural data deriving from the analysis of the deduced amino acid sequences encoded by the polynucleotides of the present invention are useful to design new drugs, more specific and therefore with a higher pharmacological potency.

Comparison of the protein sequence of the present invention with the sequences present in all the available databases showed a significant homology with members of the caspase family. Accordingly, computer modeling can be used to develop a putative tertiary structure of the proteins of the invention based on the available information of known caspases. Thus, novel ligands based on the predicted structure of human caspase-12 can be designed.

Another aspect of the present invention is the use of the human caspase-12 nucleotide sequences disclosed herein for identifying homologs in other animals. Any of the nucleotide sequences disclosed herein, or any portion thereof, can be used, for example, as probes to screen databases or nucleic acid libraries, such as, for example, genomic or cDNA libraries, to identify homologs, using screening procedures well known to those skilled in the art. Accordingly, homologs having at least 50%, more preferably at least 60%, more preferably at least 70%, more preferably at least 80%, more preferably at least 90%, more preferably at least 95%, and most preferably at least 100% homology with human caspase-12 sequences can be identified.

7. Activities/Uses

A. Uses

A number of caspases have been characterized as important effector molecules for apoptosis, whereas other caspases are involved in cytokine processing associated with inflammation. Apoptosis functions in maintaining normal tissue homeostasis in a variety of physiological processes including embryonic development, immune cell regulation, normal cellular turnover and programmed cell death of cancer cells. Thus, the dysfunction or loss of regulated apoptosis can lead to a variety of pathological disease states. For example, the loss of apoptosis can lead to the pathological accumulation of self-reactive lymphocytes such as occurs in many autoimmune diseases. Inappropriate loss of apoptosis can also lead to the accumulation of virally infected cells and of hyperproliferative cells such as neoplastic or tumor cells. Inappropriate activation of apoptosis can contribute to a variety of diseases such as AIDS, neurodegenerative diseases and ischemic injury.

Caspases have also been shown to be important for the processing of the cytokines interleukin-1β (IL-1β) and interleukin-18 (IL-18). Both IL-1β and IL-18 are expressed as inactive precursor proteins that are proteolytically processed by caspases to yield active cytokines involved in inflammatory responses. IL-1β is a multifunctional protein present in a number of different cell types. For example, IL-1β is a growth factor for acute myeloid leukemia cells, is produced by murine monocytes that migrate into Peyer's patches during inflammation, and is associated with prolonged longevity of peripheral blood monocytes in vitro. IL-18 is a crucial cytokine involved in IFN-γ production in Th1 cells and natural killer cells during inflammation [Zeuner et al., *Cell Death Differen.* (1999) 6:1075–1080].

Recent studies have also uncovered possible physiological roles for caspases apart from apoptosis. Pro-apoptotic caspase-3 is suggested to be involved in processes such as T cell proliferation, IL-2 release in PHA-stimulated Jurkat T cells, IL-16 processing in CD8[+] and CD4[+] T cells, and in cell cycle control [Zeuner et al., *Cell Death Differen.* (1999) 6:1075–1080]. Caspases have also been implicated in regulating terminal lens fiber differentiation. The mature lens fibers do not undergo cell death, however, they do exhibit nuclear degeneration similar to that seem in apoptosis. Finally, caspases have been shown to mediate CD95 inhibition of erythroid differentiation by cleaving specific transcription factors [Zeuner et al., *Cell Death Differen.* (1999) 6:1075–1080].

The report in Nakagawa et al., supra that cortical neurons isolated from caspase-12 null mutant mice were relatively resistant to induction of apoptosis by β-amyloid suggests that caspase-12 inhibitors would be effective for treating neurodegenerative diseases, particularly those associated with β-amyloid accumulation. Compared to neurons from wild-type animals, neurons from the caspase-12 null mice could be induced to undergo apoptosis by stimuli that trigger cell death pathways which act through the plasma membrane or mitochondria but not through the stress pathways of the endoplasmic reticulum. Thus, the normal signaling pathways regulating cell death in normal tissue homeostasis remain intact strongly implicating that caspase-12 is not involved. Caspase-12 may instead be involved in apoptosis in specialized tissues and in specialized situations. Furthermore, there were no developmental anomalies nor increased incidence of tumors observed in the caspase 12-null mice, suggesting that chronic use of inhibitors or antagonists of this caspase would not upset tissue homeostasis.

Data described herein indicate that human caspase-12 plays a role in regulation of cell death induced through endoplasmic reticulum stress. In organs that carry out metabolically complex functions, there is the ever constant need to change or alter the array of proteins that are expressed in order that the specialized, differentiated task of the tissue be accomplished. The endoplasmic reticulum is often the platform for synthesis of these proteins. However, various forms of cellular stress can result in the inappropriate or complete lack of folding of the newly synthesized protein in the endoplasmic reticulum. For example, drugs (e.g., doxorubicin and other cancer chemotherapeutics), toxins, chemicals and reactive oxygen species (e.g., species attending reperfusion injuries) are expected to lead to improper protein folding of nascent polypeptides. As the unfolded protein accumulates in the lumen of the endoplasmic reticulum, cells respond by attempting to up-regulate the synthesis of chaperone-type proteins. This is usually accomplished through the stress-regulated kinase (SAPK) system which is capable of activating transcriptional expression of the chaperonens. The successful execution of this process by the SAPKs ameliorates the endoplasmic reticulum stress and the cell continues to function.

Failure of the cell to alleviate the stress on the endoplasmic reticulum will result in apoptosis. Thus, diseases and conditions associated with ER stress-induced apoptosis are characterized as exhibiting a gradually developing form of apoptosis leading eventually to cell death. Although the precise signaling events that are involved are unclear, it is apparent that caspase 12 plays an important role in this death process. Caspase-12 is located on the endoplasmic reticulum and thus, may serve a key role in initiating or propagating the caspase cascade. Once initiated, the process invariably leads to cell death.

Organ failure resulting from endoplasmic reticulum stress results from apoptosis of the parenchymal cells of that tissue. Thus, in brain it is the death of neurons that is responsible for neurodegeneration, as found in the gradually developing dementias characteristic of such diseases as Alzheimer's disease, Parkinson's disease, Huntington's chorea, amyotrophic lateral sclerosis, and others. In heart, it is the death of myocytes that is responsible for failure of the heart muscle, as seen in myocardial infarctions. In kidney, it is the death of the proximal tubule cells that results in renal failure. In liver, parenchymal cell death is associated with hepatitis C and cirrhosis. In the intestine, it is the death of epithelial cells that is responsible for organ failure. Lung and skeletal muscle also are organs with similar potential responses to endoplasmic reticulum stress.

The invention thus provides a method for treating a disease or disorder associated with inappropriate apoptosis or abnormal inflammation caused by activation of human caspase-12 polypeptides comprising the step of administering to a mammal in need of such treatment an amount of a caspase inhibitor of the invention (e.g., an antisense polynucleotide or other polynucleotide that inhibits transcription or translation of human caspase-12, an antibody specific to human caspase-12, human caspase-12 variants that may act competitively to inhibit binding to substrate, ligand, receptor or adaptor molecules, or any other inhibitor identified by screening assays described herein utilizing human caspase-12 polypeptides) that is sufficient to inhibit activation of one or more human caspase-12 polypeptides. The invention also provides a method of inducing apoptosis by administering human caspase-12 polynucleotides or polypeptides of the invention for therapeutic use as anti-viral or anti-tumor agents. Inhibition of or activation of human caspase-12 by polynucleotides, polypeptides or modulators of the invention also may be used to regulate embryonic development and tissue homeostasis. Treatment methods using small molecules that mimic, agonize or antagonize the activation of one or more human caspase-12 polypeptides are also contemplated. Treatment of individuals having any of these diseases or disorders, including those described herein, is contemplated as an aspect of the invention.

Dysregulation of apoptosis has been implicated in numerous diseases such as neurodegenerative disorders including Alzheimer's disease, Parkinson's disease, Huntington's disease, and amyotrophic lateral sclerosis (ALS), cerebellar degeneration, stroke, traumatic brain injury, CNS ischemic reperfusion injury including neonatal hypoxic-ischemic brain injury or myocardial ischemic-reperfusion injury, injury caused by hypoxia, cardiovascular diseases (e.g., myocardial infarction), especially those which are associated with apoptosis of endothelial cells, degenerative liver disease, multiple sclerosis, rheumatoid arthritis, hematological disorders including lymphoma, leukemia, aplastic anemia, and myelodysplastic syndrome, osteoporosis, polycystic kidney disease, AIDS, myelodysplastic syndromes, aplastic anemia and baldness. Inhibitors or antagonists of human caspase-12 may also be useful for treating diseases of the eye such as glaucoma, retinitis pigmentosa and macular degeneration.

Inflammatory disease states include systemic inflammatory conditions and conditions associated locally with migration and attraction of monocytes, leukocytes and/or neutrophils. Inhibition of chemotaxis or chemokine activity may be useful to ameliorate pathologic inflammatory disease states. Inflammation may result from infection with pathogenic organisms (including gram-positive bacteria, gram-negative bacteria, viruses, fungi, and parasites such as protozoa and helminths), transplant rejection (including rejection of solid organs such as kidney, liver, heart, lung or cornea, as well as rejection of bone marrow transplants including Graft-Versus-Host Disease (GVHD)), or from localized chronic or acute autoimmune or allergic reactions. Autoimmune diseases include acute glomerulonephritis; rheumatoid or reactive arthritis; chronic glomerulonephritis; inflammatory bowel diseases such as Crohn's disease, ulcerative colitis and necrotizing enterocolitis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, some forms of diabetes, or any other autoimmune state where attack by the subject's own immune system results in pathologic tissue destruction. Allergic reactions include allergic asthma, chronic bronchitis, allergic rhinitis, acute and delayed hypersensitivity. Systemic inflammatory disease states include inflammation associated with trauma, burns, reperfusion following ischemic events (e.g. thrombotic events in heart, brain, intestines or peripheral vasculature, including myocardial infarction and stroke), sepsis, ARDS or multiple organ dysfunction syndrome. Inflammatory cell recruitment also occurs in atherosclerotic plaques.

Viral infections that may be treated include infections caused by herpesviruses (including CMV, HSV-1, HSV-2, VZV, EBV, HHV-6, HHV-7 and HHV-8), paramyxoviruses (including parainfluenza, mumps, measles, and respiratory syncytial virus (RSV)), picornaviruses (including enteroviruses and rhinoviruses), togaviruses, coronaviruses, arenaviruses, bunyaviruses, rhabdoviruses, orthomyxoviruses (including influenza A, B and C viruses), reoviruses (including reoviruses, rotaviruses and orbiviruses), parvoviruses, adenoviruses, hepatitis viruses (including A, B, C, D and E) and retroviruses (including HTLV and HIV). Treatment of both acute and chronic infection are contemplated.

Examples of pathological conditions resulting from increased cell survival include cancers such as lymphomas, carcinomas and hormone-dependent tumors (e.g., breast, prostate or ovarian cancer). Abnormal cellular proliferation conditions or cancers that may be treated in either adults or children include solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, astrocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Karposi's sarcoma.

As noted above, data described herein indicate that human caspase-12 plays a role in regulation of cell death induced through endoplasmic reticulum stress. Thus, it is expected that the treatment methods of the invention would be useful in treating diseases or disorders associated with endoplasmic reticulum stress that leads to protein misfolding, such as α1-AT deficiency, Cystic fibrosis, Alzheimer's disease (see above), Congenital hyperthyroid goiter, Familial hypercholesterolemia class 2, Carbohydrate-deficient glycoprotein syndrome, von Willebrand's disease, Hemophilia A, Hemophilia B, Osteogenesis imperfecta, Scurvy, Marfan syndrome, Tay-Sachs disease, Retinitis pigmentosa (see above), Leprechaunism, and Carcot-Marie-tooth type 1A. See Kaufman, R. J., *Genes & Dev.* (1999) 13(10): 1211–1233.

Concurrent treatment with another non-caspase-12-based regulator of apoptosis is also contemplated according to the invention. For example, natural factors that prevent or inhibit apoptosis include growth factors, extracellular matrix attachment, CD40 ligand, viral gene products, neutral amino acids, zinc, estrogen and androgens. Natural factors that promote apoptosis include growth factors such as tissue necrosis factor, Fas and transforming growth factor-beta, neurotransmitters, growth factor withdrawal, loss of extracellular matrix attachment, intracellular calcium and glucocorticoids.

Caspases, caspase agonists or caspase inhibitors may be targeted to a desired tissue type or location through use of antibodies or other binding partners that selectively bind to a molecule in the target tissue.

The invention thus encompasses administration of a therapeutically effective amount of a human caspase-12 inhibitor to a subject in need thereof for treatment of diseases or disorders involving inappropriate, excessive or dysfunctional apoptosis, including inflammatory disease states, neurodegenerative diseases and any other diseases or disorders described herein that are the result of inappropriate apoptosis. Suitable inhibitors include antibodies to caspase-12, antisense or other polynucleotides that inhibit expression of human caspase-12, human caspase-12 variants that are enzymatically inactive, peptide inhibitors based on caspase substrates described herein, or any inhibitors identified by the screening methods disclosed herein. Specifically excluded from the invention are treatment methods utilizing compounds already known in the art to be effective for treating these disease states.

The invention further encompasses administration of a therapeutically effective amount of human caspase-12 or an agonist to a subject in need thereof for treatment of diseases or disorders involving cell proliferation, including viral infections, cancer disease states and any other diseases or disorders described herein. Suitable agonists include human caspase-12 polynucleotides (administered, e.g., via gene therapy techniques), compounds that up-regulate expression of human caspase-12, human caspase-12 polypeptides or any agonists identified by the screening methods disclosed herein. Specifically excluded from the invention are treatment methods utilizing compounds already known in the art to be effective for treating these disease states. Corresponding methods of delivering a vector comprising a human caspase-12 polynucleotide to a subject in need thereof are also contemplated.

B. Diagnosis

Polynucleotides of the invention may also be the basis for diagnostic methods useful for identifying a genetic alteration(s) in a locus for any one of the human caspase-12 polynucleotides of the invention that underlies a disease state or states, which information is useful both for diagnosis and for selection of therapeutic strategies. Fragment polynucleotides are particularly useful as probes for detection of full-length or other fragment human caspase-12 polynucleotides. One or more fragment polynucleotides can be included in kits that are used to detect the presence of a polynucleotide encoding a human caspase-12 polypeptide, or used to detect variations in a polynucleotide sequence encoding a human caspase-12 polypeptide.

C. Therapeutics

The present compounds and methods, including nucleic acid molecules, polypeptides, antibodies, compounds identified by the screening methods described herein, have a variety of pharmaceutical applications and may be used, for example, to treat or prevent unregulated cellular growth, such as cancer cell and tumor growth.

The present invention also encompasses a method of agonizing (stimulating) or antagonizing a human caspase-12 natural binding partner associated activity in a human comprising administering to said human an agonist or antagonist to one of the above disclosed polypeptides in an amount sufficient to effect said agonism or antagonism. One embodiment of the present invention, then, is a method of treating diseases in a mammal with an agonist or antagonist of the protein of the present invention comprises administering the agonist or antagonist to a mammal in an amount sufficient to agonize or antagonize human caspase-12-associated functions.

In an effort to discover novel treatments for diseases, biomedical researchers and chemists have designed, synthesized, and tested molecules that inhibit the function of protein polypeptides. Possible peptide inhibitors include peptides based on known caspase substrates.

Mutations in genes encoding human caspase-12 polypeptides that result in loss of normal function of one or more human caspase-12 gene products underlie human disease states related to those human caspase-12 polypeptides. The invention comprehends gene therapy to restore activity of one or more human caspase-12 polypeptides to treat those disease states. Delivery of a functional human caspase-12 gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, *Nature,* supplement to vol. 392, no. 6679, pp. 25–20 (1998). For additional reviews of gene therapy technology see Friedmann, *Science,* 244:1275–1281 (1989); Verma, *Scientific American:* 68–84 (1990); and Miller, *Nature,* 357:455–460 (1992). Alternatively, it is contemplated that in other human disease states, preventing the expression of or inhibiting the activity of one or more human caspase-12 polypeptides will be useful in treating the disease states. It is contemplated that antisense therapy or gene therapy could be applied to negatively regulate the expression of one or more human caspase-12 polypeptides.

The pharmaceutical compositions optionally may include pharmaceutically acceptable (i.e., sterile and non-toxic) liquid, semisolid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma.

Compounds of the invention may be covalently or non-covalently associated with the carrier molecule, such as a linear polymer (e.g., polyethylene glycol, polylysine, dextran, etc.), a branched-chain polymer (see U.S. Pat. Nos. 4,289,872 and 5,229,490; PCT Publication WO 93/21259 published Oct. 28, 1993); a lipid; a cholesterol group (such as a steroid); or a carbohydrate or oligosaccharide. Other carriers include one or more water soluble polymer attachments such as polyoxyethylene glycol, or polypropylene glycol as described U.S. Pat. Nos.: 4,640,835, 4,496,689, 4,301,144, 4,670,417, 4,791,192 and 4,179,337. Still other useful polymers known in the art include monomethoxy-polyethylene glycol, dextran, cellulose, or other carbohydrate-based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers.

A preferred such carrier is polyethylene glycol (PEG). The PEG group may be of any convenient molecular weight and may be straight chain or branched. The average molecular weight of the PEG will preferably range from about 2 kDa to about 100 kDa, more preferably from about 5 kDa to about 50 kDa, most preferably from about 5 kDa to about 10 kDa. The PEG groups will generally be attached to the compounds of the invention via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group).

Carbohydrate groups may be covalently attached to various sites on a compound of the invention, including serine (Ser) or threonine (Thr) residues which accommodate O-linked glycosylation, and asparagine (Asn) residues which accommodate N-linked glycosylation when the Asn residue is part of the sequence Asn-Xaa-Ser/Thr, and "Xaa" is any amino acid but proline.

Compounds of the invention may be derivatized with linker components to covalently bind the compound of the invention to a carrier or other compound. Derivatization with bifunctional agents is useful for cross-linking a compound of the invention or an analog or derivative thereof, to a support matrix or to a carrier. Cross-linking agents can include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio] propioimidate yield photoactivatable intermediates that are capable of forming cross-links in the presence of light. Alternatively, reactive water-insoluble matrices such as cyanogen bromide-activated carbohydrates and the reactive substrates as described in U.S. Pat. Nos. 3,969,287; 3,691,016; 4,195,128; 4,247,642; 4,229,537; and 4,330,440 may be employed for protein immobilization.

The invention also provides compounds derivatized to include one or more antibody Fc regions. Fc regions of antibodies comprise monomeric polypeptides that may be in dimeric or multimeric forms linked by disulfide bonds or by non-covalent association. The number of intermolecular disulfide bonds between monomeric subunits of Fc molecules can be from one to four depending on the class (e.g., IgG, IgA, IgE) or subclass (e.g., IgG1, IgG2, IgG3, IgA1, IgGA2) of antibody from which the Fc region is derived. The term "Fc" as used herein is generic to the monomeric, dimeric, and multimeric forms of Fc molecules., with the Fc region being a wild-type structure or a derivatized structure.

Compounds of the invention in the pharmaceutical compositions may also include the salvage receptor binding domain of an Fc molecule as described in WO 96/32478, as well as other Fc molecules are described in WO 97/34631.

Such derivatized moieties preferably improve one or more characteristics of the compound of the invention, including for example, biological activity, solubility, absorption, biological half life, and the like. Alternatively, derivatized moieties result in compounds that have the same, or essentially the same, characteristics and/or properties of the compound that is not derivatized. The moieties may alternatively eliminate or attenuate any undesirable side effect of the compounds and the like.

When given parenterally, product compositions comprising one or more human caspase-12 polypeptides, polynucleotides, or modulators thereof are generally injected in doses ranging from 1 µg/kg to 1000 mg/kg, 0.1 mg/kg to 100 mg/kg, 0.1 mg/kg to 50 mg/kg, and more preferably at doses ranging from 1 to 20 mg/kg, given in daily doses or in equivalent doses at longer or shorter intervals, e.g., every other day, twice weekly, weekly, or twice or three times daily. The product composition may be administered by an initial bolus followed by a continuous infusion to maintain therapeutic circulating levels of drug product. Those of ordinary skill in the art will readily optimize effective dosages and administration regimens as determined by good medical practice and the clinical condition of the individual patient. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such formulations may influence the physical state, stability, rate of in vivo release, and rate of in vivo clearance of the administered agents. Depending on the route of administration, a suitable dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in the human clinical trials discussed above. Appropriate dosages may be ascertained through use of established assays for determining blood levels dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

For the treatment of cancers the expected daily dose of a hydrophobic pharmaceutical agent is between 1 to 500 mg/day, preferably 1 to 250 mg/day, and most preferably 1 to 50 mg/day. Drugs can be delivered less frequently provided plasma levels of the active moiety are sufficient to maintain therapeutic effectiveness. Plasma levels should reflect the potency of the drug. Generally, the more potent the compound the lower the plasma levels necessary to achieve efficacy.

Plasma half-life and biodistribution of the drug and metabolites in the plasma, tumors and major organs can also be determined to facilitate the selection of drugs most appropriate to inhibit a disorder. Such measurements can be carried out. For example, HPLC analysis can be performed on the plasma of animals treated with the drug and the location of radiolabeled compounds can be determined using detection methods such as X-ray, CAT scan and MRI. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out in a suitable animal model as follows: 1) the compound is administered to mice (an untreated control mouse should also be used); 2) blood samples are periodically obtained via the tail vein from one mouse in each treatment group; and 3) the samples are analyzed for red and white blood cell counts, blood cell composition and the percent of lymphocytes versus polymorphonuclear cells. A comparison of results for each dosing regime with the controls indicates if toxicity is present.

At the termination of each toxicity study, further studies can be carried out by sacrificing the animals (preferably, in accordance with the American Veterinary Medical Association guidelines Report of the American Veterinary Medical Assoc. Panel on Euthanasia, Journal of American Veterinary Medical Assoc., 202:229–249, 1993). Representative animals from each treatment group can then be examined by gross necropsy for immediate evidence of metastasis, unusual illness or toxicity. Gross abnormalities in tissue are noted and tissues are examined histologically. Compounds causing a reduction in body weight or blood components are less preferred, as are compounds having an adverse effect on major organs. In general, the greater the adverse effect the less preferred the compound.

The pharmaceutical compositions can be packaged in forms convenient for delivery, including, for example, capsule, sachet, cachet, gelatin, paper, tablets, capsules, suppositories, cachets or pellets, pills, troches or lozenges or other form. The type of packaging will generally depend on the desired route of administration.

The pharmaceutical compositions may be introduced into the subject to be treated by any conventional method including, e.g., by intravenous, intradermal, intramuscular, intramammary, intraperitoneal, intrathecal, intraocular, retrobulbar, intrapulmonary (e.g., aerosolized drug solutions) or subcutaneous injection (including depot administration for long term release); by oral, sublingual, nasal, anal, vaginal, or transdermal delivery; or by surgical implantation, e.g., embedded under the splenic capsule, brain, or in the cornea.

In one aspect, the invention provides methods for oral administration of a pharmaceutical composition of the invention. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may include liposomes that are derivatized with various polymers (e.g., U.S. Pat. No. 5,013,556). In general, the formulation will include a compound of the invention and inert ingredients which protection against degradation in the stomach and which permit release of the biologically active material in the intestine.

Compounds of the invention may be chemically modified so that oral delivery provides the desired delivery result.

Such modifications include attachment of one or more moiety to the compound molecule itself, wherein the moiety permits (a) inhibition of proteolysis; and (b) uptake into the blood stream from the stomach or intestine. Modifications that increase uptake are particularly preferred, as well as modifications that the increase overall stability of the compound and increase circulation time in the body. Examples of such moieties include polyethylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-trioxocane. Preferred for pharmaceutical usage, as indicated above, are polyethylene glycol moieties.

For the oral delivery dosage forms, it is also possible to use a salt of a modified aliphatic amino acid, such as sodium N-(8-[2-hydroxybenzoyl] amino) caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include, but are not limited to, starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment, a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the compound are for instance the fatty acids oleic acid, linoleic acid and linolenic acid.

Controlled release formulation may be desirable. The drug could be incorporated into an inert matrix which permits release by either diffusion or leaching mechanisms e.g., gums. Slowly degenerating matrices may also be incorporated into the formulation, e.g., alginates, polysaccharides. Another form of a controlled release of this therapeutic is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Also contemplated herein is pulmonary delivery of the present protein (or derivatives or modulators thereof). The protein (or derivative) is delivered to the lungs of a mammal while inhaling and traverses across the lung epithelial lining to the blood stream. (Other reports of this include Adjei et al., Pharmaceutical Research 7:565–569 (1990); Adjei et al., International Journal of Pharmaceutics 63:135–144 (1990) (leuprolide acetate); Braquet et al., Journal of Cardiovascular Pharmacology 13 (suppl. 5): s.143–146 (1989) (endothelin-1); Hubbard et al., Annals of Internal Medicine 3:206–212 (1989) (α1-antitrypsin); Smith et al., J. Clin. Invest. 84:1145–1146 (1989) (α1-proteinase); Oswein et al., "Aerosolization of Proteins", Proceedings of Symposium on Respiratory Drug Delivery II, Keystone, Colo., March, 1990 (recombinant human growth hormone); Debs et al., The Journal of Immunology 140:3482–3488 (1988) (interferon-γ and tumor necrosis factor α) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 µm (or microns), most preferably 0.5 to 5 µm, for most effective delivery to the distal lung.

Carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. Polyethylene glycol may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per ml of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery of the inventive compound is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes is also contemplated.

Additional features of the invention will be apparent from the following Examples.

EXAMPLE 1

Identification of DNAs Encoding Human Caspase-12

The cDNA encoding human caspase-12 was cloned as follows. Comparison of all of the known caspases from mammalian, vertebrate, and invertebrate species to sequences in the Celera database identified a number of partial human DNA sequences. Some of these DNA sequences, ga_7598929 (SEQ ID NO: 30), ga_7683974 (SEQ ID NO: 31), ga_9453932 (SEQ ID NO: 32), ga_9504136 (SEQ ID NO: 33), ga_12715389 (SEQ ID NO: 34), ga_13398395 (SEQ ID NO: 35), ga_13611202 (SEQ ID NO: 36), ga_15018831 (SEQ ID NO: 37), and ga_15856828 (SEQ ID NO: 38) showed homology to murine caspase-12 (EMBL Accession No. 08736; SEQ ID NO: 84) as well as human caspase-4 and human caspase-5. Programs such as Bestfit, Compare/Dotplot, Extractpeptide, Findpatterns, GAP, Lineup, Map, Motifs and Pileup (GCG Package referenced above) were used to analyze and translate the nucleotide sequences. These nucleotide sequences were translated and modified (to eliminate an internal stop codon) to optimize homology to the murine caspase-12 sequence. The optimized portion of the amino acid sequence corresponding to ga_7598929 (SEQ ID NO: 30) is set forth in SEQ ID NO: 39, the optimized portion of the amino acid sequence corresponding to ga_7683974 (SEQ ID NO: 31) is set forth in SEQ ID NO: 40, the optimized portion of the amino acid sequence corresponding to ga9453932 (SEQ ID NO: 32) is set forth in SEQ ID NO: 41, the optimized portion of the amino acid sequence corresponding to ga_9504136 (SEQ ID NO: 33) is set forth in SEQ ID NO: 42, the optimized portion of the amino acid sequence corresponding to ga_12715389 (SEQ ID NO: 34) is set forth in SEQ ID NO: 43, the optimized portion of the amino acid sequence corresponding to ga_13398395 (SEQ ID NO: 35) is set forth in SEQ ID NO: 44, two optimized portions of the amino acid sequences corresponding to ga_13611202 (SEQ ID NO: 36) corresponding to translation of two different reading frames for this nucleotide sequence are set forth in SEQ ID NOS: 45 and 46, the optimized portion of the amino acid sequence corresponding to ga_15018831 (SEQ ID NO: 37) is set forth in SEQ ID NO: 47, and two optimized portions of amino acid sequences corresponding to ga_15856828 (SEQ ID NO: 38) corresponding to translation of two different reading frames for this nucleotide sequence are set forth in SEQ ID NOS: 48 and 49.

Nucleotide sequence information based on the alignment of these optimized amino acid sequences and the murine caspase-12 amino acid sequence was utilized as the basis for designing 11 oligonucleotide primers, KW229, KW230, KW231, KW232, KW233, KW234, KW235, KW236, KW237, KW238, and KW239(SEQ ID NOS: 11, 12, 13, 14, 15, 16, 17, 18, 19, 20 and 21, respectively). Different pairwise combinations of these 11 primers were used to attempt amplification of human caspase-12 cDNA from thymus (Clontech), skeletal muscle (Clontech), and lung (Clontech) cDNA libraries using the polymerase chain reaction (PCR). For these reactions, 1 ng of cDNA library, 1.5 mM MgCl$_2$, 200 µM of each dNTP, 1.5 U Taq polymerase (GIBCO/BRL), and 0.4 µM of each of the two primers selected for a particular reaction were combined in a total volume of 50 µl with a final concentration of 10 mM Tris-HCl, pH 8.3, at room temperature and 50 mM KCl. PCR was carried out as follows: 30 cycles of 94° C. for 1 minute, 55° C. for 1 minute and 72° C. for 1.5 minutes. These experiments resulted primarily in amplification of human caspase-4 DNA sequences.

PCR reactions were also performed using a human brain cDNA library (Invitrogen) as a template. In these reactions, 2 µg of 1–6 ng/µl human brain cDNA (library mix) was used and PCR was carried out as follows: 5 cycles of 94° C. for 1 minute, 55° C. for 1 minute, and 72° C. for 1.5 minutes; followed by 30 cycles of 94° C. for 30 seconds, 65° C. for 30 seconds and 72° C. for 1 minutes. Using primers KW232 (SEQ ID NO: 14) and KW234 (SEQ ID NO: 16), an amplification product of 193 bp was obtained, which showed approximately 78% identity to murine caspase-12 using the Gap program (Wisconsin Sequence Analysis Package, Version 10 for Unix, Genetics Computer Group, University Research Park, Madison Wis.), using the default settings, which uses the algorithm of Needleman and Wunsch [*J. Mol. Biol.* 48:443–453 (1970)]. The sequence information obtained from this cDNA allowed the design of highly specific, high melting-temperature oligonucleotide primers (KW240, KW241, KW242 and KW243 (SEQ ID NOS: 22, 23, 24, 25, respectively)) to use in Rapid Amplification of cDNA Ends (RACE) PCR with Marathon-Ready cDNA from human lung (Clontech) as a template. Using primers AP1 and AP2 (Clontech), complementary to all amplified cDNA ends, and the above-described gene-specific primers, a putative human caspase-12 gene was amplified in two parts. Primers KW241 (SEQ ID NO: 23) and KW243 (SEQ ID NO: 25) were used for 5' RACE PCR and primers KW240 (SEQ ID NO: 22) and KW242 (SEQ ID NO: 24) were used for 3' RACE PCR. For all RACE PCR reactions, 5 µl of 0.1 ng/µl Marathon-Ready lung cDNA (Clontech) was combined with 1.5 mM MgCl$_2$, 200 µM of each dNTP, 1.5 U Taq polymerase, and 0.4 µM of each of two primers in a final total volume of 50 µl with a final concentration of 10 mM Tris-HCl, pH 8.3, at room temperature and 50 mM KCl. RACE PCR was carried out as follows: an initial incubation at 94° C. for 30 seconds followed by 5 cycles of 94° C. for 15 seconds and 72° C. for 4 minutes followed by 5 cycles of 94° C. for 15 seconds and 70° C. for 4 minutes followed by 25 cycles of 94° C. for 15 seconds and 68° C. for 2.5 minutes. Several cDNA amplification products, which potentially represented the 5' portion or the 3' portion of human caspase 12, were cloned and inserted into pGEM T-EASY vectors designated pKW75.seq and pKW57.seq. pKW75.seq contains the 5' portion of the gene and pKW57.seq contains the 3' portion. Sequence information derived from several isolates indicates these are previously uncharacterized and thus novel sequences. Because it was recognized that the 5' portion contained in pKW75.seq may not contain the entire 5' region of human caspase-12, primers pKW 244 (SEQ ID NO: 26) and pKW 247 (SEQ ID NO: 29) were designed and used in RACE PCR reactions to identify further 5' regions.

Human caspase-12-specific primers, which flank the entire reading frame, were designed for amplification of contiguous cDNAs from various tissues. Based on sequence information obtained from the RACE PCR products, primers KW245 (SEQ ID NO: 27) and KW246 (SEQ ID NO: 28) were designed to be used in PCR reactions to amplify contiguous human caspase-12 sequences from brain (Invitrogen) and lung (Clontech) cDNA libraries. PCR using human lung and brain cDNA libraries as templates produced products of four different sizes designated isoforms A, B, C, and D (nucleotide sequences of SEQ ID NOS: 1, 5, 9 and 10, respectively). These particular isoforms (A, B, C, and D) were isolated from brain cDNA.

FIG. 1 shows an alignment of the amino acid sequences of a human caspase-12 isoform designated KW-A (SEQ ID NO: 4) with other members of the caspase family: human caspase-1 (SEQ ID NO: 80), putative human caspase-13 (SEQ ID NO: 81), human caspase-4 (SEQ ID NO: 82), human caspase-5 (SEQ ID NO: 83), mouse caspase-12 (SEQ ID NO: 84) and mouse caspase-11 (SEQ ID NO: 85).

Amino acid sequence comparison of all of the human caspase-12 isoforms revealed approximately 60% identity to murine caspase-12 using the Gap program mentioned above, again using the default settings. Comparison of subunit portions of the human and murine amino acid sequences revealed homology of about 85% identity at the amino acid level in some cases. Furthermore, the sequences of human caspase-12 isoform-A and isoform-B contain a caspase-12 active site sequence motif (QACRG), whereas isoform-C and isoform-D do not contain the active site motif. As with the isoforms found in the other caspases (e.g., caspase 8 has at least 9 isoforms), these may have important and distinct tissue/cell-specific functions. Lack of the active site motif in isoforms-C and -D suggest that these proteins may function to inhibit caspase-12 activity. It is expected that additional isoforms, both active and inactive, may be identified in these or other tissue types, including skeletal muscle.

Comparison of the full-length assembled nucleotide sequences with the previously identified partial DNA sequences revealed that ga_7598929 (SEQ ID NO: 30), ga_9453932 (SEQ ID NO: 32), ga_9504136 (SEQ ID NO: 33), ga_12715389 (SEQ ID NO: 34), and ga_15856828 (SEQ ID NO: 38) actually corresponded to the cloned human caspase-12 cDNA.

Further additional or differentially expressed isoforms of caspase-12 were identified by probing cDNA from multiple tissue sources. PCR was performed on cDNA from multiple tissues (OriGene Technologies, Inc.) using primer pairs KW245/KW241 (SEQ ID NOS: 27 and 23, respectively) or KW231/KW241 (SEQ ID NOS: 13 and 23). Resultant DNA fragments were subcloned into the pGEM T-EASY vector and clones were analyzed for insert size. Using this approach, isoforms KW-J and KW-K (nucleotide sequences of SEQ ID NOS: 68 and 70, respectively) were identified from thyroid and spleen, respectively. KW-J has a smaller 5' region compared to the previously identified isoforms. KW-K possesses additional 5' sequence relative to the previously identified isoforms. This additional 5' DNA sequence from KW-K was used to design new primers for PCR analysis of cDNA from brain. Primer pair KW255/KW246 (SEQ ID NOS: 87 and 28) was used to amplify the 3' region of human caspase-12. Primer pair KW256/KW245 (SEQ ID NOS: 88 and 27 ) was used to amplify additional 5' clones. Using this strategy, three additional isoforms that differ in their 3' sequence were identified from brain. These isoforms, designated KW-G, KW-H and KW-I (nucleotide sequences set forth in SEQ ID NOS: 62, 64 and 66, respectively), all lack the enzymatic active site sequence. Additional PCR was performed on brain cDNA to amplify similar isoforms that contain active site sequences. Using primer KW234 (SEQ ID NO: 16), which anneals to an active site sequence, with KW255 (SEQ ID NO: 87) in PCR of human brain cDNA, two additional isoforms were identified.

These isoforms were designated KW-E and KW-F (nucleotide sequences set forth in SEQ ID NOS: 58 and 60, respectively).

FIG. 2 shows an alignment of the amino acid sequences of isoforms KW-A (SEQ ID NO: 51), KW-B (SEQ ID NO: 53), KW-C (SEQ ID NO: 55), KW-D (SEQ ID NO: 57), KW-E (SEQ ID NO: 59), KW-F (SEQ ID NO: 61), KW-G (SEQ ID NO: 63), KW-H (SEQ ID NO: 65), KW-I (SEQ ID NO: 67), KW-J (SEQ ID NO: 69), and KW-K (SEQ ID NO: 71) as well as hCaspase-12.

FIG. 3 shows an alignment of a non-naturally occurring variant human caspase-12 isoform, designated hCaspase-12 (SEQ ID NO: 77) in the Figure and described in more detail in Example 3B below, with murine caspase-12 (SEQ ID NO: 84).

FIG. 4 shows an alignment of the amino acid sequences of the non-naturally occurring variant hCaspase-12 (SEQ ID NO: 77), murine caspase-12 (SEQ ID NO: 84), human caspase-1 (SEQ ID NO: 80), human caspase-2 (SEQ ID NO: 97), human caspase-3 (SEQ ID NO: 98), human caspase-4 (SEQ ID NO: 82), human caspase-5 (SEQ ID NO: 83), human caspase-6 (SEQ ID NO: 99), human caspase-7 (SEQ ID NO: 100), human caspase-8 (SEQ ID NO: 101), human caspase-9 (SEQ ID NO: 102), human caspase-10 (SEQ ID NO: 103), human caspase-13 (SEQ ID NO: 104), and human caspase-14 (SEQ ID NO: 105). FIG. 5 shows an alignment of the amino acid sequences of hCaspase-12 (SEQ ID NO: 77) and the most closely related human caspases, caspase-4, –5, -13 and -1.

EXAMPLE 2

Tissue Expression Analysis and Subcellular Localization

A. Tissue Expression

Tissue expression profiling experiments were done to identify additional or differentially expressed isoforms of caspase-12. Two rounds of PCR were performed on cDNA from multiple tissues (Sure-RACE, OriGene Technologies, Inc.). For the Sure-RACE PCR, a master PCR mix, consisting of 10 mM Tris-HCl, pH 8.3, 50 mM KCl, 1.5 mM MgCl$_2$, 0.2 mM each dNTP, 0.5 U Taq DNA polymerase, 0.2 µM KW243 primer and 0.2 µM APP-1 Sure-RACE adaptor primer, was used. The cycling parameters were as follows: an initial incubation at 94° C. for 3 minutes followed by 5 cycles of 94° C. for 15 seconds, and 72° C. for 2.5 minutes; followed by 5 cycles of 94° C. for 15 seconds, and 70° C. for 2.5 minutes; followed by 5 cycles of 94° C. for 15 seconds and 65° C. for 30 seconds, then 72° C. for 2.5 minutes; followed by 15 cycles of 94° C. for 30 seconds, then 62° C. for 30 seconds, then 72° C. for 2.5 minutes, and finally incubating at 72° C. for 10 minutes. Secondary PCR reactions using aliquots from the resultant reaction products were conducted using primer pairs KW245/KW241 (SEQ ID NOS: 27 and 23) or KW231/KW241 (SEQ ID NOS: 13 and 23). A similar reaction mix with these gene-specific primers was used with the following cycling parameters: initial incubation at 94° C. for 2 minutes, followed by 35 cycles of 94° C. for 30 seconds, then 67° C. for 30 seconds, and then 72° C. for 1.5 minutes. An aliquot of the reaction products was resolved by agarose gel electrophoresis. The PCR products from the KW231/KW241 amplification are shown in FIG. 6. These results demonstrate that human caspase-12 is ubiquitously expressed in human tissues and that caspase-12 isoforms of various sizes are expressed in the different tissues.

In addition to the tissue-specific expression studies, temporal mRNA expression and/or expression in tissues from patients suffering from a disease condition (including any condition mentioned herein) can also be examined. Conventional Northern blot or in situ hybridization techniques can be used.

B. Subcellular Localization to the Endoplasmic Reticulum

Immunofluorescence cell staining was utilized to demonstrate the subcellular localization of human caspase-12 in the endoplasmic reticulum. Neuroblastoma SH-EP cells (Scaffidi et al, *J. Biol. Chem.* (1977) 272(43):26953–26958) were grown on glass coverslips that were treated with poly-L-lysine. Individual coverslips were washed twice with PBS and fixed with 4% formalin in PBS at 37° C. for 20 minutes. The coverslips were washed twice with PBS, then permeabilized with 0.1% Triton X-100 in PBS for 10 minutes at 37° C. Coverslips were again washed twice in PBS and blocked by the addition of 5% BSA in PBS for 30 minutes at 37° C. Anti-caspase-12 polyclonal antibody (prepared against peptide WSHHLEEIFQKVQHSFE as described below in Example 4) was diluted to 3 µg/ml in TBST (10 mM Tris-HCl, pH 8.0, 150 mM NaCl, and 0.1% Tween-20) with 2% BSA. hnmunostaining of GRP-78, an ER-resident protein, was used as a positive control to evaluate the subcellular localization of human caspase-12. GRP-78 is a well-characterized member of a family of glucose-regulated proteins and is an ER-localized protein. Immunostaining with antibody to GRP-78 demonstrates a distinctive pattern of expression which is considered typical of ER localization. To perform the immunostaining studies, antibody to GRP 78 (Santa Cruz) was diluted to 1 µg/ml in TBST with 2% BSA. For demonstration of co-localization, antibodies were combined at the concentrations indicated above. Coverslips were incubated at 37° C. for 1 hour, then washed with 3 changes of phosphate-buffered saline (PBS) for 10 minutes each at 37° C. For fluorescence detection of caspase-12, Cy3-goat ant-rabbit IgG (ZYMED) was diluted 1:60 in TBST, 2% BSA and used as a labeled secondary antibody. For fluorescence detection of GRP 78, cells were incubated with Alexa-488 donkey anti-goat antibody (Molecular Probes) at a dilution of 1:1000 in TBST, 2% BSA. For co-localization of proteins, the same secondary antibodies were combined at appropriate concentrations in TBST, 2% BSA. Coverslips were incubated at 37° C. for 1 hour and washed with 3 changes of PBS for 10 minutes each. Coverslips were mounted on glass slides and cells were examined by confocal fluorescence microscopy (Zeiss). FIG. 7 demonstrates dual fluorescence immunostaining in a single cell. Caspase-12 protein is visualized as red fluorescence in FIG. 7-A; GRP 78 is visualized as green fluorescence in FIG. 7-B. An image overlay of the caspase-12 scan with the GRP 78 scan is shown in FIG. 7-C. A yellow signal indicates co-localization of fluorescence when the single images are overlaid. The results of these experiments finely localized the subcellular position of human caspase-12 in the endoplasmic reticulum, and not in the mitochondria, golgi apparatus, nucleus, or on the cell surface.

EXAMPLE 3

Recombinant Expression of Human Caspase-12 Natural and Variant Polypeptides in Host Cells A full-length expression clone of human caspase-12 was generated by mutagenesis of the DNA sequence found in the largest naturally occurring isoform from spleen, KW-K. A BLAST search of the KW-K nucleotide sequence, against the High-Throughput Genomics (HTG) database (National Center for Biotechnology Information), identified an homologous sequence on human chromosome 11. Using this information, mutagenesis of KW-K was performed to obtain a continuous open reading frame. Chromosome 11 sequence (Genbank Acc. No. AC00975) from nucleotides 15967–16142 aligned with nucleotides 361–544 of KW-K (SEQ ID: 70), provided that a "C" was inserted after base 403 of KW-K. Additionally, the BLAST search identified chromosome 11 sequences (Genbank Acc. Nos. AC009795 (bases 15954–16136); AP002004 (bases 90010–90191); AC009799 (bases 28786–28968)) which align with nucleotides 361–542 of KW-K (SEQ ID NO: 70). The chromosomal sequences indicated a "C" should replace the "T" at nucleotide 476 in the KW-K (SEQ ID: 70) sequence. The mutagenesis was more easily accomplished by making those changes using the isoform KW-K sequence as template and then subcloning the amplified fragment into the KW-A isoform (SEQ ID NO: 1) in the pGEM-T vector (Promega). The resultant plasmid, pKW-19, contains the KW-A sequence (nucleotides 1–1026 of SEQ ID NO: 1) and is cloned into the T-A cloning site of pGEM-T. The first step in the mutagenesis was the introduction of a "C" to shift the reading frame. The 87 bp EcoRI fragment from pKW-19 (nucleotides 234–319 of SEQ ID NO: 1) was excised by restriction endonuclease digestion. The EcoRI fragment was subsequently replaced by the larger EcoRI fragment from KW-K, which also contains an additional "C." For generation of the EcoRI fragment with the additional nucleotide, the KW-K isoform was used as a template in a PCR amplification using primers KW245/KW258 (SEQ ID NOS: 27 and 89, respectively). Digestion of the PCR product with EcoRI resulted in a 180 bp fragment corresponding to nucleotides 242–422 of SEQ ID NO: 70. The KW 258 primer spans one caspase-12 EcoRI site and also includes an extra base intended to shift the reading frame once introduced into the gene. This 180 bp EcoRI fragment was ligated with the larger fragment obtained be digesting pKW-19 with EcoRI, after purifying it from the undesired smaller EcoRI fragment. The desired construction was confirmed by restriction endonuclease digestion with EcoRI to detect the presence of a larger fragment and orientation was confirmed by digestion with HindIII. The resulting plasmid, named pKW-19-5, was mutagenized through PCR amplification using vector primer SP6 (GIBCO/BRL) and KW259 (SEQ ID NO: 90). KW259 spans the BglII site of caspase-12 and includes a nucleotide substitution that changes an internal stop codon to an Arg codon. The amplification product was digested with PstI and BglII and ligated into the larger BglII/PstI of pKW-19, after purifying it from the undesired PstI/BglII fragment. The caspase-12 gene that resulted from this mutagenesis is designated RIK-2 (SEQ ID NO: 72). This gene was cloned into various vectors for expression in bacterial or mammalian cells. Using PCR amplification of the RIK-2 template and primers KW262/KW254 (SEQ ID NOS: 93 and 86), the gene was cloned into mammalian expression vectors pcDNA3.1 (Invitrogen), pTRE (Clontech), and pIRES-hrGFP-1a (Invitrogen). Both of the KW262 and KW254 primers encode BamHI restriction enzyme sites; in addition, KW262 encodes a Kozak consensus translation initiation sequence for enhanced protein expression, followed by 21 nucleotides of caspase-12 sequence.

A. Production of Variants and Vectors for Expression in Bacterial Cells

For expression in bacterial cells, the RIK-2 DNA template was amplified by PCR using primers KW260/KW254 (SEQ ID NOS: 91 and 86). KW260 encodes a BamHI restriction site and additional nucleotides for subcloning into the pRSET-B expression vector (Invitrogen). With this vector, proteins are expressed as fusions with a 6-His purification tag.

A variant of the caspase-12 gene that is missing the CARD domain (ΔCARD) was constructed by PCR amplification of the RIK-2 template using primers KW269/KW254 (SEQ ID NOS: 96 and 86 above). KW269 contains a BamHI restriction enzyme site, a Kozak consensus sequence and an initiation codon. The resulting construct was designated RIK-4 (SEQ ID NO: 74). RIK-4 was amplified using primers KW261/KW254 (SEQ ID NOS: 92 and 86 above) and the resulting PCR product was cloned into pRSET-B for bacterial cell expression of the 6-His fusion protein.

All naturally occurring human caspase-12 isoforms identified thus far possess a non-conserved amino acid, Ser, at position 205. However, a multiple sequence alignment of all previously known human caspases demonstrated an absolutely conserved Gly at this position. Site-directed mutagenesis was performed on RIK-2 to convert Ser-205 to Gly. This was accomplished using the Quick Change Site-Directed Mutagenesis Kit (Stratagene) according to the manufacturer's protocol and primers containing the desired mutation, KW264 (SEQ ID NO: 94) and KW265 (SEQ ID NO: 95). Template plasmid DNA was selectively eliminated and the mutated plasmid DNA was transformed into $E.\ coli$ DH5α cells rendered competent using a conventional technique. Existing expression constructs were mutagenized in this manner to convert Ser-205 to Gly. The plasmid that resulted from mutagenizing the full-length KW-K gene in this manner was designated hCaspase-12 (SEQ ID NO: 76). The plasmid that resulted from mutagenizing the ΔCARD variant in this manner was designated RIK-5 (SEQ ID NO: 78).

Other plasmids described herein could be mutagenized in a similar manner; alternatively, convenient restriction enzyme sites may be utilized to insert this mutation by substituting a suitable fragment from RIK-5 containing the Ser-205 to Gly mutation for the corresponding fragment of another isoform or derivative thereof.

B. Expression in Bacterial Cells

The hCaspase-12 gene or ΔCARD caspase-12 (RIK-5) gene was cloned into pRSET-B for expression as a 6-His fusion protein. The plasmids were transformed into Epicurian Coli® BL21 (DE21) pLysS competent cells (Stratagene). Transformants were identified by their ability to grow on LB plates containing 100 μg/ml ampicillin. Clones containing expression plasmids were grown overnight at 37° C. in liquid LB medium containing 100 μg/ml ampicillin. The overnight culture was used to inoculate a larger culture at a ratio of 1:100 (v/v). The cells were grown to an optical density (600 nm) of 0.2 at 37° C. IPTG (Isopropyl-β-D-thiogalactopyranoside) was added to a final concentration of 0.4 mM and the cells were incubated at 30° C. for 6 hours. The cells were pelleted by centrifugation, washed in PBS and resuspended in IMAC Ni$^{2+}$ immobilized metal affinity chromatography lysis buffer (20 mM HEPES, pH 7.5, 15 mM KCl, 0.02% Na-azide) at ⅓₇ the original culture volume. Cell lysates were freeze-thawed twice, followed by a 1-minute, constant sonication at 20% duty cycle. Lysates were clarified by centrifugation at 14,000 rpm at 4° C. for 30 minutes. NaCl was added to the supernatant to a final concentration of 0.5M. An aliquot of this "partially purified" protein preparation was removed and subjected to Western blot as described below.

The human caspase-12 proteins in the remaining supernatant were further purified using IMAC. The affinity resin was prepared as follows: Chelating Sepharose FF (Pharmacia) resin was washed four times with 10 volumes of distilled water per wash to remove ethanol. The resin was charged by incubating in 2% NiSO$_4$ (w/v) in distilled water for 1 hour at 4° C. The resin was washed extensively with water to remove unbound $Ni^{2+}$. The resin was washed and equilibrated with IMAC "A" buffer (20 mM HEPES, pH 7.5, 0.5M NaCl, 0.02% Na azide). Protein supernatant was added to the resin (10:1 volume of supernatant to packed volume of resin) in a tube and rocked at 4° C. for 1 hour. The resin was washed 3 times with IMAC "A" buffer to remove unbound proteins The resin was then washed with a mixture of 95% IMAC "A" buffer and 5% IMAC "B" buffer (20 mM HEPES, pH 7.5, 0.5M NaCl, 500 mM imidazole, 0.02% Na azide) to elute proteins bound with low affinity. The resin was finally washed with a mixture of 92% IMAC "A" buffer and 8% IMAC "B" buffer, poured into a disposable column, and allowed to drain by gravity flow. His-Caspase-12 proteins were eluted from the column by the addition of IMAC elution buffer (a mixture of 60% IMAC "A" buffer and 40% IMAC "B" buffer) which contains imidazole at a final concentration of 200 mM. Fractions were collected and assayed for caspase-12 protein as follows.

The partially purified and more completely purified preparations of both recombinant human caspase-12 (containing the Ser-205 to Gly mutation) and the ΔCARD variant (containing the same mutation) were subjected to Western blot analysis using an anti-human caspase-12 polyclonal antibody prepared against peptide WSHHLEEIFQKVQH-SFE (containing an epitope near the C-terminus of human caspase-12) as described in Example 4.

Western blots of bacterially-expressed and IMAC-purified human caspase-12 and ΔCARD caspase-12 showed that the antibody recognized proteins of the expected molecular weights, based upon the sequence information. However, the partially purified caspase-12 protein preparations additionally contained a lower molecular weight protein (about 20 kDa) that was immunoreactive with the anti-caspase-12 antibody. This low molecular weight protein was not present in the supernatants upon IMAC purification. The presence of this band may indicate that the caspase-12 protein was autolytically processed during expression, inasmuch as no proteases found in bacteria have been reported to process any procaspase to the characteristic mature subunits observed upon caspase activation.

C. Expression in Mammalian Cells

For expression of recombinant hCaspase-12, mammalian cell expression plasmids were introduced into HEK293 cells using FuGENE transfection reagent (Roche Molecular Biochemicals). Expression of the full-length hCaspase-12 and ΔCARD caspase-12 (RIK-5) proteins was confirmed by Western blot analysis using anti-caspase-12 polyclonal antibody prepared against peptide WSHHLEEIFQKVQHSFE as described below in Example 4. Cells were harvested 48 hours post-transfection and lysed in detergent buffer (20 mM HEPES pH 7.3, 100 mM NaCl, 1 mM EDTA, 1 mM EGTA, 1 mM $Na_3VO_4$, 0.1 mM molybdic acid, 10 mM $MgCl_2$, 10 mM β-glycerophosphate, 5 mM PNPP, 1 mM PMSF, 0.5% NP-40, 1 mM NaF, 5 μg/ml leupeptin, 5 μg/ml pepstatin, and 1 mM DTT. The recombinantly expressed caspase-12 proteins were of the predicted molecular weights, based upon the sequence information.

Alternatively, human caspase-12 proteins of the invention can be produced by expressing a polynucleotide encoding caspase-12 in a suitable host cell using a suitable expression vector and using standard genetic engineering techniques. For example, one of the sequences encoding human caspase-12 described in Example 1 is subcloned into the commercial expression vector pzeoSV2 (Invitrogen, San Diego, Calif.) and transfected into Chinese Hamster Ovary (CHO) cells (ATCC CRL-1781) using the transfection reagent FuGENE 6 and the transfection protocol provided in the product insert. Additional eukaryotic cell lines, such as African Green Monkey Kidney cells (COS-7, ATCC CRL-1651) or Human Kidney cells (HEK293, ATCC CRL-1573), also may be suitable. Cells stably expressing human caspase-12 may be selected by growth in the presence of 100 mg/ml zeocin (Stratagene, La Jolla, Calif.). Optionally, the human caspase-12 polypeptide is purified from the cells using standard chromatographic techniques. To facilitate purification, antiserum (or antisera) is raised against one or more synthetic peptide sequences that correspond to portions of the amino acid sequence of human caspase-12, and the antiserum is used to affinity purify human caspase-12 protein. The human caspase-12 gene may also be expressed in-frame with a tag sequence (e.g., polyhistidine, hemagglutinin, FLAG) to facilitate purification. Moreover, it will be appreciated that many of the uses for human caspase-12 polypeptides, such as assays described below, do not require purification of caspase-12 protein from the host cell.

EXAMPLE 4

Generation of Antibodies to Human Caspase-12 Proteins

A peptide corresponding to amino acids 331–347 (WSHHLEEIFQKVQHSFE, SEQ ID NO: 107) of the human caspase-12 protein was synthesized for generation of a rabbit polyclonal antibody to human caspase-12. The C-12 peptide, $H_2$N-Cys-Gly-Gly-Trp-Ser-His-His-Leu-Glu-Glu-Ile-Phe-Gln-Lys-Val-Gln-His-Ser-Phe-Glu-$CO_2$H (SEQ ID NO: 108) was coupled to Keyhole Limpet Hemocyanin (KLH); Pierce Chemical Co. and used as an immunogen for injection into rabbits using standard dosing schedules for raising polyclonal antibodies. Antibody to caspase-12 was purified from immune antiserum by peptide affinity chromatography using immobilized C-12 peptide.

Standard techniques are employed to generate other polyclonal or monoclonal antibodies to human caspase-12 protein, and to generate useful antigen-binding fragments thereof or variants thereof, including "humanized" variants. Such protocols can be found, for example, in Sambrook et al., *Molecular Cloning: a Laboratory Manual.* Second Edition, Cold Spring Harbor, N.Y.: Cold Spring Harbor Laboratory (1989); Harlow et al. (Eds), *Antibodies A Laboratory Manual;* Cold Spring Harbor Laboratory; Cold Spring Harbor, N.Y. (1988); and other documents cited below. In one embodiment, recombinant human caspase-12 polypeptides (or cells or cell membranes containing such polypeptides) are used as an antigen to generate the antibodies. In another embodiment, one or more peptides having amino acid sequences corresponding to an immunogenic portion of human caspase-12 (e.g., 6, 7, 8, 9, 10, 11, 12, 13, 14, 15, 16,17,18, 19, 20, or more amino acids of contiguous caspase-12 sequence) are used as antigen. The antigen may be mixed with an adjuvant, carrier, or diluent and/or linked to a hapten to increase antibody production.

A. Polyclonal or Monoclonal Antibodies

As one exemplary protocol, recombinant human caspase-12 polypeptide or a synthetic fragment thereof is used to immunize a mouse for generation of monoclonal antibodies (or larger mammal, such as a rabbit, for polyclonal antibodies). To increase antigenicity, peptides are conjugated to KLH (Pierce Chemical Co.), according to the manufacturer's recommendations. For an initial injection, the antigen is emulsified with Freund's Complete Adjuvant and injected subcutaneously. At intervals of two to three weeks, additional aliquots of human caspase-12-specific antigen are emulsified with Freund's Incomplete Adjuvant and injected subcutaneously. Prior to the final booster injection, a serum sample is taken from the immunized mouse or mice and assayed by Western blot to confirm the presence of antibodies that immunoreact with human caspase-12. Serum from the immunized animals may be used as a polyclonal antisera or used to isolate polyclonal antibodies that recognize human caspase-12. Alternatively, the mice are sacrificed and their spleens removed for generation of monoclonal antibodies.

To generate monoclonal antibodies, the spleens are placed in 10 ml serum-free RPMI 1640, and single cell suspensions are formed by grinding the spleens in serum-free RPMI 1640, supplemented with 2 mM L-glutamine, 1 mM sodium pyruvate, 100 units/ml penicillin, and 100 µg/ml streptomycin (RPMI) (Gibco, Canada). The cell suspensions are filtered and washed by centrifugation and resuspended in serum-free RPMI. Thymocytes taken from three naive Balb/c mice are prepared in a similar manner and used as a Feeder Layer. NS-1 myeloma cells, kept in log phase in RPMI with 10% fetal bovine serum (FBS) (Hyclone Laboratories, Inc., Logan, Utah) for three days prior to fusion, are centrifuged and washed as well.

To produce hybridoma fusions, spleen cells from the immunized mice are combined with NS-1 cells and centrifuged, and the supernatant is aspirated. The cell pellet is dislodged by tapping the tube, and 2 ml of 37° C. PEG 1500 (50% in 75 mM HEPES, pH 8.0) (Boehringer Mannheim) is stirred into the pellet, followed by the addition of serum-free RPMI. Thereafter, the cells are centrifuged and resuspended in RPMI containing 15% FBS, 100 µM sodium hypoxanthine, 0.4 µM aminopterin, 16 µM thymidine (HAT) (Gibco), 25 units/ml of IL-6 (Boehringer Mannheim) and $1.5 \times 10^6$ thymocytes/ml and plated onto 10 Corning flat-bottom 96-well tissue culture plates (Corning, Corning N.Y.).

On days 2, 4, and 6 after the fusion, 100 µl of medium is removed from the wells of the fusion plates and replaced with fresh medium. On day 8, the fusions are screened by ELISA, testing for the presence of mouse IgG that binds to human caspase-12. Selected fusion wells are further cloned by dilution until monoclonal cultures producing anti-human caspase-12 antibodies are obtained.

B. Humanization of Anti-Human Caspase-12 Monoclonal Antibodies

Human caspase-12-neutralizing antibodies comprise one class of therapeutics useful as antagonists. The following description provides protocols to improve the utility of anti-human caspase-12 protein monoclonal antibodies as therapeutics in humans, by "humanizing" the monoclonal antibodies to improve their serum half-life and render them less immunogenic in human hosts (i.e., to prevent human antibody response to non-human anti-human caspase-12 antibodies).

The principles of humanization have been described in the literature and are facilitated by the modular arrangement of antibody proteins. To minimize the possibility of binding complement, a humanized antibody of the IgG4 isotype is preferred.

For example, a level of humanization is achieved by generating chimeric antibodies comprising the variable domains of non-human antibody proteins of interest with the constant domains of human antibody molecules. (See, e.g., Morrison et al., Adv. Immunol, 44:65–92 (1989)). The variable domains of human caspase-12 neutralizing anti-human caspase-12 antibodies are cloned from the genomic DNA of a B-cell hybridoma or from cDNA generated from mRNA isolated from the hybridoma of interest. The V region gene fragments are linked to exons encoding human antibody constant domains, and the resultant construct is expressed in suitable mammalian host cells (e.g., myeloma or CHO cells).

To achieve an even greater level of humanization, only those portions of the variable region gene fragments that encode antigen-binding complementarity determining regions ("CDR") of the non-human monoclonal antibody genes are cloned into human antibody sequences. (See, e.g., Jones et al., Nature 321:522–525 (1986); Riechmann et al., Nature 332:323–327 (1988); Verhoeyen et al., Science 239:1534–36 (1988); and Tempest et al., Bio/Technology 9:266–71 (1991)). If necessary, the β-sheet framework of the human antibody surrounding the CDR3 regions also is modified to more closely mirror the three-dimensional structure of the antigen-binding domain of the original monoclonal antibody. (See Kettleborough et al., Protein Engin. 4:773–783 (1991): and Foote et al., J. Mol. Biol. 224:487–499 (1992)).

In an alternative approach, the surface of a non-human monoclonal antibody of interest is humanized by altering selected surface residues of the non-human antibody, e.g., by site-directed mutagenesis, while retaining all of the interior and contacting residues of the non-human antibody. (See Padlan, Molecular Immunol. 28(4/5):489–98 (1991)).

The foregoing approaches are employed using human caspase-12-neutralizing anti-human caspase-12 monoclonal antibodies and the hybridomas that produce them to generate humanized human caspase-12-neutralizing antibodies useful as therapeutics to treat or ameliorate (i.e., palliate) conditions wherein human caspase-12 expression or ligand-mediated human caspase-12 signaling is detrimental.

C. Human Caspase-12-Neutralizing Antibodies from Phage Display

Human caspase-12-neutralizing antibodies are generated by phage-display techniques such as those described in Aujame et al., Human Antibodies 8(4):155–168 (1997); Hoogenboom, TIBTECH 15:62–70 (1997); and Rader et al., Curr. Opin. Biotechnol. 8:503–508 (1997), all of which are incorporated by reference. For example, antibody variable regions in the form of Fab fragments or linked single chain Fv fragments are fused to the amino terminus of filamentous phage minor coat-protein pIII. Expression of the fusion protein and incorporation thereof into the mature phage coat results in phage particles that present an antibody on their surface and contain the genetic material encoding the antibody. A phage library comprising such constructs is expressed in bacteria, and the library is panned (i.e., screened) for human caspase-12-specific phage antibodies using labeled or immobilized human caspase-12 as the antigen-probe.

D. Human Caspase-12-Neutralizing Antibodies from Transgenic Mice

Human caspase-12 protein-neutralizing antibodies are generated in transgenic mice essentially as described in Bruggemann et al., Immunol. Today 17(8):391–97 (1996) and Bruggemann et al., Curr. Opin. Biotechnol. 8:455–58 (1997). Transgenic mice carrying human V gene segments in germline configuration and that express these transgenes in their lymphoid tissue are immunized with a human caspase-12 composition using conventional immunization protocols. Hybridomas are generated using B cells from the immunized mice using conventional protocols and screened to identify hybridomas secreting anti-human caspase-12 human antibodies (e.g. as described above).

EXAMPLE 5

Examination of Protease Activity and Substrate Specificity of Human Caspase-12

All caspases exhibit enzymatic activity. Sequence analysis of human caspase-12 indicates that it shares high homology at the amino acid level to those regions of caspases involved in proteolysis.

A. Assays of Proteolytic Activity using Peptide Substrates

Proteolytic activities of caspases can be determined using the fluorogenic tetrapeptide substrates acetyl-Asp-Glu-Val-Asp-α-(4-methyl-coumaryl-7-amide) (Ac-DEVD-AMC) and acetyl-Tyr-Val-Ala-Asp-α-(4-methyl-coumaryl-7-amide) (Ac-YVAD-AMC) which contain sequences that correspond to the cleavage sites within the caspase substrates PARP and IL-1β, respectively. Caspase-3 cleaves Ac-DEVD-AMC but not Ac-YVAD-AMC, whereas caspase-1 cleaves only the latter substrate. Additional fluorescent peptide substrates that can be used include DEDD-R110 (Rhodamine-110 derivatized peptide), VEKD-R110, ATAD-R110, VETD-R110, LEHD-R110, and IETD-R110.

Enzymatic activity and substrate specificity of human caspase-12 can be analyzed using Ac-DEVD-AMC and Ac-YVAD-AMC. Briefly, human caspase-12 is expressed and isolated as in Example 3. Approximately 200 μg of human caspase-12 protein is incubated in buffer containing approximately 50 μM Ac-DEVD-AMC or Ac-YVAD-AMC at room temperature for varying periods of time. Proteolytic activity is determined by measuring AMC release by spectrofluorometry at an excitation wavelength of 380 nm and an emission wavelength of 460 nm. Reactions using DEDD-R110, VEKD-R110, ATAD-R110, VETD-R110, LEHD-R110 or IETD-R110 as substrates are carried out in buffer containing 10 mM PIPES, pH 7.4, 2 mM EDTA, 0.1% CHAPS, and 5 mM dithiothreitol). Reactions are monitored using an excitation wavelength of 496 nm and an emission wavelength of 520 nm at 30° C. for varying periods of time.

B. Assays of Proteolytic Activity Using Procaspase-3 Substrate

Lysates which contain recombinant caspases produced by expression in E. coli often contain fragments indicative of autoprocessing. Because the autolysis in caspase-12 lysates observed in Example 3B above is indicative of enzymatic activity, the enzymatic activity of partially purified human caspase-12 lysates was evaluated using procaspase-3 as a potential substrate. Caspase-3 is an effector caspase, which is cleaved at Asp175 by initiator caspases-8 and -9 to give the mature 19 kDa and 11 kDa subunits of the active enzyme. Processing of procaspase-3 was evaluated by Western blot analysis using an antibody that binds to full-length caspase-3 and another antibody that binds to the larger B subunit and that is specific for activated enzyme.

For use as a substrate for caspase-12, procaspase-3 was immunoprecipitated from SH-EP cell lysates using an antibody to full-length caspase-3 (Upstate Biotechnology, Inc.) and isolated on Protein G-Plus/Protein A agarose (Oncogene Science). To evaluate the enzymatic activity of partially purified caspase-12 protein, aliquots of immunoprecipitated procaspase-3 were incubated for 2 hours at 37° C. with a partially purified preparation of hCaspase-12, a partially purified preparation of ΔCARD caspase-12, and a similarly treated control (non-caspase protein) preparation, in a reaction buffer containing 25 mM HEPES, pH 7.5, 0.1% CHAPS, and 1 mM DTT. Reactions were terminated by the addition of loading buffer and incubation at 70° C. for 10 minutes. Samples were electrophoresed under reducing conditions on NuPAGE 4–12% Bis-Tris gels using NuPAGE MOPS Running buffer (Invitrogen). Following electrophoresis, proteins were transferred to an Immobilon P membrane (Millipore). The non-specific protein binding to the membrane was blocked by incubation with 5% BSA. Caspase-3 processing/activation by caspase-12 was detected by incubating with an anti-caspase-3 antibody (Upstate Biotechnology) which recognizes all subunits of caspase-3. Following incubation with an anti-rabbit HRP-conjugated antibody (Santa Cruz Biotechnology), immunoreactivity was detected by chemiluminescence using SuperSignal West PICO reagent (Pierce). Processing of procaspase-3 by caspase-12 to mature subunits was confirmed by Western blot using the Cleaved Caspase-3 (D175) Antibody (New England Biolabs) which is specific to only the active subunit (p19) of caspase-3.

Figure 8:
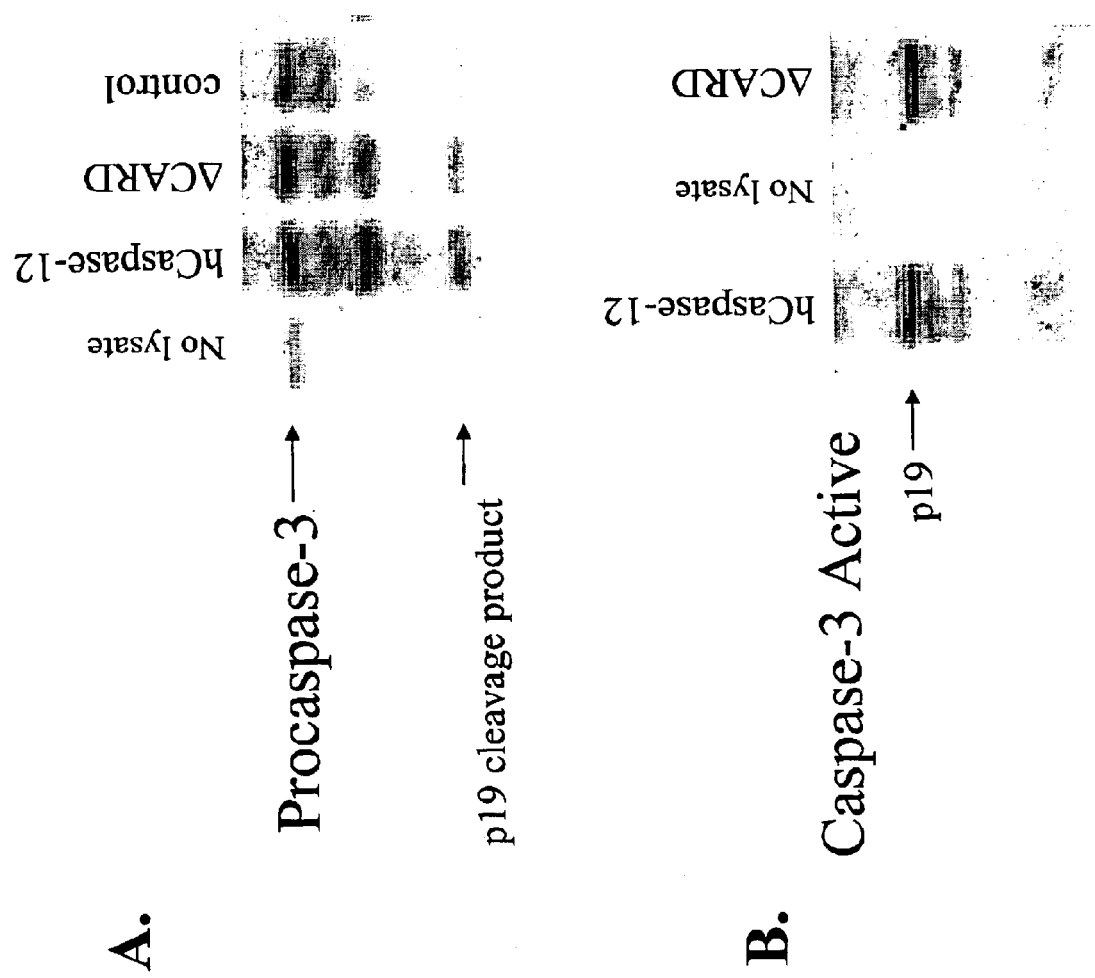
FIG. 8 is a Western blot.

FIGS. 8-A and 8-B show the results of this Western blot analysis. FIG. 8-A (Western blot with antibody to full-length caspase-3) shows that when procaspase-3 was incubated with recombinant human caspase-12 or the ΔCARD variant, lower molecular weight bands indicative of cleaved mature subunits were observed. No procaspase-3 processing was observed in reactions with the control, non-caspase protein preparations. These low molecular weight bands contained substantially greater amounts of protein than the corresponding faint bands observed in the control lane. FIG. 8-B (Western blot with antibody specific to the active enzyme) confirms that an immunoreactive band was present in the reactions where procaspase-3 was incubated with recombinant human caspase-12 or the ΔCARD variant.

These results suggest that human caspase-12 was able to cleave procaspase-3 to subunits of appropriate molecular weight, because there is no reported protease of bacterial origin that shows Asp-Xaa cleavage specificity.

C. Further Assay on a Peptide Substrate

The enzymatic activity of the partially purified hCaspase-12 and ΔCARD proteins was further evaluated in a fluorimetric assay allowing quantitation. The caspase activity of partially purified hCaspase-12 and ΔCARD protein preparations was compared to a control (non-caspase protein) preparation, using the Homogeneous Caspase Assay (Roche Biochemicals) according to the manufacturer's protocol. The assay measures the amount of free rhodamine-110, following its release from the substrate DEVD-R110, a caspase recognition sequence. Following a two-hour incubation of DEVD-R110 substrate with dilutions of the various protein preparations, free rhodamine-110 was quantitated fluorimetrically. Measured fluorescence intensity (RFU) for each preparation was 807 for hCaspase-12, 445 for ΔCARD, and 31 for the control. These results demonstrate that the recombinant human caspase-12 protein preparations exhibited proteolytic activity.

EXAMPLE 6

Analysis of the Over-Expression of Human Caspase-12

Over-expression of several members of the caspase family, including caspase-8, results in induction of apoptosis. Induction of cell death mediated by over-expression of human pro-caspase-12 can be determined using several cell or cell-free systems. For example, Sf9 baculovirus cells are infected with recombinant baculovirus encoding full-length human caspase-12. Cells are then examined for morphological signs of apoptosis including blebbing of the cytoplasmic membrane, condensation of nuclear chromatin, and release of small apoptotic bodies by microscopy. Internucleochromosomal DNA cleavage, another hallmark of apoptosis, is examined by electrophoresis of total cellular DNA isolated from the Sf9 cells. Sf9 cells that are infected with baculovirus containing vector only and Sf9 cells infected with recombinant baculovirus encoding caspase-3 are also analyzed as negative and positive controls, respectively.

Alternatively, the capability of human caspase-12 overexpression to induce apoptosis is assayed by transiently transfecting MCF-7 breast carcinoma cells, embryonic kidney 293 cells, HeLa cells or the like with an expression vector encoding human caspase-12, and assaying for morphological changes characteristic of programmed cell death. Overexpression of human caspase-12 induced by transfection of SH-EP (Scaffidi et al., above) and HEK293 cells with relevant clones in the pcDNA3.1 vector did not result in significant apoptosis of the transfected cells under these conditions. In the absence of a specific death stimulus/signal, elevated expression of caspase-12 will not trigger apoptosis. However, activation of human caspase-12 could be observed and was evaluated as described in Example 8 below.

EXAMPLE 7

Assays to Identify Modulators of Human Caspase-12 Protein Activity

Set forth below are assays for identifying modulators (agonists and antagonists) of human caspase-12 protein activity (e.g., proteolytic activity, or binding of human caspase-12 to adaptor molecules, receptor molecules, substrates or other ligands). Among the modulators that can be identified by these assays are natural ligand compounds of human caspase-12, synthetic analogs and derivatives of natural ligands, antibodies, antibody fragments, and/or antibody-like compounds derived from natural antibodies or from antibody-like combinatorial libraries, and/or synthetic compounds identified through high-throughput screening of libraries, and the like. All modulators that bind human caspase-12 protein are useful for identifying human caspase-12 protein in tissue samples (e.g., for diagnostic purposes, pathological purposes, and the like). Agonist and antagonist modulators are useful for up-regulating and down-regulating human caspase-12 activity, respectively, to treat disease states characterized by abnormal levels of human caspase-12 activity. Human caspase-12 binding molecules also may be used to deliver a therapeutic compound or a label to cells that express human caspase-12 protein (e.g., by attaching the compound or label to the binding molecule). The assays may be performed using single putative or candidate modulators, and/or may be performed using a known agonist in combination with candidate antagonists (or vice versa). Any assays known in the art for detecting caspase activity may be used, including the enzymatic assays described above in Example 5.

EXAMPLE 8

Studies of Activation of Human Caspase-12
A. Activation of Human Caspase-12 as Part of the Extrinsic Pathway The role of hCaspase-12 in cell death pathways was examined using cells of a neuroblastoma cell line, SH-EP. In the extrinsic (or receptor-induced) cell death pathway, caspase-8 is the apical caspase that cleaves effector caspases such as caspase-3, which cleaves many cellular substrates. Caspase activation, indicated by cleavage of the proform of the enzyme in cell lysates, was evaluated by Western blot analysis.

The expression vector pIRES-hrGFP-1a harboring the hCaspase-12 or RIK-5 gene was transfected into SH-EP cells using Superfect transfection reagent (Qiagen). At 24 hours post-transfection, 250 ng/ml αFas-antibody (CH-11, Upstate Biotechnology) was added and incubated for 18 hours to induce the extrinsic cell death pathway. Culture medium and cells were harvested and lysed in detergent buffer. Cleavage of exogenous hCaspase-12 was evaluated by Western blot analysis using anti-human caspase-12 antibody (prepared against peptide WSHHLEEIFQKVQHSFE as described in Example 4).

Figure 9:
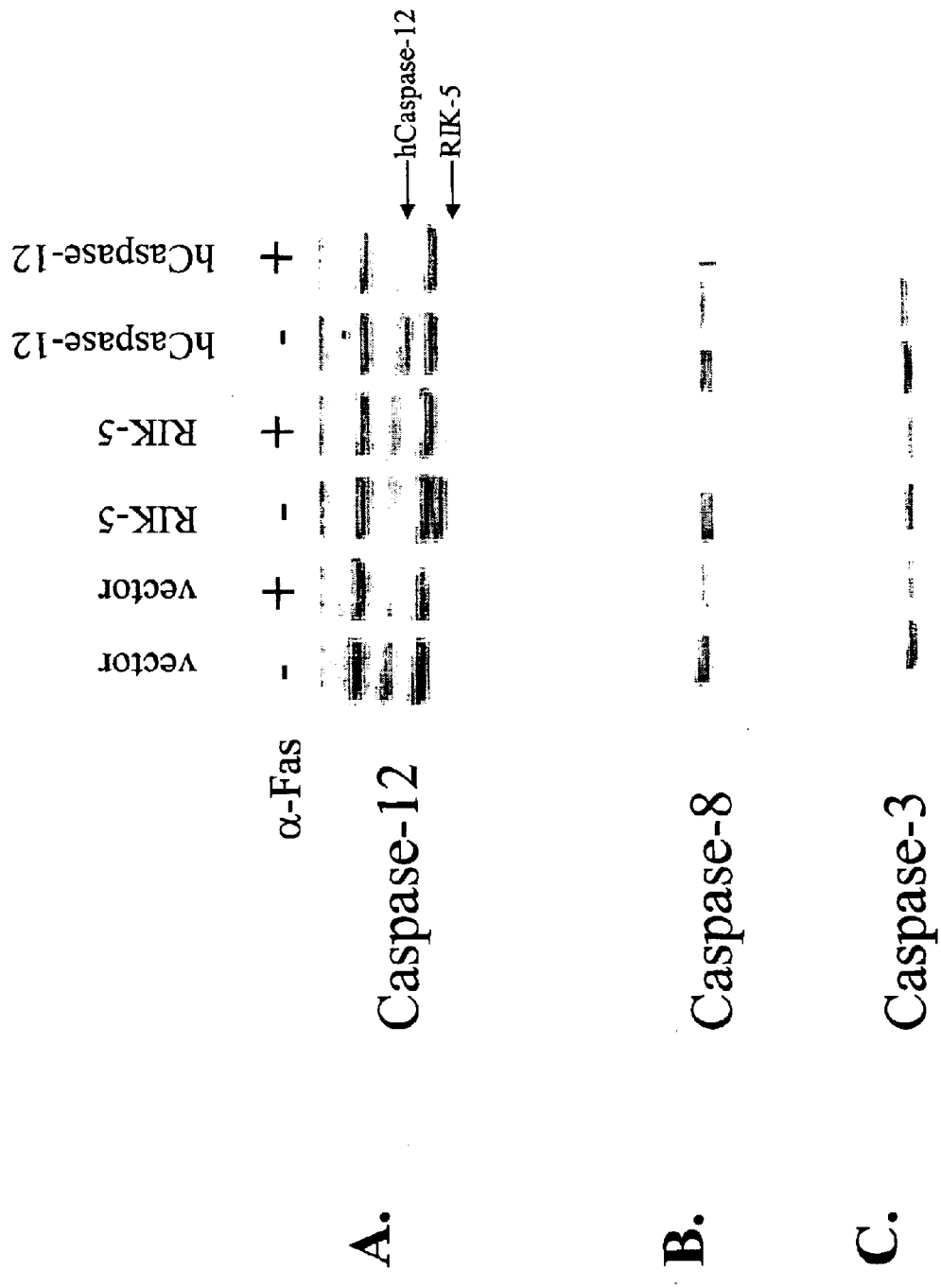
FIG. 9 shows Western blots of hCaspase-12 expression in culture.

The results, shown in FIG. 9-A, demonstrated that hCaspase-12 and RIK-5 proteins were cleaved in cultures undergoing apoptosis. FIGS. 9-B and 9-C are control Western blots using antibodies to caspase-8 (Upstate Biotechnology) or caspase-3 (Santa Cruz Biotechnology) that demonstrated activation of these caspases, as evidenced by the reduced amount of proform of the enzyme relative to uninduced cultures. These results indicate that human caspase-12 is a substrate of caspases that are activated upon Fas receptor engagement.

B. Activation of Human Caspase-12 in Response to ER Stress

Reports in the literature indicated a strong activation of murine caspase-12 in response to agents which induce an endoplasmic reticulum (ER) stress response, such as tunicamycin or the $Ca^{2+}$ ionophore A23187. The activation of endogenous human caspase-12 by these ER stress-inducing agents in SH-EP and HEK293 cells was evaluated by Western blot analysis of cell lysates. SH-EP is a neuroblastoma cell line that endogenously expresses human caspase-12 at detectable levels. HEK293 is a transformed kidney cell line that lacks detectable caspase-12.

Figure 10:
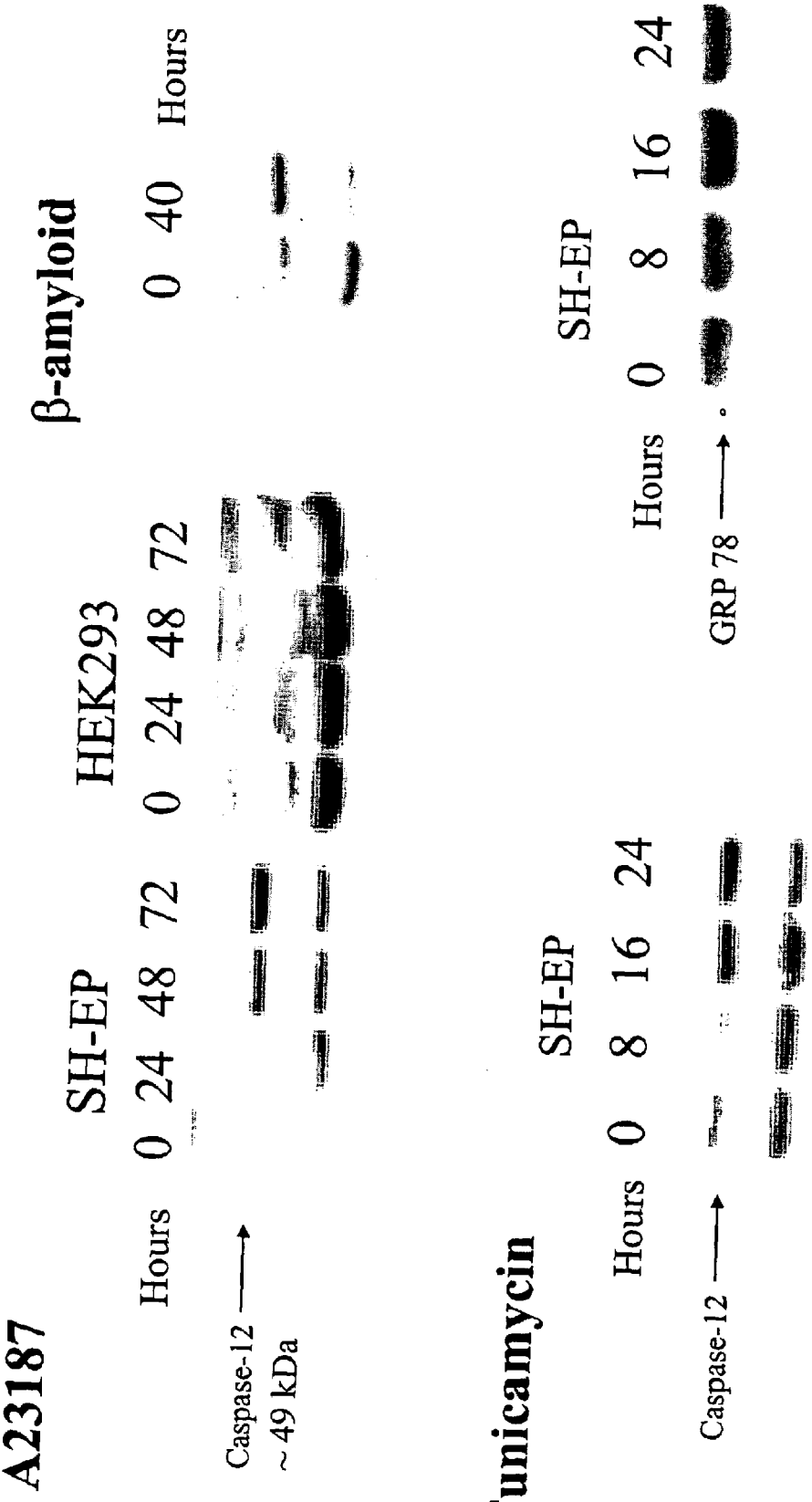
FIG. 10, panels A and B, shows Western blots of NuPAGE gels containing caspase-12 expression products from cultures treated with 1 μg/ml tunicamycin or 2 μM A23187 (Calbiochem) and harvested over time. The experimental antibody is described in Example 8A.

Cell cultures were treated with 1 µg/ml tunicamycin or 2 µM A23187 (Calbiochem) and harvested over time. Cells were lysed in detergent buffer, cellular proteins resolved on NuPAGE gels and subjected to Western blot analysis using the same antibody as in Example 8A above. Results, depicted in FIGS. 10-A and 10-B, show that strong induction of caspase-12 protein occurs in SH-EP cells upon treatment with either tunicamycin or A23187 and that induction is time-dependent. FIG. 10-D depicts a control Western blot using an antibody against GRP 78 (Santa Cruz Biotechnology) that demonstrated induction of this ER-resident protein upon tunicamycin treatment, consistent with the literature (Nakagowa et al., Nature (2000) 403:98–103). In a similar experiment, results of which are depicted in FIG. 10-C, induction of human caspase-12 was observed in cultures treated with 40 µM β-amyloid [25–35] (BACHEM) for 40 hours. This is consistent with an earlier report (Nakagowa et al., supra) that demonstrated that cells from a caspase-12$^{-/-}$ mouse are more resistant to beta-amyloid-induced apoptosis.

The biological significance of caspase-12 up-regulation by the ER stress-inducing agent A23187 in apoptosis was further investigated. SH-EP cells were treated with 2 µM A23187 for 40 hours to induce expression of endogenous caspase-12. One control culture was left untreated. Of the four cultures treated with A23187, one culture received 10 μg/ml cycloheximide (CHX) to block new protein synthesis and two cultures were subjected to an apoptotic stimulus, either 250 ng/ml α-Fas antibody for 24 hours or 1200 microjoules UV irradiation. The cultures were harvested after 6.5 hours. Western blot analysis of caspase-12 expression and activation was done as described above in Example 8A, using similar protein loads for each condition tested.

Figure 11:
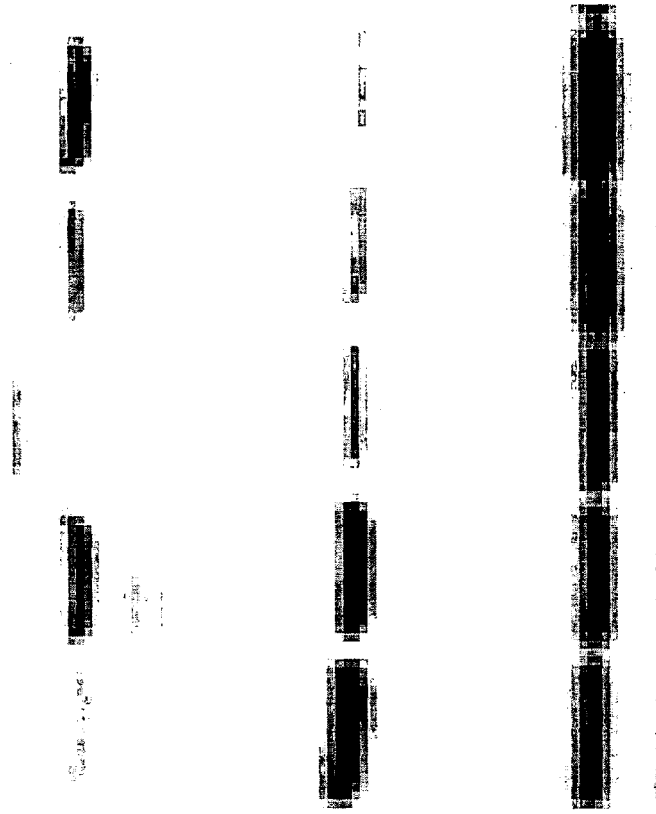
FIG. 11 shows Western blots of induced expression of endogenous caspase-12 in SH-EP cells treated with 2 μM A23187 for 40 hours. One control culture was left untreated. Of the four cultures treated with A23187, one culture received 10 μg/ml cycloheximide (CHX) to block new protein synthesis and two cultures were subjected to an apoptotic stimulus, either 250 ng/ml α-Fas antibody for 24 hours or 1200 microjoules UV irradiation. The cultures were harvested after 6.5 hours. Western blot analysis of caspase-12 expression and activation was done as described above in Example 8A, using similar protein loads for each condition tested.

The results displayed in FIG. 11-A demonstrated that expression of caspase-12 is induced upon treatment with A23187 and is inhibited by the presence of cycloheximide, indicating that ER-stress-induced processing via A23187 requires protein expression. In cultures subjected to UV irradiation, caspase-12 is cleaved, as evidenced by the loss of the proenzyme. However, in cultures treated with α-Fas antibody, the caspase-12 proenzyme remains intact. Control Western blots using an antibody to caspase-3 demonstrated activation of caspase-3 in induced cultures.

Additional experiments of were conducted to evaluate the effect of a caspase or calpain inhibitor on SH-EP cells subjected to ER stress. Z-VAD-fmk (Z=benzyloxycarbonyl group at the N-terminus of Val-Ala-DL-Asp(OMe)-fluoromethylketone; BACHEM) is a general caspase inhibitor that inhibits most of the known caspases, to varying extents. Calpeptin is an inhibitor of calpains, a family of calcium-dependent proteases that proteolyze a variety of cellular proteins. SH-EP cells were treated with 2 μM A23187 for 40 hours to induce expression of endogenous caspase-12. One culture was pre-incubated with 50 μM Z-VAD-fmk, and another was pre-incubated with 10 μM calpeptin (Calbiochem) for 1 hour prior to UV irradiation. Cultures were harvested 6.5 hours after UV irradiation, lysates were prepared and proteins were resolved by NuPAGE gel electrophoresis. Caspase activation was evaluated by Western blot using antibodies to caspase-12 as described above in Example 8A. The results, displayed in FIG. 12-A, demonstrate caspase-12 cleavage and presumed activation after UV irradiation, as judged by the loss of the proenzyme band (lane 2). Inclusion of a general caspase inhibitor (ZVAD-fmk) reduces cleavage of pro-caspase-12 (lane 3). Likewise, cleavage of procaspase-12 is reduced by the presence of the calpain inhibitor (lane 4). Lysates from the same cultures, subjected to Western blots using an anti-caspase-3 antibody (Upstate Biotechnology, Inc.), showed that cleavage of caspase-3 following UV irradiation (lane 2) was inhibited by the presence of the caspase inhibitor Z-VAD-fmk (lane 3) but was not affected by the calpain inhibitor (lane 4). These results demonstrate caspase-12 cleavage/activation is dependent upon calpain activity Thus, the pathways responsible for caspase-12 activation differ considerably from those involved in activation of the key executioner caspase, caspase-3. Additionally, the calcium/calpain-regulated feature of the caspase-12 activation pathway ties this caspase to cellular events in tissues in which calcium levels are critical for function.

EXAMPLE 9

Calpain II Cleavage of Human Caspase-12

An alteration in intracellular calcium homeostasis can induce an ER stress response which results in apoptosis. As illustrated in Example 8 above, treatment of cells with the calcium ionophore A23187 (which elevates calcium concentration in the cytosol) results in up-regulation of endogenous caspase-12. A link between calcium levels and caspase-12 may involve the calpains, a family of calcium-dependent proteases that are activated by elevated intracellular calcium and that proteolyze a variety of cellular proteins. Elevated calpain activity has been linked to degenerative conditions or diseases of the brain and other tissues, including but not limited to stroke, cerebral vasospasm, and kidney failure (Vanderklish et al., Int. J. Exp. Pathol. (2000) 81(5):323–39). Calcium metabolism has been implicated in cardiac arrythmias and heart-related contractile dysfunction (Shorofsky et al., Am. J. Med. (2001) 110(2):127–40), as well as coronary artery disease (Tzivoni Clin. Cardiol. (2001) 24(2):102–06); Ca channelopathy-related diseases or disorders such as episodic ataxia-type 2, spinocerebellar ataxia type 6, familial hemiplegic migraine, hypokalemic periodic paralysis, central core disease, malignant hyperthermia syndrome, congenital stationary night blindness (Celesia. Clin. Neurophysiol. (2001) 112(1):2–18); and a variety of neurodegenerative diseases (Deigner et al., Expert Opin. Investig. Drugs (2000) 9(4):747–64). Consistent with Deigner et al., many neurological diseases or disorders are degenerative (e.g., Alzheiner's disease), consistent with a gradual and prolonged form of apoptosis, while others arise as acute pathological states (e.g., cerebral ischemia). Paschen Cell Calcium (2001) 29(1):1–11.

Figure 13:
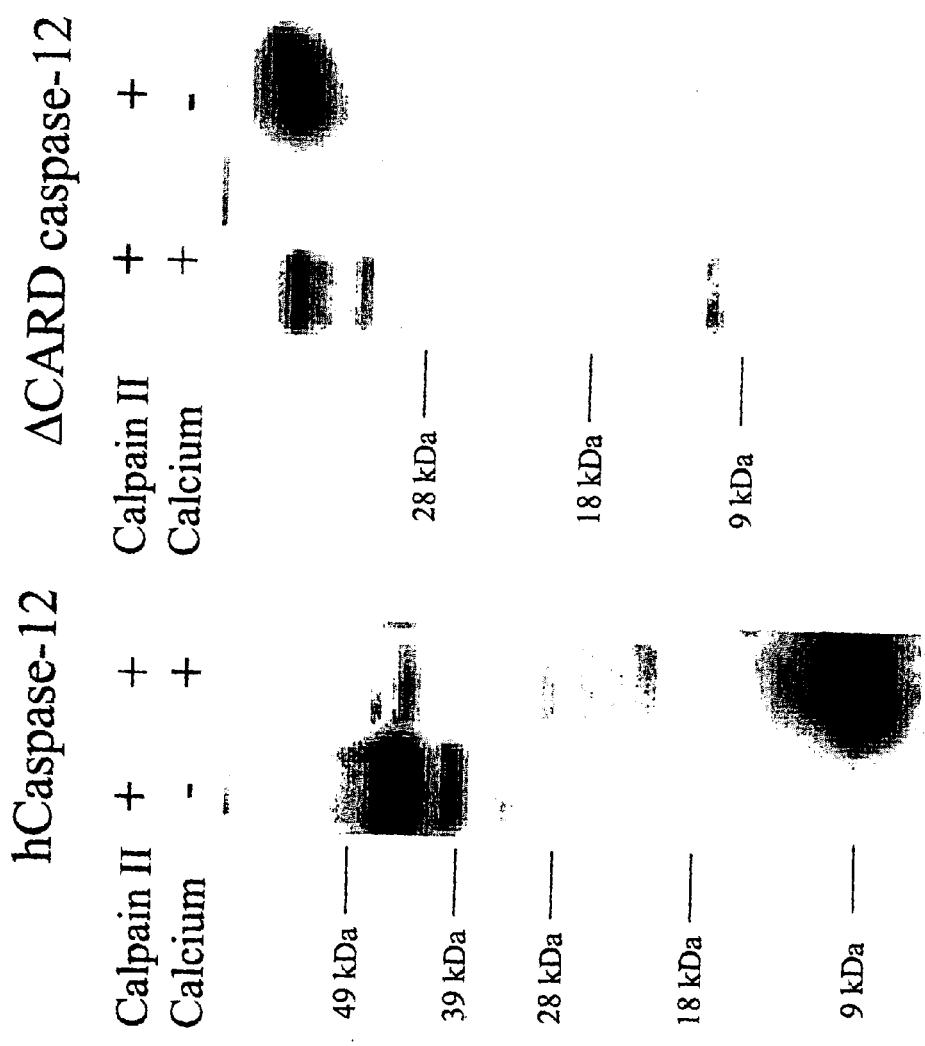
FIG. 13, panels A and B, shows Western blots (see Example 8A) revealing the action of calpain on caspase-12 using an in vitro assay. Affinity-purified hCaspase-12 and ΔCARD caspase-12 were prepared as described in Example 3B and incubated with 0.012 U/μl calpain II (Calbiochem) in solutions containing 150 mM NaCl, 20 mM Tris-HCl, pH 7.5, and 1 mM DTT. Calpain II was activated by the addition of 5 mM $CaCl_2$, while corresponding control cultures were not activated by addition of calcium.

The relationship between calpain and caspase-12 was explored in vitro as follows. Affinity-purified hCaspase-12 and ΔCARD caspase-12 prepared as described in Example 3B above, were incubated with 0.012 U/μl calpain II (Calbiochem) in solutions containing 150 mM NaCl, 20 mM Tris-HCl, pH 7.5, and 1 mM DTT. Calpain II was activated by the addition of 5 mM $CaCl_2$, while corresponding control cultures were not activated by addition of calcium. Cleavage of human caspase-12 was evaluated by Western blot analysis as described in Example 8A above. Results are depicted in FIGS. 13-A and 13-B and show that calpain II cleaves both hCaspase-12 and the ΔCARD variant and that this cleavage is calcium dependent. Thus, the activation and processing of caspase-12 is closely tied to cellular calcium levels. It is anticipated that calpain will process caspase-12 by recognizing the cleavage site "ASADT" at positions 269–272 of hCaspase-12 (SEQ ID NO: 77), with cleavage occurring between residues 271 and 272. Because cellular calcium is an important regulatory feature in health and disease, the signaling pathway to caspase-12 may have multiple branches that can result in activation of this caspase.

Moreover, another aspect of the invention, related to the studies described here, involves the design of peptide modulators of calpain activity that are based on the caspase-12 sequence. Preferably, such peptide modulators, e.g., inhibitors, will include the "ASADT" sequence (residues 269–272 of SEQ ID NO: 77) or variations or derivatives thereof.

While the present invention has been described in terms of specific embodiments, it is understood that variations and modifications will occur to those in the art, all of which are intended as aspects of the present invention. Accordingly, only such limitations as appear in the claims should be placed on the invention.

What is claimed is:

1. A purified and isolated caspase polypeptide comprising the amino acid sequence set forth in SEQ ID NO: 77.

2. A purified and isolated fusion polypeptide comprising a caspase polypeptide according to claim 1.

3. A method for identifying a candidate inhibitor of human caspase-12 comprising the steps of:

contacting a composition comprising a caspase polypeptide according to claim 1 with a substrate, and measuring enzymatic activity of said caspase polypeptide in the presence and absence of a test compound, wherein a decrease in enzymatic activity means that the test compound is a candidate inhibitor.

4. A method for identifying a candidate activator of human caspase-12 comprising the steps of:

contacting a composition comprising a caspase polypeptide according to claim 1 with a substrate, and measuring enzymatic activity of said caspase polypeptide in the presence and absence of a test compound, wherein an increase in enzymatic activity means that the test compound is a candidate activator.

5. A method for identifying a compound that binds to human caspase-12 comprising the steps of:

contacting a composition comprising a caspase polypeptide according to claim 1 with a test compound, and measuring binding of said test compound to said caspase polypeptide.

* * * * *